(12) United States Patent
Dey et al.

(10) Patent No.: US 11,713,327 B2
(45) Date of Patent: Aug. 1, 2023

(54) HETEROARYL HETEROCYCLYL COMPOUNDS FOR THE TREATMENT OF AUTOIMMUNE DISEASE

(71) Applicant: Hoffmann-La Roche Inc., Little Falls, NJ (US)

(72) Inventors: Fabian Dey, Basel (CH); Buyu Kou, Shanghai (CN); Haixia Liu, Shanghai (CN); Hong Shen, Shanghai (CN); Xiaoqing Wang, Shanghai (CN); Weixing Zhang, Shanghai (CN); Zhisen Zhang, Shanghai (CN); Zhiwei Zhang, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 90 days.

(21) Appl. No.: 17/251,494

(22) PCT Filed: Jun. 11, 2019

(86) PCT No.: PCT/EP2019/065091
§ 371 (c)(1),
(2) Date: Dec. 11, 2020

(87) PCT Pub. No.: WO2019/238616
PCT Pub. Date: Dec. 19, 2019

(65) Prior Publication Data
US 2021/0300947 A1 Sep. 30, 2021

(30) Foreign Application Priority Data

Jun. 12, 2018 (WO) ................ PCT/CN2018/090783
Sep. 12, 2018 (EP) ..................................... 18193919
Apr. 16, 2019 (WO) ................ PCT/CN2019/082889

(51) Int. Cl.
| | |
|---|---|
| C07D 519/00 | (2006.01) |
| C07D 413/14 | (2006.01) |
| C07D 417/14 | (2006.01) |
| C07D 471/04 | (2006.01) |
| C07D 487/04 | (2006.01) |
| C07D 498/10 | (2006.01) |

(52) U.S. Cl.
CPC ......... *C07D 519/00* (2013.01); *C07D 413/14* (2013.01); *C07D 417/14* (2013.01); *C07D 471/04* (2013.01); *C07D 487/04* (2013.01); *C07D 498/10* (2013.01)

(58) Field of Classification Search
CPC .. C07D 519/00; C07D 413/14; C07D 417/14; C07D 471/04; C07D 487/04; C07D 498/10
USPC .................................................... 514/210.16
See application file for complete search history.

(56) References Cited

U.S. PATENT DOCUMENTS

| | | |
|---|---|---|
| 2015/0105370 A1 | 4/2015 | Carlson et al. |
| 2017/0174653 A1 | 6/2017 | Sherer et al. |
| 2019/0185469 A1 | 6/2019 | Dyckman et al. |
| 2021/0253575 A1 | 8/2021 | Dey et al. |
| 2021/0269451 A1 | 9/2021 | Liu et al. |
| 2021/0300924 A1 | 9/2021 | Liu et al. |
| 2021/0323977 A1 | 10/2021 | Liu et al. |
| 2021/0340134 A1 | 11/2021 | Qiu et al. |
| 2021/0340136 A1 | 11/2021 | Zhu et al. |
| 2021/0355122 A1 | 11/2021 | Dey et al. |
| 2021/0395239 A1 | 12/2021 | Dey et al. |
| 2022/0112187 A1 | 4/2022 | Liu et al. |

FOREIGN PATENT DOCUMENTS

| | | |
|---|---|---|
| EP | 3 623 369 A1 | 3/2020 |
| WO | 2015/057655 A1 | 4/2015 |
| WO | 2015/057659 A1 | 4/2015 |
| WO | 2019/028302 A1 | 2/2017 |
| WO | 2017/106607 A1 | 6/2017 |
| WO | 2018/005586 A1 | 1/2018 |
| WO | 2018/026620 A1 | 2/2018 |
| WO | 2018/031434 A1 | 2/2018 |
| WO | 2018/047081 A1 | 3/2018 |
| WO | 2018/049089 A1 | 3/2018 |
| WO | 2019/018354 A1 | 1/2019 |
| WO | 2019/028301 A1 | 2/2019 |
| WO | 2019/099336 A1 | 5/2019 |

(Continued)

OTHER PUBLICATIONS

Alper, P., et al., "Discovery of potent, orally bioavailable in vivo efficacious antagonists of the TLR7/8 pathway" Bioorg Med Chem Lett 30(17):127366 (1-5) (Sep. 1, 2020).

(Continued)

*Primary Examiner* — Kahsay Habte
(74) *Attorney, Agent, or Firm* — Genentech, Inc.; Richard G. A. Bone

(57) ABSTRACT

The present invention relates to compounds of formula (I), ab (I), wherein R1 to R3 and L are as described herein, and their pharmaceutically acceptable salt, enantiomer or diastereomer thereof, and compositions including the compounds and methods of using the compounds.

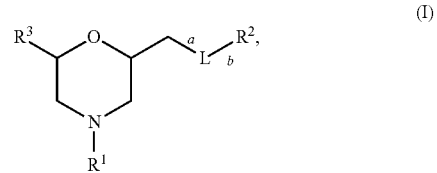

(I)

17 Claims, No Drawings

(56) References Cited

FOREIGN PATENT DOCUMENTS

| | | |
|---|---|---|
| WO | 2019/118799 A1 | 6/2019 |
| WO | 2019/123294 A2 | 6/2019 |
| WO | 2019/125849 A1 | 6/2019 |
| WO | 2019/126081 A1 | 6/2019 |
| WO | 2019/126082 A1 | 6/2019 |
| WO | 2019/126083 A1 | 6/2019 |
| WO | 2019/126113 A1 | 6/2019 |
| WO | 2019/126242 A1 | 6/2019 |
| WO | 2019/126253 A1 | 6/2019 |
| WO | 2019/220390 A1 | 11/2019 |
| WO | 2019/238629 A1 | 12/2019 |
| WO | 2020/043271 A1 | 3/2020 |
| WO | 2020/048583 A1 | 3/2020 |
| WO | 2020/048595 A1 | 3/2020 |
| WO | 2020/048596 A1 | 3/2020 |
| WO | 2020/048605 A1 | 3/2020 |
| WO | 2020/052738 A1 | 3/2020 |
| WO | 2020/064792 A1 | 4/2020 |
| WO | 2020/094749 A1 | 5/2020 |
| WO | 2021/048200 A1 | 3/2021 |
| WO | 2021/052892 A1 | 3/2021 |
| WO | 2021/099406 A1 | 5/2021 |

OTHER PUBLICATIONS

International Preliminary Report on Patentability for PCT/EP2019/065091 dated Dec. 15, 2020, pp. 1-9.

International Search Report for PCT/EP2019/065091 dated Aug. 19, 2019, pp. 1-13.

Knoepfel, T., et al., "Target-Based Identification and Optimization of 5-Indazol-5-yl Pyridones as Toll-like Receptor 7 and 8 Antagonists Using a Biochemical TLR8 Antagonist Competition Assay" J Med Chem 63(15):8276-8295 (Jul. 30, 2020).

Mussari et al., "Discovery of Potent and Orally Bioavailable Small Molecule Antagonists of Toll-like Receptors 7/8/9 (TLR7/8/9)" ACS Med. Chem. Lett. 11:1751-1758 ( 2020).

U.S. Appl. No. 17/756,221, filed May 19, 2022 entitled "Spiro(isobenzofuranazetidine) Compounds for the Treatment of Autoimmune Disease".

U.S. Appl. No. 17/761,150, filed Mar. 16, 2022 entitled "Piperidinyl Amine Compounds for the Treatment of Autoimmune Disease".

U.S. Appl. No. 17/641,894, filed Mar. 10, 2020 entitled: "Quinoline Compounds for the Treatment of Autoimmune Disease".

HETEROARYL HETEROCYCLYL COMPOUNDS FOR THE TREATMENT OF AUTOIMMUNE DISEASE

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with nonspecific anti-inflammatory or immunosuppressive drugs. However, long term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al *Lancet* 2011, 377, 721). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as autoinflammation diseases.

Toll Like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7,8,9 is considered as a key node in a broad of autoimmune and auto-inflammatory diseases (Krieg, A. M. et al. Immunol. Rev. 2007, 220, 251. Jiménez-Dalmaroni, M. J. et al *Autoimmun Rev.* 2016, 15, 1. Chen, J. Q., et al. *Clinical Reviews in Allergy & Immunology* 2016, 50, 1). Anti-RNA and anti-DNA antibodies are well established diagnostic markers of SLE, and these antibodies can deliver both self-RNA and self-DNA to endosomes. While self-RNA complexes can be recognized by TLR7 and TLR8, self-DNA complexes can trigger TLR9 activation. Indeed, defective clearance of self-RNA and self-DNA from blood and/or tissues is evident in SLE (Systemic Lupus Erythematosus) patients. TLR7 and TLR9 have been reported to be upregulated in SLE tissues, and correlate with chronicity and activity of lupus nephritis, respectively. In B cells of SLE patients, TLR7 expression correlates with anti-RNP antibody production, while TLR9 expression with IL-6 and anti-dsDNA antibody levels. Consistently, in lupus mouse models, TLR7 is required for anti-RNA antibodies, and TLR9 is required for anti-nucleosome antibody. On the other hand, overexpression of TLR7 or human TLR8 in mice promotes autoimmunity and auto-inflammation. Moreover, activation of TLR8 specifically contributes to inflammatory cytokine secretion of mDC/macrophages, neutrophil NETosis, induction of Th17 cells, and suppression of Treg cells. In addition to the described role of TLR9 in promoting autoantibody production of B cells, activation of TLR9 by self-DNA in pDC also leads to induction of type I IFNs and other inflammatory cytokines. Given these roles of TLR9 in both pDC and B cells, both as key contributors to the pathogenesis of autoimmune diseases, and the extensive presence of self-DNA complexes that could readily activate TLR9 in many patients with autoimmune diseases, it may have extra benefit to further block self-DNA mediated TLR9 pathways on top of inhibition of TLR7 and TLR8 pathways. Taken together, TLR7, 8, and 9 pathways represent new therapeutic targets for the treatment of autoimmune and auto-inflammatory diseases, for which no effective steroid-free and non-cytotoxic oral drugs exist, and inhibition of all these pathways from the very upstream may deliver satisfying therapeutic effects. As such, we invented oral compounds that target and suppress TLR7, TLR8 and TLR9 for the treatment of autoimmune and auto-inflammatory diseases.

SUMMARY OF THE INVENTION

The present invention relates to novel compounds of formula (I) or (Ia),

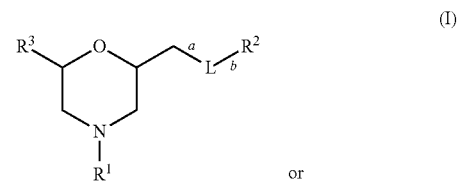

or

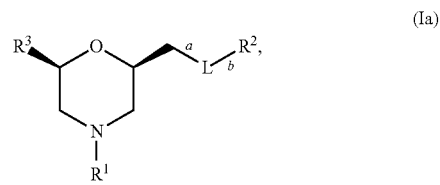

wherein
$R^1$ is

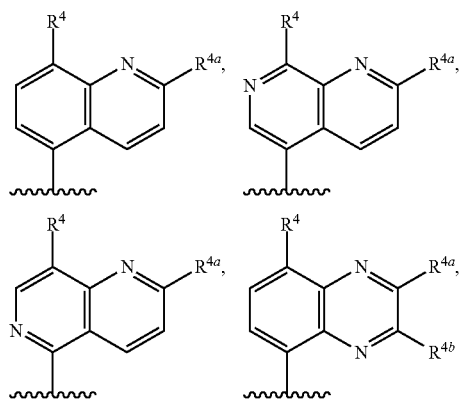

-continued

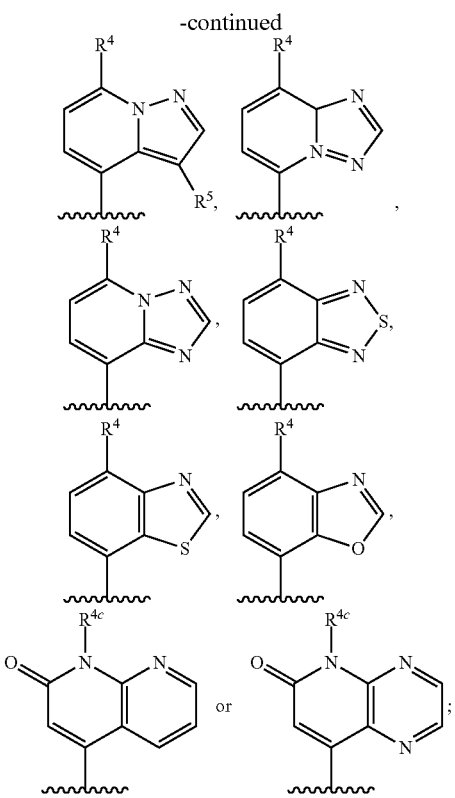

wherein R⁴ is $C_{1-6}$alkyl, $C_{1-6}$alkoxy, halo$C_{1-6}$alkyl, halogen, nitro or cyano; $R^{4a}$ is H or deuterium; $R^{4b}$ is H, deuterium or $C_{1-6}$alkyl; $R^{4c}$ is $C_{1-6}$alkyl or $C_{3-7}$cycloalkyl; $R^5$ is H or halogen;

R² is 1,2,3,4-tetrahydroisoquinolinyl which is unsubstituted or substituted by $C_{1-6}$alkoxy, hydroxy or hydroxy$C_{1-6}$alkyl;
2,3-dihydro-1H-pyrrolo[3,4-c]pyridinyl;
3,4-dihydro-1H-isoquinolinyl di-substituted by hydroxy and $C_{1-6}$alkyl;
4,5,6,7-tetrahydropyrazolo[1,5-a]pyrazinyl;
4,5,6,7-tetrahydrothiazolo[5,4-c]pyridinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl which is unsubstituted or substituted by $C_{1-6}$alkyl;
5,6,7,8-tetrahydro-2,7-naphthyridinyl which is unsubstituted or substituted by $C_{1-6}$alkyl;
5,6,7,8-tetrahydropyrido[3,4-b]pyrazinyl which is unsubstituted or substituted by $C_{1-6}$alkyl;
5,6,7,8-tetrahydropyrido[3,4-d]pyrimidinyl;
5,6,7,8-tetrahydropyrido[4,3-d]pyrimidinyl;
6,7-dihydro-5H-pyrrolo[3,4-b]pyridinyl which is unsubstituted or substituted by $C_{1-6}$alkyl;
6,7-dihydro-5H-pyrrolo[3,4-d]pyrimidinyl;
7,8-dihydro-5H-1,6-naphthyridinyl substituted by $C_{1-6}$alky; or
isoindolinyl which is unsubstituted or substituted by hydroxy$C_{1-6}$alkyl or $C_{1-6}$alkyl;

R³ is $C_{1-6}$alkyl;

L is 1,4-diazepanyl; hydroxy-1,4-diazepanyl; piperazinyl; (hydroxy$C_{1-6}$alkyl)piperazinyl; 1,6-diazaspiro[3.3]heptanyl; aminoazetidinyl; pyrrolidinylamino; or 3-oxa-7,9-diazabicyclo[3.3.1]nonanyl; 2,3,4a,5,7,7a-hexahydropyrrolo[3,4-b][1,4]oxazinyl; 3,3-dimethyl-piperazinyl; 3,7-diazabicyclo[4.2.0]octanyl; or 5-oxa-2,8-diazaspiro[3.5]nonanyl; or a pharmaceutically acceptable salt thereof.

Another object of the present invention is related to novel compounds of formula (I) or (Ia), their manufacture, medicaments based on a compound in accordance with the invention and their production as well as the use of compounds of formula (I) or (Ia) as TLR7 and/or TLR8 and/or TLR9 antagonist, and for the treatment or prophylaxis of systemic lupus erythematosus or lupus nephritis. The compounds of formula (I) or (Ia) show superior TLR7 and/or TLR8 and/or TLR9 antagonism activity. In addition, the compounds of formula (I) or (Ia) also show good cytotoxicity, solubility, hPBMC, human microsome stability and SDPK profiles, as well as low CYP inhibition.

DETAILED DESCRIPTION OF THE INVENTION

Definitions

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "halogen" and "halo" are used interchangeably herein and denote fluoro, chloro, bromo, or iodo.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to (i) a compound of formula (I),

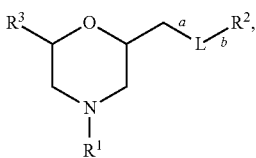

wherein
$R^1$ is

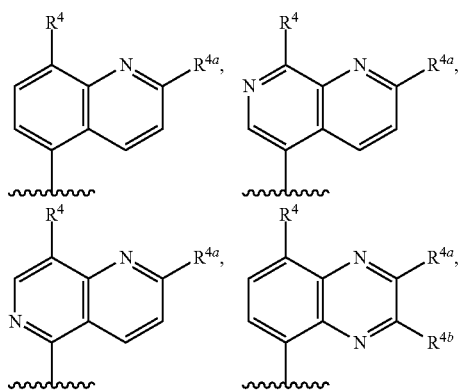

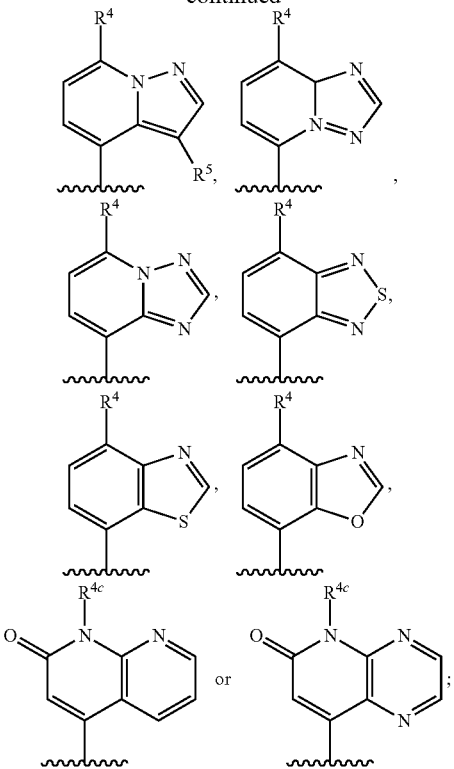

wherein $R^4$ is $C_{1-6}$alkyl, $C_{1-6}$alkoxy, halo$C_{1-6}$alkyl, halogen, nitro or cyano; $R^{4a}$ is H or deuterium; $R^{4b}$ is H, deuterium or $C_{1-6}$alkyl; $R^{4c}$ is $C_{1-6}$alkyl or $C_{3-7}$cycloalkyl; $R^5$ is H or halogen;

$R^2$ is 1,2,3,4-tetrahydroisoquinolinyl which is unsubstituted or substituted by $C_{1-6}$alkoxy, hydroxy or hydroxy$C_{1-6}$alkyl;
  2,3-dihydro-1H-pyrrolo[3,4-c]pyridinyl;
  3,4-dihydro-1H-isoquinolinyl di-substituted by hydroxy and $C_{1-6}$alkyl;
  4,5,6,7-tetrahydropyrazolo[1,5-a]pyrazinyl;
  4,5,6,7-tetrahydrothiazolo[5,4-c]pyridinyl;
  5,6,7,8-tetrahydro-1,6-naphthyridinyl;
  5,6,7,8-tetrahydro-1,7-naphthyridinyl;
  5,6,7,8-tetrahydro-2,6-naphthyridinyl which is unsubstituted or substituted by $C_{1-6}$alkyl;
  5,6,7,8-tetrahydro-2,7-naphthyridinyl which is unsubstituted or substituted by $C_{1-6}$alkyl;
  5,6,7,8-tetrahydropyrido[3,4-b]pyrazinyl which is unsubstituted or substituted by $C_{1-6}$alkyl;
  5,6,7,8-tetrahydropyrido[3,4-d]pyrimidinyl;
  5,6,7,8-tetrahydropyrido[4,3-d]pyrimidinyl;
  6,7-dihydro-5H-pyrrolo[3,4-b]pyridinyl which is unsubstituted or substituted by $C_{1-6}$alkyl;
  6,7-dihydro-5H-pyrrolo[3,4-d]pyrimidinyl;
  7,8-dihydro-5H-1,6-naphthyridinyl substituted by $C_{1-6}$alkyl; or
  isoindolinyl which is unsubstituted or substituted by hydroxy$C_{1-6}$alkyl or $C_{1-6}$alkyl;

$R^3$ is $C_{1-6}$alkyl;
L is 1,4-diazepanyl; hydroxy-1,4-diazepanyl; piperazinyl; (hydroxy$C_{1-6}$alkyl)piperazinyl; 1,6-diazaspiro[3.3]heptanyl; aminoazetidinyl; pyrrolidinylamino; or 3-oxa-7,9-diazabicyclo[3.3.1]nonanyl; 2,3,4a,5,7,7a-hexahydropyrrolo[3,4-b][1,4]oxazinyl; 3,3-dimethyl-piperazinyl; 3,7- diazabicyclo[4.2.0]octanyl; or 5-oxa-2,8-diazaspiro[3.5]
nonanyl; or a pharmaceutically acceptable salt thereof.

A further embodiment of present invention is (ii) a
compound of formula (I), wherein
R¹ is wherein R⁴ is $C_{1-6}$alkyl, $C_{1-6}$alkoxy, halo$C_{1-6}$alkyl or cyano;
R$^{4a}$ is H or deuterium; R$^{4b}$ is H, deuterium or $C_{1-6}$alkyl; R$^{4c}$
is $C_{1-6}$alkyl or $C_{3-7}$cycloalkyl; R⁵ is halogen;
R² is 1,2,3,4-tetrahydroisoquinolinyl which is unsubstituted
or substituted by $C_{1-6}$alkoxy, hydroxy or hydroxy$C_{1-6}$alkyl;
2,3-dihydro-1H-pyrrolo[3,4-c]pyridinyl;
3,4-dihydro-1H-isoquinolinyl di-substituted by hydroxy
and $C_{1-6}$alkyl;
4,5,6,7-tetrahydropyrazolo[1,5-a]pyrazinyl;
4,5,6,7-tetrahydrothiazolo[5,4-c]pyridinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl which is unsubstituted or substituted by $C_{1-6}$alkyl;
5,6,7,8-tetrahydro-2,7-naphthyridinyl which is unsubstituted or substituted by $C_{1-6}$alkyl;
5,6,7,8-tetrahydropyrido[3,4-b]pyrazinyl which is unsubstituted or substituted by $C_{1-6}$alkyl;
5,6,7,8-tetrahydropyrido[3,4-d]pyrimidinyl;
5,6,7,8-tetrahydropyrido[4,3-d]pyrimidinyl;
6,7-dihydro-5H-pyrrolo[3,4-b]pyridinyl which is unsubstituted or substituted by $C_{1-6}$alkyl;
6,7-dihydro-5H-pyrrolo[3,4-d]pyrimidinyl;
7,8-dihydro-5H-1,6-naphthyridinyl substituted by $C_{1-6}$alkyl; or
isoindolinyl which is unsubstituted or substituted by
hydroxy$C_{1-6}$alkyl or $C_{1-6}$alkyl;
R³ is $C_{1-6}$alkyl;
L is 1,4-diazepanyl; hydroxy-1,4-diazepanyl; piperazinyl;
(hydroxy$C_{1-6}$alkyl)piperazinyl; 1,6-diazaspiro[3.3]heptanyl;
aminoazetidinyl; pyrrolidinylamino; or 3-oxa-7,9-
diazabicyclo[3.3.1]nonanyl; 2,3,4a,5,7,7a-hexahydropyr-
rolo[3,4-b][1,4]oxazinyl; 3,3-dimethyl-piperazinyl; 3,7-
diazabicyclo[4.2.0]octanyl; or 5-oxa-2,8-diazaspiro[3.5]
nonanyl; or a pharmaceutically acceptable salt thereof.

An another embodiment of present invention is (iii) a
compound of formula (Ia), (Ia)

wherein
R¹ is or wherein R⁴ is $C_{1-6}$alkyl, $C_{1-6}$alkoxy, halo$C_{1-6}$alkyl or cyano;
R$^{4a}$ is H or deuterium; R$^{4b}$ is H, deuterium or $C_{1-6}$alkyl; R$^{4c}$
is $C_{1-6}$alkyl or $C_{3-7}$cycloalkyl; R⁵ is halogen;
R² is 1,2,3,4-tetrahydroisoquinolinyl which is unsubstituted
or substituted by $C_{1-6}$alkoxy,
hydroxy or hydroxy$C_{1-6}$alkyl;
2,3-dihydro-1H-pyrrolo[3,4-c]pyridinyl;
3,4-dihydro-1H-isoquinolinyl di-substituted by hydroxy
and $C_{1-6}$alkyl;
4,5,6,7-tetrahydropyrazolo[1,5-a]pyrazinyl;
4,5,6,7-tetrahydrothiazolo[5,4-c]pyridinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl which is unsubstituted or substituted by $C_{1-6}$alkyl;
5,6,7,8-tetrahydro-2,7-naphthyridinyl which is unsubstituted or substituted by $C_{1-6}$alkyl;
5,6,7,8-tetrahydropyrido[3,4-b]pyrazinyl which is unsubstituted or substituted by $C_{1-6}$alkyl;
5,6,7,8-tetrahydropyrido[3,4-d]pyrimidinyl;
5,6,7,8-tetrahydropyrido[4,3-d]pyrimidinyl;
6,7-dihydro-5H-pyrrolo[3,4-b]pyridinyl which is unsubstituted or substituted by $C_{1-6}$alkyl;
6,7-dihydro-5H-pyrrolo[3,4-d]pyrimidinyl;
7,8-dihydro-5H-1,6-naphthyridinyl substituted by $C_{1-6}$alkyl; or
isoindolinyl which is unsubstituted or substituted by
hydroxy$C_{1-6}$alkyl or $C_{1-6}$alkyl;

$R^3$ is $C_{1-6}$alkyl;

L is 1,4-diazepanyl; hydroxy-1,4-diazepanyl; piperazinyl; (hydroxyC$_{1-6}$alkyl)piperazinyl; 1,6-diazaspiro[3.3]heptanyl; aminoazetidinyl; pyrrolidinylamino; or 3-oxa-7,9-diazabicyclo[3.3.1]nonanyl; 2,3,4a,5,7,7a-hexahydropyrrolo[3,4-b][1,4]oxazinyl; 3,3-dimethyl-piperazinyl; 3,7-diazabicyclo[4.2.0]octanyl; or 5-oxa-2,8-diazaspiro[3.5]nonanyl; or a pharmaceutically acceptable salt thereof.

A further embodiment of present invention is (iv) a compound of formula (I) or (Ia) according to any one of (i) to (iii), wherein $R^1$ is

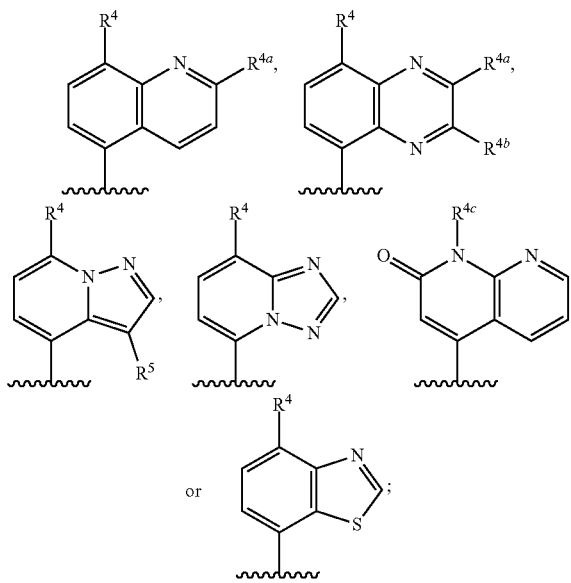

wherein $R^4$ is methyl, trifluoromethyl, methoxy or cyano; $R^{4a}$ is H or deuterium; $R^{4b}$ is H, deuterium or methyl; $R^{4c}$ is methyl, ethyl or isopropyl; $R^5$ is fluoro;
$R^2$ is 1-(hydroxymethyl)-1,2,3,4-tetrahydroisoquinolin-6-yl; 1,2,3,4-tetrahydroisoquinolin-7-yl; 1-methylisoindolin-5-yl; 2-(2-hydroxyethyl)isoindolin-5-yl; 2,3-dihydro-1H-pyrrolo[3,4-c]pyridin-6-yl; 2-methyl-6,7-dihydro-5H-pyrrolo[3,4-b]pyridin-3-yl; 3-methyl-5,6,7,8-tetrahydropyrido[3,4-b]pyrazin-2-yl; 4,5,6,7-tetrahydropyrazolo[1,5-a]pyrazin-1-yl; 4,5,6,7-tetrahydrothiazolo[5,4-c]pyridin-2-yl; 4-hydroxy-1,2,3,4-tetrahydroisoquinolin-6-yl; 4-hydroxy-2-methyl-3,4-dihydro-1H-isoquinolin-6-yl; 4-methoxy-1,2,3,4-tetrahydroisoquinolin-6-yl; 5,6,7,8-tetrahydro-1,6-naphthyridin-2-yl; 5,6,7,8-tetrahydro-1,6-naphthyridin-3-yl; 5,6,7,8-tetrahydro-1,7-naphthyridin-2-yl; 5,6,7,8-tetrahydro-1,7-naphthyridin-3-yl; 5,6,7,8-tetrahydro-2,6-naphthyridin-1-yl; 5,6,7,8-tetrahydro-2,6-naphthyridin-3-yl; 5,6,7,8-tetrahydro-2,7-naphthyridin-3-yl; 5,6,7,8-tetrahydropyrido[3,4-b]pyrazin-2-yl; 5,6,7,8-tetrahydropyrido[3,4-b]pyrazin-3-yl; 5,6,7,8-tetrahydropyrido[3,4-d]pyrimidin-2-yl; 5,6,7,8-tetrahydropyrido[4,3-d]pyrimidin-2-yl; 5,6,7,8-tetrahydropyrido[4,3-d]pyrimidin-4-yl; 5-methyl-5,6,7,8-tetrahydro-2,6-naphthyridin-3-yl; 5-methyl-6,7-dihydro-5H-pyrrolo[3,4-b]pyridin-2-yl; 6,7-dihydro-5H-pyrrolo[3,4-b]pyridin-2-yl; 6,7-dihydro-5H-pyrrolo[3,4-b]pyridin-3-yl; 6,7-dihydro-5H-pyrrolo[3,4-d]pyrimidin-2-yl; 6,7-dihydro-5H-pyrrolo[3,4-d]pyrimidin-4-yl; 6-methyl-5,6,7,8-tetrahydro-2,7-naphthyridin-3-yl; 6-methyl-7,8-dihydro-5H-1,6-naphthyridin-2-yl; 7-methyl-5,6,7,8-tetrahydro-2,6-naphthyridin-3-yl; 7-methyl-6,7-dihydro-5H-pyrrolo[3,4-b]pyridin-2-yl; 7-methyl-6,7-dihydro-5H-pyrrolo[3,4-b]pyridin-3-yl; 8-methyl-5,6,7,8-tetrahydro-2,7-naphthyridin-3-yl; isoindolin-4-yl; or isoindolin-5-yl;

$R^3$ is methyl;

L is 1,4-diazepanyl; hydroxy-1,4-diazepanyl; piperazinyl; (hydroxymethyl)piperazinyl; 1,6-diazaspiro[3.3]heptanyl; aminoazetidinyl; pyrrolidinylamino; or 3-oxa-7,9-diazabicyclo[3.3.1]nonanyl; 2,3,4a,5,7,7a-hexahydropyrrolo[3,4-b][1,4]oxazinyl; 3,3-dimethyl-piperazinyl; 3,7-diazabicyclo[4.2.0]octanyl; or 5-oxa-2,8-diazaspiro[3.5]nonanyl; or a pharmaceutically acceptable salt thereof.

A further embodiment of present invention is (v) a compound of formula (I) or (Ia) according to any one of (i) to (iv), wherein $R^1$ is

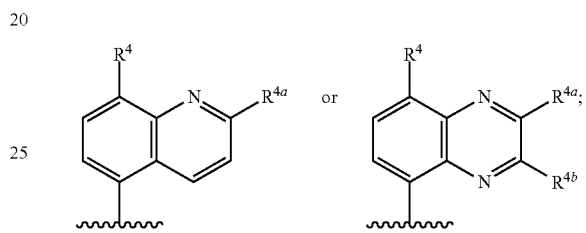

wherein $R^4$ is cyano; $R^{4a}$ is H or deuterium; $R^{4b}$ is H or deuterium.

A further embodiment of present invention is (vi) a compound of formula (I) or (Ia) according to any one of (i) to (v), wherein L is

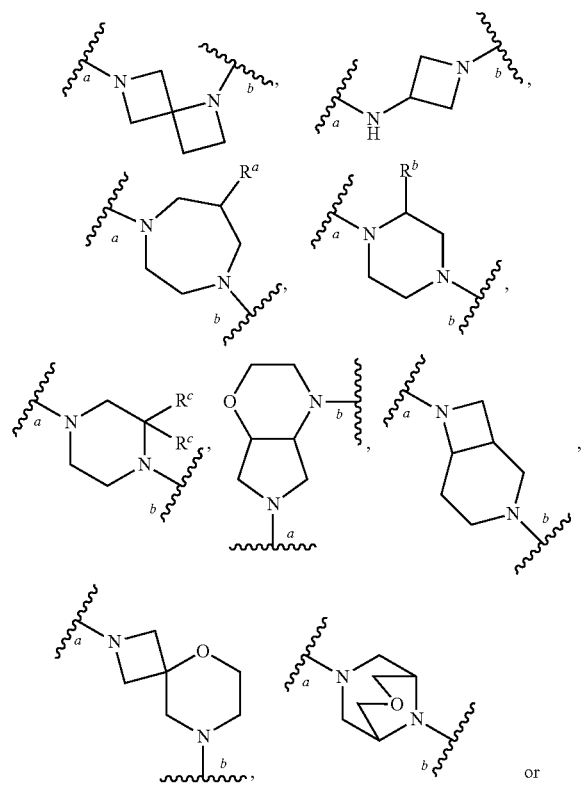

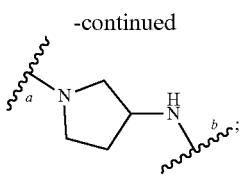

wherein $R^a$ is H or hydroxy; $R^b$ is H or hydroxy$C_{1-6}$alkyl; $R^c$ is $C_{1-6}$alkyl.

A further embodiment of present invention is (vii) a compound of formula (I) or (Ia) according to any one of (i) to (vi), wherein L is

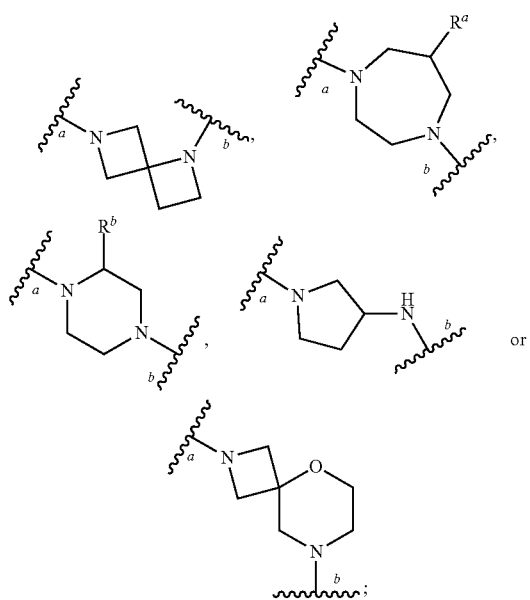

wherein $R^a$ is H; $R^b$ is H or hydroxy$C_{1-6}$alkyl.

A further embodiment of present invention is (viii) a compound of formula (I) or (Ia) according to any one of (i) to (vii), wherein L is

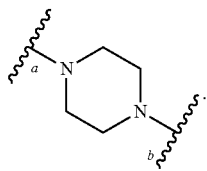 [SMILES: *N1CCN(*)CC1]

Another embodiment of present invention is (ix) a compound of formula (I) or (Ia) according to any one of (i) to (viii), wherein $R^2$ is 1,2,3,4-tetrahydroisoquinolinyl which is unsubstituted or substituted by hydroxy; 5,6,7,8-tetrahydro-1,6-naphthyridinyl; 5,6,7,8-tetrahydro-2,6-naphthyridinyl which is unsubstituted or substituted by $C_{1-6}$alkyl; 5,6,7,8-tetrahydro-2,7-naphthyridinyl; or 6,7-dihydro-5H-pyrrolo[3,4-b]pyridinyl which is unsubstituted or substituted by $C_{1-6}$alkyl.

A further embodiment of present invention is (x) a compound of formula (I) or (Ia) according to any one of (i) to (ix), wherein $R^2$ is 1,2,3,4-tetrahydroisoquinolin-6-yl; 4-hydroxy-1,2,3,4-tetrahydroisoquinolin-6-yl; 5,6,7,8-tetrahydro-1,6-naphthyridin-2-yl; 5,6,7,8-tetrahydro-1,6-naphthyridin-3-yl; 5,6,7,8-tetrahydro-2,6-naphthyridin-3-yl; 5,6,7,8-tetrahydro-2,7-naphthyridin-3-yl; 5-methyl-5,6,7,8-tetrahydro-2,6-naphthyridin-3-yl; 5-methyl-6,7-dihydro-5H-pyrrolo[3,4-b]pyridin-2-yl; 6,7-dihydro-5H-pyrrolo[3,4-b]pyridin-2-yl; 6,7-dihydro-5H-pyrrolo[3,4-b]pyridin-3-yl; or 7-methyl-5,6,7,8-tetrahydro-2,6-naphthyridin-3-yl.

A further embodiment of present invention is (xi) a compound of formula (I) or (Ia) according to any one of (i) to (x), wherein
$R^1$ is

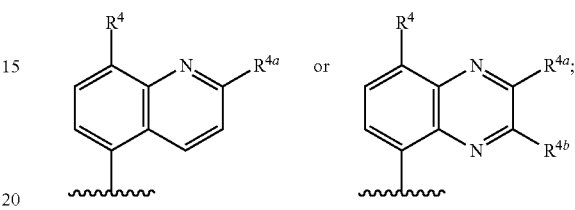

wherein $R^4$ is cyano; $R^{4a}$ is H or deuterium; $R^{4b}$ is H or deuterium;
$R^2$ is 1,2,3,4-tetrahydroisoquinolinyl which is unsubstituted or substituted by hydroxy; 5,6,7,8-tetrahydro-1,6-naphthyridinyl; 5,6,7,8-tetrahydro-2,6-naphthyridinyl which is unsubstituted or substituted by $C_{1-6}$alkyl; 5,6,7,8-tetrahydro-2,7-naphthyridinyl; or 6,7-dihydro-5H-pyrrolo[3,4-b]pyridinyl which is unsubstituted or substituted by $C_{1-6}$alkyl;
$R^3$ is $C_{1-6}$alkyl;
L is

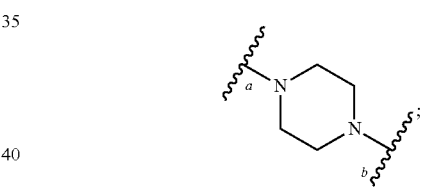

or a pharmaceutically acceptable salt thereof.

A further embodiment of present invention is (xii) a compound of formula (I) or (Ia) according to any one of (i) to (xi), wherein
$R^1$ is

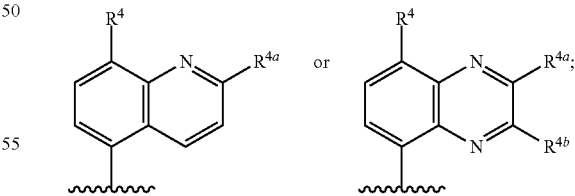

wherein $R^4$ is cyano; $R^{4a}$ is H or deuterium;
$R^{4b}$ is H or deuterium;
$R^2$ is 1,2,3,4-tetrahydroisoquinolin-6-yl; 4-hydroxy-1,2,3,4-tetrahydroisoquinolin-6-yl; 5,6,7,8-tetrahydro-1,6-naphthyridin-2-yl; 5,6,7,8-tetrahydro-1,6-naphthyridin-3-yl; 5,6,7,8-tetrahydro-2,6-naphthyridin-3-yl; 5,6,7,8-tetrahydro-2,7-naphthyridin-3-yl; 5-methyl-5,6,7,8-tetrahydro-2,6-naphthyridin-3-yl; 5-methyl-6,7-dihydro-5H-pyrrolo[3,4-b]pyridin-2-yl; 6,7-dihydro-5H-pyrrolo[3,4- b]pyridin-2-yl; 6,7-dihydro-5H-pyrrolo[3,4-b]pyridin-3-yl; or 7-methyl-5,6,7,8-tetrahydro-2,6-naphthyridin-3-yl;
$R^3$ is methyl;
L is

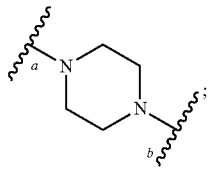 [SMILES: *N1CCN(*)CC1]

or a pharmaceutically acceptable salt thereof.

The present invention relates to (i') a compound of formula (I),

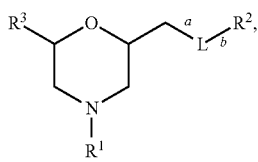
(I)

wherein
$R^1$ is

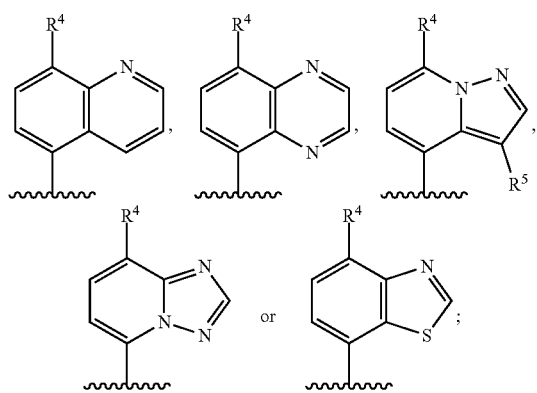

wherein $R^4$ is cyano; $R^5$ is halogen;
$R^2$ is 1,2,3,4-tetrahydroisoquinolinyl which is unsubstituted or substituted by hydroxy or
hydroxyC$_{1-6}$alkyl;
2,3-dihydro-1H-pyrrolo[3,4-c]pyridinyl;
4,5,6,7-tetrahydropyrazolo[1,5-a]pyrazinyl;
4,5,6,7-tetrahydrothiazolo[5,4-c]pyridinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl;
5,6,7,8-tetrahydro-2,7-naphthyridinyl;
5,6,7,8-tetrahydropyrido[3,4-b]pyrazinyl;
5,6,7,8-tetrahydropyrido[3,4-d]pyrimidinyl;
5,6,7,8-tetrahydropyrido[4,3-d]pyrimidinyl;
6,7-dihydro-5H-pyrrolo[3,4-b]pyridinyl substituted by C$_{1-6}$alkyl;
6,7-dihydro-5H-pyrrolo[3,4-d]pyrimidinyl;
7,8-dihydro-5H-1,6-naphthyridinyl substituted by C$_{1-6}$alkyl; or
isoindolinyl which is unsubstituted or substituted by hydroxyC$_{1-6}$alkyl or C$_{1-6}$alkyl;
$R^3$ is C$_{1-6}$alkyl;
L is 1,4-diazepanyl; hydroxy-1,4-diazepanyl; piperazinyl; (hydroxyC$_{1-6}$alkyl)piperazinyl; 1,6-diazaspiro[3.3]heptanyl; aminoazetidinyl; pyrrolidinylamino; or 3-oxa-7,9-diazabicyclo[3.3.1]nonanyl;
or a pharmaceutically acceptable salt, enantiomer or diastereomer thereof.

An another embodiment of present invention is (ii') a compound of formula (Ia),

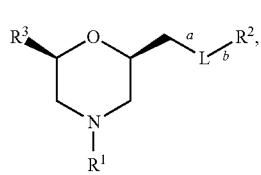
(Ia)

wherein
$R^1$ is

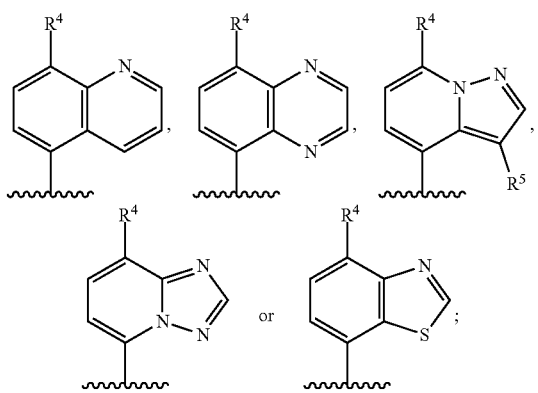

wherein $R^4$ is cyano; $R^5$ is halogen;
$R^2$ is 1,2,3,4-tetrahydroisoquinolinyl which is unsubstituted or substituted by hydroxy or
hydroxyC$_{1-6}$alkyl;
2,3-dihydro-1H-pyrrolo[3,4-c]pyridinyl;
4,5,6,7-tetrahydropyrazolo[1,5-a]pyrazinyl;
4,5,6,7-tetrahydrothiazolo[5,4-c]pyridinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl;
5,6,7,8-tetrahydro-2,7-naphthyridinyl;
5,6,7,8-tetrahydropyrido[3,4-b]pyrazinyl;
5,6,7,8-tetrahydropyrido[3,4-d]pyrimidinyl;
5,6,7,8-tetrahydropyrido[4,3-d]pyrimidinyl;
6,7-dihydro-5H-pyrrolo[3,4-b]pyridinyl substituted by C$_{1-6}$alkyl;
6,7-dihydro-5H-pyrrolo[3,4-d]pyrimidinyl;
7,8-dihydro-5H-1,6-naphthyridinyl substituted by C$_{1-6}$alky; or
isoindolinyl which is unsubstituted or substituted by hydroxyC$_{1-6}$alkyl or C$_{1-6}$alkyl;
$R^3$ is C$_{1-6}$alkyl;
L is 1,4-diazepanyl; hydroxy-1,4-diazepanyl; piperazinyl; (hydroxyC$_{1-6}$alkyl)piperazinyl; 1,6-diazaspiro[3.3]heptanyl; aminoazetidinyl; pyrrolidinylamino; or 3-oxa-7,9-diazabicyclo[3.3.1]nonanyl;

or a pharmaceutically acceptable salt, enantiomer or diastereomer thereof.

A further embodiment of present invention is (iii') a compound of formula (I) or (Ia) according to (i) or (ii), wherein R¹ is

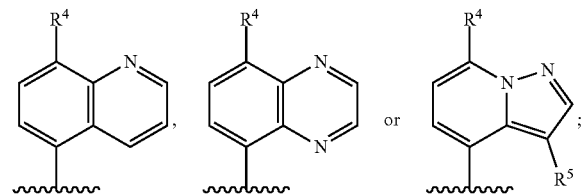

wherein R⁴ is cyano, R⁵ is halogen.

A further embodiment of present invention is (iv') a compound of formula (I) or (Ia) according to (iii), wherein L is

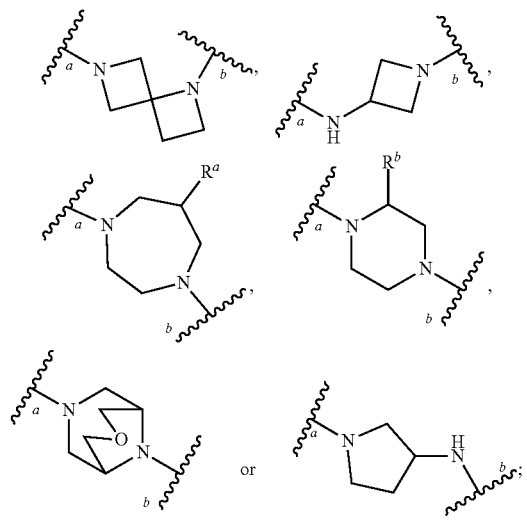

wherein $R^a$ is H or hydroxy; R is H or hydroxyC$_{1-6}$alkyl.

A further embodiment of present invention is (v') a compound of formula (I) or (Ia) according to (iv), wherein L is

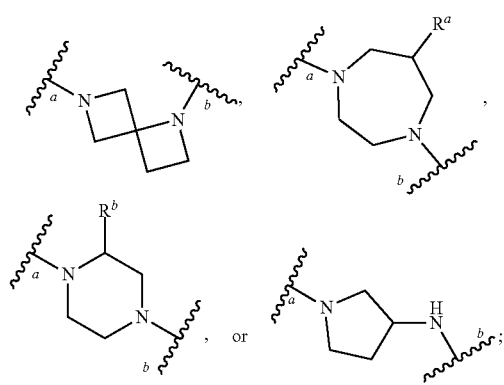

wherein $R^a$ is H; $R^b$ is H or hydroxyC$_{1-6}$alky

A further embodiment of present invention is (vi') a compound of formula (I) or (Ia) according to (v), wherein L is

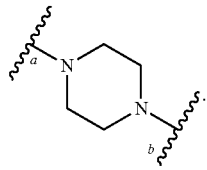 [SMILES: *N1CCN(*)CC1]

A further embodiment of present invention is (vii') a compound of formula (I) or (Ia) according to (vi), wherein R² is 1,2,3,4-tetrahydroisoquinolinyl which is unsubstituted or substituted by hydroxy; 6,7-dihydro-5H-pyrrolo[3,4-b]pyridinyl; 5,6,7,8-tetrahydro-1,6-naphthyridinyl; 5,6,7,8-tetrahydro-2,7-naphthyridinyl; or 5,6,7,8-tetrahydro-2,6-naphthyridinyl.

Another embodiment of present invention is (viii') a compound of formula (I) or (Ia) according to (i) or (ii), wherein
R¹ is

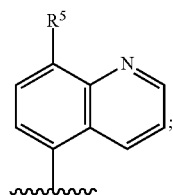

wherein R⁵ is cyano;
R² is 1,2,3,4-tetrahydroisoquinolinyl which is unsubstituted or substituted by hydroxy; 6,7-dihydro-5H-pyrrolo[3,4-b]pyridinyl; 5,6,7,8-tetrahydro-1,6-naphthyridinyl; 5,6,7,8-tetrahydro-2,7-naphthyridinyl; or 5,6,7,8-tetrahydro-2,6-naphthyridinyl;
R³ is C$_{1-6}$alkyl;
L is

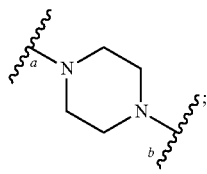 [SMILES: *N1CCN(*)CC1]

or a pharmaceutically acceptable salt, enantiomer or diastereomer thereof.

A further embodiment of present invention is (ix') a compound of formula (I) or (Ia) according to (viii), wherein R¹ is

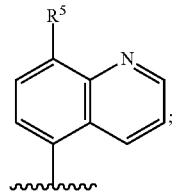

wherein R⁵ is cyano;
R² is 1,2,3,4-tetrahydroisoquinolinyl;
  hydroxy-1,2,3,4-tetrahydroisoquinolinyl;
  6,7-dihydro-5H-pyrrolo[3,4-b]pyridinyl;
  5,6,7,8-tetrahydro-1,6-naphthyridinyl;
  5,6,7,8-tetrahydro-2,7-naphthyridinyl; or
  5,6,7,8-tetrahydro-2,6-naphthyridinyl;
R³ is methyl;
L is

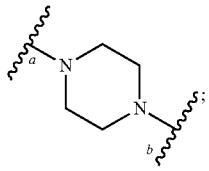 [SMILES: *N1CCN(*)CC1]

or a pharmaceutically acceptable salt, enantiomer or diastereomer thereof.

Another embodiment of present invention is that (xi) a compound of formula (I) or (Ia) selected from the following:
  5-[(2R,6S)-2-methyl-6-[[4-(4,5,6,7-tetrahydropyrazolo[1,5-a]pyrazin-2-yl)piperazin-1-yl]methyl]morpholin-4-yl]quinoline-8-carbonitrile;
  5-[(2S,6R)-2-[(4-isoindolin-4-ylpiperazin-1-yl)methyl]-6-methyl-morpholin-4-yl]quinoline-8-carbonitrile;
  5-[(2S,6R)-2-[[(3S)-3-(hydroxymethyl)-4-isoindolin-5-yl-piperazin-1-yl]methyl]-6-methyl-morpholin-4-yl]quinoline-8-carbonitrile;
  5-[(2S,6R)-2-[[(3R)-3-(hydroxymethyl)-4-isoindolin-5-yl-piperazin-1-yl]methyl]-6-methyl-morpholin-4-yl]quinoline-8-carbonitrile;
  5-[(2R,6S)-2-methyl-6-[[4-(1,2,3,4-tetrahydroisoquinolin-6-yl)piperazin-1-yl]methyl]morpholin-4-yl]quinoline-8-carbonitrile;
  5-[(2S,6R)-2-[[4-(6,7-dihydro-5H-pyrrolo[3,4-d]pyrimidin-4-yl)piperazin-1-yl]methyl]-6-methyl-morpholin-4-yl]quinoline-8-carbonitrile;
  5-[(2S,6R)-2-[(4-isoindolin-5-ylpiperazin-1-yl)methyl]-6-methyl-morpholin-4-yl]quinoline-8-carbonitrile;
  7-[(2S,6R)-2-[[4-(6,7-dihydro-5H-pyrrolo[3,4-b]pyridin-3-yl)piperazin-1-yl]methyl]-6-methyl-morpholin-4-yl]-1,3-benzothiazole-4-carbonitrile;
  5-[(2R,6S)-2-methyl-6-[[4-(1,2,3,4-tetrahydroisoquinolin-7-yl)piperazin-1-yl]methyl]morpholin-4-yl]quinoline-8-carbonitrile;
  5-[(2S,6R)-2-[[4-(6,7-dihydro-5H-pyrrolo[3,4-b]pyridin-3-yl)piperazin-1-yl]methyl]-6-methyl-morpholin-4-yl]quinoline-8-carbonitrile;
  5-[(2S,6R)-2-[[4-(6,7-dihydro-5H-pyrrolo[3,4-d]pyrimidin-2-yl)piperazin-1-yl]methyl]-6-methyl-morpholin-4-yl]quinoline-8-carbonitrile;
  5-[(2R,6S)-2-methyl-6-[[4-(5,6,7,8-tetrahydropyrido[3,4-d]pyrimidin-2-yl)piperazin-1-yl]methyl]morpholin-4-yl]quinoline-8-carbonitrile;
  5-[(2S,6R)-2-[[3-(hydroxymethyl)-4-isoindolin-5-yl-piperazin-1-yl]methyl]-6-methyl-morpholin-4-yl]quinoline-8-carbonitrile;
  5-[(2R,6S)-2-methyl-6-[[4-(5,6,7,8-tetrahydro-1,6-naphthyridin-2-yl)piperazin-1-yl]methyl]morpholin-4-yl]quinoline-8-carbonitrile;
  5-[(2S,6R)-2-[[2-(hydroxymethyl)-4-isoindolin-5-yl-piperazin-1-yl]methyl]-6-methyl-morpholin-4-yl]quinoline-8-carbonitrile;
  5-[(2S,6R)-2-[[4-[2-(2-hydroxyethyl)isoindolin-5-yl]piperazin-1-yl]methyl]-6-methyl-morpholin-4-yl]quinoline-8-carbonitrile;
  5-[(2R,6R)-2-methyl-6-[[4-(5,6,7,8-tetrahydropyrido[3,4-b]pyrazin-2-yl)piperazin-1-yl]methyl]morpholin-4-yl]quinoline-8-carbonitrile;
  5-[(2S,6R)-2-[[4-(2,3-dihydro-1H-pyrrolo[3,4-c]pyridin-6-yl)piperazin-1-yl]methyl]-6-methyl-morpholin-4-yl]quinoline-8-carbonitrile;
  5-[(2R,6S)-2-methyl-6-[[4-(5,6,7,8-tetrahydro-2,7-naphthyridin-3-yl)piperazin-1-yl]methyl]morpholin-4-yl]quinoline-8-carbonitrile;
  5-[(2R,6S)-2-methyl-6-[[4-(5,6,7,8-tetrahydro-2,6-naphthyridin-3-yl)piperazin-1-yl]methyl]morpholin-4-yl]quinoline-8-carbonitrile;
  5-[(2R,6S)-2-methyl-6-[[4-(5,6,7,8-tetrahydro-1,6-naphthyridin-3-yl)piperazin-1-yl]methyl]morpholin-4-yl]quinoline-8-carbonitrile;
  5-[(2S,6R)-2-[[4-(4-hydroxy-1,2,3,4-tetrahydroisoquinolin-6-yl)piperazin-1-yl]methyl]-6-methyl-morpholin-4-yl]quinoline-8-carbonitrile;
  5-[(2R,6S)-2-methyl-6-[[4-(5,6,7,8-tetrahydro-1,7-naphthyridin-3-yl)piperazin-1-yl]methyl]morpholin-4-yl]quinoline-8-carbonitrile;
  5-[(2S,6R)-2-[[4-[1-(hydroxymethyl)-1,2,3,4-tetrahydroisoquinolin-6-yl]piperazin-1-yl]methyl]-6-methyl-morpholin-4-yl]quinoline-8-carbonitrile;
  8-[(2S,6R)-2-[[4-(6,7-dihydro-5H-pyrrolo[3,4-b]pyridin-3-yl)piperazin-1-yl]methyl]-6-methyl-morpholin-4-yl]quinoxaline-5-carbonitrile;
  4-[(2S,6R)-2-[[4-(6,7-dihydro-5H-pyrrolo[3,4-b]pyridin-3-yl)piperazin-1-yl]methyl]-6-methyl-morpholin-4-yl]-3-fluoro-pyrazolo[1,5-a]pyridine-7-carbonitrile;
  5-[(2R,6S)-2-methyl-6-[[4-(5,6,7,8-tetrahydro-1,6-naphthyridin-3-yl)piperazin-1-yl]methyl]morpholin-4-yl]-[1,2,4]triazolo[1,5-a]pyridine-8-carbonitrile;
  5-[(2R,6S)-2-methyl-6-[[4-(1-methylisoindolin-5-yl)piperazin-1-yl]methyl]morpholin-4-yl]quinoline-8-carbonitrile;
  5-[(2R,6S)-2-methyl-6-[[4-(5,6,7,8-tetrahydropyrido[4,3-d]pyrimidin-2-yl)piperazin-1-yl]methyl]morpholin-4-yl]quinoline-8-carbonitrile;
  5-[(2S,6R)-2-[[4-(6,7-dihydro-5H-pyrrolo[3,4-b]pyridin-2-yl)piperazin-1-yl]methyl]-6-methyl-morpholin-4-yl]quinoline-8-carbonitrile;
  5-[(2R,6S)-2-methyl-6-[[4-(4,5,6,7-tetrahydrothiazolo[5,4-c]pyridin-2-yl)piperazin-1-yl]methyl]morpholin-4-yl]quinoline-8-carbonitrile;
  5-[(2S,6R)-2-[[3-(6,7-dihydro-5H-pyrrolo[3,4-d]pyrimidin-2-ylamino)pyrrolidin-1-yl]methyl]-6-methyl-morpholin-4-yl]quinoline-8-carbonitrile;
  5-[(2R,6S)-2-methyl-6-[[4-(4,5,6,7-tetrahydrothiazolo[5,4-c]pyridin-2-yl)-1,4-diazepan-1-yl]methyl]morpholin-4-yl]quinoline-8-carbonitrile;
  5-[(2R,6S)-2-methyl-6-[[4-(6-methyl-7,8-dihydro-5H-1,6-naphthyridin-2-yl)piperazin-1-yl]methyl]morpholin-4-yl]quinoline-8-carbonitrile;
  5-[(2S,6R)-2-[[(6R)-6-hydroxy-4-(5,6,7,8-tetrahydro-1,6-naphthyridin-2-yl)-1,4-diazepan-1-yl]methyl]-6-methyl-morpholin-4-yl]quinoline-8-carbonitrile;
  5-[(2S,6R)-2-[[(6S)-6-hydroxy-4-(5,6,7,8-tetrahydro-1,6-naphthyridin-2-yl)-1,4-diazepan-1-yl]methyl]-6-methyl-morpholin-4-yl]quinoline-8-carbonitrile;
  5-[(2R,6S)-2-methyl-6-[[1-(5,6,7,8-tetrahydro-1,6-naphthyridin-2-yl)-1,6-diazaspiro[3.3]heptan-6-yl]methyl]morpholin-4-yl]quinoline-8-carbonitrile;

5-[(2S,6R)-2-[[9-(6,7-dihydro-5H-pyrrolo[3,4-b]pyridin-3-yl)-3-oxa-7,9-diazabicyclo[3.3.1]nonan-7-yl]methyl]-6-methyl-morpholin-4-yl]quinoline-8-carbonitrile;

5-[(2S,6R)-2-[[3-(isoindolin-5-ylamino)pyrrolidin-1-yl]methyl]-6-methyl-morpholin-4-yl]quinoline-8-carbonitrile;

5-[(2R,6S)-2-methyl-6-[[4-(5,6,7,8-tetrahydropyrido[4,3-d]pyrimidin-2-yl)-1,4-diazepan-1-yl]methyl]morpholin-4-yl]quinoline-8-carbonitrile;

5-[(2R,6S)-2-methyl-6-[[4-(5,6,7,8-tetrahydropyrido[3,4-b]pyrazin-3-yl)piperazin-1-yl]methyl]morpholin-4-yl]quinoline-8-carbonitrile;

5-[(2R,6S)-2-methyl-6-[[4-(5-methyl-6,7-dihydro-5H-pyrrolo[3,4-b]pyridin-3-yl)piperazin-1-yl]methyl]morpholin-4-yl]quinoline-8-carbonitrile;

5-[(2S,6R)-2-[[[1-(6,7-dihydro-5H-pyrrolo[3,4-d]pyrimidin-2-yl)azetidin-3-yl]amino]methyl]-6-methyl-morpholin-4-yl]quinoline-8-carbonitrile;

5-[(2S,6R)-2-[[[1-(6,7-dihydro-5H-pyrrolo[3,4-b]pyridin-3-yl)azetidin-3-yl]amino]methyl]-6-methyl-morpholin-4-yl]quinoline-8-carbonitrile;

5-[(2R,6S)-2-methyl-6-[[8-(1,2,3,4-tetrahydroisoquinolin-6-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,7-naphthyridin-2-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,7-naphthyridin-3-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,6-naphthyridin-3-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-2,6-naphthyridin-3-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,6-naphthyridin-2-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydropyrido[3,4-b]pyrazin-2-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydropyrido[4,3-d]pyrimidin-2-yl)-5-oxa-2,8-diazaspiro[3.5]nonan-2-yl]methyl]morpholin-4-yl]quinoline-8-carbonitrile;

5-[(2S,6R)-2-[[(4aR,7aR)-4-(5,6,7,8-tetrahydro-1,7-naphthyridin-3-yl)-2,3,4a,5,7,7a-hexahydropyrrolo[3,4-b][1,4]oxazin-6-yl]methyl]-6-methylmorpholin-4-yl]quinoline-8-carbonitrile;

cis-5-[(2R,6S)-2-methyl-6-[[4-(5,6,7,8-tetrahydro-1,6-naphthyridin-2-yl)-2,3,4a,5,7,7a-hexahydropyrrolo[3,4-b][1,4]oxazin-6-yl]methyl]morpholin-4-yl]quinoline-8-carbonitrile;

trans-5-[(2R,6S)-2-methyl-6-[[3-(5,6,7,8-tetrahydro-1,6-naphthyridin-2-yl)-3,7-diazabicyclo[4.2.0]octan-7-yl]methyl]morpholin-4-yl]quinoline-8-carbonitrile;

5-[(2S,6R)-2-[[3,3-dimethyl-4-(5,6,7,8-tetrahydro-1,6-naphthyridin-3-yl)piperazin-1-yl]methyl]-6-methyl-morpholin-4-yl]quinoline-8-carbonitrile;

5-[(2R,6S)-2-methyl-6-[[3-(5,6,7,8-tetrahydropyrido[4,3-d]pyrimidin-2-ylamino)pyrrolidin-1-yl]methyl]morpholin-4-yl]quinoline-8-carbonitrile;

5-[(2S,6R)-2-[[4-(4-methoxy-1,2,3,4-tetrahydroisoquinolin-6-yl)piperazin-1-yl]methyl]-6-methyl-morpholin-4-yl]quinoline-8-carbonitrile;

5-[(2S,6R)-2-[[4-(4-hydroxy-2-methyl-3,4-dihydro-1H-isoquinolin-6-yl)piperazin-1-yl]methyl]-6-methyl-morpholin-4-yl]quinoline-8-carbonitrile;

5-[(2R,6S)-2-methyl-6-[[4-(3-methyl-5,6,7,8-tetrahydropyrido[3,4-b]pyrazin-2-yl)piperazin-1-yl]methyl]morpholin-4-yl]quinoline-8-carbonitrile;

5-[(2R,6S)-2-methyl-6-[[4-(5,6,7,8-tetrahydropyrido[4,3-d]pyrimidin-4-yl)piperazin-1-yl]methyl]morpholin-4-yl]quinoline-8-carbonitrile;

5-[(2R,6S)-2-methyl-6-[[4-(5,6,7,8-tetrahydro-2,6-naphthyridin-1-yl)piperazin-1-yl]methyl]morpholin-4-yl]quinoline-8-carbonitrile;

5-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-1[(5R)-5-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-[(7R)-7-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-[(7S)-7-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-[(7S)-7-methyl-6,7-dihydro-5H-pyrrolo[3,4-b]pyridin-3-yl]piperazin-1-yl]methyl]morpholin-4-yl]quinoline-8-carbonitrile;

5-[(2R,6S)-2-methyl-6-[[4-[(7R)-7-methyl-6,7-dihydro-5H-pyrrolo[3,4-b]pyridin-3-yl]piperazin-1-yl]methyl]morpholin-4-yl]quinoline-8-carbonitrile;

5-[(2R,6S)-2-methyl-6-[[4-(5,6,7,8-tetrahydro-1,7-naphthyridin-2-yl)piperazin-1-yl]methyl]morpholin-4-yl]quinoline-8-carbonitrile;

5-[(2R,6S)-2-methyl-6-[[4-[(6R)-6-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(6S)-6-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(5R)-5-methyl-5,6,7,8-tetrahydro-2,6-naphthyridin-3-yl]piperazin-1-yl]methyl]morpholin-4-yl]quinoline-8-carbonitrile;

5-[(2R,6S)-2-methyl-6-[[4-[(5S)-5-methyl-5,6,7,8-tetrahydro-2,6-naphthyridin-3-yl]piperazin-1-yl]methyl]morpholin-4-yl]quinoline-8-carbonitrile;

5-[(2R,6S)-2-methyl-6-[[4-[(7S)-7-methyl-5,6,7,8-tetrahydro-2,6-naphthyridin-3-yl]piperazin-1-yl]methyl]morpholin-4-yl]quinoline-8-carbonitrile;

5-[(2R,6S)-2-methyl-6-[[4-[(7R)-7-methyl-5,6,7,8-tetrahydro-2,6-naphthyridin-3-yl]piperazin-1-yl]methyl]morpholin-4-yl]quinoline-8-carbonitrile;

8-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoxaline-5-carbonitrile;

8-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoxaline-5-carbonitrile;

8-[(2R,6S)-2-methyl-6-[[4-(5,6,7,8-tetrahydro-2,6-naphthyridin-3-yl)piperazin-1-yl]methyl]morpholin-4-yl]quinoxaline-5-carbonitrile;

8-[(2R,6S)-2-methyl-6-[[4-1[(7S)-7-methyl-5,6,7,8-tetrahydro-2,6-naphthyridin-3-yl]piperazin-1-yl]methyl]morpholin-4-yl]quinoxaline-5-carbonitrile;

8-[(2R,6S)-2-methyl-6-[[4-1[(7R)-7-methyl-5,6,7,8-tetrahydro-2,6-naphthyridin-3-yl]piperazin-1-yl]methyl]morpholin-4-yl]quinoxaline-5-carbonitrile;

8-[(2R,6S)-2-methyl-6-[[4-1[(6R)-6-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-[(6S)-6-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-1[(8S)-8-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-1[(8R)-8-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-1[(5R)-5-methyl-5,6,7,8-tetrahydro-2,6-naphthyridin-3-yl]piperazin-1-yl]methyl]morpholin-4-yl]quinoxaline-5-carbonitrile;

8-[(2R,6S)-2-methyl-6-[[4-[(5S)-5-methyl-5,6,7,8-tetrahydro-2,6-naphthyridin-3-yl]piperazin-1-yl]methyl]morpholin-4-yl]quinoxaline-5-carbonitrile;

(2R,6S)-4-(8-methoxyquinoxalin-5-yl)-2-methyl-6-[[4-(5,6,7,8-tetrahydro-2,6-naphthyridin-3-yl)piperazin-1-yl]methyl]morpholine;

2-methyl-8-[(2R,6S)-2-methyl-6-[[4-(5,6,7,8-tetrahydro-2,6-naphthyridin-3-yl)piperazin-1-yl]methyl]morpholin-4-yl]quinoxaline-5-carbonitrile;

(2R,6S)-2-methyl-6-[[4-(5,6,7,8-tetrahydro-2,6-naphthyridin-3-yl)piperazin-1-yl]methyl]-4-[8-(trifluoromethyl)quinoxalin-5-yl]morpholine;

(2R,6S)-2-methyl-4-(8-methylquinoxalin-5-yl)-6-[[4-[(5R)-5-methyl-5,6,7,8-tetrahydro-2,6-naphthyridin-3-yl]piperazin-1-yl]methyl]morpholine;

(2R,6S)-2-methyl-4-(8-methylquinoxalin-5-yl)-6-[[4-[(5S)-5-methyl-5,6,7,8-tetrahydro-2,6-naphthyridin-3-yl]piperazin-1-yl]methyl]morpholine;

2,3-dideuterio-8-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoxaline-5-carbonitrile;

2,3-dideuterio-8-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoxaline-5-carbonitrile;

2,3-dideuterio-8-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoxaline-5-carbonitrile;

2,3-dideuterio-8-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoxaline-5-carbonitrile;

2-deuterio-5-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoline-8-carbonitrile;

2-deuterio-5-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoline-8-carbonitrile;

1-methyl-4-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]-1,8-naphthyridin-2-one;

1-isopropyl-4-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]-1,8-naphthyridin-2-one; and 1-methyl-4-[(2R,6S)-2-methyl-6-[[4-(5,6,7,8-tetrahydro-2,6-naphthyridin-3-yl)piperazin-1-yl]methyl]morpholin-4-yl]-1,8-naphthyridin-2-one;

or a pharmaceutically acceptable salt, enantiomer or diastereomer thereof.

A number of compounds used as reference herein were disclosed in patent US20150105370 showing TLR7 and TLR9 potency data summarized in table 1 (TLR8 data is not available). Compounds in Table 1 are all characterized with an aromatic ring at the terminal position (phenyl or pyridinyl). However, according to the potency data disclosed, only some of the compounds in Table 1 showed good TLR7 potency, and all of which were lack of TLR9 potency. More examples disclosed in US20150105370 with same structural characteristics confirmed such trend, which suggests the terminal aryl/heteroaryl ring is not favorable for TLR9 activity.

Meanwhile, more analogues of the compounds disclosed in US20150105370, such as compound R1, compound R2 which bear some substituents on the terminal aryl ring, were synthesized to confirm the SAR (structure-activity-relationship). But according to the potency data shown in Table 2, the substituents on the terminal aryl ring may not necessarily improve the potency of TLR9. Therefore, the skill of the art shall not obtain any incitation from the information disclosed in US20150105370 to further optimize such chemical structures.

Surprisingly, the compounds of this invention significantly improved TLR9 potency (>8 folds compared to ER-888286) while keeping excellent TLR7 and TLR8 potency. In another embodiment, hERG profile and safety ratio were greatly improved as compared with reference compounds from US20150105370 and reference compounds R1 and R2 synthesized herein (see table 3). The compounds of formula (I) or (Ia) also showed good hPBMC, cytotoxicity, solubility, human microsome stability and SDPK profiles, as well as low CYP inhibition.

TABLE 1

TLR7 and TLR9 potency of compounds disclosed in US20150105370

| Compound | Structure | HEK/hTLR7 IC50 (μM) | HEK/hTLR9 IC50 (μM) |
|---|---|---|---|
| ER-887258 | 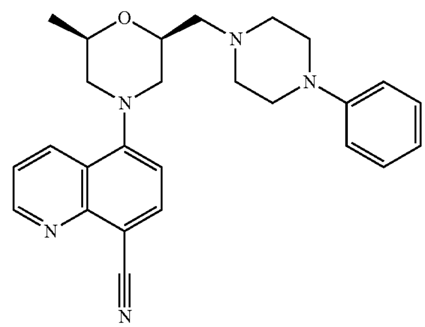 [SMILES: C[C@@H]1CN(c2ccc(C#N)c3ncccc23)C[C@H](CN2CCN(c3ccccc3)CC2)O1] | 0.0852 | >2.0 |
| ER-888285 | 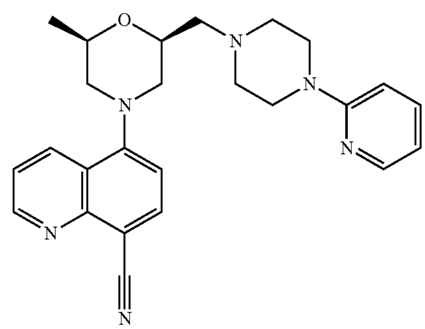 [SMILES: C[C@@H]1CN(c2ccc(C#N)c3ncccc23)C[C@H](CN2CCN(c3ccccn3)CC2)O1] | 0.120 | >2.0 |
| ER-888286 | 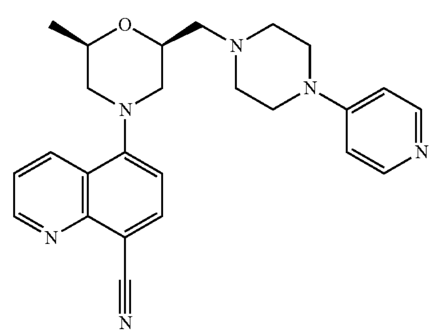 [SMILES: C[C@@H]1CN(c2ccc(C#N)c3ncccc23)C[C@H](CN2CCN(c3ccncc3)CC2)O1] | 1.370 | >2.0 |
| ER-894544 | 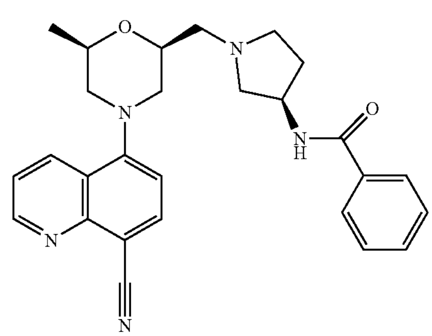 [SMILES: C[C@@H]1CN(c2ccc(C#N)c3ncccc23)C[C@H](CN2CC[C@@H](NC(=O)c3ccccc3)C2)O1] | 0.043 | >6.2 |

TABLE 1-continued

TLR7 and TLR9 potency of compounds disclosed in US20150105370

| Compound | Structure | HEK/hTLR7 IC50 (μM) | HEK/hTLR9 IC50 (μM) |
|---|---|---|---|
| ER-894160 | 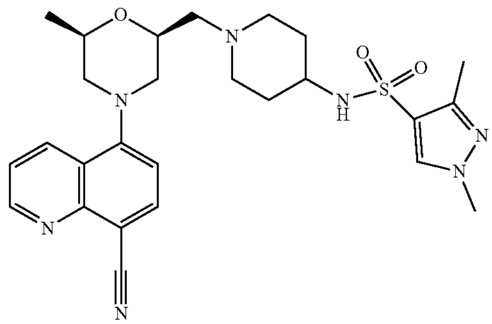 [SMILES: Cc1nn(C)cc1S(=O)(=O)NC1CCN(C[C@H]2CN(c3ccc(C#N)c4ncccc34)C[C@@H](C)O2)CC1] | 0.1990 | >10.0 |
| ER-894155 | 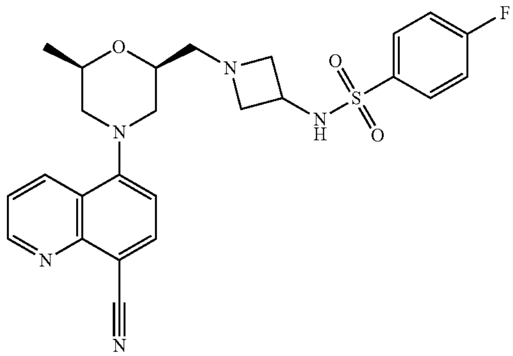 [SMILES: C[C@@H]1CN(c2ccc(C#N)c3ncccc23)C[C@H](CN2CC(NS(=O)(=O)c3ccc(F)cc3)C2)O1] | 0.2820 | >10.0 |

Synthesis

The compounds of the present invention can be prepared by any conventional means. Suitable processes for synthesizing these compounds as well as their starting materials are provided in the schemes below and in the examples. All substituents, in particular, $R^1$ to $R^4$ are as defined above unless otherwise indicated. Furthermore, and unless explicitly otherwise stated, all reactions, reaction conditions, abbreviations and symbols have the meanings well known to a person of ordinary skill in organic chemistry.

General synthetic routes for preparing the compound of formula (I) or (Ia) are shown below.

Scheme 1

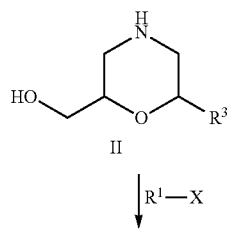

II

↓ $R^1$—X

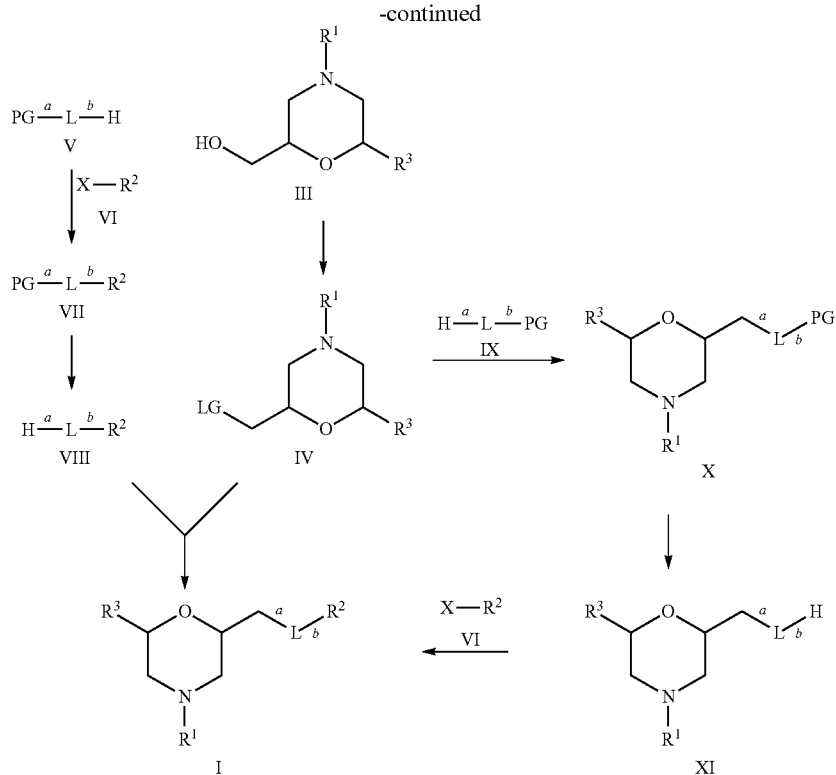

Wherein X is halogen; LG is leaving group, such as OTf, OTs and OMs; PG is protecting group, such as Boc and Cbz.

The coupling of compound of formula (II) with R¹—X can be achieved by direct coupling at elevated temperature in the presence of a base, such as DIPEA or $K_2CO_3$, or under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as RuPhos Pd G2, and a base, such as $Cs_2CO_3$, to provide compound of formula (III). Subsequently the hydroxy group of compound of formula (III) is converted to a leaving group, such as OTf, OTs, or OMs, under basic condition, such as DIPEA, TEA, $K_2CO_3$ or 2,6-dimethylpyridine, with $Tf_2O$, TsCl or MsCl. The coupling of compound of formula (V) with (VI) can be achieved by direct coupling at high temperature in the presence of a base, such as DIPEA or $K_2CO_3$, or under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as RuPhos Pd G2, BrettPhos Pd G3, XPhos Pd G3, $Pd_2(dba)_3$/BINAP or $Pd_2(dba)_3$/XantPhos and a base, such as $Cs_2CO_3$ or t-BuONa, to provide compound of formula (VII). The protecting group of compound of formula (VII) can be removed at high temperature or under acidic condition, such as TFA, or under hydrogenation condition with a catalyst, such as Pd/C or $Pd(OH)_2$/C. Compound of formula (VIII) is further coupled with compound of formula (IV) in the presence of a base, such as $K_2CO_3$, DIPEA or $Cs_2CO_3$, to afford compound of formula (I). On the other hand, in a basic condition, such as $K_2CO_3$, DIPEA, or $Cs_2CO_3$, compound of formula (IV) is reacted with (IX) to give compound of formula (X). The protecting group can be removed at high temperature or under acidic condition, such as TFA, or under hydrogenation condition with a catalyst, such as Pd/C or $Pd(OH)_2$/C to give compound of formula (XI) which is further coupled with (VI) under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as Ruphos Pd G2, and a base, such as $Cs_2CO_3$, to provide compound of formula (I). In some embodiment, the coupling of compound of formula (VIII) and (IV) or formula (XI) and (VI) may give a product containing a protecting group, e.g. Boc or Cbz, originated from (VIII) or (VI), which will be removed before affording the final compound of formula (I).

Compounds of this invention can be obtained as mixtures of diastereomers or enantiomers, which can be separated by methods well known in the art, e.g. (chiral) HPLC or SFC.

This invention also relates to a process for the preparation of a compound of formula (I) or (Ia) comprising any of the following steps:

a) the coupling of compound of formula (IV),

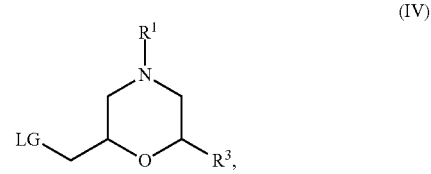

(IV)

with compound of formula (VIII) in the presence of a base;

b) the Buchwald-Hartwig amination of compound of formula (XI),

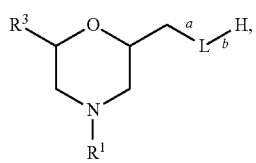

with compound of formula (VI) in the presence of a catalyst and a base;

wherein in step a), the base can be, for example, $K_2CO_3$, DIPEA or $Cs_2CO_3$;

in step b), the catalyst can be, for example, Ruphos Pd G2; the base can be, for example, DIPEA or $Cs_2CO_3$;

A compound of formula (I) or (Ia) when manufactured according to the above process is also an object of the invention.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:
ACN: acetonitrile
ACECl: 1-chloroethyl chloroformate
AIBN: 2,2'-azobis(2-methylpropionitrile)
BINAP: (2,2'-bis(diphenylphosphino)-1,1'-binaphthyl)
Boc$_2$O: di-tert butyl dicarbonate
BrettPhos Pd G3: [(2-di-cyclohexylphosphino-3,6-dimethoxy-2',4',6'-triisopropyl-1,1'-biphenyl)-2-(2'-amino-1,1'-biphenyl)]palladium(II) methanesulfonate
t-Bu XPhosPd G3: [(2-di-tert-butylphosphino-2',4',6'-triisopropyl-1,1'-biphenyl)-2-(2'-amino-1,1'-biphenyl)] palladium(II) methanesulfonate
CbzCl: benzylchloroformate
cataCXium A Pd G2: chloro[(di(1-adamantyl)-N-butylphosphine)-2-(2-aminobiphenyl)]palladium(II)
DAST: diethylaminosulfur trifluoride
DCM: dichloromethane
DIAD: diisopropyl azodicarboxylate
DIPEA: N,N-diisopropylethylamine
DMA: dimethylacetamide
DMEDA: 1,2-dimethylethylenediamine
DMFDMA: N,N-dimethylformamide dimethyl acetal
EtOAc or EA: ethyl acetate
FA: formic acid
HATU: hexafluorophosphate azabenzotriazole tetramethyl uronium
HLM human liver microsome
$IC_{50}$: half inhibition concentration
IPA: isopropanol
LCMS liquid chromatography-mass spectrometry
MS: mass spectrometry
NCS: N-chlorosuccinimide
NMP: N-methylpyrrolidin-2-one
PdCl$_2$(dtbpf) 1,1'-bis(di-tert-butylphosphino)ferrocene palladium dichloride
Pd$_2$(dba)$_3$: tris(dibenzylideneacetone)dipalladium(0)
PdCl$_2$(dppf): 1,1'-bis(diphenylphosphino)ferrocene palladium dichloride
PE: petroleum ether
prep-HPLC: preparative high performance liquid chromatography
prep-TLC: preparative thin layer chromatography
PPh$_3$: triphenylphosphine
Rf: retention factor
rt: room temperature
RuPhos Pd G2: chloro(2-dicyclohexylphosphino-2',6'-diisopropoxy-1,1'-biphenyl)[2-(2'-amino-1,1'-biphenyl)]palladium(II) 2nd generation
SelectFluor: 1-chloromethyl-4-fluoro-1,4-diazoniabicyclo [2.2.2]octane bis(tetrafluoroborate)
SFC: supercritical fluid chromatography
TEA: trimethylamine
Teoc-OSu: 1-[2-(trimethylsilyl)ethoxycarbonyloxy]pyrrolidin-2,5-dione
TFA: trifluoroacetic acid
Tf$_2$O: trifluoromethanesulfonic anhydride
THF: tetrahydrofuran
v/v: volume ratio
XantPhos: 4,5-bis(diphenylphosphino)-9,9-dimethylxanthene
XPhos: 2-dicyclohexylphosphino-2',4',6'-triisopropylbiphenyl
XPhos Pd G2: chloro(2-dicyclohexylphosphino-2',4',6'-triisopropyl-1,1'-biphenyl)[2-(2'-amino-1,1'-biphenyl)]palladium(II)

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 µm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 µm, OBD™ 30×100 mm) column, SunFire™ Prep-C18 (5 µm, OBD™ 30×100 mm) column, Phenomenex Synergi-C18 (10 µm, 25×150 mm) or Phenomenex Gemini-C18 (10 µm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 µm, 30×250 mm), AS (10 µm, 30×250 mm) or AD (10 µm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3$—$H_2O$ in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;

Acidic condition II: A: 0.0375% TFA in $H_2O$; B: 0.01875% TFA in acetonitrile;

Basic condition I: A: 0.1% $NH_3.H_2O$ in $H_2O$; B: acetonitrile;

Basic condition II: A: 0.025% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

Preparative Examples

The following examples are intended to illustrate the meaning of the present invention but should by no means represent a limitation within the meaning of the present invention:

Intermediate A

[(2R,6R)-4-(8-cyano-5-quinolyl)-6-methyl-morpholin-2-yl]methyl trifluoromethanesulfonate

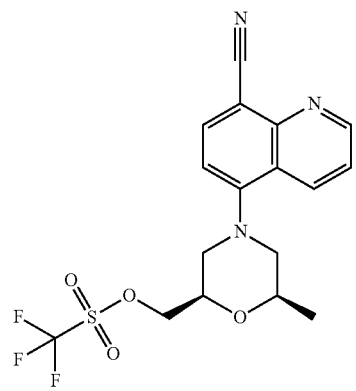

The title compound was prepared according to the following scheme:

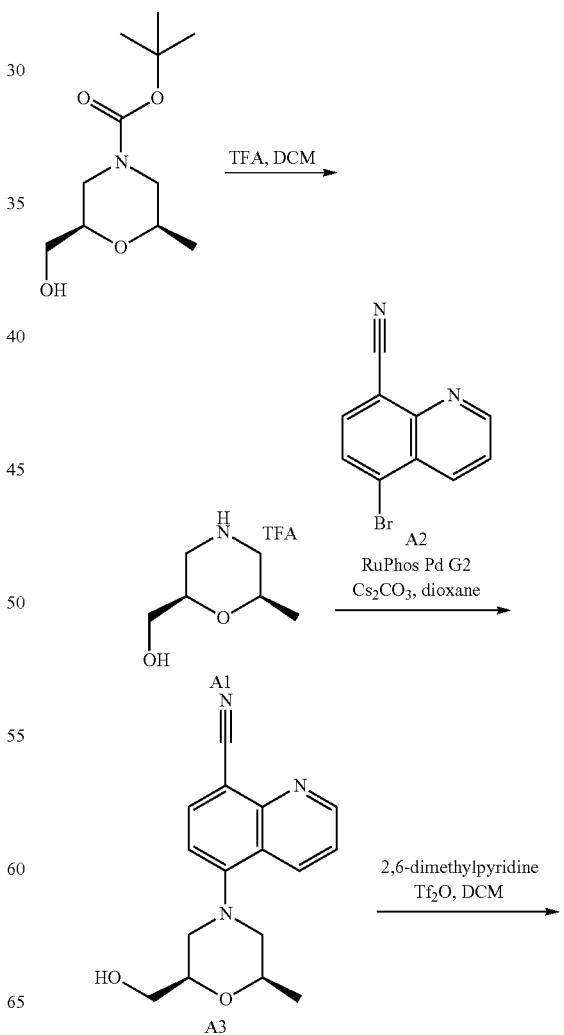

33
-continued

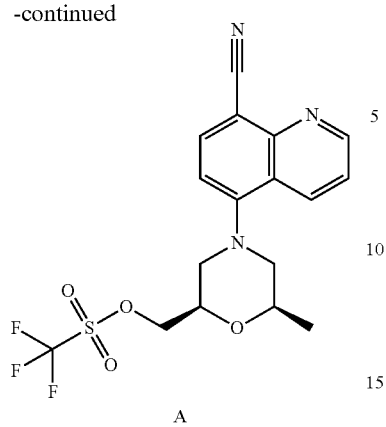

A

Step 1: Preparation of [(2R,6R)-6-methylmorpholin-2-yl]methanol; 2,2,2-trifluoroacetic acid (Compound A1)

To a solution of tert-butyl (2R,6R)-2-(hydroxymethyl)-6-methylmorpholine-4-carboxylate (CAS: 1700609-48-8, Vendor: WuXi Apptec, 1.35 g, 5.84 mmol) in DCM (10 mL) was added 2,2,2-trifluoroacetic acid (2.66 g, 23.30 mmol). After being stirred at rt for 3 hrs, the reaction mixture was concentrated in vacuo to give the crude product compound A1 (1.43 g) which was used in next step directly. MS: calc'd 132 (MH$^+$), measured 132 (MH$^+$).

Step 2: Preparation of 5-[(2R,6R)-2-(hydroxymethyl)-6-methyl-morpholin-4-yl]quinoline-8-carbonitrile (Compound A3)

The mixture of 5-bromoquinoline-8-carbonitrile (compound A2, CAS: 507476-70-2, Vendor: BePharm, 1.50 g, 6.42 mmol), [(2R,6R)-6-methylmorpholin-2-yl]methanol; 2,2,2-trifluoroacetic acid (compound A1, 1.43 g, 5.83 mmol), RuPhos Pd G2 (136 mg, 175 µmol) and Cs$_2$CO$_3$ (5.70 g, 17.50 mmol) in 1,4-dioxane (10 mL) was charged with N$_2$, and heated to 90° C. overnight. After being cooled down, the solid was filtered off and washed with EA (10 mL) twice. The filtrate was concentrated and the residue was purified by flash column (EA/PE=0 to 100%) to afford compound A3 (709 mg) as a light yellow solid. MS: calc'd 284 (MH$^+$), measured 284 (MH$^+$).

Step 3: Preparation of [(2R,6R)-4-(8-cyano-5-quinolyl)-6-methyl-morpholin-2-yl]methyl trifluoromethanesulfonate (Intermediate A)

To a flask was added 5-[(2R,6R)-2-(hydroxymethyl)-6-methyl-morpholin-4-yl]quinoline-8-carbonitrile (compound A3, 709 mg, 2.50 mmol), DCM (10 mL) and 2,6-dimethylpyridine (536 mg, 577 µL, 5.00 mmol). Then the reaction mixture was cooled with ice bath and trifluoromethanesulfonic anhydride (1.06 g, 634 µL, 3.75 mmol) was added dropwise. After being stirred for 2 hrs, the mixture was concentrated and purified by flash column (EA/PE=0 to 40%) to give Intermediate A (720 mg) as a yellow solid. MS: calc'd 416 (MH$^+$), measured 416 (MH$^+$).

34

Intermediate B

[(2R,6R)-4-(4-cyano-1,3-benzothiazol-7-yl)-6-methyl-morpholin-2-yl]methyl trifluoromethanesulfonate

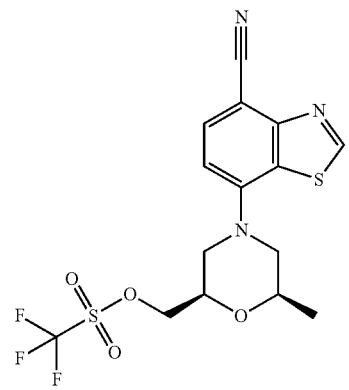 [SMILES: C[C@@H]1CN(c2ccc(C#N)c3ncsc23)C[C@H](COS(=O)(=O)C(F)(F)F)O1]

The title compound was prepared according to the following scheme:

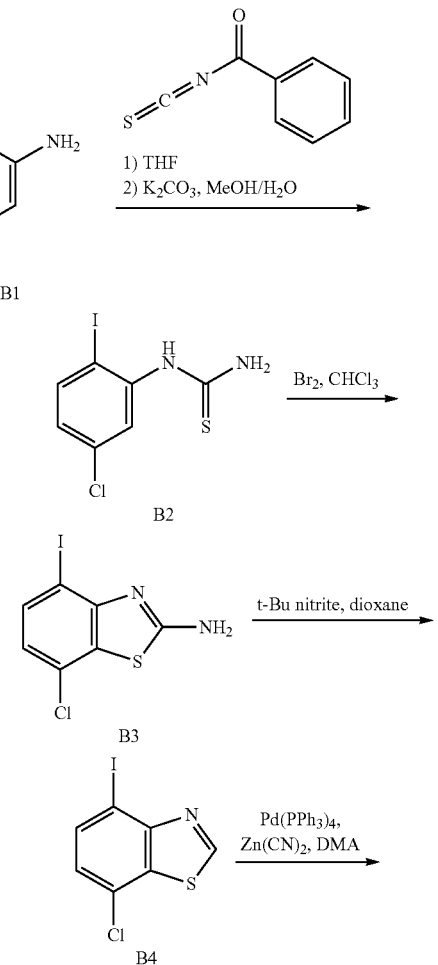

-continued

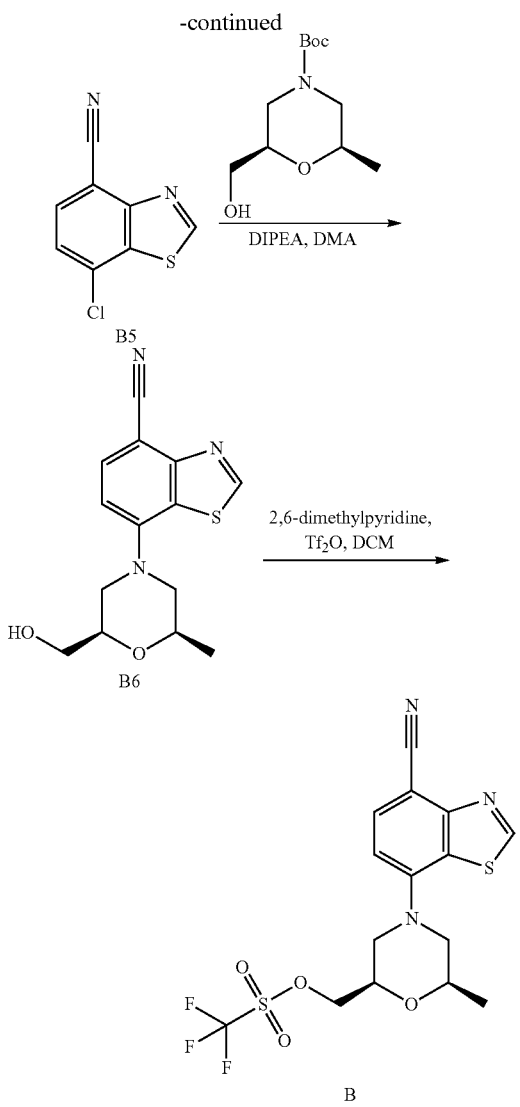

Step 1: Preparation of 1-(5-chloro-2-iodophenyl)thiourea (Compound B2)

To a solution of 5-chloro-2-iodo-aniline (compound B1, 5.00 g, 19.70 mmol) in THF (87 mL) was added benzoyl isothiocyanate (6.40 g, 39.40 mmol) at 10-20° C. After the reaction was stirred at 20° C. for 16 hrs, the solvent was removed and the solid was washed with EtOH/PE (50 mL, v/v=4/1), followed by air-drying to afford an intermediate (8.70 g). The intermediate was further dissolved in methanol (100 mL) and treated with a solution of $K_2CO_3$ (8.20 g, 59.20 mmol) in water (40 mL). After the reaction mixture was heated at 70° C. for 4 hrs, the solvent was removed under vacuum followed by addition of water (20 mL). The solid was collected by filtration, further washed with water (20 mL), and dried to give compound B2 (5.00 g) as a yellow solid.

Step 2: Preparation of 7-chloro-4-iodo-1,3-benzothiazol-2-amine (Compound B3)

To a solution of 1-(5-chloro-2-iodophenyl)thiourea (compound B2, 4.00 g, 12.80 mmol) in $CHCl_3$ (32 mL) was added bromine (0.66 mL, 12.80 mmol). The reaction mixture was heated at 78° C. for 18 hrs. After being cooled down, the solvent was removed under vacuum and the solid was dissolved in DCM/MeOH (100 mL, v/v=1/1), followed by addition of aqueous solution of $Na_2S_2O_3$ (20 mL). Then the solvent was removed under vacuum and water (30 mL) was added. After filtration, the solid was collected and dried to give compound B3 (3.50 g) as a yellow solid. MS: calc'd 311 ($MH^+$), measured 311 ($MH^+$).

Step 3: Preparation of 7-chloro-4-iodo-1,3-benzothiazole (Compound B4)

To a solution of 7-chloro-4-iodo-1,3-benzothiazol-2-amine (compound B3, 3.00 g, 9.70 mmol) in 1,4-dioxane (60 mL) was added tert-butyl nitrite (2.00 g, 19.30 mmol). After being stirred at 90° C. for 18 hrs, the reaction mixture was concentrated and purified by flash column to give a crude product, which was triturated in PE (15 mL) to give compound B4 (1.50 g) as a white solid. MS: calc'd 296 ($MH^+$), measured 296 ($MH^+$).

Step 4: Preparation of 7-chloro-1,3-benzothiazole-4-carbonitrile (Compound B5)

To a solution of 7-chloro-4-iodo-1,3-benzothiazole (compound B4, 1.50 g, 5.10 mmol) in DMA (40 mL) was added $Zn(CN)_2$ (0.89 g, 7.60 mmol) and $Pd(PPh_3)_4$ (0.20 g, 0.17 mmol). After being stirred at 100° C. for 18 hrs, the reaction mixture was poured into water (100 mL). The solid was collected by filtration, and dissolved in EtOAc (400 mL), washed with brine, dried over anhydrous $Na_2SO_4$ and concentrated to give compound B5 (0.90 g) as a white solid. MS: calc'd 195 ($MH^+$), measured 195 ($MH^+$).

Step 5: Preparation of 7-[(2R,6R)-2-(hydroxymethyl)-6-methyl-morpholin-4-yl]-1,3-benzothiazole-4-carbonitrile (Compound B6)

To a solution of tert-butyl (2R,6R)-2-(hydroxymethyl)-6-methyl-morpholine-4-carboxylate (61 mg, 0.26 mmol) in DCM (2 mL) was added HCl (0.5 mL, 10% in MeOH) at rt. After being stirred at rt for 2 hrs, the reaction mixture was concentrated and the residue was dissolved in DMA (0.5 mL). To the solution was added 7-chloro-1,3-benzothiazole-4-carbonitrile (compound B5, 52 mg, 0.31 mmol) and DIPEA (0.13 mL, 0.77 mmol). After the reaction mixture was stirred at 150° C. for 2 hrs, water (10 mL) was added. The mixture was then cooled down and extracted with EtOAc (10 mL). The organic layer was washed with brine, dried over anhydrous $Na_2SO_4$, and concentrated to give a crude product which was purified by prep-TLC (PE/EA=2/1) to give compound B6 (15 mg) as a yellow gum. MS: calc'd 290 ($MH^+$), measured 290 ($MH^+$).

Step 6: Preparation of [(2R,6R)-4-(4-cyano-1,3-benzothiazol-7-yl)-6-methyl-morpholin-2-yl]methyl trifluoromethanesulfonate (Intermediate B)

To a solution of 7-[(2R,6R)-2-(hydroxymethyl)-6-methyl-morpholin-4-yl]-1,3-benzothiazole-4-carbonitrile (compound B6, 15 mg, 0.05 mmol) in DCM (1 mL) was added 2,6-dimethylpyridine (22 mg, 0.21 mmol) and trifluoromethanesulfonic anhydride (29 mg, 0.10 mmol). After being stirred at 0° C. for 1 h, the reaction mixture was poured into ice-water (10 mL) and extracted with DCM (10 mL), dried over Na$_2$SO$_4$, and concentrated to give Intermediate B (20 mg) as a yellow solid. MS: calc'd 422 (MH$^+$), measured 422 (MH$^+$).

Intermediate C

[(2R,6R)-4-(8-cyanoquinoxalin-5-yl)-6-methyl-morpholin-2-yl]methyl trifluoromethanesulfonate

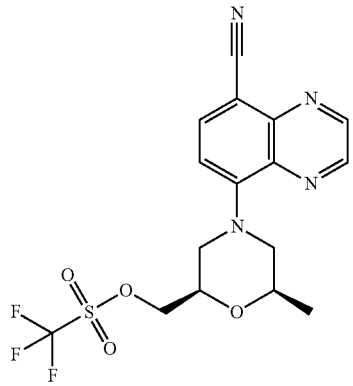 [SMILES: C[C@@H]1CN(c2ccc(C#N)c3nccnc23)C[C@H](COS(=O)(=O)C(F)(F)F)O1]

The title compound was prepared in analogy to the preparation of Intermediate A by using 8-bromoquinoxaline-5-carbonitrile (Synthesis refers to US 20170174653 A1) instead of 5-bromoquinoline-8-carbonitrile (compound A2). Intermediate C (825 mg) was obtained as an off-white solid. MS: calc'd 417 (MH$^+$), measured 417 (MH$^+$).

Intermediate D

[(2R,6R)-4-(7-cyanopyrazolo[1,5-a]pyridin-4-yl)-6-methyl-morpholin-2-yl]methyl trifluoromethanesulfonate

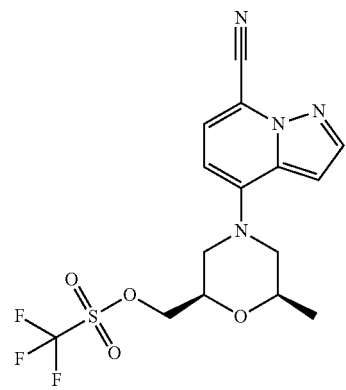 [SMILES: C[C@@H]1CN(c2ccc(C#N)n3nccc23)C[C@H](COS(=O)(=O)C(F)(F)F)O1]

The title compound was prepared in analogy to the preparation of Intermediate A by using 4-chloropyrazolo[1,5-a]pyridine-7-carbonitrile (CAS: 1268520-74-6, Vendor: PharmaBlock) instead of 5-bromoquinoline-8-carbonitrile (compound A2). Intermediate D (166 mg) was obtained as a white solid. MS: calc'd 405 (MH$^+$), measured 405 (MH$^+$).

Intermediate E

[(2R,6R)-4-(7-cyano-3-fluoro-pyrazolo[1,5-a]pyridin-4-yl)-6-methyl-morpholin-2-yl]methyl trifluoromethanesulfonate

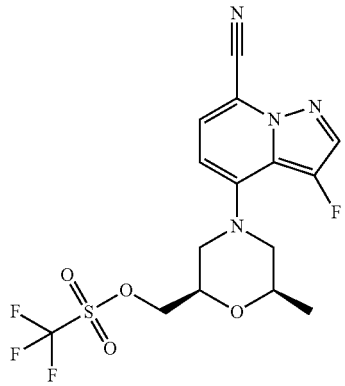 [SMILES: C[C@@H]1CN(c2ccc(C#N)n3ncc(F)c23)C[C@H](COS(=O)(=O)C(F)(F)F)O1]

The title compound was prepared according to the following scheme:

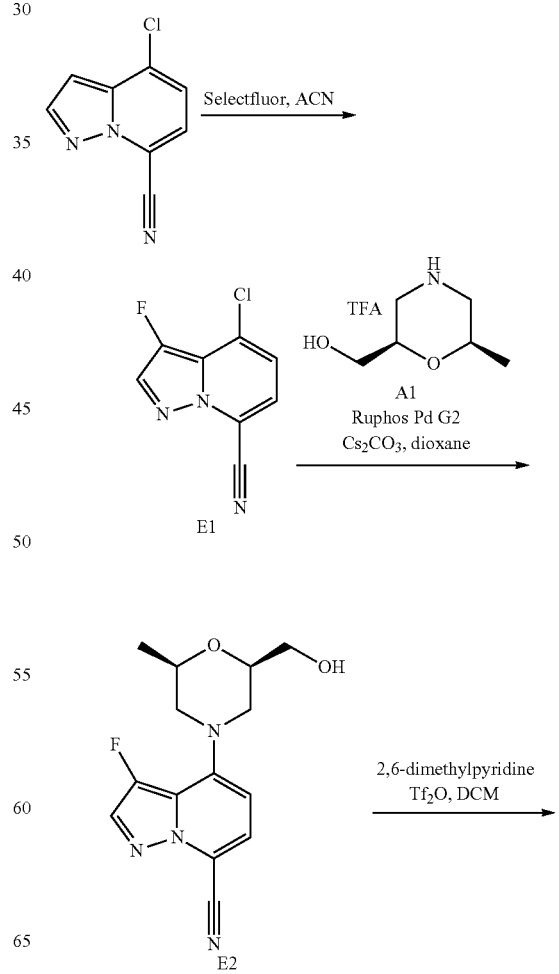

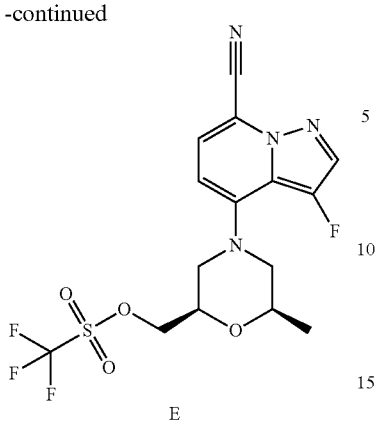

E

Step 1: Preparation of 4-chloro-3-fluoro-pyrazolo[1,5-a]pyridine-7-carbonitrile (Compound E1)

To a solution of 4-chloropyrazolo[1,5-a]pyridine-7-carbonitrile (CAS: 1268520-74-6, Vendor: Pharmablock, 600 mg, 3.38 mmol) in acetonitrile (50 mL) was added SelectFluor (2.39 g, 6.76 mmol). After being stirred at rt for 24 hrs, the mixture was concentrated and diluted with water (30 mL), extracted with DCM (30 mL) twice. The organic layer was washed with sat. NH$_4$Cl and brine, dried over Na$_2$SO$_4$, and concentrated to give a crude product which was purified by flash column to give compound E1 (419 mg) as a light yellow powder. MS: calc'd 196 (MH$^+$), measured 196 (MH$^+$). $^1$H NMR (400 MHz, METHANOL-d$_4$) δ=8.17 (d, J=3.5 Hz, 1H), 7.55 (d, J=7.6 Hz, 1H), 7.35 (d, J=7.7 Hz, 1H).

Step 2: Preparation of 3-fluoro-4-[(2R,6R)-2-(hydroxymethyl)-6-methyl-morpholin-4-yl]pyrazolo[1,5-a]pyridine-7-carbonitrile (Compound E2)

To a solution of 4-chloro-3-fluoropyrazolo[1,5-a]pyridine-7-carbonitrile (compound E1, 419 mg, 2.14 mmol), [(2R,6R)-6-methylmorpholin-2-yl]methanol; 2,2,2-trifluoroacetic acid (compound A1, 526 mg, 2.14 mmol) and Cs$_2$CO$_3$ (2.79 g, 8.57 mmol) in 1,4-dioxane (10 mL) was added RuPhos Pd G2 (116 mg, 0.15 mmol) under N$_2$. The reaction mixture was heated at 90° C. for 2 hrs. After being cooled down, the mixture was diluted with EtOAc and filtered through celite. The filtrate was concentrated to give a brown oil which was purified by flash column to give compound E2 (325 mg) as a yellow oil. MS: calc'd 291 (MH$^+$), measured 291 (MH$^+$).

Step 3: Preparation of (2R,6R)-4-(7-cyanopyrazolo[1,5-a]pyridin-4-yl)-6-methyl-morpholin-2-yl]methyl trifluoromethanesulfonate (Intermediate E)

To a solution of 3-fluoro-4-[(2R,6R)-2-(hydroxymethyl)-6-methyl-morpholin-4-yl]pyrazolo[1,5-a]pyridine-7-carbonitrile (compound E2, 325 mg, 1.12 mmol) in DCM (3 mL) was added 2,6-dimethylpyridine (240 mg, 258 µL, 2.24 mmol) and Tf$_2$O (474 mg, 284 µL, 1.68 mmol) at rt. After being stirred for 1.5 hrs, the mixture was diluted with DCM, washed with sat. NH$_4$Cl and brine. The organic layer was dried over Na$_2$SO$_4$ and concentrated to give the crude product which was purified by flash column to give Intermediate E (180 mg) as a yellow solid. MS: calc'd 423 (MH$^+$), measured 423 (MH$^+$).

Intermediate F

[(2R,6R)-4-(8-cyano-[1,2,4]triazolo[1,5-a]pyridin-5-yl)-6-methyl-morpholin-2-yl]methyl trifluoromethanesulfonate

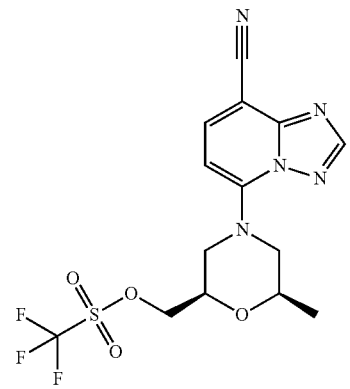 [SMILES: C[C@@H]1CN(c2ccc(C#N)c3ncnn23)C[C@H](COS(=O)(=O)C(F)(F)F)O1]

The title compound was prepared according to the following scheme:

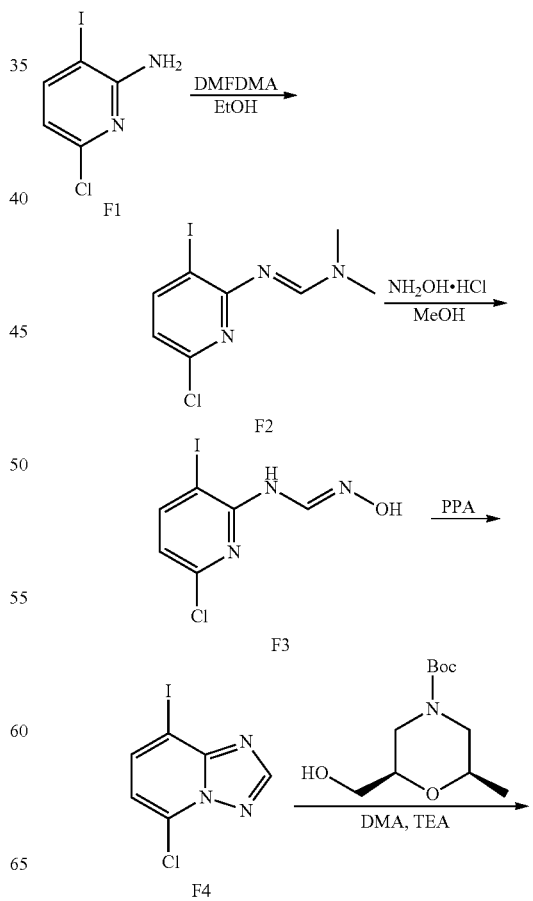

-continued

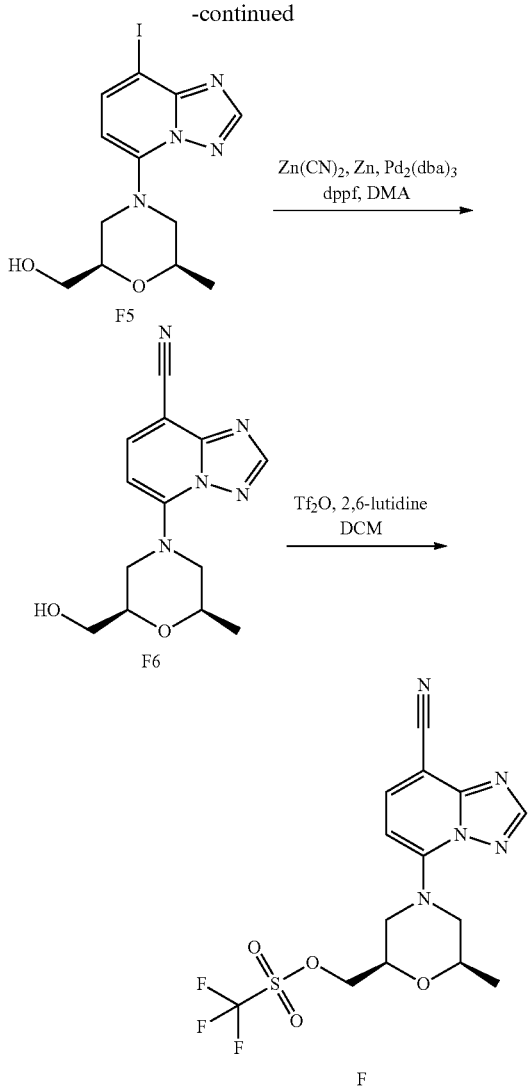

Step 1: Preparation of N'-(6-chloro-3-iodo-2-pyridyl)-N,N-dimethyl-formamidine (Compound F2)

To a solution of 6-chloro-3-iodo-pyridin-2-amine (compound F1, CAS: 800402-06-6, Vendor: BePharm, 25.00 g, 98.25 mmol) in ethanol (340 mL) was added N,N-dimethylformamide dimethyl acetal (19.55 g, 164.07 mmol). After being heated at 90° C. for 18 hrs, the mixture was concentrated to give compound F2 (30.41 g) as a light yellow solid. MS: calc'd 310 (MH$^+$), measured 310 (MH$^+$).

Step 2: Preparation of N-(6-chloro-3-iodo-2-pyridyl)-N'-hydroxy-formamidine (Compound F3)

To a solution of N'-(6-chloro-3-iodo-2-pyridyl)-N,N-dimethyl-formamidine (compound F2, 30.00 g, 96.92 mmol) in methanol (300 mL) was added hydroxylamine hydrochloride (10.10 g, 145.38 mmol). After being stirred at 15° C. for 1.5 hrs, the mixture was filtered. The solid was dried to give compound F3 (24.00 g) as a white solid. MS: calc'd 298 (MH$^+$), measured 298 (MH$^+$).

Step 3: Preparation of 5-chloro-8-iodo-[1,2,4]triazolo[1,5-a]pyridine (Compound F4)

A solution of N-(6-chloro-3-iodo-2-pyridyl)-N'-hydroxyformamidine (compound F3, 10.00 g, 33.62 mmol) in polyphosphoric acid (66.00 g, 275.07 mmol) was heated at 80° C. for 4 hrs. The mixture was then poured into ice water (500 mL) and basified with 50% KOH solution to pH=8, extracted with DCM (200 mL) twice. The combined organic layer was washed with brine (100 mL), dried over anhydrous Na$_2$SO$_4$, filtered and concentrated to give compound F4 (9.30 g) as a white solid. MS: calc'd 280 (MH$^+$), measured 280 (MH$^+$).

Step 4: Preparation of [(2R,6R)-4-(8-iodo-[1,2,4]triazolo[1,5-a]pyridin-5-yl)-6-methyl-morpholin-2-yl]methanol (Compound F5)

To a solution of tert-butyl (2R,6R)-2-(hydroxymethyl)-6-methyl-morpholine-4-carboxylate (CAS: 1700609-48-8, Vendor: WuXi Apptec, 497 mg, 2.15 mmol) in DCM (10 mL) was added HCl (2.50 mL, 10% in MeOH) at rt. After the reaction mixture was stirred at rt for 2 hrs, the solvent was removed, and the residue was dissolved in DMA (4 mL). To the solution was added 5-chloro-8-iodo-[1,2,4]triazolo[1,5-a]pyridine (compound F4, 600 mg, 2.15 mmol) and triethylamine (1.50 mL, 10.73 mmol). After being stirred at 100° C. for 18 hrs, the mixture was concentrated and purified by flash column (EA/Isohexane=70%) to give compound F5 (500 mg) as a colorless gum. MS: calc'd 375 (MH$^+$), measured 375 (MH$^+$).

Step 5: Preparation of 5-[(2R,6R)-2-(hydroxymethyl)-6-methyl-morpholin-4-yl]-[1,2,4]triazolo[1,5-a]pyridine-8-carbonitrile (Compound F6)

To a solution of [(2R,6R)-4-(8-iodo-[1,2,4]triazolo[1,5-a]pyridin-5-yl)-6-methyl-morpholin-2-yl]methanol (compound F5, 500 mg, 1.34 mmol) and zinc cyanide (314 mg, 2.67 mmol) in N,N-dimethylacetamide (2 mL) was added zinc (87 mg, 1.34 mmol), 1,1'-bis(diphenylphosphino)ferrocene (74 mg, 0.13 mmol) and tris(dibenzylideneacetone)dipalladium (0) (122 mg, 0.13 mmol). The mixture was stirred at 120° C. under N$_2$ atmosphere for 4 hrs, then filtered. The filtrate was purified by flash column (EA/PE=80%) to give compound F6 (300 mg) as a white solid. MS: calc'd 274 (MH$^+$), measured 274 (MH$^+$).

Step 6: Preparation of [(2R,6R)-4-(8-cyano-[1,2,4]triazolo[1,5-a]pyridin-5-yl)-6-methyl-morpholin-2-yl]methyl trifluoromethanesulfonate (Intermediate F)

To a solution of 5-[(2R,6R)-2-(hydroxymethyl)-6-methyl-morpholin-4-yl]-[1,2,4]triazolo[1,5-a]pyridine-8-carbonitrile (compound F6, 150 mg, 0.55 mmol) and 2,6-lutidine (0.09 mL, 0.77 mmol) in DCM (10 mL) was added trifluoromethanesulfonic anhydride (0.08 mL, 1.10 mmol) at 0° C. After being stirred at 0° C. for 1 h, the reaction mixture was quenched with water (30 mL) and extracted with EA (30 mL). The organic layer was dried and concentrated, and purified by prep-TLC (EA/PE=50%) to give Intermediate F (100 mg) as a yellow solid. MS: calc'd 406 (MH$^+$), measured 406 (MH$^+$).

Intermediate G

[(2R,6R)-6-methyl-4-(8-methylquinoxalin-5-yl)morpholin-2-yl]methyl trifluoromethanesulfonate

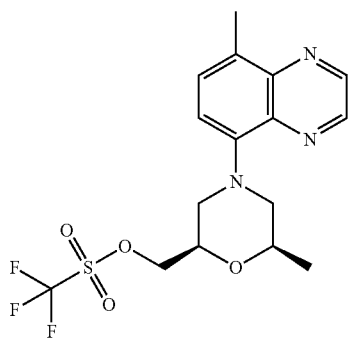 [SMILES: Cc1ccc(N2C[C@H](COS(=O)(=O)C(F)(F)F)O[C@H](C)C2)c2nccnc12]

The title compound was prepared in analogy to the preparation of Intermediate A by using 5-bromo-8-methylquinoxaline (CAS: 1360599-43-4, Vendor: Bepharm) instead of 5-bromoquinoline-8-carbonitrile (compound A2), replacing RuPhos Pd G2 and $Cs_2CO_3$ with $Pd_2(dba)_3$, BINAP and t-BuONa in the Buchwald-Hartwig amination reaction. Intermediate G (200 mg) was obtained as a brown solid. MS: calc'd 406 ($MH^+$), measured 406 ($MH^+$).

Intermediate H

[(2R,6R)-4-(8-methoxyquinoxalin-5-yl)-6-methyl-morpholin-2-yl]methyl trifluoromethanesulfonate

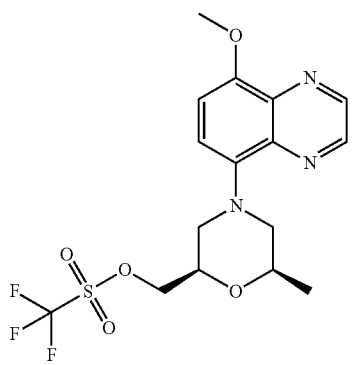 [SMILES: COc1ccc(N2C[C@H](COS(=O)(=O)C(F)(F)F)O[C@H](C)C2)c2nccnc12]

The title compound was prepared in analogy to the preparation of Intermediate A by using 5-bromo-8-methoxyquinoxaline (compound H1) instead of 5-bromoquinoline-8-carbonitrile (compound A2). Intermediate H (56 mg) was obtained as a yellow gum. MS: calc'd 422 ($MH^+$), measured 422 ($MH^+$).

The compound H1 was prepared according to the following scheme:

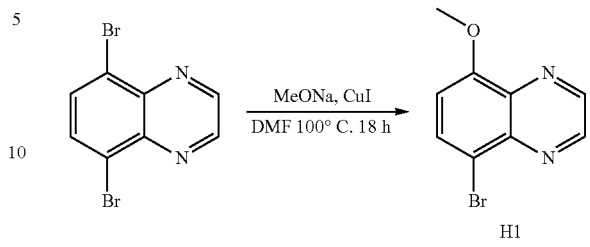

Preparation of 5-bromo-8-methoxy-quinoxaline (compound H1)

A solution of 5,8-dibromoquinoxaline (800 mg, 2.78 mmol), cuprous iodide (529 mg, 2.78 mmol), sodium methoxide (5.4 M in MeOH, 0.57 mL, 3.06 mmol) in DMF (20 mL) was stirred at 100° C. for 18 hrs. After concentration, the mixture was purified by flash column (PE/EA=2/1) to give compound H1 (310 mg) as a yellow solid. MS calc'd 239 ($MH^+$), measured 239 ($MH^+$).

Intermediate I

[(2R,6R)-4-(8-cyano-3-methyl-quinoxalin-5-yl)-6-methyl-morpholin-2-yl]methyl trifluoromethanesulfonate The title compound was prepared in analogy to the preparation of Intermediate A by using 8-bromo-2-methyl-quinoxaline-5-carbonitrile (compound 12) instead of 5-bromoquinoline-8-carbonitrile (compound A2). Intermediate I (150 mg) was obtained as a dark gum with 51% purity. MS: calc'd 431 ($MH^+$), measured 431 ($MH^+$).

The compound 12 was prepared according to the following scheme:

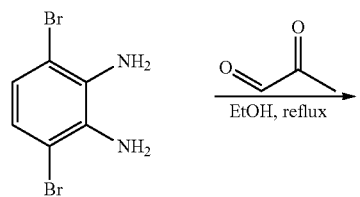

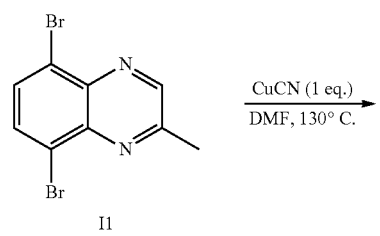

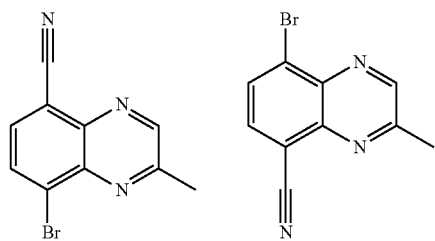

Step 1: Preparation of 5,8-dibromo-2-methyl-quinoxaline (Compound I1)

A mixture of 3,6-dibromobenzene-1,2-diamine (3500 mg, 13.16 mmol), pyruvic aldehyde (4267 mg, 23.69 mmol) in ethanol (35 mL) was degassed and purged with N$_2$ for 3 times. After being stirred at 85° C. under reflux in N$_2$ atmosphere for 2 hrs, the mixture was filtrated and the solid was washed with EtOH (50 mL), and dried under reduced pressure to give compound I1 (2200 mg) as a yellow solid. MS: calc'd 301 (MH$^+$), measured 301 (MH$^+$).

Step 2: Preparation of 8-bromo-2-methyl-quinoxaline-5-carbonitrile and 8-bromo-3-methyl-quinoxaline-5-carbonitrile (Compound I2 and I2')

A mixture of 5,8-dibromo-2-methyl-quinoxaline (compound I1, 1200 mg, 3.97 mmol) and cuprous cyanide (356 mg, 3.97 mmol) in DMF (10 mL) was stirred at 130° C. for 5 hrs. After being cooled down, the reaction mixture was diluted with H$_2$O (100 mL), and extracted with DCM (40 mL) for five times. The combined organic layer was dried over Na$_2$SO$_4$, filtered and concentrated. The residue was purified by prep-TLC (PE/EA=5/1) to give the mixture of compound I2 and I2' (200 mg) as a yellow solid. MS: calc'd 248 (MH$^+$), measured 248 (MH$^+$).

Intermediate J

[(2R,6R)-6-methyl-4-[8-(trifluoromethyl)quinoxalin-5-yl]morpholin-2-yl]methyl trifluoromethanesulfonate

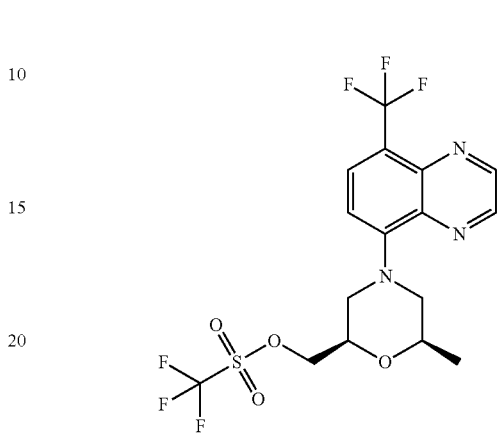

The title compound was prepared in analogy to the preparation of Intermediate A by using 5-bromo-8-(trifluoromethyl)quinoxaline (CAS: 2101944-93-6, Vendor: Bepharm) instead of 5-bromoquinoline-8-carbonitrile (compound A2). Intermediate J (200 mg) was obtained as a brown solid. MS: calc'd 460 (MH$^+$), measured 460 (MH$^+$).

Intermediate K

[(2R,6R)-4-(8-cyano-2,3-dideuterio-quinoxalin-5-yl)-6-methyl-morpholin-2-yl]methyl trifluoromethanesulfonate

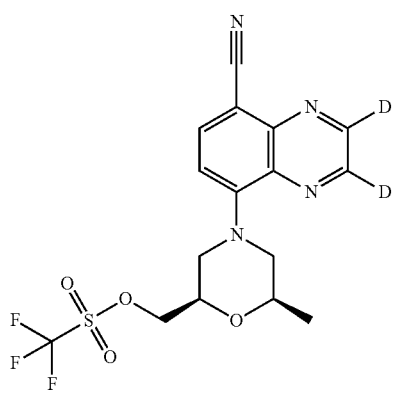 [SMILES: [2H]c1nc2c(C#N)ccc(N3C[C@H](COS(=O)(=O)C(F)(F)F)O[C@H](C)C3)c2nc1[2H]]

The title compound was prepared in analogy to the preparation of Intermediate A by using 8-bromo-2,3-dideuterio-quinoxaline-5-carbonitrile (compound K8) instead of 5-bromoquinoline-8-carbonitrile (compound A2). Intermediate K (200 mg) was obtained as a yellow solid. MS: calc'd 419 (MH$^+$), measured 419 (MH$^+$).

The compound K8 was prepared according to the following scheme:

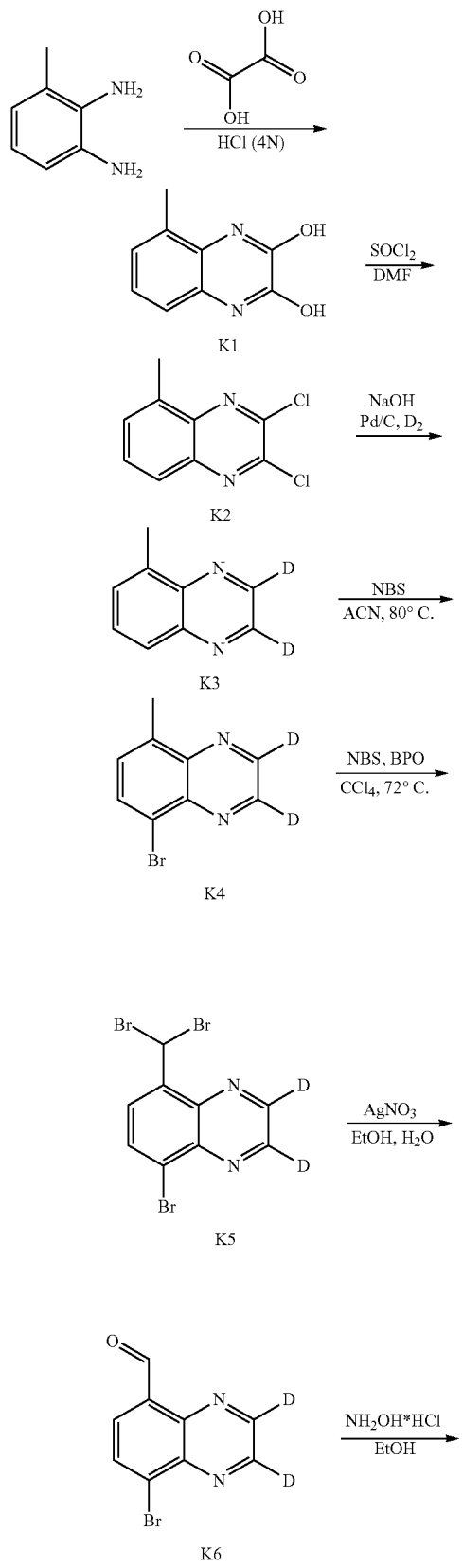

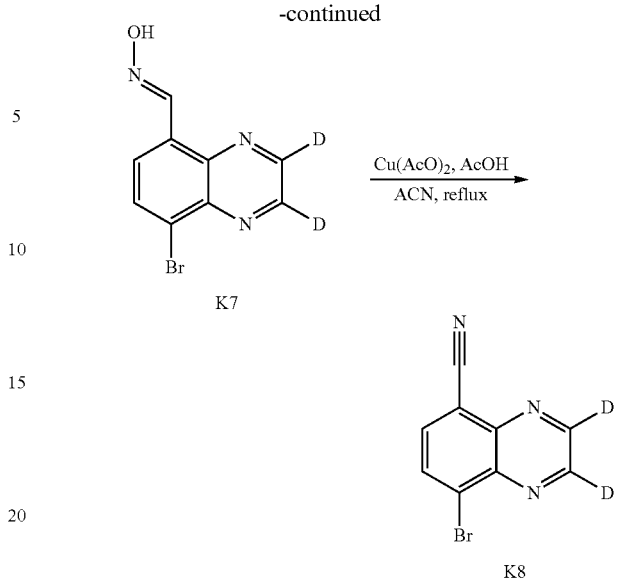

Step 1: Preparation of 5-methylquinoxaline-2,3-diol (Compound K1)

To the solution of 2,3-diaminotoluene (CAS: 2687-25-4, Vendor: Aldrich, 150 g, 1228 mmol) and hydrogenchloride (4 N, 3750 mL) was added oxalic acid (221 g, 2456 mmol). The mixture was stirred at 100° C. for 3 hrs. After being cooled down, the mixture was poured into 3000 mL ice-water. A black solid was appeared. The mixture was filtered, and the wet-cake was washed with 500 mL water and dried under vacuum to give compound K1 (230 g) as a black solid. MS calc'd 177 (MH$^+$), measured 177 (MH$^+$).

Step 2: Preparation of 2,3-dichloro-5-methyl-quinoxaline (Compound K2)

To the solution of 5-methylquinoxaline-2,3-diol (compound K1, 220 g, 1249 mmol) in 1,2-dichloroethane (500 mL) was added thionyl chloride (500 mL, 2498 mmol) and DMF (0.97 mL, 12.49 mmol). The final mixture was stirred at 80° C. for 6 hrs. After being cooled down, the mixture was concentrated to give a crude product which was purified by flash column (PE/EA=5/1) to give compound K2 (152 g) as a yellow solid. MS calc'd 213 (MH$^+$), measured 213 (MH$^+$).

Step 3: Preparation of 2,3-dideuterio-5-methyl-quinoxaline (Compound K3)

To the solution of 2,3-dichloro-5-methyl-quinoxaline (compound K2, 46 g, 215.90 mmol) in 1,4-dioxane (760 mL) and deuterium oxide (160 mL) was added 2 N aqueous solution of NaOH in D$_2$O (215.9 mL, 431.80 mmol) and Pd/C (10 wt. %, 9200 mg). The mixture was stirred at rt under deuterium atmosphere for 3 hrs. Then the mixture was filtered and diluted with 800 mL water, extracted with 250 mL EA for three times. The combined organic layer was washed with 300 mL water twice and 200 mL brine once. After dried over Na$_2$SO$_4$, the organic layer was concentrated to give the crude product which was purified by flash column (PE/EA=10/1) to give compound K3 (16 g) as a brown oil. MS calc'd 147 (MH$^+$), measured 147 (MH$^+$).

Step 4: Preparation of 5-bromo-2,3-dideuterio-8-methyl-quinoxaline (Compound K4)

A solution of 2,3-dideuterio-5-methyl-quinoxaline (compound K3, 10 g, 58.14 mmol), N-bromosuccinimide (20697 mg, 116.29 mmol) in ACN (250 mL) was stirred at 80° C. for 18 hrs. After being cooled down, the solution was concentrated to give a crude solid which was washed with 300 mL water. The crude product was purified by flash column (PE/EA=5/1) to give compound K4 (8500 mg) as a light yellow solid. MS calc'd 225 (MH$^+$), measured 225 (MH$^+$).

Step 5: Preparation of 5-bromo-2,3-dideuterio-8-(dibromomethyl)quinoxaline (Compound K5)

A solution of 5-bromo-2,3-dideuterio-8-methyl-quinoxaline (compound K4, 8500 mg, 37.76 mmol), N-bromosuccinimide (26886 mg, 151.06 mmol), 2,2'-azobis(2-methylpropionitrile) (1240 mg, 7.55 mmol) in carbon tetrachloride (250 mL) was stirred at 80° C. for 18 hrs. After being cooled down, the mixture was concentrated to give an oil which was diluted with 300 mL water. The mixture was stirred for 1 h and filtered. The wet-cake was purified by flash column (PE/EA=10/1) to give compound K5 (10000 mg) as a yellow solid. MS calc'd 381 (MH$^+$), measured 381 (MH$^+$).

Step 6: Preparation of 8-bromo-2,3-dideuterio-quinoxaline-5-carbaldehyde (Compound K6)

A solution of silver nitrate (17747 mg, 104.47 mmol) in water (200 mL) was added to the solution of 5-bromo-2,3-dideuterio-8-(dibromomethyl)quinoxaline (compound K5, 10000 mg, 26.12 mmol) in ethanol (400 mL). After being stirred at rt for 2 hrs, the mixture was concentrated to about 300 mL and filtered. The filtrate was diluted with 500 mL water and extracted with 200 mL EA for three times. The combined organic layer was washed with 200 mL water twice and 100 mL brine once, dried over Na$_2$SO$_4$ and concentrated to give the crude product (batch 1). The wet-cake was stirred in 500 mL DCM for 1 h, filtered and the wet-cake was washed with 100 mL DCM twice. The filtrate was concentrated to give the crude product as an oil (batch 2). The two batches were combined to give compound K6 (5500 mg) as a yellow solid. MS calc'd 239 (MH$^+$), measured 239 (MH$^+$).

Step 7: Preparation of (5E)-8-bromo-2,3-dideuterio-quinoxaline-5-carbaldehyde oxime (Compound K7)

A solution of 8-bromo-2,3-dideuterio-quinoxaline-5-carbaldehyde (compound K6, 5500 mg, 23.01 mmol), hydroxylamine hydrochloride (2078 mg, 29.91 mmol), sodium acetate (4150 mg, 50.61 mmol) in ethanol (250 mL) was stirred at 70° C. for 16 hrs. After being cooled down, the solution was concentrated to give a residue which was treated with 300 mL water and stirred for 0.5 h. The suspension was filtered, and the wet-cake was treated with 300 mL MeCN. After concentration, the compound K7 (4500 mg) was obtained as a yellow solid. MS calc'd 254 (MH$^+$), measured 254 (MH$^+$).

Step 8: Preparation of 8-bromo-2,3-dideuterio-quinoxaline-5-carbonitrile (Compound K8)

A solution of (5E)-8-bromo-2,3-dideuterio-quinoxaline-5-carbaldehyde oxime (compound K7, 4500 mg, 17.71 mmol), copper(II) acetate (965 mg, 5.31 mmol), acetic acid (1382 mg, 23.02 mmol) in acetonitrile (120 mL) was stirred at 80° C. for 18 hrs. After being cooled down, the solution was concentrated to give an oil which was dissolved in 500 mL DCM. The suspension was stirred for 1 h, filtered, and the wet-cake was washed with 100 mL DCM twice. The filtrate was concentrated and purified by flash column (PE/EA/DCM=3/1/1) to give compound K8 (2600 mg) as a yellow solid. MS calc'd 236 (MH$^+$), measured 236 (MH$^+$).

Intermediate L

[(2R,6R)-4-(8-cyano-2-deuterio-5-quinolyl)-6-methyl-morpholin-2-yl]methyl trifluoromethanesulfonate

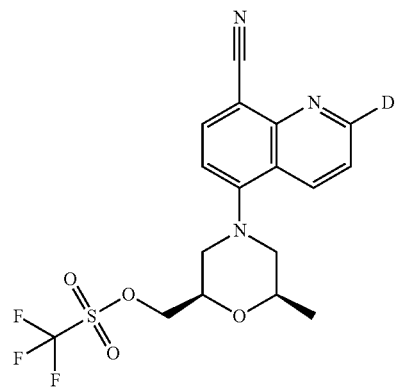 [SMILES: [2H]c1ccc2c(N3C[C@H](COS(=O)(=O)C(F)(F)F)O[C@H](C)C3)ccc(C#N)c2n1]

The title compound was prepared in analogy to the preparation of Intermediate B by using 2-deuterio-5-fluoro-quinoline-8-carbonitrile (compound L5) instead of 7-chloro-1,3-benzothiazole-4-carbonitrile (compound B5). Intermediate L (10.55 g) was obtained as a yellow solid. MS: calc'd 417 (MH$^+$), measured 417 (MH$^+$).

The compound L5 was prepared according to the following scheme:

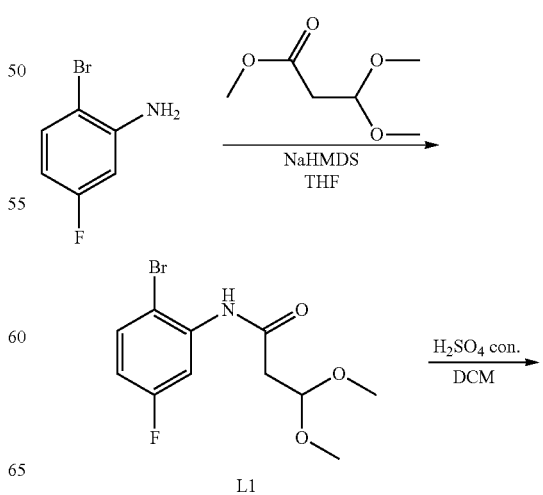

L1

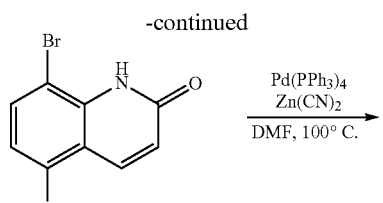

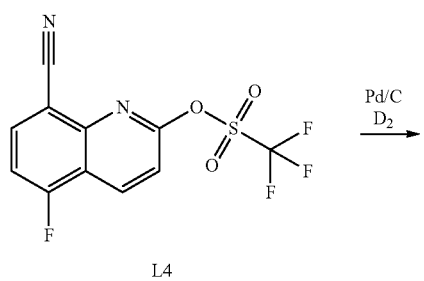

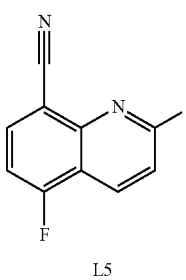

Step 1: Preparation of N-(2-bromo-5-fluoro-phenyl)-3,3-dimethoxy-propanamide (Compound L1)

To the solution of 2-bromo-5-fluoroaniline (CAS: 1003-99-2, Vendor: TCI, 50 g, 263.14 mmol) and methyl 3,3-dimethoxypropionate (CAS: 7424-91-1, Vendor: Accela, 45 mL, 315.77 mmol) in THF (150 mL) was added NaHMDS in THF (1 M, 394 mL, 394.72 mmol) dropwise at 0° C. After being stirred at 0° C. for 10 mins, the mixture was warmed up to 15° C. and stirred for 18 hrs. The reaction was quenched by addition of 100 mL sat. $NH_4Cl$ and concentrated to about 300 mL. The solution was diluted with 500 mL water and extracted with 200 mL EA for three times. The combined organic layer was washed with 200 mL water twice and 100 ml brine, dried over $Na_2SO_4$ and concentrated to give the crude product L1 (100 g) as a brown oil. MS calc'd 321 ($MH^+$), measured 321 ($MH^+$).

Step 2: Preparation of 8-bromo-5-fluoro-1H-quinolin-2-one (Compound L2)

A solution of N-(2-bromo-5-fluoro-phenyl)-3,3-dimethoxy-propanamide (compound L1, 100 g, 238.46 mmol) in DCM (500 mL) was added to concentrated sulfuric acid (300 mL) at 0° C. After being stirred at 15° C. for 2 hrs, the mixture was poured slowly into 2000 mL ice-water, a yellow precipitate was appeared. The mixture was filtered, and the wet-cake was washed with 500 mL water, 200 mL isopropyl alcohol and 300 mL PE. The solid was dried by sucking in vacuum to give compound L2 (50 g) as a yellow solid. MS calc'd 242 ($MH^+$), measured 242 ($MH^+$).

Step 3: Preparation of 5-fluoro-2-oxo-1H-quinoline-8-carbonitrile (Compound L3)

A solution of 8-bromo-5-fluoro-1H-quinolin-2-one (compound L2, 50 g, 206.58 mmol), zinc cyanide (48.50 g, 413.15 mmol), $Pd(PPh_3)_4$ (24.29 g, 21.02 mmol) in DMF (1000 mL) was stirred at 120° C. for 5 hrs. After being cooled down, the reaction mixture was quenched with 300 mL saturated $NH_4Cl$, diluted with 2000 mL water and extracted with 500 mL DCM for three times. The combined organic layer was washed with 500 mL water twice and 200 mL brine once, dried over $Na_2SO_4$ and concentrated to give the crude product which was purified by flash column (PE/EA=3/1) to give compound L3 (29 g) as a yellow solid. MS calc'd 189 ($MH^+$), measured 189 ($MH^+$).

Step 4: Preparation of (8-cyano-5-fluoro-2-quinolyl) trifluoromethanesulfonate (Compound L4)

To the solution of 5-fluoro-2-oxo-1H-quinoline-8-carbonitrile (compound L3, 17000 mg, 90.35 mmol), 2,6-dimethylpyridine (38705 mg, 361.39 mmol) in DCM (500 mL) was added trifluoromethanesulfonic anhydride (50975 mg, 180.70 mmol) at 0° C. After being stirred at 0° C. for 1 h, the mixture was diluted with 500 mL water and extracted with 200 mL DCM for three times. The combined organic layer was washed with 200 mL water twice and 100 mL brine once, dried over $Na_2SO_4$ and concentrated to give the crude product which was purified by flash column (PE/EA=5/1) to give compound L4 (23000 mg) as a yellow solid. MS calc'd 321 ($MH^+$), measured 321 ($MH^+$).

Step 5: Preparation of 2-deuterio-5-fluoro-quinoline-8-carbonitrile (Compound L5)

To the solution of (8-cyano-5-fluoro-2-quinolyl) trifluoromethanesulfonate (compound L4, 23000 mg, 71.83 mmol) in THF (230 mL) and deuterium oxide (100 mL) was added potassium carbonate (19853 mg, 143.65 mmol) and Pd/C (10 wt. %, 6000 mg). The mixture was stirred at 40° C. for 5 hrs under deuterium atmosphere. Then the mixture was filtered and the filtrate was concentrated and purified by flash column (PE/EA=5/1) to give compound L5 (11400 mg) as a light yellow solid. MS calc'd 174 ($MH^+$), measured 174 ($MH^+$).

Intermediate M

[(2R,6R)-6-methyl-4-(1-methyl-2-oxo-1,8-naphthyridin-4-yl)morpholin-2-yl]methyl trifluoromethanesulfonate

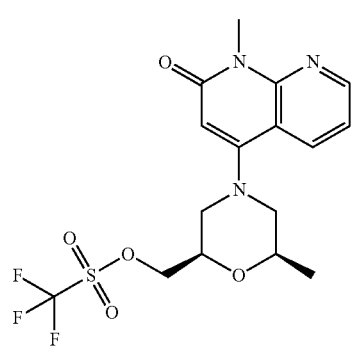 [SMILES: C[C@@H]1CN(c2cc(=O)n(C)c3ncccc23)C[C@H](COS(=O)(=O)C(F)(F)F)O1]

The title compound was prepared in analogy to the preparation of Intermediate A by using 4-bromo-1-methyl-1,8-naphthyridin-2-one (compound M1) instead of 5-bromoquinoline-8-carbonitrile (compound A2). Intermediate M (140 mg) was obtained as a yellow solid. MS: calc'd 422 (MH$^+$), measured 422 (MH$^+$).

The compound M1 was prepared according to the following scheme:

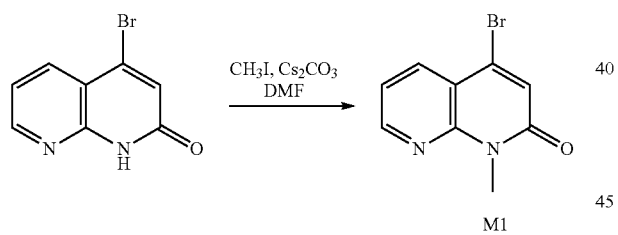

M1

Preparation of 4-bromo-1-methyl-1,8-naphthyridin-2-one (Compound M1)

To the solution of 4-bromo-1,8-naphthyridin-2 (1H)-one (CAS: 72235-36-0, Vendor: Accela, 370 mg, 1.64 mmol) in DMF (15 mL) was added iodomethane (2.33 g, 16.40 mmol) and Cs$_2$CO$_3$ (1.07 g, 3.29 mmol). The reaction mixture was stirred at 80° C. overnight. After being cooled down, the reaction was quenched by addition of ice-water (30 mL). The solid was collected by filtration to give crude compound M1 (419 mg) which was used directly for next step. MS calc'd 239 (MH$^+$), measured 239 (MH$^+$). $^1$H NMR (400 MHz, METHANOL-d$_4$) δ=8.72 (dd, J=1.7, 4.7 Hz, 1H), 8.39 (dd, J=1.7, 7.9 Hz, 1H), 7.43 (dd, J=4.7, 8.0 Hz, 1H), 7.20 (s, 1H), 3.83 (s, 3H).

Intermediate N

[(2R,6R)-4-(1-ethyl-2-oxo-1,8-naphthyridin-4-yl)-6-methyl-morpholin-2-yl]methyl trifluoromethanesulfonate

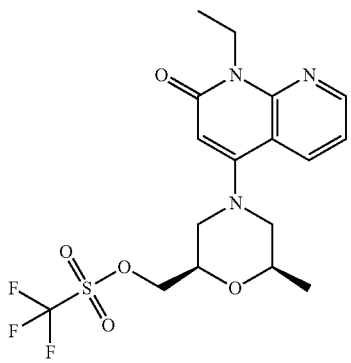 [SMILES: CCn1c(=O)cc(N2C[C@H](COS(=O)(=O)C(F)(F)F)O[C@H](C)C2)c2cccnc21]

The title compound was prepared in analogy to the preparation of Intermediate M by using iodoethane instead of iodomethane. Intermediate N (56 mg) was obtained as a yellow solid. MS: calc'd 436 (MH$^+$), measured 436 (MH$^+$).

Intermediate O

[(2R,6R)-4-(1-isopropyl-2-oxo-1,8-naphthyridin-4-yl)-6-methyl-morpholin-2-yl]methyl trifluoromethanesulfonate

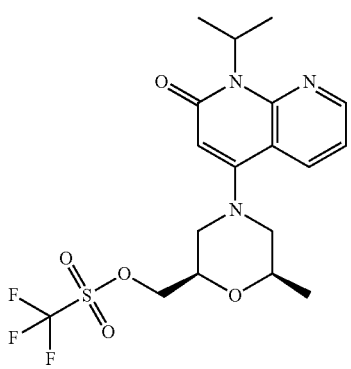 [SMILES: CC(C)n1c(=O)cc(N2C[C@H](COS(=O)(=O)C(F)(F)F)O[C@H](C)C2)c2cccnc21]

The title compound was prepared in analogy to the preparation of Intermediate M by using 2-iodopropane instead of iodomethane. Intermediate O (78 mg) was obtained as a yellow solid. MS: calc'd 450 (MH$^+$), measured 450 (MH$^+$).

Reference Compound R1

5-[(2S,6R)-2-[[4-(4-methoxyphenyl)piperazin-1-yl]methyl]-6-methyl-morpholin-4-yl]quinoline-8-carbonitrile

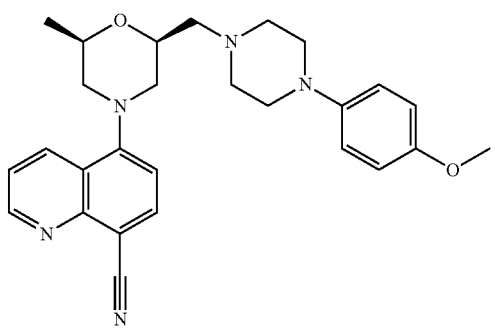

The title compound was prepared according to the following scheme:

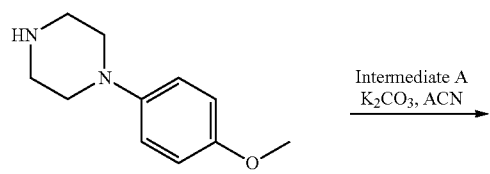

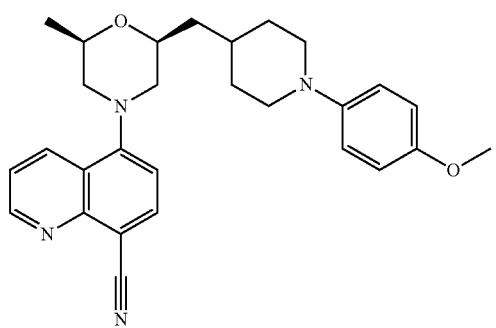 [SMILES: COc1ccc(N2CCN(C[C@H]3CN(c4ccc(C#N)c5ncccc45)C[C@@H](C)O3)CC2)cc1]

R1

To a flask was added [(2R,6R)-4-(8-cyano-5-quinolyl)-6-methyl-morpholin-2-yl]methyl trifluoromethanesulfonate (Intermediate A, 30 mg, 72 µmol), 1-(4-methoxyphenyl)piperazine (CAS: 38212-30-5, Vendor: Accela, 21 mg, 108 µmol), potassium carbonate (30 mg, 217 µmol) and acetonitrile (4 mL). After being stirred at 85° C. for 2 hrs, the mixture was filtered through celite and purified by prep-HPLC to give compound R1 (22 mg) as a yellow solid. MS: calc'd 458 (MH+), measured 458 (MH+). $^1$H NMR (400 MHz, METHANOL-d$_4$) δ=9.00 (dd, J=1.7, 4.2 Hz, 1H), 8.67 (dd, J=1.7, 8.6 Hz, 1H), 8.18 (d, J=8.1 Hz, 1H), 7.66 (dd, J=4.3, 8.6 Hz, 1H), 7.30 (d, J=7.9 Hz, 1H), 7.05-6.98 (m, 2H), 6.93-6.85 (m, 2H), 4.55-4.46 (m, 1H), 4.26-4.16 (m, 1H), 3.89-3.56 (m, 7H), 3.50-3.37 (m, 6H), 3.25-3.00 (m, 2H), 2.84-2.71 (m, 2H), 1.33 (d, J=6.2 Hz, 3H).

Reference Compound R2

5-[(2S,6R)-2-[[4-(4-chlorophenyl)piperazin-1-yl]methyl]-6-methyl-morpholin-4-yl]quinoline-8-carbonitrile

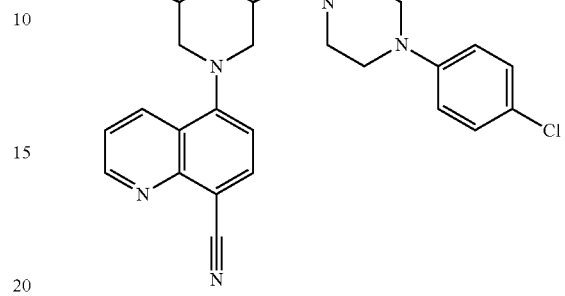

The title compound was prepared in analogy to the preparation of compound R1 by using 1-(4-cholophenyl)piperazine (CAS: 38212-33-8, Vendor: BePharm) instead of 1-(4-methoxyphenyl)piperazine. Compound R2 (24 mg) was obtained as a yellow solid. MS: calc'd 462 (MH+), measured 462 (MH+). $^1$H NMR (400 MHz, METHANOL-d$_4$) δ=9.00 (dd, J=1.6, 4.3 Hz, 1H), 8.67 (dd, J=1.7, 8.6 Hz, 1H), 8.17 (d, J=8.1 Hz, 1H), 7.66 (dd, J=4.3, 8.6 Hz, 1H), 7.34-7.26 (m, 3H), 7.07-6.98 (m, 2H), 4.55-4.47 (m, 1H), 4.25-4.15 (m, 1H), 3.99-3.55 (m, 3H), 3.55-3.32 (m, 7H), 3.28-3.04 (m, 2H), 2.85-2.71 (m, 2H), 1.33 (d, J=6.2 Hz, 3H).

Example 1

5-[(2R,6S)-2-methyl-6-[[4-(4,5,6,7-tetrahydropyrazolo[1,5-a]pyrazin-2-yl)piperazin-1-yl]methyl]morpholin-4-yl]quinoline-8-carbonitrile

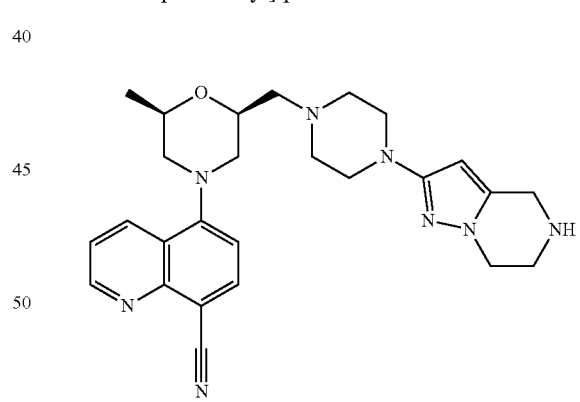

The title compound was prepared according to the following scheme:

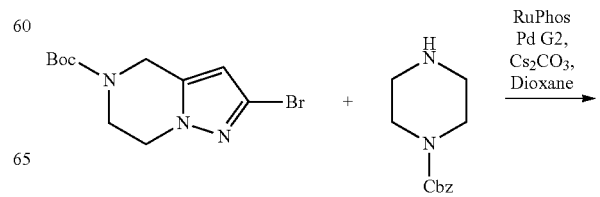

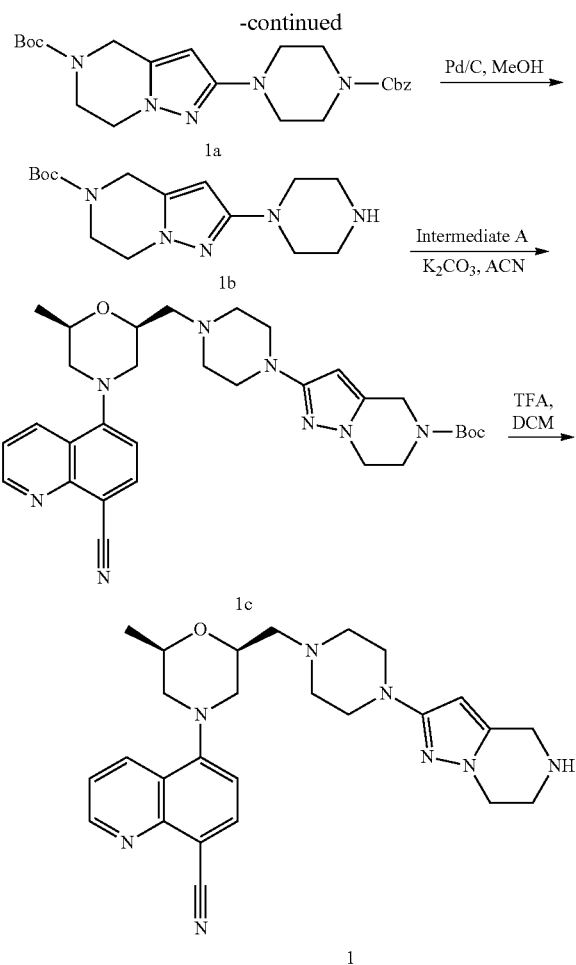

Step 1: Preparation of tert-butyl 2-(4-benzyloxycarbonylpiperazin-1-yl)-6,7-dihydro-4H-pyrazolo[1,5-a]pyrazine-5-carboxylate (Compound 1a)

To a flask was added tert-butyl 2-bromo-6,7-dihydro-4H-pyrazolo[1,5-a]pyrazine-5-carboxylate (CAS: 1250998-21-0, Vendor: WuXi Apptec, 300 mg, 993 μmol), benzyl piperazine-1-carboxylate (437 mg, 1.99 mmol), $Cs_2CO_3$ (970 mg, 2.98 mmol) and 1,4-dioxane (6 mL), the suspension was bubbled with $N_2$ for 5 mins and Ruphos Pd G2 (39 mg, 50 μmol) was added. The mixture was heated at 120° C. under microwave for 3 hrs. The mixture was then diluted with EA (10 mL), and filtered through celite. The filtrate was concentrated to give a brown oil which was purified by flash column (EA/PE=0 to 50%) to give compound 1a (55 mg) as a yellow solid. MS: calc'd 442 ($MH^+$), measured 442 ($MH^+$).

Step 2: Preparation of tert-butyl 2-piperazin-1-yl-6,7-dihydro-4H-pyrazolo[1,5-a]pyrazine-5-carboxylate (Compound 1b)

To a flask containing tert-butyl 2-(4-benzyloxycarbonylpiperazin-1-yl)-6,7-dihydro-4H-pyrazolo[1,5-a]pyrazine-5-carboxylate (compound 1a, 55 mg, 125 μmol) was added Pd/C (10 wt. %, 13 mg, 125 μmol) and MeOH (10 mL). The reaction mixture was stirred at rt under hydrogen balloon for 18 hrs, then filtered and concentrated to give the crude compound 1b (38 mg) which was used in the next step without purification. MS: calc'd 308 ($MH^+$), measured 308 ($MH^+$).

Step 3: Preparation of tert-butyl 2-[4-[[(2S,6R)-4-(8-cyano-5-quinolyl)-6-methyl-morpholin-2-yl]methyl]piperazin-1-yl]-6,7-dihydro-4H-pyrazolo[1,5-a]pyrazine-5-carboxylate (Compound 1c)

To a tube was added [(2R,6R)-4-(8-cyano-5-quinolyl)-6-methyl-morpholin-2-yl]methyl trifluoromethanesulfonate (Intermediate A, 40 mg, 96 μmol), tert-butyl 2-piperazin-1-yl-6,7-dihydro-4H-pyrazolo[1,5-a]pyrazine-5-carboxylate (compound 1b, 38 mg, 125 μmol), $K_2CO_3$ (67 mg, 481 μmol) and acetonitrile (5 mL). The mixture was heated to reflux for 2 hrs. After being cooled down, the mixture was diluted with acetonitrile and filtered through celite. The filtrate was concentrated to give compound 1c (55 mg) which was used in next step without purification. MS: calc'd 573 ($MH^+$), measured 573 ($MH^+$).

Step 4: Preparation of 5-[(2R,6S)-2-methyl-6-[[4-(4,5,6,7-tetrahydropyrazolo[1,5-a]pyrazin-2-yl)piperazin-1-yl]methyl]morpholin-4-yl]quinoline-8-carbonitrile (Example 1)

To a solution of tert-butyl 2-[4-[[(2S,6R)-4-(8-cyano-5-quinolyl)-6-methyl-morpholin-2-yl]methyl]piperazin-1-yl]-6,7-dihydro-4H-pyrazolo[1,5-a]pyrazine-5-carboxylate (compound 1c, 55 mg, 96 μmol) in DCM (2 mL) was added TFA (0.30 mL). After being stirred at rt for 3 hrs, the mixture was concentrated to give a yellow oil which was purified by prep-HPLC to give Example 1 (44 mg) as a yellow solid. MS: calc'd 473 ($MH^+$), measured 473 ($MH^+$). $^1H$ NMR (400 MHz, METHANOL-$d_4$) δ=9.01 (dd, J=1.5, 4.2 Hz, 1H), 8.68 (dd, J=1.6, 8.6 Hz, 1H), 8.18 (d, J=7.9 Hz, 1H), 7.67 (dd, J=4.3, 8.6 Hz, 1H), 7.30 (d, J=8.1 Hz, 1H), 5.92 (s, 1H), 4.57-4.49 (m, 1H), 4.48 (s, 2H), 4.28 (t, J=5.8 Hz, 2H), 4.25-4.16 (m, 1H), 4.03-3.55 (m, 6H), 3.52-3.36 (m, 6H), 3.30-3.08 (m, 2H), 2.86-2.69 (m, 2H), 1.33 (d, J=6.2 Hz, 3H).

Example 2

5-[(2S,6R)-2-[(4-isoindolin-4-ylpiperazin-1-yl)methyl]-6-methyl-morpholin-4-yl]quinoline-8-carbonitrile

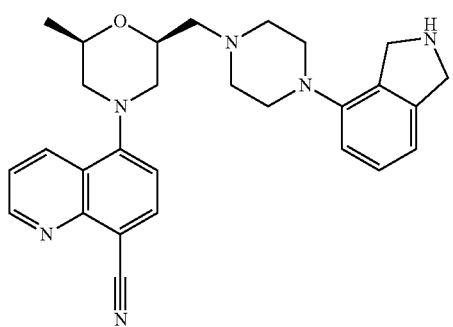 [SMILES: C[C@@H]1CN(c2ccc(C#N)c3ncccc23)C[C@H](CN2CCN(c3cccc4c3CNC4)CC2)O1]

The title compound was prepared in analogy to the preparation of Example 1 by using tert-butyl 4-bromoisoindoline-2-carboxylate (CAS: 1035235-27-8, Vendor:

BePharm) instead of tert-butyl 2-bromo-6,7-dihydro-4H-pyrazolo[1,5-a]pyrazine-5-carboxylate. Example 2 (38 mg) was obtained as a yellow solid. MS: calc'd 469 (MH⁺), measured 469 (MH⁺). ¹H NMR (400 MHz, METHANOL-d₄) δ=9.02 (dd, J=1.6, 4.3 Hz, 1H), 8.69 (dd, J=1.6, 8.6 Hz, 1H), 8.19 (d, J=8.1 Hz, 1H), 7.68 (dd, J=4.2, 8.6 Hz, 1H), 7.49-7.42 (m, 1H), 7.31 (d, J=8.1 Hz, 1H), 7.21 (d, J=7.5 Hz, 1H), 7.16 (d, J=8.1 Hz, 1H), 4.66 (d, J=5.4 Hz, 4H), 4.59-4.50 (m, 1H), 4.27-4.16 (m, 1H), 3.83 (br s, 2H), 3.56-3.38 (m, 8H), 3.32-3.16 (m, 2H), 2.87-2.71 (m, 2H), 1.35 (d, J=6.2 Hz, 3H).

Example 3

5-[(2S,6R)-2-[[(3S)-3-(hydroxymethyl)-4-isoindolin-5-yl-piperazin-1-yl]methyl]-6-methyl-morpholin-4-yl]quinoline-8-carbonitrile

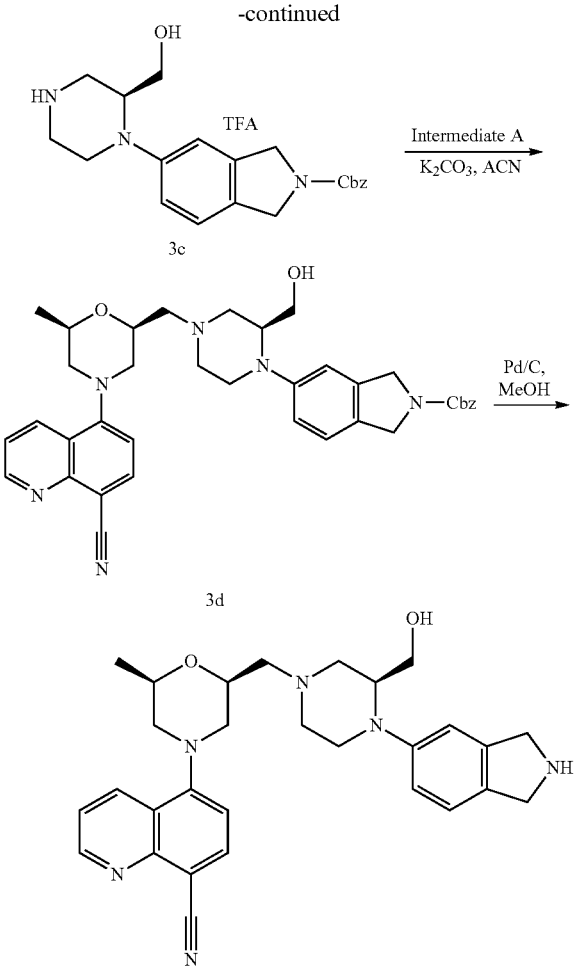

The title compound was prepared according to the following scheme:

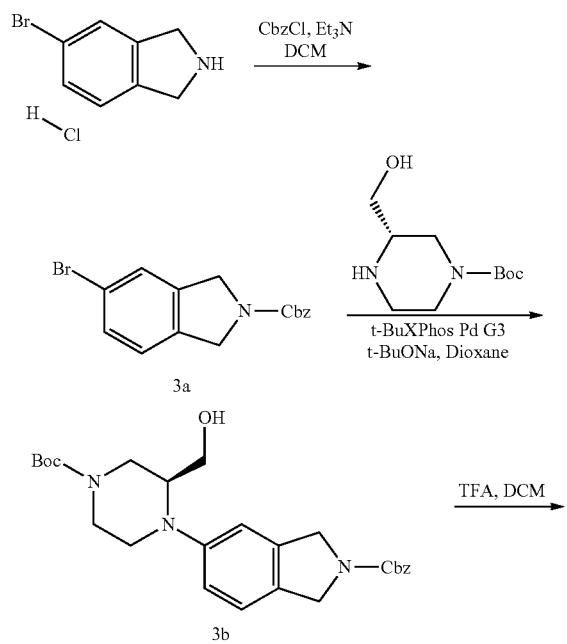

Step 1: Preparation of benzyl 5-bromoisoindoline-2-carboxylate (Compound 3a)

To a flask was added 5-bromoisoindoline hydrochloride (CAS: 919346-89-7, Vendor: PharmaBlock, 1.00 g, 4.26 mmol), TEA (1.29 g, 1.78 mL, 12.80 mmol) and DCM (20 mL). Then it was cooled with ice bath and Cbz-Cl (873 mg, 730 μL, 5.12 mmol) was added dropwise. After being stirred at rt for 1 h, the mixture was diluted with water (20 mL) and extracted with EA (20 mL) twice. The combined organic layer was dried over Na₂SO₄ and concentrated to give a brown oil which was purified by flash column (EA/PE=0 to 20%) to give compound 3a (1.10 g) as a white solid. MS: calc'd 332, 334 (MH⁺), measured 332, 334 (MH⁺).

Step 2: Preparation of benzyl 5-[(2S)-4-tert-butoxycarbonyl-2-(hydroxymethyl)piperazin-1-yl]isoindoline-2-carboxylate (Compound 3b)

To a flask was added benzyl 5-bromoisoindoline-2-carboxylate (compound 3a, 200 mg, 602 μmol), tert-butyl (3S)-3-(hydroxymethyl)piperazine-1-carboxylate (CAS: 314741-40-7, Vendor: PharmaBlock, 195 mg, 903 μmol), sodium tert-butoxide (116 mg, 1.20 mmol) and 1,4-dioxane (4 mL), the suspension was bubbled with N₂ for 5 mins and t-BuXPhos Pd G3 (48 mg, 60 μmol) was added. The mixture was heated at 90° C. under microwave for 2 hrs. After being cooled down, the mixture was diluted with EA (10 mL) and filtered through celite. The filtrate was concentrated to give a brown oil which was purified by flash column (MeOH/DCM=0 to 10%) to give compound 3b (183 mg) as a light yellow oil. MS: calc'd 468 (MH+), measured 468 (MH+).

Step 3: Preparation of benzyl 5-[(2S)-2-(hydroxymethyl)piperazin-1-yl]isoindoline-2-carboxylate; 2,2,2-trifluoroacetic acid (Compound 3c)

To a solution of benzyl 5-[(2S)-4-tert-butoxycarbonyl-2-(hydroxymethyl)piperazin-1-yl]isoindoline-2-carboxylate (compound 3b, 183 mg, 391 μmol) in DCM (5 mL) was added TFA (1 mL). After being stirred at rt for 3 hrs, the reaction mixture was concentrated in vacuo to give the crude compound 3c (188 mg) which was used in next step directly. MS: calc'd 368 (MH+), measured 368 (MH+).

Step 4: Preparation of benzyl 5-[(2S)-4-[[(2S,6R)-4-(8-cyano-5-quinolyl)-6-methyl-morpholin-2-yl]methyl]-2-(hydroxymethyl)piperazin-1-yl]isoindoline-2-carboxylate (Compound 3d)

To a tube was added [(2R,6R)-4-(8-cyano-5-quinolyl)-6-methyl-morpholin-2-yl]methyl trifluoromethanesulfonate (Intermediate A, 40 mg, 96 μmol), benzyl 5-[(2S)-2-(hydroxymethyl)piperazin-1-yl]isoindoline-2-carboxylate; 2,2,2-trifluoroacetic acid (compound 3c, 188 mg, 390 μmol), potassium carbonate (67 mg, 481 μmol) and acetonitrile (5 mL). The mixture was heated at 55° C. for 2 hrs. After being cooled down, the mixture was diluted with acetonitrile and filtered through celite. The filtrate was concentrated and purified by flash column (EA/PE=0 to 90%) to give the desired product compound 3d (22 mg) as a yellow solid. MS: calc'd 633 (MH+), measured 633 (MH+).

Step 5: Preparation of 5-[(2S,6R)-2-[[(3S)-3-(hydroxymethyl)-4-isoindolin-5-yl-piperazin-1-yl]methyl]-6-methyl-morpholin-4-yl]quinoline-8-carbonitrile (Example 3)

To a flask containing benzyl 5-[(2S)-4-[[(2S,6R)-4-(8-cyano-5-quinolyl)-6-methyl-morpholin-2-yl]methyl]-2-(hydroxymethyl)piperazin-1-yl]isoindoline-2-carboxylate (compound 3d, 22 mg, 35 μmol) was added Pd/C (10 wt. %, 20 mg, 188 μmol) and MeOH (2 mL). The reaction mixture was stirred at rt under hydrogen balloon for 2 hrs, then filtered and concentrated. The residue was purified by prep-HPLC to give Example 3 (2 mg) as a light yellow solid. MS: calc'd 499 (MH+), measured 499 (MH+). 1H NMR (400 MHz, METHANOL-d4) δ=9.03 (dd, J=1.6, 4.3 Hz, 1H), 8.71 (dd, J=1.7, 8.7 Hz, 1H), 8.20 (d, J=7.9 Hz, 1H), 7.69 (dd, J=4.3, 8.6 Hz, 1H), 7.36 (br s, 1H), 7.33 (d, J=7.9 Hz, 1H), 7.10 (br s, 2H), 4.59 (br d, J=13.3 Hz, 5H), 4.41-4.29 (m, 1H), 4.27-4.19 (m, 1H), 4.19-4.10 (m, 1H), 4.03-3.94 (m, 1H), 3.93-3.80 (m, 2H), 3.79-3.69 (m, 2H), 3.52-3.40 (m, 5H), 3.17-3.13 (m, 1H), 2.90-2.75 (m, 2H), 1.34 (d, J=6.2 Hz, 3H).

Example 4

5-[(2S,6R)-2-[[(3R)-3-(hydroxymethyl)-4-isoindolin-5-yl-piperazin-1-yl]methyl]-6-methyl-morpholin-4-yl]quinoline-8-carbonitrile

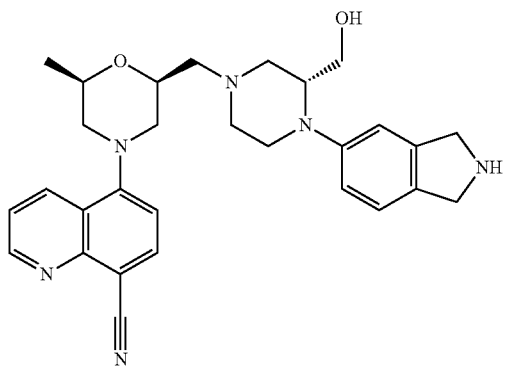 [SMILES: C[C@@H]1CN(c2ccc(C#N)c3ncccc23)C[C@H](CN2CCN(c3ccc4c(c3)CNC4)[C@@H](CO)C2)O1]

The title compound was prepared in analogy to the preparation of Example 3 by using tert-butyl (3R)-3-(hydroxymethyl)piperazine-1-carboxylate (CAS: 278788-66-2, Vendor: Accela ChemBio Inc) instead of tert-butyl (3S)-3-(hydroxymethyl)piperazine-1-carboxylate. Example 4 (8 mg) was obtained as a light yellow solid. MS: calc'd 499 (MH+), measured 499 (MH+). 1H NMR (400 MHz, METHANOL-d4) δ=9.02 (dd, J=1.6, 4.2 Hz, 1H), 8.70 (dd, J=1.7, 8.6 Hz, 1H), 8.20 (d, J=8.1 Hz, 1H), 7.68 (dd, J=4.3, 8.6 Hz, 1H), 7.38 (br d, J=8.6 Hz, 1H), 7.32 (d, J=8.1 Hz, 1H), 7.11 (br s, 2H), 4.67-4.50 (m, 5H), 4.41-4.29 (m, 1H), 4.28-4.19 (m, 1H), 4.18-4.04 (m, 1H), 4.02-3.82 (m, 3H), 3.79-3.61 (m, 2H), 3.56-3.38 (m, 6H), 2.88-2.70 (m, 2H), 1.32 (d, J=6.4 Hz, 3H).

Example 5

5-[(2R,6S)-2-methyl-6-[[4-(1,2,3,4-tetrahydroisoquinolin-6-yl)piperazin-1-yl]methyl]morpholin-4-yl]quinoline-8-carbonitrile

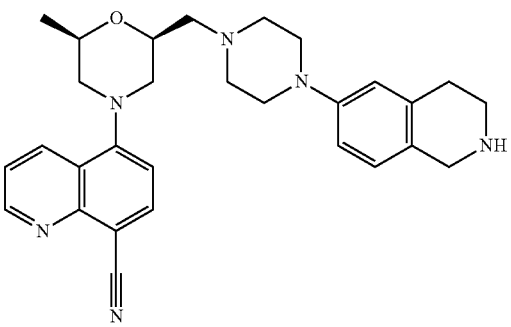

The title compound was prepared in analogy to the preparation of Example 1 by using tert-butyl 6-bromo-3,4-dihydro-1H-isoquinoline-2-carboxylate (CAS: 893566-74-0, Vendor: Titan) instead of tert-butyl 2-bromo-6,7-dihydro-4H-pyrazolo[1,5-a]pyrazine-5-carboxylate, and replacing MeOH with isopropanol in the hydrogenation reaction. Example 5 (17 mg) was obtained as a yellow solid. MS:

calc'd 483 (MH+), measured 483 (MH+). ¹H NMR (400 MHz, METHANOL-d₄) δ=9.00 (dd, J=1.6, 4.2 Hz, 1H), 8.67 (dd, J=1.6, 8.5 Hz, 1H), 8.17 (d, J=7.9 Hz, 1H), 7.66 (dd, J=4.3, 8.7 Hz, 1H), 7.29 (d, J=8.0 Hz, 1H), 7.17 (d, J=8.5 Hz, 1H), 7.01 (dd, J=2.4, 8.5 Hz, 1H), 6.93 (d, J=2.1 Hz, 1H), 4.60-4.51 (m, 1H), 4.31 (s, 2H), 4.25-4.16 (m, 1H), 4.05-3.34 (m, 13H), 3.31-3.19 (m, 1H), 3.12 (t, J=6.3 Hz, 2H), 2.85-2.70 (m, 2H), 1.34 (d, J=6.3 Hz, 3H).

Example 6

5-[(2S,6R)-2-[[4-(6,7-dihydro-5H-pyrrolo[3,4-d]pyrimidin-4-yl)piperazin-1-yl]methyl]-6-methyl-morpholin-4-yl]quinoline-8-carbonitrile

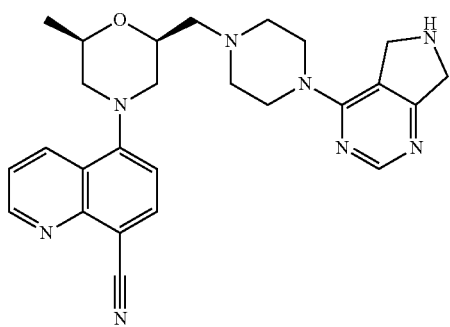 [SMILES: C[C@@H]1CN(c2ccc(C#N)c3ncccc23)C[C@H](CN2CCN(c3ncnc4c3CNC4)CC2)O1]

The title compound was prepared according to the following scheme:

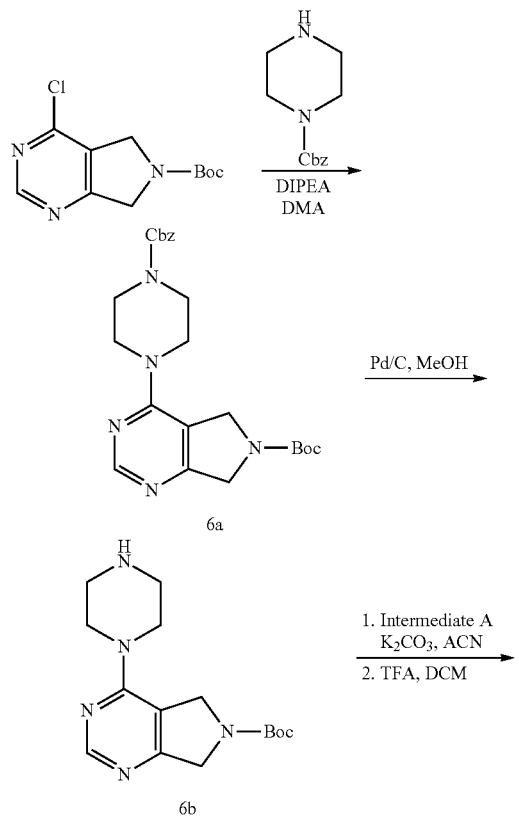

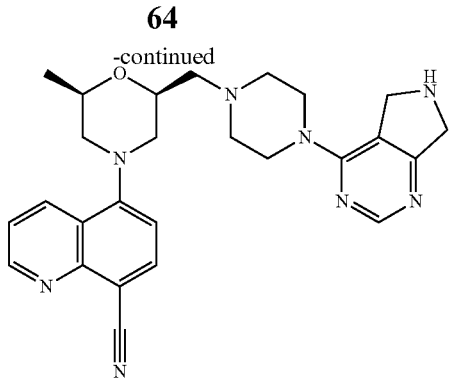

Step 1: Preparation of tert-butyl 4-(4-benzyloxycarbonylpiperazin-1-yl)-5,7-dihydropyrrolo[3,4-d]pyrimidine-6-carboxylate (Compound 6a)

To a flask was added tert-butyl 4-chloro-5,7-dihydropyrrolo[3,4-d]pyrimidine-6-carboxylate (CAS: 1053657-15-0, Vendor: PharmaBlock, 150 mg, 587 μmol), benzyl piperazine-1-carboxylate (129 mg, 587 μmol), DIPEA (227 mg, 307 μL, 1.76 mmol) and DMA (2 mL). The reaction mixture was bubbled with N₂ for 5 mins and then heated at 120° C. under microwave for 2 hrs. After being cooled down, the mixture was concentrated to give a brown oil which was purified by flash column (EA/PE=0 to 70%) to give compound 6a (221 mg) as a light yellow oil. MS: calc'd 440 (MH+), measured 440 (MH+).

Step 2: Preparation of tert-butyl 4-piperazin-1-yl-5,7-dihydropyrrolo[3,4-d]pyrimidine-6-carboxylate (Compound 6b)

To a flask containing tert-butyl 4-(4-benzyloxycarbonylpiperazin-1-yl)-5,7-dihydropyrrolo[3,4-d]pyrimidine-6-carboxylate (compound 6a, 221 mg, 503 μmol) was added Pd/C (10 wt. %, 11 mg, 101 μmol) and MeOH (5 mL). The reaction mixture was stirred at rt under hydrogen balloon for 18 hrs, then filtered and concentrated to give the crude compound 6b (154 mg) which was used in the next step without further purification. MS: calc'd 306 (MH+), measured 306 (MH+).

Step 3: Preparation of 5-[(2S,6R)-2-[[4-(6,7-dihydro-5H-pyrrolo[3,4-d]pyrimidin-4-yl)piperazin-1-yl]methyl]-6-methyl-morpholin-4-yl]quinoline-8-carbonitrile (Example 6)

To a tube was added [(2R,6R)-4-(8-cyano-5-quinolyl)-6-methyl-morpholin-2-yl]methyl trifluoromethanesulfonate (Intermediate A, 50 mg, 120 μmol), tert-butyl 4-piperazin-1-yl-5,7-dihydropyrrolo[3,4-d]pyrimidine-6-carboxylate (compound 6b, 44 mg, 144 μmol), potassium carbonate (50 mg, 361 μmol) and acetonitrile (6 mL). The mixture was heated at 55° C. for 2 hrs. After being cooled down, the mixture was diluted with acetonitrile and filtered through celite. The filtrate was concentrated to give a yellow oil which was dissolved in DCM (6 mL) and TFA (625 μL, 120 μmol) was added. After being stirred at rt for 2 hrs, the mixture was concentrated to give an oil which was purified by prep-HPLC to give Example 6 (32 mg) as a light yellow solid. MS: calc'd 471 (MH+), measured 471 (MH+). ¹H NMR (400 MHz, METHANOL-d₄) δ=9.00 (dd, J=1.6, 4.3

Hz, 1H), 8.68 (dd, J=1.7, 8.6 Hz, 1H), 8.37 (s, 1H), 8.17 (d, J=8.1 Hz, 1H), 7.66 (dd, J=4.3, 8.6 Hz, 1H), 7.27 (d, J=7.9 Hz, 1H), 4.35 (s, 2H), 4.27-4.17 (m, 1H), 4.16-4.06 (m, 1H), 4.01 (s, 2H), 3.78 (t, J=5.0 Hz, 4H), 3.53-3.38 (m, 2H), 2.80-2.50 (m, 8H), 1.28 (d, J=6.2 Hz, 3H).

Example 7

5-[(2S,6R)-2-[(4-isoindolin-5-ylpiperazin-1-yl)methyl]-6-methyl-morpholin-4-yl]quinoline-8-carbonitrile

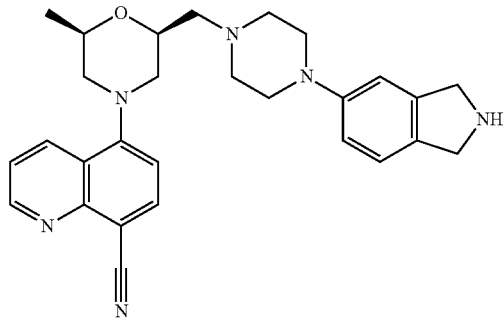

The title compound was prepared in analogy to the preparation of Example 1 by using tert-butyl 5-bromoisoindoline-2-carboxylate (compound 7a) instead of tert-butyl 2-bromo-6,7-dihydro-4H-pyrazolo[1,5-a]pyrazine-5-carboxylate. Example 7 (46 mg) was obtained as a yellow solid. MS: calc'd 469 (MH$^+$), measured 469 (MH$^+$). $^1$H NMR (400 MHz, METHANOL-d$_4$) δ=9.02 (dd, J=2.0 Hz, 4.4 Hz, 1H), 8.69 (dd, J=1.6 Hz, 8.4 Hz, 1H), 8.19 (d, J=8.0 Hz, 1H), 7.67 (dd, J=4.4 Hz, 8.8 Hz, 1H), 7.38 (d, J=9.2 Hz, 1H), 7.31 (d, J=8.4 Hz, 1H), 7.13-7.12 (m, 2H), 4.60-4.57 (m, 5H), 4.24-4.19 (m, 1H), 3.89-3.79 (m, 10H), 3.39-3.30 (m, 2H), 2.84-2.73 (m, 2H), 1.34 (d, J=6.4 Hz, 3H).

The compound 7a was prepared according to the following scheme:

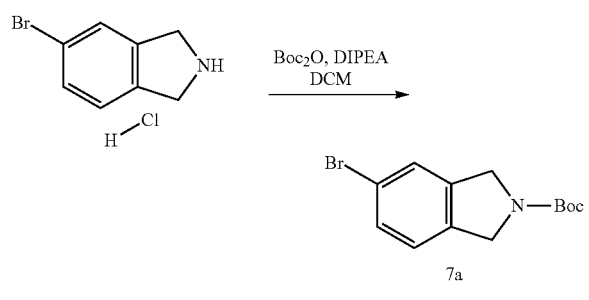

Preparation of tert-butyl 5-bromoisoindoline-2-carboxylate (compound 7a) To a solution of 5-bromoisoindoline hydrochloride (CAS: 919346-89-7, Vendor: PharmaBlock, 1.00 g, 4.26 mmol) and DIPEA (2.42 mL, 13.90 mmol) in DCM (21 mL) was added Boc$_2$O (1.16 g, 5.33 mmol) at 0° C. After being stirred at rt for 18 hrs, the mixture was washed with 1 N HCl (10 mL) five times, and brine (10 mL) twice, dried over Na$_2$SO$_4$, filtered and concentrated to give compound 7a (1.00 g) as a white solid. MS: calc'd 298 (MH$^+$), measured 242 (MH$^+$-56).

Example 8

7-[(2S,6R)-2-[[4-(6,7-dihydro-5H-pyrrolo[3,4-b]pyridin-3-yl)piperazin-1-yl]methyl]-6-methyl-morpholin-4-yl]-1,3-benzothiazole-4-carbonitrile

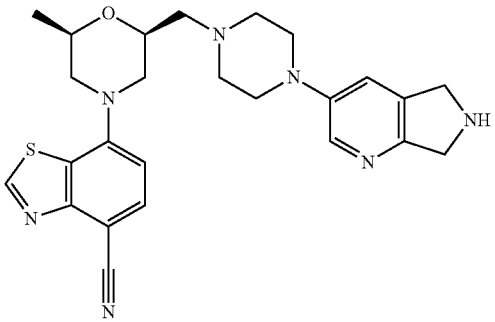 [SMILES: C[C@@H]1CN(c2ccc(C#N)c3ncsc23)C[C@H](CN2CCN(c3cnc4c(c3)CNC4)CC2)O1]

The title compound was prepared in analogy to the preparation of Example 7 by using 3-bromo-6,7-dihydro-5H-pyrrolo[3,4-b]pyridine hydrochloride (CAS: 1394117-24-8, Vendor: PharmaBlock) and Intermediate B instead of 5-bromoisoindoline hydrochloride and Intermediate A. Example 8 (20 mg) was obtained as a white solid. MS: calc'd 476 (MH$^+$), measured 476 (MH$^+$). $^1$H NMR (400 MHz, METHANOL-d$_4$) δ=9.40 (s, 1H), 8.08 (d, J=2.6 Hz, 1H), 7.90 (d, J=8.3 Hz, 1H), 7.40 (s, 1H), 7.14 (d, J=8.3 Hz, 1H), 4.21 (s, 2H), 4.10 (s, 2H), 4.08-4.01 (m, 1H), 3.99-3.90 (m, 1H), 3.87 (br d, J=12.2 Hz, 1H), 3.70 (br d, J=11.9 Hz, 1H), 3.28 (t, J=5.0 Hz, 4H), 2.89-2.80 (m, 2H), 2.78-2.69 (m, 4H), 2.68-2.56 (m, 2H), 1.30 (d, J=6.2 Hz, 3H).

Example 9

5-[(2R,6S)-2-methyl-6-[[4-(1,2,3,4-tetrahydroisoquinolin-7-yl)piperazin-1-yl]methyl]morpholin-4-yl]quinoline-8-carbonitrile

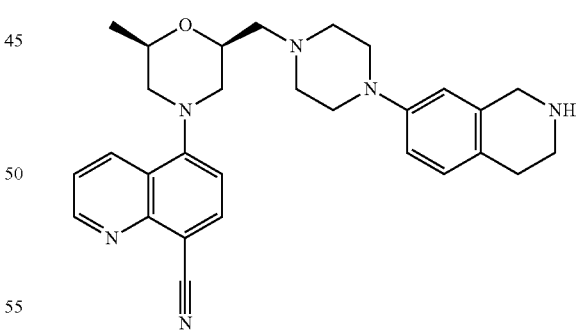

The title compound was prepared in analogy to the preparation of Example 5 by using tert-butyl 7-bromo-3,4-dihydro-1H-isoquinoline-2-carboxylate (CAS: 258515-65-0, Vendor: BePharm) instead of tert-butyl 6-bromo-3,4-dihydro-1H-isoquinoline-2-carboxylate. Example 9 (35 mg) was obtained as a yellow solid. MS: calc'd 483 (MH$^+$), measured 483 (MH$^+$). $^1$H NMR (300 MHz, METHANOL-d$_4$) δ=8.96 (dd, J=1.3, 4.1 Hz, 1H), 8.64 (dd, J=1.4, 8.6 Hz, 1H), 8.13 (d, J=8.1 Hz, 1H), 7.63 (dd, J=4.2, 8.6 Hz, 1H), 7.25 (d, J=8.1 Hz, 1H), 7.19 (d, J=8.5 Hz, 1H), 7.03 (dd, J=2.3, 8.5 Hz, 1H), 6.88 (s, 1H), 4.55 (br t, J=9.3 Hz, 1H), 4.35 (s, 2H), 4.26-4.13 (m, 1H), 3.99-3.36 (m, 13H), 3.27-3.15 (m, 1H), 3.06 (br t, J=6.2 Hz, 2H), 2.84-2.68 (m, 2H), 1.32 (d, J=6.2 Hz, 3H).

Example 10

5-[(2S,6R)-2-[[4-(6,7-dihydro-5H-pyrrolo[3,4-b]pyridin-3-yl)piperazin-1-yl]methyl]-6-methyl-morpholin-4-yl]quinoline-8-carbonitrile

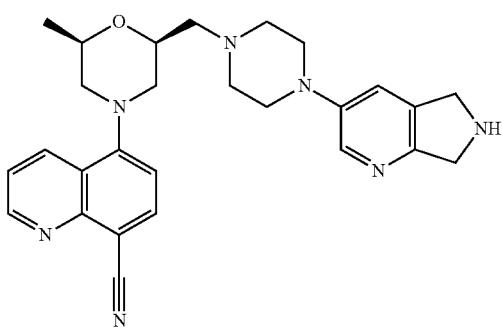 [SMILES: C[C@@H]1CN(c2ccc(C#N)c3ncccc23)C[C@H](CN2CCN(c3cnc4c(c3)CNC4)CC2)O1]

The title compound was prepared in analogy to the preparation of Example 7 by using 3-bromo-6,7-dihydro-5H-pyrrolo[3,4-b]pyridine hydrochloride instead of 5-bromoisoindoline hydrochloride. Example 10 (18 mg) was obtained as a yellow solid. MS: calc'd 470 (MH+), measured 470 (MH+). $^1$H NMR (400 MHz, METHANOL-d$_4$) δ=8.98 (dd, J=1.6, 4.1 Hz, 1H), 8.66 (dd, J=1.5, 8.5 Hz, 1H), 8.35 (d, J=2.0 Hz, 1H), 8.15 (d, J=8.0 Hz, 1H), 7.64 (dd, J=4.1, 8.7 Hz, 1H), 7.57 (d, J=2.0 Hz, 1H), 7.27 (d, J=8.0 Hz, 1H), 4.69 (s, 2H), 4.53 (s, 3H), 4.24-4.14 (m, 1H), 3.60 (br s, 6H), 3.50-3.32 (m, 6H), 2.83-2.68 (m, 2H), 1.32 (d, J=6.3 Hz, 3H).

Example 11

5-[(2S,6R)-2-[[4-(6,7-dihydro-5H-pyrrolo[3,4-d]pyrimidin-2-yl)piperazin-1-yl]methyl]-6-methyl-morpholin-4-yl]quinoline-8-carbonitrile

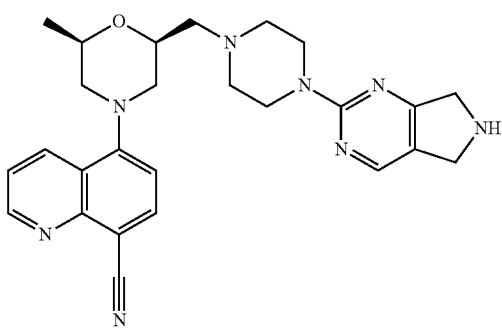

The title compound was prepared in analogy to the preparation of Example 6 by using tert-butyl 2-chloro-5,7-dihydropyrrolo[3,4-d]pyrimidine-6-carboxylate (compound 11a) instead of tert-butyl 4-chloro-5,7-dihydropyrrolo[3,4-d]pyrimidine-6-carboxylate, and replacing MeOH by THF in the hydrogenation reaction. Example 11 (30 mg) was obtained as a yellow solid. MS: calc'd 471 (MH+), measured 471 (MH+). $^1$H NMR (400 MHz, METHANOL-d$_4$) δ=8.96 (d, J=4.3 Hz, 1H), 8.63 (d, J=8.3 Hz, 1H), 8.46 (s, 1H), 8.12 (d, J=8.0 Hz, 1H), 7.62 (dd, J=4.3, 8.5 Hz, 1H), 7.24 (d, J=8.0 Hz, 1H), 4.61 (s, 2H), 4.54 (br t, J=9.3 Hz, 1H), 4.47 (s, 2H), 4.24-4.15 (m, 1H), 4.13-3.47 (m, 4H), 3.47-3.32 (m, 6H), 3.13 (br s, 2H), 2.81-2.67 (m, 2H), 1.31 (d, J=6.3 Hz, 3H).

The compound 11a was prepared according to the following scheme:

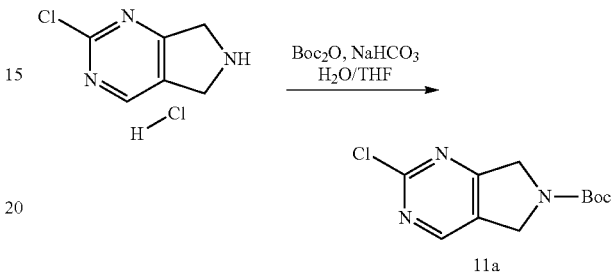

Preparation of tert-butyl 2-chloro-5,7-dihydropyrrolo[3,4-d]pyrimidine-6-carboxylate (Compound 11a)

To a solution of 2-chloro-6,7-dihydro-5H-pyrrolo[3,4-d]pyrimidine hydrochloride (CAS: 1314790-85-6, Vendor: PharmaBlock, 200 mg, 1.04 mmol) in THF (4 mL) and water (2 mL) was added NaHCO$_3$ (442 mg, 4.17 mmol) and Boc$_2$O (273 mg, 1.25 mmol) at 0° C. After being stirred at rt for 4 hrs, the reaction mixture was concentrated to dryness and the residue was taken up in EtOAc (50 mL). The organic layer was washed with water (50 mL) twice and brine (50 mL) once, dried over Na$_2$SO$_4$, filtered and concentrated. The residue was purified by flash column (EA/PE=1/3) to give compound 11a (220 mg) as a white solid. MS: calc'd 256 (MH+), measured 256 (MH+).

Example 12

5-[(2R,6S)-2-methyl-6-[[4-(5,6,7,8-tetrahydropyrido[3,4-d]pyrimidin-2-yl)piperazin-1-yl]methyl]morpholin-4-yl]quinoline-8-carbonitrile

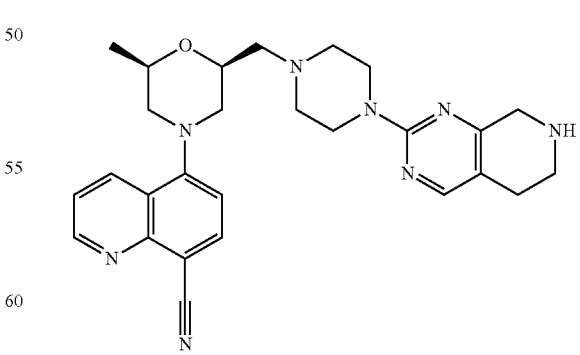

The title compound was prepared in analogy to the preparation of Example 6 by using tert-butyl 2-chloro-6,8-dihydro-5H-pyrido[3,4-d]pyrimidine-7-carboxylate (CAS: 1196156-15-6, Vendor: PharmaBlock) instead of tert-butyl 4-chloro-5,7-dihydropyrrolo[3,4-d]pyrimidine-6-carboxylate, and replacing MeOH by isopropanol/NH$_3$.H$_2$O (v/v=200/1) in the hydrogenation reaction. Example 12 (17 mg) was obtained as a yellow solid. MS: calc'd 485 (MH$^+$), measured 485 (MH$^+$). $^1$H NMR (400 MHz, METHANOL-d$_4$) δ=9.01 (dd, J=4.3, 1.6 Hz, 1H), 8.68 (dd, J=8.7, 1.6 Hz, 1H), 8.38 (s, 1H), 8.19 (d, J=8.0 Hz, 1H), 7.67 (dd, J=8.6, 4.3 Hz, 1H), 7.30 (d, J=8.0 Hz, 1H), 4.89-4.76 (m, 2H), 4.59-4.50 (m, 1H), 4.29-4.15 (m, 3H), 3.89-3.59 (m, 2H), 3.54 (br t, J=6.2 Hz, 3H), 3.48-3.37 (m, 5H), 3.32-3.20 (m, 2H), 3.00 (t, J=6.1 Hz, 2H), 2.85-2.71 (m, 2H), 1.34 (d, J=6.3 Hz, 3H).

Example 13

5-[(2S,6R)-2-[[3-(hydroxymethyl)-4-isoindolin-5-yl-piperazin-1-yl]methyl]-6-methyl-morpholin-4-yl]quinoline-8-carbonitrile

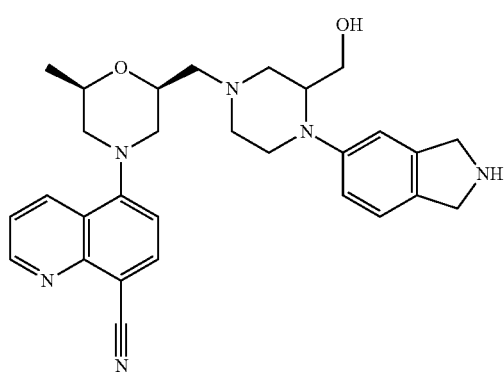 [SMILES: C[C@@H]1CN(c2ccc(C#N)c3ncccc23)C[C@H](CN2CCN(c3ccc4c(c3)CNC4)C(CO)C2)O1]

The title compound was prepared in analogy to the preparation of Example 7 by using benzyl 3-(hydroxymethyl)piperazine-1-carboxylate (CAS: 191739-40-9, Vendor: BePharm) instead of benzyl piperazine-1-carboxylate, and replacing MeOH with isopropanol in the hydrogenation reaction. Example 13 (5 mg) was obtained as a light yellow solid. MS: calc'd 499 (MH$^+$), measured 499 (MH$^+$). $^1$H NMR (400 MHz, METHANOL-d$_4$) δ=8.98 (d, J=4.3 Hz, 1H), 8.68 (br d, J=8.2 Hz, 1H), 8.16 (d, J=8.1 Hz, 1H), 7.66 (dd, J=4.2, 8.5 Hz, 1H), 7.27 (d, J=8.1 Hz, 2H), 7.04-6.90 (m, 2H), 4.53 (d, J=12.1 Hz, 4H), 4.22 (br d, J=8.2 Hz, 1H), 4.17-4.04 (m, 1H), 3.97-3.82 (m, 2H), 3.63 (br d, J=12.0 Hz, 1H), 3.55-3.48 (m, 1H), 3.45-3.35 (m, 3H), 3.21-3.12 (m, 1H), 2.99 (br d, J=10.5 Hz, 1H), 2.78-2.55 (m, 4H), 2.54-2.36 (m, 2H), 1.36-1.23 (m, 3H).

Example 14

5-[(2R,6S)-2-methyl-6-[[4-(5,6,7,8-tetrahydro-1,6-naphthyridin-2-yl)piperazin-1-yl]methyl]morpholin-4-yl]quinoline-8-carbonitrile

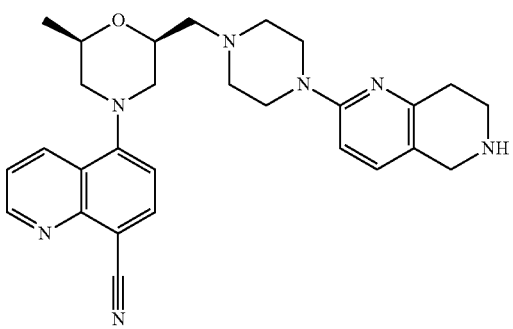

The title compound was prepared in analogy to the preparation of Example 7 by using 2-chloro-5,6,7,8-tetrahydro-1,6-naphthyridine (CAS: 210539-05-2, Vendor: BePharm) instead of 5-bromoisoindoline hydrochloride, replacing RuPhos Pd G2, Cs$_2$CO$_3$ and 1,4-dioxane with Pd$_2$(dba)$_3$, XantPhos, t-BuONa and toluene in the Buchwald-Hartwig amination reaction, replacing DIPEA with TEA in the Boc protection reaction and replacing MeOH with isopropanol in the hydrogenation reaction. Example 14 (21 mg) was obtained as a yellow solid. MS: calc'd 484 (MH$^+$), measured 484 (MH$^+$). $^1$H NMR (400 MHz, METHANOL-d$_4$) δ=9.01 (dd, J=1.6, 4.3 Hz, 1H), 8.68 (dd, J=1.5, 8.6 Hz, 1H), 8.18 (d, J=8.1 Hz, 1H), 7.67 (dd, J=4.3, 8.6 Hz, 1H), 7.51 (d, J=8.8 Hz, 1H), 7.30 (d, J=8.1 Hz, 1H), 6.91 (d, J=8.8 Hz, 1H), 4.54 (br d, J=8.2 Hz, 1H), 4.30 (s, 2H), 4.26-4.17 (m, 1H), 3.98-3.34 (m, 12H), 3.33-3.19 (m, 2H), 3.10 (t, J=6.4 Hz, 2H), 2.84-2.71 (m, 2H), 1.34 (d, J=6.2 Hz, 3H).

Example 15

5-[(2S,6R)-2-[[2-(hydroxymethyl)-4-isoindolin-5-yl-piperazin-1-yl]methyl]-6-methyl-morpholin-4-yl]quinoline-8-carbonitrile

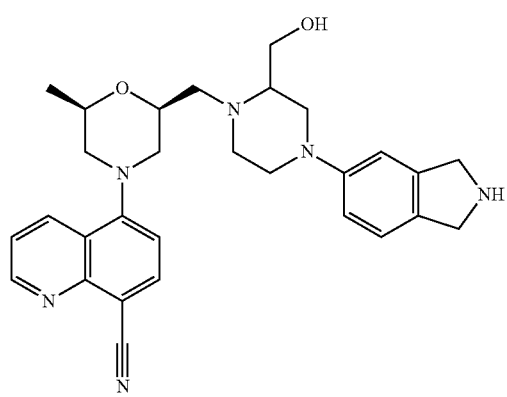 [SMILES: C[C@@H]1CN(c2ccc(C#N)c3ncccc23)C[C@H](CN2CCN(c3ccc4c(c3)CNC4)CC2CO)O1]

The title compound was prepared in analogy to the preparation of Example 1 by using tert-butyl 5-[4-benzyloxycarbonyl-3-(hydroxymethyl)piperazin-1-yl]isoindoline-2-carboxylate (compound 15c) instead of tert-butyl 2-(4-benzyloxycarbonylpiperazin-1-yl)-6,7-dihydro-4H-pyrazolo[1,5-a]pyrazine-5-carboxylate (compound 1a). Example 15 (14 mg) was obtained as a yellow solid. MS: calc'd 499 (MH$^+$), measured 499 (MH$^+$). $^1$H NMR (400 MHz, METHANOL-d$_4$) δ=9.00 (dd, J=4.2, 1.5 Hz, 1H), 8.68 (dd, J=8.6, 1.5 Hz, 1H), 8.18 (d, J=7.9 Hz, 1H), 7.67 (dd, J=8.6, 4.3 Hz, 1H), 7.39-7.34 (m, 1H), 7.30 (d, J=8.1 Hz, 1H), 7.13 (br s, 2H), 4.59 (d, J=14.8 Hz, 5H), 4.27-4.04 (m, 2H), 4.03-3.40 (m, 11H), 3.29 (br s, 1H), 2.85 (t, J=11.0 Hz, 1H), 2.79-2.69 (m, 1H), 1.37-1.29 (m, 3H).

The compound 15c was prepared according to the following scheme:

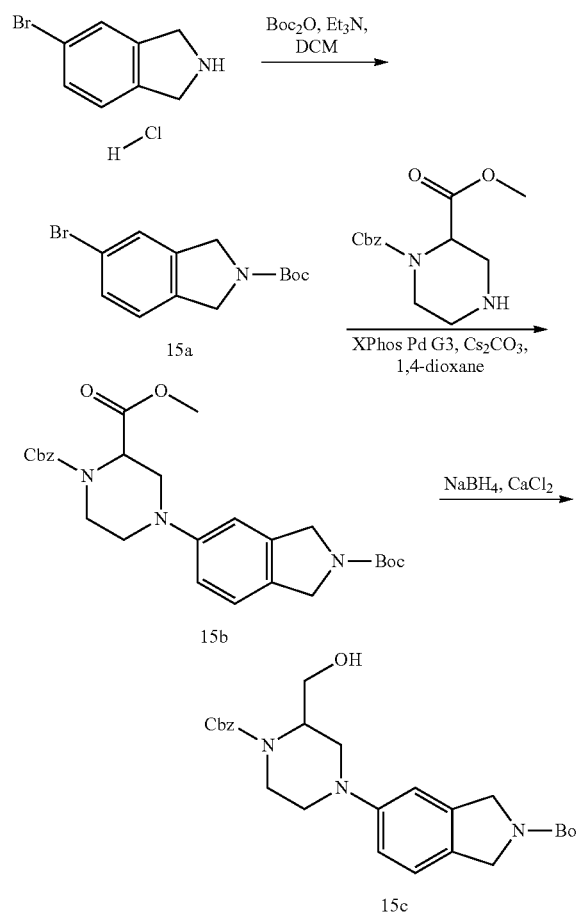

Step 1: Preparation of tert-butyl 5-bromoisoindoline-2-carboxylate (Compound 15a)

To a solution of 5-bromoisoindoline hydrochloride (2.50 g, 10.66 mmol) in DCM (20 mL) was added TEA (4.46 mL, 31.98 mmol) and Boc$_2$O (2.79 g, 12.79 mmol) at 0° C. After being stirred at rt for 4 hrs, the mixture was diluted with DCM (100 mL), washed with water (30 mL) and brine (30 mL), dried over anhydrous Na$_2$SO$_4$, concentrated to give a crude product which was purified by flash column (PE/EtOAc=10/1) to give compound 15a (2.50 g) as a white solid. MS: calc'd 298 (MH$^+$), measured 242 (MH$^+$−56).

Step 2: Preparation of O1-benzyl O2-methyl 4-(2-tert-butoxycarbonylisoindolin-5-yl)piperazine-1,2-dicarboxylate (Compound 15b)

To a solution of tert-butyl 5-bromoisoindoline-2-carboxylate (compound 15a, 1.12 g, 3.75 mmol) in 1,4-dioxane (10 mL) was added O1-benzyl O2-methyl piperazine-1,2-dicarboxylate (CAS: 126937-43-7, Vendor: BePharm, 950 mg, 3.41 mmol), Cs$_2$CO$_3$ (1.67 g, 5.12 mmol) and XPhos Pd G3 (289 mg, 0.34 mmol). The mixture was stirred at 100° C. under N$_2$ for 12 hrs. After being cooled down, the mixture was filtered and concentrated. The residue was diluted with EtOAc (10 mL) and washed with water (3 mL) and brine (3 mL), dried over anhydrous Na$_2$SO$_4$, concentrated to give a crude product which was purified by flash column (PE/EtOAc=3/1) to give compound 15b (420 mg) as a yellow oil. MS: calc'd 496 (MH$^+$), measured 496 (MH$^+$).

Step 3: Preparation of tert-butyl 5-[4-benzyloxycarbonyl-3-(hydroxymethyl)piperazin-1-yl]isoindoline-2-carboxylate (Compound 15c)

To a solution of O1-benzyl O2-methyl 4-(2-tert-butoxycarbonylisoindolin-5-yl)piperazine-1,2-dicarboxylate (compound 15b, 220 mg, 0.44 mmol) and calcium chloride (69 mg, 0.62 mmol) in THF (2 mL) and ethanol (2 mL) was added sodium borohydride (40 mg, 1.07 mmol). The mixture was stirred at 15° C. for 18 hrs. After being quenched with saturated NH$_4$Cl, the reaction mixture was extracted with EtOAc (10 mL) three times. The organic layer was washed with water (10 mL) and brine (10 mL). The organic layer was dried over Na$_2$SO$_4$, filtered and concentration and then purified by prep-TLC (petroleum/EtOAc=1/1) to give compound 15c (80 mg) as a colorless oil. MS: calc'd 468 (MH$^+$), measured 468 (MH$^+$).

Example 16

5-[(2S,6R)-2-[[4-[2-(2-hydroxyethyl)isoindolin-5-yl]piperazin-1-yl]methyl]-6-methyl-morpholin-4-yl]quinoline-8-carbonitrile

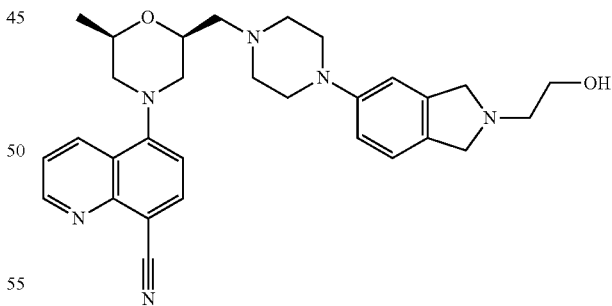

The title compound was prepared according to the following scheme:

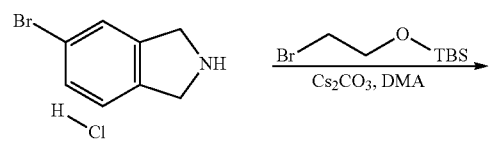

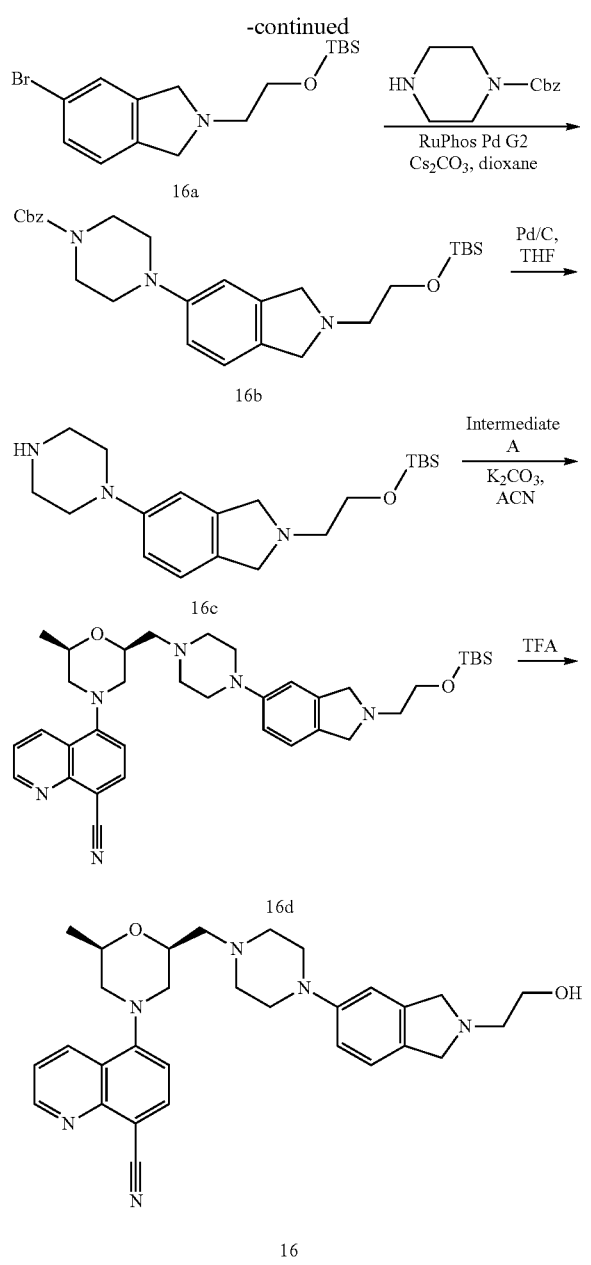

Step 1: Preparation of 2-(5-bromoisoindolin-2-yl)ethoxy-tert-butyl-dimethyl-silane (Compound 16a)

To a solution of 5-bromoisoindoline hydrochloride (400 mg, 1.71 mmol) in DMA (2 mL) was added cesium carbonate (1.67 g, 5.12 mmol) and (2-bromoethoxy)-tert-butyldimethylsilane (449 mg, 1.88 mmol). After being stirred at 100° C. for 12 hrs, the mixture was diluted by EtOAc (100 mL), filtered and concentrated. The residue was purified by flash column (EA/PE=1/3) to give compound 16a (200 mg) as a yellow oil. MS: calc'd 356 (MH$^+$), measured 356 (MH$^+$).

Step 2: Preparation of benzyl-4-[2-[2-[tert-butyl(dimethyl)silyl]oxyethyl]isoindolin-5-yl]piperazine-1-carboxylate (Compound 16b)

To a solution of 2-(5-bromoisoindolin-2-yl)ethoxy-tert-butyl-dimethyl-silane (compound 16a, 200 mg, 0.56 mmol) in 1,4-dioxane (2 mL) was added benzyl piperazine-1-carboxylate (136 mg, 0.62 mmol), Cs$_2$CO$_3$ (549 mg, 1.68 mmol) and RuPhos Pd G2 (22 mg, 0.03 mmol). After being stirred at 85° C. for 12 hrs, the mixture was diluted by EtOAc (100 mL), filtered and concentrated. The residue was purified by flash column (EA/PE=2/1) to give compound 16b (90 mg) as a yellow oil. MS: calc'd 496 (MH$^+$), measured 496 (MH$^+$).

Step 3: Preparation of tert-butyl-dimethyl-[2-(5-piperazin-1-ylisoindolin-2-yl)ethoxy]silane (Compound 16c)

To a solution of benzyl 4-[2-[2-[tert-butyl(dimethyl)silyl]oxyethyl]isoindolin-5-yl]piperazine-1-carboxylate (compound 16b, 90 mg, 0.18 mmol) in THF (5 mL) was added Pd/C (10 wt. %, 50 mg, 0.18 mmol). The reaction mixture was stirred at rt under H$_2$ balloon atmosphere for 5 hrs, then filtered and the filtrate was concentrated to give compound 16c (40 mg) as a colorless gum which was used into next step without further purification. MS: calc'd 362 (MH$^+$), measured 362 (MH$^+$).

Step 4: Preparation of 5-[(2S,6R)-2-[[4-[2-[2-[tert-butyl(dimethyl)silyl]oxyethyl]isoindolin-5-yl]piperazin-1-yl]methyl]-6-methyl-morpholin-4-yl]quinoline-8-carbonitrile (Compound 16d)

To a solution of tert-butyl-dimethyl-[2-(5-piperazin-1-ylisoindolin-2-yl)ethoxy]silane (compound 16c, 38 mg, 0.11 mmol) in acetonitrile (1 mL) was added potassium carbonate (17 mg, 0.12 mmol) and [(2R,6R)-4-(8-cyano-5-quinolyl)-6-methyl-morpholin-2-yl]methyl trifluoromethanesulfonate (Intermediate A, 20 mg, 0.05 mmol). After being stirred at 60° C. for 3 hrs, the mixture was filtered and concentrated to give compound 16d (30 mg) as a yellow gum. MS: calc'd 627 (MH$^+$), measured 627 (MH$^+$).

Step 5: Preparation of 5-[(2S,6R)-2-[[4-[2-(2-hydroxyethyl)isoindolin-5-yl]piperazin-1-yl]methyl]-6-methyl-morpholin-4-yl]quinoline-8-carbonitrile (Example 16)

The solution of 5-[(2S,6R)-2-[[4-[2-[2-[tert-butyl(dimethyl)silyl]oxyethyl]isoindolin-5-yl]piperazin-1-yl]methyl]-6-methyl-morpholin-4-yl]quinoline-8-carbonitrile (compound 16d, 30 mg, 0.05 mmol) in trifluoroacetic acid (5 mL) was stirred at 40° C. for 5 hrs. The mixture was concentrated and the residue was purified by prep-HPLC to give Example 16 (15 mg) as a yellow solid. MS: calc'd 513 (MH$^+$), measured 513 (MH$^+$). $^1$H NMR (400 MHz, METHANOL-d$_4$) δ=9.00 (dd, J=1.6, 4.3 Hz, 1H), 8.67 (dd, J=1.7, 8.6 Hz, 1H), 8.18 (d, J=8.1 Hz, 1H), 7.66 (dd, J=4.4, 8.6 Hz, 1H), 7.37-7.27 (m, 2H), 7.13-7.08 (m, 2H), 4.83 (br s, 1H), 4.65-4.48 (m, 3H), 4.24-3.95 (m, 3H), 3.95-3.89 (m, 2H), 3.88-3.63 (m, 4H), 3.54-3.53 (m, 1H), 3.57-3.52 (m, 1H), 3.49-3.35 (m, 7H), 2.82-2.71 (m, 2H), 1.32 (d, J=6.4 Hz, 3H).

Example 17

5-[(2R,6S)-2-methyl-6-[[4-(5,6,7,8-tetrahydropyrido[3,4-b]pyrazin-2-yl)piperazin-1-yl]methyl]morpholin-4-yl]quinoline-8-carbonitrile

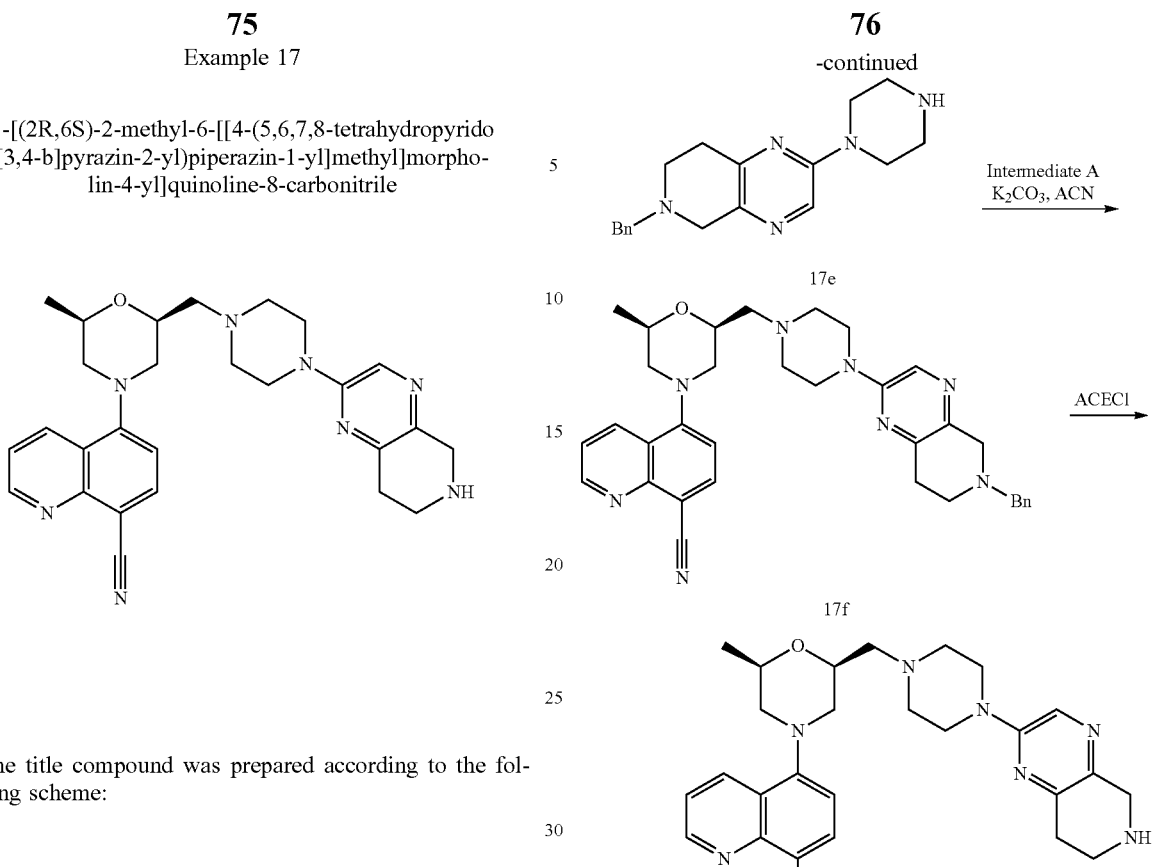

The title compound was prepared according to the following scheme:

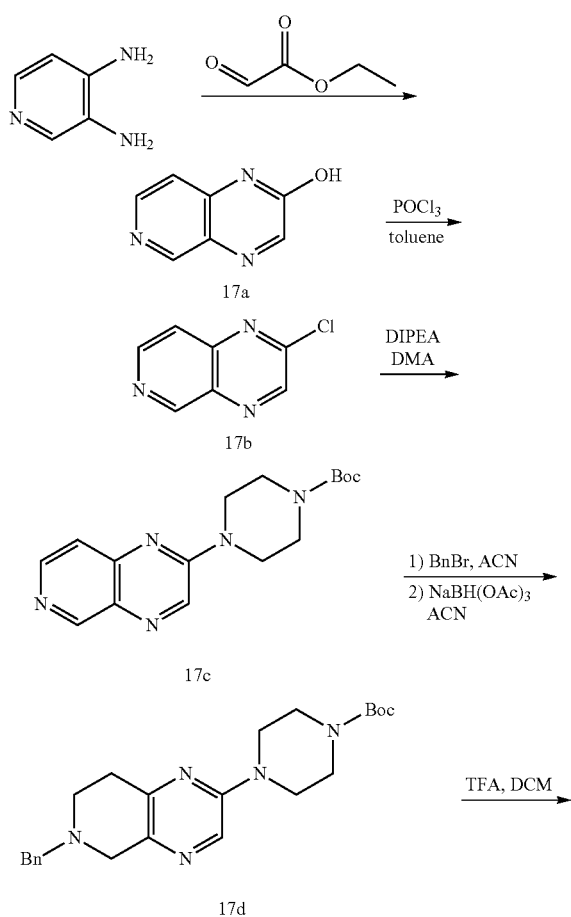

Step 1: Preparation of pyrido[3,4-b]pyrazin-2-ol (Compound 17a)

To a solution of 3,4-diaminopyridine (CAS: 54-96-6, Vendor: Alfa Aesar, 13.00 g, 119.12 mmol) in ethanol (170 mL) was added ethyl glyoxalate (25.63 mL, 131.04 mmol). The mixture was stirred at 20° C. for 0.5 h and then at 90° C. for 18 hrs. After being cooled down, the mixture was filtered and washed with EtOH (10 mL). The solid was dried to give the crude compound 17a (8.00 g) as a yellow solid, which was used for the next step without purification.

Step 2: Preparation of 2-chloropyrido[3,4-b]pyrazine (Compound 17b)

To a solution of pyrido[3,4-b]pyrazin-2-ol (compound 17a, 8.00 g, 54.37 mmol) in toluene (238 mL) was added trichlorophosphate (26.05 mL, 271.87 mmol) and DMF (10 µL). After being stirred at 100° C. for 18 hrs, the reaction mixture was quenched with aq. NaHCO$_3$, and filtered. The filtrate was extracted with EA (100 mL) twice. The organic layer was washed with brine (20 mL), and dried over anhydrous Na$_2$SO$_4$, filtered and concentrated to give compound 17b (2.00 g) as a yellow solid, which was used for the next step without further purification. MS: calc'd 166 (MH$^+$), measured 166 (MH$^+$).

Step 3: Preparation of tert-butyl 4-pyrido[3,4-b] pyrazin-2-ylpiperazine-1-carboxylate (Compound 17c)

To a solution of 2-chloropyrido[3,4-b]pyrazine (compound 17b, 2.00 g, 12.08 mmol) in N,N-dimethylacetamide (40 mL) was added N,N-diisopropylethylamine (4.21 mL, 24.16 mmol) and 1-Boc-piperazine (4.50 g, 24.16 mmol). After being stirred at 100° C. for 1 h, the mixture was diluted with EA (100 mL) and washed with brine (20 mL). The organic layer was dried over $Na_2SO_4$, filtered and concentrated. The residue was purified by flash column (PE/EA=1/1) to give compound 17c (930 mg) as a yellow solid. MS: calc'd 316 ($MH^+$), measured 316 ($MH^+$).

Step 4: Preparation of tert-butyl 4-(6-benzyl-7,8-dihydro-5H-pyrido[3,4-b]pyrazin-2-yl)piperazine-1-carboxylate (Compound 17d)

To a solution of tert-butyl 4-pyrido[3,4-b]pyrazin-2-ylpiperazine-1-carboxylate (compound 17c, 430 mg, 1.36 mmol) in acetonitrile (5 mL) was added benzyl bromide (0.17 mL, 1.40 mmol). The mixture was heated at 80° C. for 1.5 hrs. After being cooled down, the mixture was filtered and dried to give tert-butyl 4-(6-benzylpyrido[3,4-b]pyrazin-6-ium-2-yl)piperazine-1-carboxylate bromide (330 mg) as a yellow solid, which was used for the next step without purification.

To a solution of tert-butyl 4-(6-benzylpyrido[3,4-b]pyrazin-6-ium-2-yl)piperazine-1-carboxylate bromide (330 mg, 0.68 mmol) in acetonitrile (5 mL) was added sodium triacetoxyborohydride (719 mg, 3.39 mmol) at 0° C. After being stirred at 20° C. for 3 hrs, the reaction mixture was quenched with aq. $NaHCO_3$ (10 mL) and keep the temperature below 10° C. and extracted by EtOAc (30 ml). The organic layer was washed with water (10 mL) and brine (10 mL), dried over $Na_2SO_4$ and concentrated to give compound 17d (200 mg) as a yellow solid. MS: calc'd 410 ($MH^+$), measured 410 ($MH^+$).

Step 5: Preparation of 6-benzyl-2-piperazin-1-yl-7,8-dihydro-5H-pyrido[3,4-b]pyrazine (Compound 17e)

To a solution of tert-butyl 4-(6-benzyl-7,8-dihydro-5H-pyrido[3,4-b]pyrazin-2-yl)piperazine-1-carboxylate (compound 17d, 80 mg, 0.20 mmol) in DCM (2 mL) was added trifluoroacetic acid (2 mL). After being stirred at 20° C. for 1 h, the mixture was concentrated and the residue was adjusted to pH=8 with aq.$NaHCO_3$. The mixture was extracted with DCM (20 mL) three times. The organic layer was dried over $Na_2SO_4$, filtered and concentrated to give compound 17e (60 mg) as a yellow solid, which was used for the next step without purification.

Step 6: Preparation of 5-[(2S,6R)-2-[[4-(6-benzyl-7,8-dihydro-5H-pyrido[3,4-b]pyrazin-2-yl)piperazin-1-yl]methyl]-6-methyl-morpholin-4-yl]quinoline-8-carbonitrile (Compound 17f)

To a solution of 6-benzyl-2-piperazin-1-yl-7,8-dihydro-5H-pyrido[3,4-b]pyrazine (compound 17e, 60 mg, 0.19 mmol) in acetonitrile (4 mL) was added potassium carbonate (50 mg, 0.36 mmol) and [(2R,6R)-4-(8-cyano-5-quinolyl)-6-methyl-morpholin-2-yl]methyl trifluoromethanesulfonate (Intermediate A, 60 mg, 0.14 mmol). After being stirred at 55° C. for 0.5 h, the mixture was diluted by EA (10 mL), filtered and concentrated to give compound 17f (90 mg) as a yellow gum. MS: calc'd 575 ($MH^+$), measured 575 ($MH^+$).

Step 7: Preparation of 5-[(2R,6S)-2-methyl-6-[[4-(5,6,7,8-tetrahydropyrido[3,4-b]pyrazin-2-yl)piperazin-1-yl]methyl]morpholin-4-yl]quinoline-8-carbonitrile (Example 17)

To a solution of 5-[(2S,6R)-2-[[4-(6-benzyl-7,8-dihydro-5H-pyrido[3,4-b]pyrazin-2-yl)piperazin-1-yl]methyl]-6-methyl-morpholin-4-yl]quinoline-8-carbonitrile (compound 17f, 90 mg, 0.16 mmol) in 1,2-dichloroethane (4 mL) was added 1-chloroethyl chloroformate (45 mg, 0.32 mmol) at 0° C. The reaction mixture was stirred at 25° C. for 2 hrs. After the solvent was removed, methanol (4 mL) was added. Then the mixture was further heated at 72° C. for 5 hrs. After the solvent was removed, the residue was purified by prep-HPLC to give Example 17 (13 mg) as a yellow solid. MS: calc'd 485 ($MH^+$), measured 485 ($MH^+$). $^1H$ NMR (400 MHz, METHANOL-$d_4$) δ=9.02 (dd, J=1.6, 4.4 Hz, 1H), 8.69 (dd, J=1.6, 8.4 Hz, 1H), 8.30 (s, 1H), 8.19 (d, J=8.0 Hz 1H), 7.67 (dd, J=4.4, 8.8 Hz, 1H), 7.31 (d, J=8.0 Hz 1H), 4.55-4.50 (m, 1H), 4.35 (s, 2H), 4.26-4.15 (m, 1H), 3.84-3.75 (m, 1H), 3.68-3.36 (m, 8H), 3.32-3.25 (m, 4H), 3.18-3.08 (m, 3H), 2.85-2.70 (m, 2H), 1.34 (d, J=6.4 Hz 3H).

Example 18

5-[(2S,6R)-2-[[4-(2,3-dihydro-1H-pyrrolo[3,4-c]pyridin-6-yl)piperazin-1-yl]methyl]-6-methyl-morpholin-4-yl]quinoline-8-carbonitrile

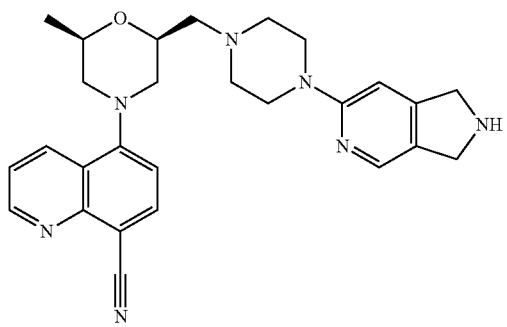

The title compound was prepared in analogy to the preparation of Example 7 by using 6-chloro-2,3-dihydro-1H-pyrrolo[3,4-c]pyridine hydrochloride (CAS: 905273-90-7, Vendor: Wuhan Kaymke Chemical Co., Ltd.) instead of 5-bromoisoindoline hydrochloride, replacing RuPhos Pd G2, $Cs_2CO_3$ and 1,4-dioxane by $Pd_2(dba)_3$, XantPhos, t-BuONa and toluene in the Buchwald-Hartwig amination reaction, and replacing DIPEA by TEA in the Boc protection reaction. Example 18 (26 mg) was obtained as a yellow solid. MS: calc'd 470 ($MH^+$), measured 470 ($MH^+$). $^1H$ NMR (400 MHz, METHANOL-$d_4$) δ=9.02 (d, J=4.2 Hz, 1H), 8.69 (dd, J=8.6, 1.7 Hz, 1H), 8.27 (s, 1H), 8.19 (d, J=7.8 Hz, 1H), 7.68 (dd, J=8.6, 4.2 Hz, 1H), 7.31 (d, J=7.9 Hz, 1H), 7.04 (s, 1H), 5.02-4.91 (m, 2H), 4.61 (d, J=7.8 Hz, 4H), 4.54 (br d, J=9.7 Hz, 1H), 4.27-4.18 (m, 1H), 3.79-3.34 (m, 10H), 2.86-2.71 (m, 2H), 1.35 (d, J=6.2 Hz, 3H).

Example 19

5-[(2R,6S)-2-methyl-6-[[4-(5,6,7,8-tetrahydro-2,7-naphthyridin-3-yl)piperazin-1-yl]methyl]morpholin-4-yl]quinoline-8-carbonitrile

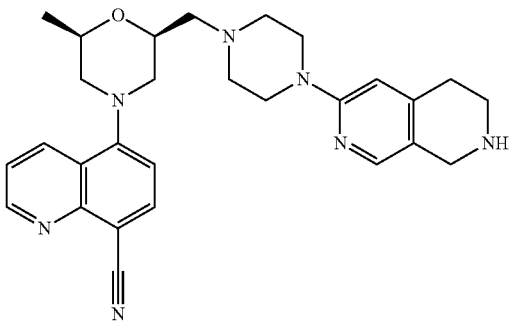 [SMILES: C[C@@H]1CN(c2ccc(C#N)c3ncccc23)C[C@H](CN2CCN(c3cc4c(cn3)CNCC4)CC2)O1]

The title compound was prepared in analogy to the preparation of Example 7 by using 6-chloro-1,2,3,4-tetrahydro-2,7-naphthyridine hydrochloride (CAS: 1335053-26-3, Vendor: BePharm) instead of 5-bromoisoindoline hydrochloride, replacing RuPhos Pd G2 and Cs$_2$CO$_3$ with Pd(OAc)$_2$, (R)-BINAP and t-BuONa in the Buchwald-Hartwig amination reaction and replacing MeOH with isopropanol in the hydrogenation reaction. Example 19 (18 mg) was obtained as a yellow solid. MS: calc'd 484 (MH$^+$), measured 484 (MH$^+$). $^1$H NMR (400 MHz, METHANOL-d$_4$) δ=8.98 (dd, J=1.6, 4.3 Hz, 1H), 8.65 (dd, J=1.7, 8.6 Hz, 1H), 8.15 (d, J=8.1 Hz, 1H), 8.09 (s, 1H), 7.64 (dd, J=4.3, 8.7 Hz, 1H), 7.27 (d, J=8.1 Hz, 1H), 6.88 (s, 1H), 4.58-4.48 (m, 1H), 4.32 (s, 2H), 4.24-4.14 (m, 1H), 4.14-3.53 (m, 6H), 3.50 (t, J=6.5 Hz, 3H), 3.46-3.33 (m, 5H), 3.12 (t, J=6.4 Hz, 2H), 2.83-2.69 (m, 2H), 1.32 (d, J=6.1 Hz, 3H).

Example 20

5-[(2R,6S)-2-methyl-6-[[4-(5,6,7,8-tetrahydro-2,6-naphthyridin-3-yl)piperazin-1-yl]methyl]morpholin-4-yl]quinoline-8-carbonitrile

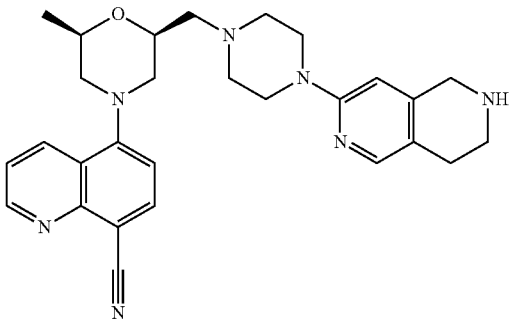

The title compound was prepared in analogy to the preparation of Example 1 by using tert-butyl 7-chloro-3,4-dihydro-2,6-naphthyridine-2 (1H)-carboxylate (CAS: 1060816-50-3, Vendor: Shanghai Hong-chuang Pharma Tech Co., Ltd.) instead of tert-butyl 2-bromo-6,7-dihydro-4H-pyrazolo[1,5-a]pyrazine-5-carboxylate, replacing RuPhos Pd G2, Cs$_2$CO$_3$ and 1,4-dioxane with Pd$_2$(dba)$_3$, XantPhos, t-BuONa and toluene in the Buchwald-Hartwig amination reaction and replacing MeOH with isopropanol in the hydrogenation reaction. Example 20 (33 mg) was obtained as a yellow solid. MS: calc'd 484 (MH$^+$), measured 484 (MH$^+$). $^1$H NMR (400 MHz, METHANOL-d$_4$) δ=8.99 (dd, J=1.5, 4.2 Hz, 1H), 8.67 (dd, J=1.6, 8.6 Hz, 1H), 8.17-8.12 (m, 2H), 7.65 (dd, J=4.3, 8.6 Hz, 1H), 7.28 (d, J=8.1 Hz, 1H), 6.90 (s, 1H), 4.55 (br t, J=9.3 Hz, 1H), 4.40 (s, 2H), 4.27-4.17 (m, 1H), 4.17-3.34 (m, 14H), 3.06 (t, J=6.2 Hz, 2H), 2.85-2.68 (m, 2H), 1.33 (d, J=6.2 Hz, 3H).

Example 21

5-[(2R,6S)-2-methyl-6-[[4-(5,6,7,8-tetrahydro-1,6-naphthyridin-3-yl)piperazin-1-yl]methyl]morpholin-4-yl]quinoline-8-carbonitrile

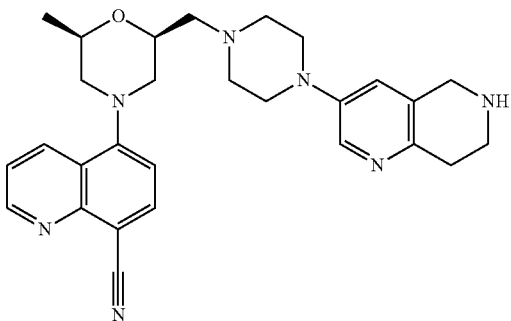 [SMILES: C[C@@H]1CN(c2ccc(C#N)c3ncccc23)C[C@H](CN2CCN(c3cnc4c(c3)CNCC4)CC2)O1]

The title compound was prepared in analogy to the preparation of Example 7 by using 3-bromo-5,6,7,8-tetrahydro-1,6-naphthyridine hydrochloride (CAS: 1159010-96-4, Vendor: PharmaBlock) instead of 5-bromoisoindoline hydrochloride, replacing RuPhos Pd G2, Cs$_2$CO$_3$ and 1,4-dioxane with Pd$_2$(dba)$_3$, XantPhos, t-BuONa and toluene in the Buchwald-Hartwig amination reaction and replacing MeOH with isopropanol in the hydrogenation reaction. Example 21 (34 mg) was obtained as a brown solid. MS: calc'd 484 (MH$^+$), measured 484 (MH$^+$). $^1$H NMR (400 MHz, METHANOL-d$_4$) δ=8.98 (dd, J=1.5, 4.2 Hz, 1H), 8.65 (dd, J=1.6, 8.6 Hz, 1H), 8.47 (d, J=2.7 Hz, 1H), 8.14 (d, J=8.1 Hz, 1H), 7.87 (d, J=2.4 Hz, 1H), 7.64 (dd, J=4.2, 8.6 Hz, 1H), 7.26 (d, J=8.1 Hz, 1H), 4.63-4.49 (m, 3H), 4.26-4.15 (m, 1H), 4.09-3.50 (m, 10H), 3.50-3.38 (m, 4H), 3.33-3.26 (m, 2H), 2.85-2.68 (m, 2H), 1.33 (d, J=6.4 Hz, 3H).

Example 22

5-[(2S,6R)-2-[[4-(4-hydroxy-1,2,3,4-tetrahydroiso-quinolin-6-yl)piperazin-1-yl]methyl]-6-methyl-morpholin-4-yl]quinoline-8-carbonitrile

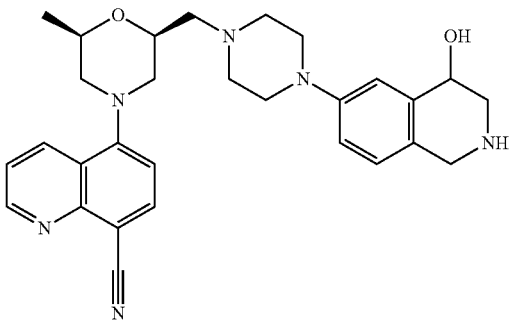 [SMILES: C[C@@H]1CN(c2ccc(C#N)c3ncccc23)C[C@H](CN2CCN(c3ccc4c(c3)C(O)CNC4)CC2)O1]

The title compound was prepared in analogy to the preparation of Example 5 by using tert-butyl-6-bromo-4-hydroxy-3,4-dihydro-1H-isoquinoline-2-carboxylate (compound 22f) instead of tert-butyl 6-bromo-3,4-dihydro-1H-isoquinoline-2-carboxylate. Example 22 (12 mg) was obtained as a yellow solid. MS: calc'd 499 (MH$^+$), measured 499 (MH$^+$). $^1$H NMR (400 MHz, METHANOL-d$_4$) δ=9.02 (dd, J=1.7, 4.3 Hz, 1H), 8.69 (dd, J=1.8, 8.5 Hz, 1H), 8.20 (d, J=7.9 Hz, 1H), 7.68 (dd, J=4.2, 8.5 Hz, 1H), 7.32 (d, J=8.1 Hz, 1H), 7.23 (d, J=8.7 Hz, 1H), 7.16-7.08 (m, 2H), 4.96-4.91 (m, 1H), 4.54 (br s, 1H), 4.40-4.30 (m, 2H), 4.23 (br s, 1H), 3.85-3.41 (m, 13H), 3.27-3.13 (m, 1H), 2.87-2.72 (m, 2H), 1.35 (d, J=6.2 Hz, 3H).

The compound 22f was prepared according to the following scheme:

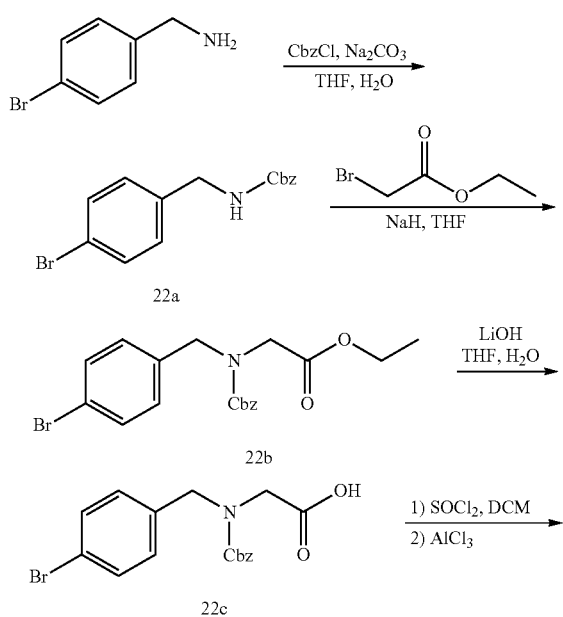

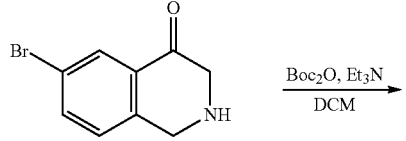

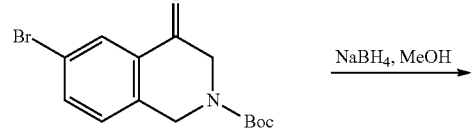

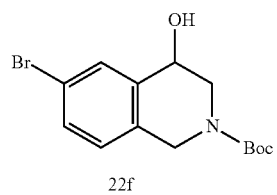

Step 1: Preparation of benzyl N-[(4-bromophenyl)methyl]carbamate (Compound 22a)

To a solution of 4-bromobenzylamine (20.00 g, 107.50 mmol) and sodium carbonate (34.18 g, 322.49 mmol) in THF/water (450 mL, v/v=2/1) was added benzyl chloroformate (36.68 g, 215.00 mmol) at 0° C. After being stirred at 25° C. for 2 hrs, the reaction mixture was quenched by addition of water (200 mL) and extracted with EA (200 mL) twice. The combined organic layer was dried over Na$_2$SO$_4$, filtered and concentrated. The residue was purified by flash column (EtOAc/isohexane=30%) to give compound 22a (23.00 g) as a white solid. MS: calc'd 320 (MH$^+$), measured 320 (MH$^+$).

Step 2: Preparation of ethyl 2-[benzyloxycarbonyl-[(4-bromophenyl)methyl]amino]acetate (Compound 22b)

To a solution of benzyl N-[(4-bromophenyl)methyl]carbamate (22.00 g, 68.71 mmol) in THF (264 mL) was added sodium hydride (3.92 g, 97.90 mmol) at 0° C. The mixture was stirred for 30 mins, and then ethyl bromoacetate (8.38 mL, 75.58 mmol) was added. After being stirred at 20° C. for another 18 hrs, the reaction mixture was quenched by addition of water (30 mL) and extracted with EA (20 mL) twice. The organic layer was washed with brine (20 mL), dried over anhydrous Na$_2$SO$_4$, filtered and concentrated. The residue was purified by flash column to give compound 22b (20.00 g) as a colorless oil. MS: calc'd 406 (MH$^+$), measured 406 (MH$^+$).

Step 3: Preparation of 2-[benzyloxycarbonyl-[(4-bromophenyl)methyl]amino]acetic acid (Compound 22c)

To a solution of ethyl 2-[benzyloxycarbonyl-[(4-bromophenyl)methyl]amino]acetate (20.00 g, 49.23 mmol) in THF (300 mL) was added the solution of lithium hydroxide monohydrate (2.48 g, 59.07 mmol) in water (100 mL) at 0° C. dropwise. After being stirred at 25° C. for 4 hrs, the reaction mixture was quenched by addition of water (200 mL) and extracted with MTBE (100 mL). The aqueous was acidified to pH=3, and extracted with EA (200 mL) twice. The organic layer was dried and concentrated to give compound 22c (18.00 g) as a colorless oil. MS: calc'd 400 (M+Na$^+$), measured 400 (M+Na$^+$).

Step 4: Preparation of 6-bromo-2,3-dihydro-1H-isoquinolin-4-one (Compound 22d)

To a solution of 2-[benzyloxycarbonyl-[(4-bromophenyl)methyl]amino]acetic acid (10.00 g, 26.44 mmol) in DCM (215 mL) was added thionyl chloride (3.15 mL, 39.66 mmol). After being refluxed for 3 hrs, the reaction mixture was concentrated. The residue was dissolved in DCM (215 mL) and aluminum chloride (14.10 g, 105.76 mmol) was added at 0° C. The solution was stirred at 20° C. for 18 hrs and then diluted with ice-water, and neutralized to pH=7-8 with aq.NaHCO$_3$. The mixture was filtered and washed with DCM (500 mL) five times. The organic layer was washed with brine (200 mL), dried over anhydrous Na$_2$SO$_4$, filtered and concentrated to give the crude product compound 22d (6.00 g) as a yellow solid. MS: calc'd 226 (MH$^+$), measured 226 (MH$^+$).

Step 5: Preparation of tert-butyl 6-bromo-4-oxo-1,3-dihydroisoquinoline-2-carboxylate (Compound 22e)

To a solution of 6-bromo-2,3-dihydro-1H-isoquinolin-4-one (2.00 g, 8.85 mmol) in DCM (20 mL) was added triethylamine (3.17 mL, 22.73 mmol) and Boc$_2$O (2.90 g, 13.27 mmol) at 0° C. After being stirred at 25° C. for 18 hrs, the reaction mixture was concentrated and purified by flash column to give compound 22e (1.00 g) as a yellow solid.

Step 6: Preparation of tert-butyl 6-bromo-4-hydroxy-3,4-dihydro-1H-isoquinoline-2-carboxylate (Compound 22f)

To a solution of tert-butyl 6-bromo-4-oxo-1,3-dihydroisoquinoline-2-carboxylate (400 mg, 1.23 mmol) in methanol (13 mL) was added sodium borohydride (56 mg, 1.47 mmol) at 0° C. After being stirred at 0° C. for 2 hrs, the reaction was quenched by addition of water (10 mL), and the mixture was extracted with DCM (10 mL) three times. The organic layer was dried over Na$_2$SO$_4$, filtered and concentrated to give compound 22f (350 mg) as a yellow gum. MS: calc'd 328 (MH$^+$), measured 328 (MH$^+$).

Example 23

5-[(2R,6S)-2-methyl-6-[[4-(5,6,7,8-tetrahydro-1,7-naphthyridin-3-yl)piperazin-1-yl]methyl]morpholin-4-yl]quinoline-8-carbonitrile

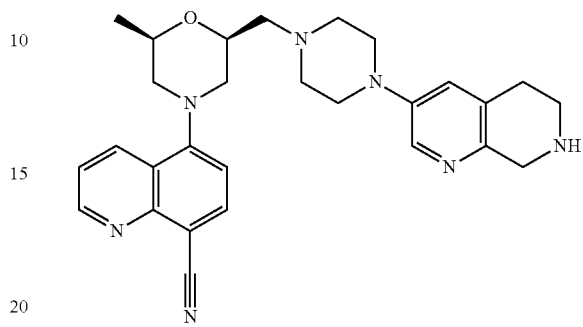

The title compound was prepared in analogy to the preparation of Example 21 by using 3-bromo-5,6,7,8-tetrahydro-1,7-naphthyridine (CAS: 1196156-01-0, Vendor: PharmaBlock) instead of 3-bromo-5,6,7,8-tetrahydro-1,6-naphthyridine hydrochloride. Example 23 (27 mg) was obtained as a yellow solid. MS: calc'd 484 (MH$^+$), measured 484 (MH$^+$). $^1$H NMR (400 MHz, METHANOL-d$_4$) δ=8.96 (dd, J=1.6, 4.3 Hz, 1H), 8.64 (dd, J=1.6, 8.7 Hz, 1H), 8.33 (d, J=2.7 Hz, 1H), 8.12 (d, J=7.8 Hz, 1H), 7.62 (dd, J=4.4, 8.6 Hz, 1H), 7.51 (d, J=2.4 Hz, 1H), 7.25 (d, J=8.1 Hz, 1H), 4.59-4.50 (m, 1H), 4.39 (s, 2H), 4.24-4.15 (m, 1H), 4.14-3.51 (m, 9H), 3.50-3.34 (m, 5H), 3.18 (t, J=6.2 Hz, 2H), 2.82-2.68 (m, 2H), 1.35-1.27 (m, 3H).

Example 24

5-[(2S,6R)-2-[[4-[1-(hydroxymethyl)-1,2,3,4-tetrahydroisoquinolin-6-yl]piperazin-1-yl]methyl]-6-methyl-morpholin-4-yl]quinoline-8-carbonitrile

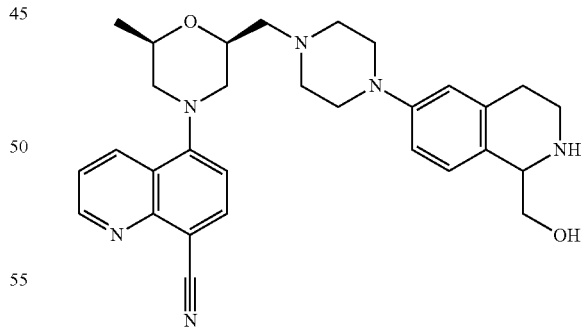

The title compound was prepared according to the following scheme:

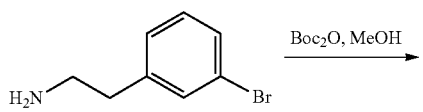

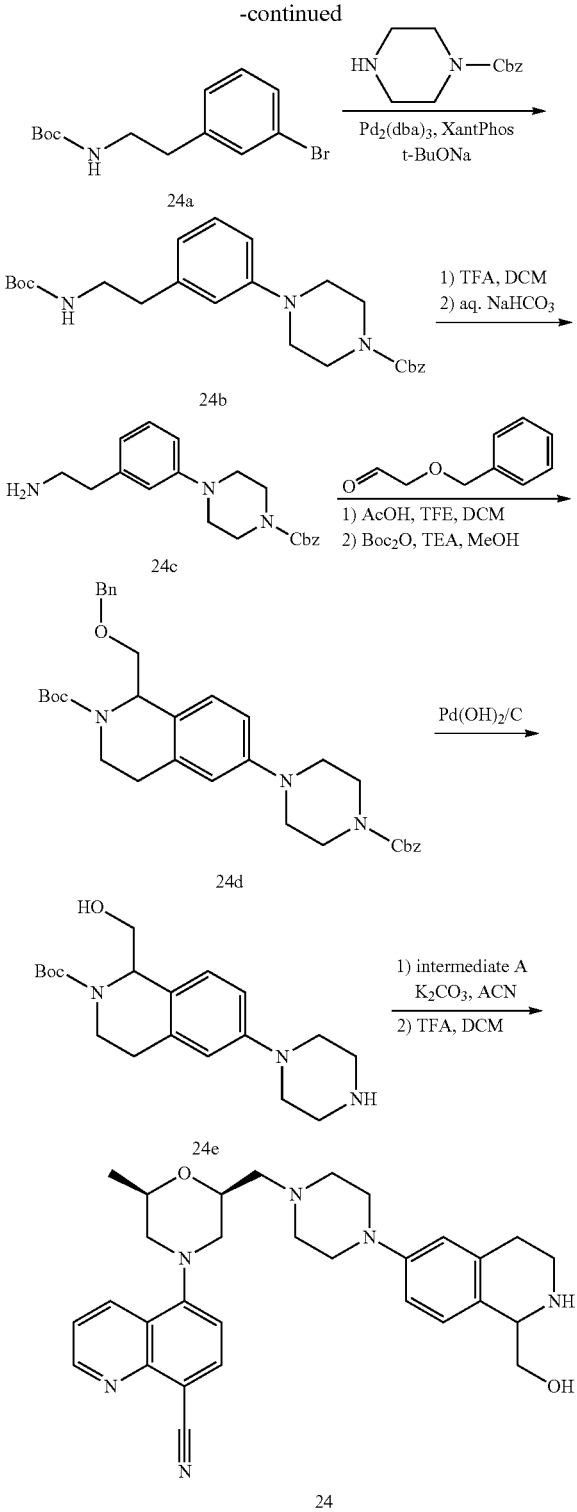

Step 1: Preparation of tert-butyl N-[2-(3-bromophenyl)ethyl]carbamate (Compound 24a)

To a solution of 3-bromophenethylamine (CAS: 58971-11-2, Vendor: Aldrich, 3.00 g, 14.99 mmol) in methanol (60 mL) was added Boc$_2$O (4.58 g, 20.99 mmol) at 0° C. After being stirred at 25° C. for 18 hrs, the mixture was concentrated and the residue was dissolved in DCM (50 mL). The mixture was then washed with 5% citric acid (20 mL) and brine (20 mL), dried over Na$_2$SO$_4$, filtered and concentrated to give the crude compound 24a (4.00 g) as a colorless oil, which was used for the next step without purification. MS: calc'd 300 (MH$^+$), measured 300 (MH$^+$).

Step 2: Preparation of benzyl 4-[3-[2-(tert-butoxycarbonylamino)ethyl]phenyl]piperazine-1-carboxylate (Compound 24b)

To a solution of tert-butyl N-[2-(3-bromophenyl)ethyl]carbamate (compound 24a, 1.00 g, 3.33 mmol), benzyl piperazine-1-carboxylate (734 mg, 3.33 mmol), sodium tert-butoxide (640 mg, 6.66 mmol), 9,9-dimethyl-4,5-bis(diphenylphosphino)xanthene (386 mg, 0.67 mmol) in toluene (28 mL) was added tris(dibenzylideneacetone)dipalladium (0) (305 mg, 0.33 mmol) and the mixture was stirred at 90° C. under N$_2$ atmosphere for 18 hrs. Then the mixture was concentrated and purified by flash column (PE/EA=5/1) to give compound 24b (600 mg) as a yellow oil. MS: calc'd 440 (MH$^+$), measured 440 (MH$^+$).

Step 3: Preparation of benzyl 4-[3-(2-aminoethyl)phenyl]piperazine-1-carboxylate (Compound 24c)

To a solution of benzyl 4-[3-[2-(tert-butoxycarbonylamino)ethyl]phenyl]piperazine-1-carboxylate (compound 24b, 600 mg, 1.37 mmol) in DCM (5 mL) was added trifluoroacetic acid (1.00 mL, 12.98 mmol) at 0° C. After being stirred at 25° C. for 2 hrs, the mixture was concentrated and the residue was neutralized to pH=7-8 by addition of aq. NaHCO$_3$. The mixture was extracted with DCM (20 mL) three times. The organic layer was dried over Na$_2$SO$_4$, filtered and concentrated to give the desired product compound 24c (400 mg) as a yellow gum. MS: calc'd 340 (MH$^+$), measured 340 (MH$^+$).

Step 4: Preparation of tert-butyl 6-(4-benzyloxycarbonylpiperazin-1-yl)-1-(benzyloxymethyl)-3,4-dihydro-1H-isoquinoline-2-carboxylate (Compound 24d)

To a solution of benzyl 4-[3-(2-aminoethyl)phenyl]piperazine-1-carboxylate (compound 24c, 200 mg, 0.59 mmol) in DCM/2,2,2-trifluoroethanol (3.5 mL, v/v=6/1) was added 4 A Molecular sieve (200 mg), acetic acid (88 mg, 1.47 mmol) and a solution of benzyloxyacetaldehyde (97 mg, 0.65 mmol) in DCM (1 mL) at 0° C. After being stirred at 10° C. for 18 hrs, the mixture was filtered and concentrated to give the crude benzyl 4-[1-(benzyloxymethyl)-1,2,3,4-tetrahydroisoquinolin-6-yl]piperazine-1-carboxylate (280 mg) as a yellow gum, which was used for the next step without purification.

To a solution of benzyl 4-[1-(benzyloxymethyl)-1,2,3,4-tetrahydroisoquinolin-6-yl]piperazine-1-carboxylate (280 mg, 0.59 mmol) in methanol (5 mL) was added triethylamine (0.25 mL, 1.78 mmol), Boc$_2$O (259 mg, 1.19 mmol) at 0° C. After being stirred at 15° C. for 2 hrs, the mixture was concentrated and the residue was purified by prep-TLC (PE:EA=2:1) to give compound 24d (160 mg) as a yellow gum. MS: calc'd 572 (MH$^+$), measured 572 (MH$^+$).

Step 5: Preparation of tert-butyl 1-(hydroxymethyl)-6-piperazin-1-yl-3,4-dihydro-1H-isoquinoline-2-carboxylate (Compound 24e)

To a solution of tert-butyl 6-(4-benzyloxycarbonylpiperazin-1-yl)-1-(benzyloxymethyl)-3,4-dihydro-1H-isoquinoline-2-carboxylate (compound 24d, 160 mg, 0.28 mmol) in MeOH/THF (5 mL, v/v=1/1) was added Pd(OH)$_2$/C (10 wt. %, 50 mg, 0.38 mmol). The mixture was stirred at 45° C. for 36 hrs under H$_2$ balloon. After filtration, the solvent was removed to give compound 24e (70 mg) as a yellow gum, which was used for the next step without purification. MS: calc'd 348 (MH$^+$), measured 348 (MH$^+$).

Step 6: Preparation of 5-[(2S,6R)-2-[[4-[1-(hydroxymethyl)-1,2,3,4-tetrahydroisoquinolin-6-yl]piperazin-1-yl]methyl]-6-methyl-morpholin-4-yl]quinoline-8-carbonitrile (Example 24)

To a solution of tert-butyl 1-(hydroxymethyl)-6-piperazin-1-yl-3,4-dihydro-1H-isoquinoline-2-carboxylate (compound 24e, 22 mg, 0.06 mmol) in acetonitrile (3 mL) was added potassium carbonate (17 mg, 0.12 mmol) and [(2R,6R)-4-(8-cyano-5-quinolyl)-6-methyl-morpholin-2-yl]methyl trifluoromethanesulfonate (Intermediate A, 20 mg, 0.05 mmol). After being stirred at 55° C. for 0.5 h, the mixture was diluted with EA (10 mL), filtered and concentrated to give a yellow gum which was used in next step directly.

The crude product was dissolved in DCM (2 mL), and trifluoroacetic acid (0.52 mL, 6.69 mmol) was added. After being stirred at 20° C. for 1 h, the mixture was concentrated and the residue was dissolved in acetonitrile (10 mL) which was basified to pH=7 with solid NaHCO$_3$. After filtration, the solvent was removed and the residue was purified by prep-HPLC to give Example 24 (12 mg) as a white solid. MS: calc'd 513 (MH$^+$), measured 513 (MH$^+$). $^1$H NMR (400 MHz, METHANOL-d$_4$) δ=9.00 (dd, J=2.0, 4.4 Hz, 1H), 8.67 (dd, J=1.6, 8.8 Hz, 1H), 8.17 (d, J=8.0 Hz, 1H), 7.66 (dd, J=4.4, 8.8 Hz, 1H), 7.30 (d, J=8.0 Hz, 1H), 7.23 (d, J=8.8 Hz, 1H), 7.02 (dd, J=2.0, 8.4 Hz, 1H), 6.93 (d, J=2.4 Hz, 1H), 4.59-4.46 (m, 2H), 4.28-4.16 (m, 1H), 4.15-4.07 (m, 1H), 3.43 (br s, 15H), 3.16-3.08 (m, 2H), 2.86-2.71 (m, 2H), 1.33 (d, J=6.4 Hz, 3H).

Example 25

8-[(2S,6R)-2-[[4-(6,7-dihydro-5H-pyrrolo[3,4-b]pyridin-3-yl)piperazin-1-yl]methyl]-6-methyl-morpholin-4-yl]quinoxaline-5-carbonitrile

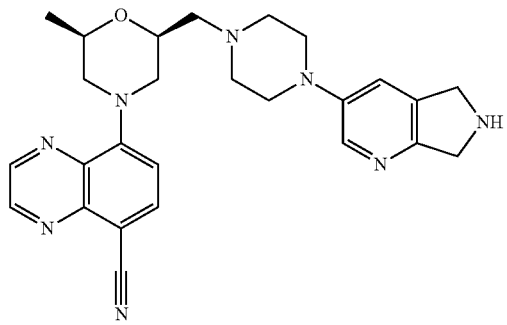 [SMILES: C[C@@H]1CN(c2ccc(C#N)c3nccnc23)C[C@H](CN2CCN(c3cnc4c(c3)CNC4)CC2)O1]

The title compound was prepared in analogy to the preparation of Example 8 by using Intermediate C instead of Intermediate B. Example 25 (11 mg) was obtained as a yellow solid. MS: calc'd 471 (MH$^+$), measured 471 (MH$^+$). $^1$H NMR (400 MHz, METHANOL-d$_4$) δ=8.97 (d, J=1.7 Hz, 1H), 8.89 (d, J=1.7 Hz, 1H), 8.34 (d, J=2.7 Hz, 1H), 8.14 (d, J=8.1 Hz, 1H), 7.56 (d, J=2.2 Hz, 1H), 7.25 (d, J=8.3 Hz, 1H), 4.68 (s, 2H), 4.53 (s, 2H), 4.51-4.43 (m, 1H), 4.30 (br d, J=12.0 Hz, 1H), 4.18-4.10 (m, 2H), 4.05-3.53 (m, 6H), 3.53-3.33 (m, 4H), 2.90-2.78 (m, 2H), 1.33 (d, J=6.1 Hz, 3H).

Example 26

4-[(2S,6R)-2-[[4-(6,7-dihydro-5H-pyrrolo[3,4-b]pyridin-3-yl)piperazin-1-yl]methyl]-6-methyl-morpholin-4-yl]-3-fluoro-pyrazolo[1,5-a]pyridine-7-carbonitrile

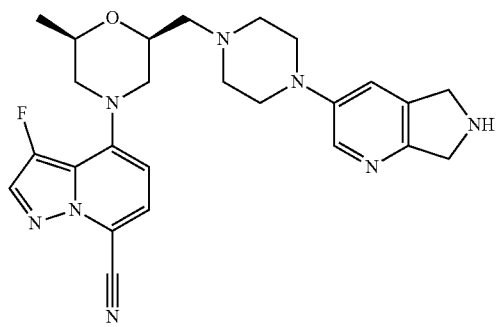 [SMILES: C[C@@H]1CN(c2ccc(C#N)n3ncc(F)c23)C[C@H](CN2CCN(c3cnc4c(c3)CNC4)CC2)O1]

The title compound was prepared in analogy to the preparation of Example 8 by using Intermediate E instead of Intermediate B. Example 26 (16 mg) was obtained as a yellow solid. MS: calc'd 477 (MH$^+$), measured 477 (MH$^+$). $^1$H NMR (400 MHz, METHANOL-d$_4$) δ=8.36 (d, J=2.2 Hz, 1H), 8.01 (d, J=3.5 Hz, 1H), 7.57 (d, J=2.3 Hz, 1H), 7.45 (d, J=7.9 Hz, 1H), 6.56 (d, J=8.1 Hz, 1H), 4.70 (s, 2H), 4.55 (s, 2H), 4.43-4.33 (m, 1H), 4.12-4.00 (m, 1H), 3.61 (br t, J=11.2 Hz, 8H), 3.53-3.34 (m, 4H), 2.85-2.67 (m, 2H), 1.32 (d, J=6.2 Hz, 3H).

Example 27

5-[(2R,6S)-2-methyl-6-[[4-(5,6,7,8-tetrahydro-1,6-naphthyridin-3-yl)piperazin-1-yl]methyl]morpholin-4-yl]-[1,2,4]triazolo[1,5-a]pyridine-8-carbonitrile

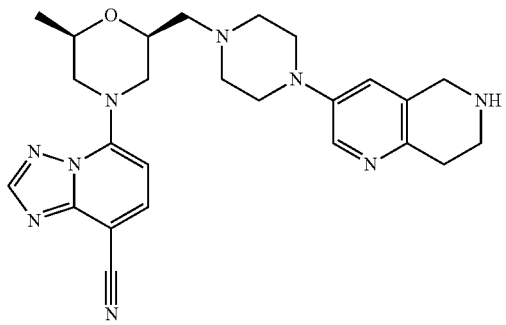 [SMILES: C[C@@H]1CN(c2ccc(C#N)c3ncnn23)C[C@H](CN2CCN(c3cnc4c(c3)CNCC4)CC2)O1]

The title compound was prepared in analogy to the preparation of Example 21 by using Intermediate F instead of Intermediate A. Example 27 (19 mg) was obtained as a white solid. MS: calc'd 474 (MH$^+$), measured 474 (MH$^+$). $^1$H NMR (400 MHz, METHANOL-d$_4$) δ=8.50 (s, 1H), 8.36 (d, J=2.6 Hz, 1H), 8.12 (d, J=8.3 Hz, 1H), 7.50 (s, 1H), 6.72

(d, J=8.3 Hz, 1H), 4.56-4.39 (m, 4H), 4.32 (br d, J=12.5 Hz, 1H), 4.16-4.05 (m, 1H), 3.98-3.34 (m, 12H), 3.20 (t, J=6.4 Hz, 2H), 3.02-2.87 (m, 2H), 1.36 (d, J=6.2 Hz, 3H).

Example 28

5-[(2R,6S)-2-methyl-6-[[4-(1-methylisoindolin-5-yl)piperazin-1-yl]methyl]morpholin-4-yl]quinoline-8-carbonitrile

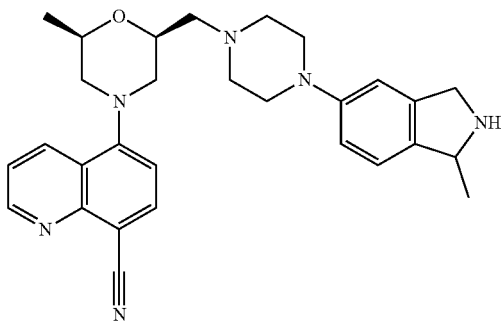 [SMILES: CC1NCc2cc(N3CCN(C[C@H]4CN(c5ccc(C#N)c6ncccc56)C[C@@H](C)O4)CC3)ccc21]

The title compound was prepared in analogy to the preparation of Example 5 by using tert-butyl 5-bromo-1-methyl-isoindoline-2-carboxylate (compound 28a) instead of tert-butyl 6-bromo-3,4-dihydro-1H-isoquinoline-2-carboxylate. Example 28 (40 mg) was obtained as a white solid. MS: calc'd 483 (MH$^+$), measured 483 (MH$^+$). $^1$H NMR (400 MHz, METHANOL-d$_4$) δ=9.02 (dd, J=1.5, 4.2 Hz, 1H), 8.69 (dd, J=1.5, 8.6 Hz, 1H), 8.19 (d, J=8.1 Hz, 1H), 7.67 (dd, J=4.3, 8.6 Hz, 1H), 7.35-7.29 (m, 2H), 7.16-7.10 (m, 2H), 4.97 (q, J=6.7 Hz, 1H), 4.64-4.47 (m, 3H), 4.27-4.14 (m, 1H), 4.06-3.35 (m, 11H), 3.15 (br s, 1H), 2.89-2.68 (m, 2H), 1.67 (d, J=6.7 Hz, 3H), 1.34 (d, J=6.2 Hz, 3H).

The compound 28a was prepared according to the following scheme:

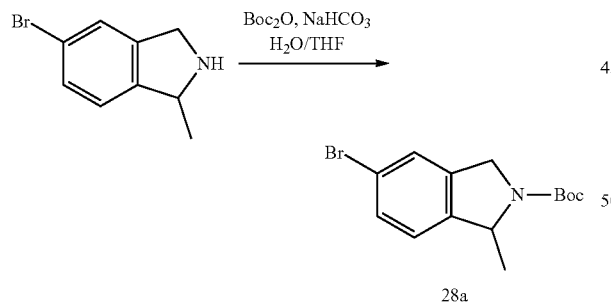

Preparation of tert-butyl 5-bromo-1-methyl-isoindoline-2-carboxylate (Compound 28a)

A solution of 5-bromo-1-methylisoindoline (CAS: 335428-62-1, Vendor: BePharm, 250 mg, 1.18 mmol), Boc$_2$O (386 mg, 1.77 mmol) and sodium hydrogen carbonate (396 mg, 4.71 mmol) in THF (5 mL) and water (5 mL) was stirred at 25° C. under N$_2$ for 2 hrs. After being quenched by addition of water (20 mL), the reaction mixture was extracted with EA (20 mL). The organic layer was dried and concentrated under vacuum and purified by prep-TLC (EA/PE=1/3, Rf=0.3) to give compound 28a (300 mg) as a colorless gum. MS calc'd 312 (MH$^+$), measured 312 (MH$^+$).

Example 29

5-[(2R,6S)-2-methyl-6-[[4-(5,6,7,8-tetrahydropyrido[4,3-d]pyrimidin-2-yl)piperazin-1-yl]methyl]morpholin-4-yl]quinoline-8-carbonitrile

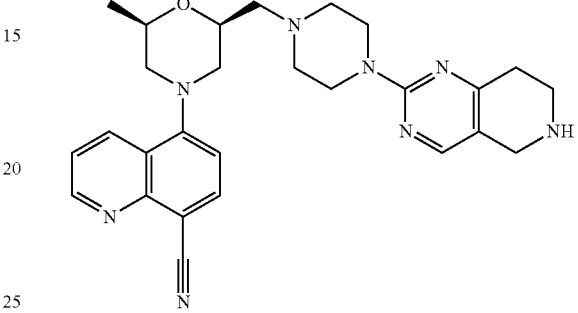

The title compound was prepared in analogy to the preparation of Example 6 by using tert-butyl 2-chloro-7,8-dihydro-5H-pyrido[4,3-d]pyrimidine-6-carboxylate (compound 29a) instead of tert-butyl 4-chloro-5,7-dihydropyrrolo[3,4-d]pyrimidine-6-carboxylate. Example 29 (11 mg) was obtained as a light yellow powder. MS: calc'd 485 (MH$^+$), measured 485 (MH$^+$). $^1$H NMR (400 MHz, METHANOL-d$_4$) δ=9.02 (dd, J=1.7, 4.2 Hz, 1H), 8.69 (dd, J=1.7, 8.6 Hz, 1H), 8.34 (s, 1H), 8.19 (d, J=7.9 Hz, 1H), 7.67 (dd, J=4.3, 8.6 Hz, 1H), 7.31 (d, J=8.1 Hz, 1H), 4.57-4.49 (m, 1H), 4.31 (s, 2H), 4.27-4.17 (m, 1H), 3.60 (t, J=6.5 Hz, 5H), 3.49-3.39 (m, 5H), 3.39-3.34 (m, 3H), 3.31-3.18 (m, 1H), 3.08 (t, J=6.4 Hz, 2H), 2.85-2.79 (m, 1H), 2.78-2.72 (m, 1H), 1.35 (d, J=6.4 Hz, 3H).

The compound 29a was prepared according to the following scheme:

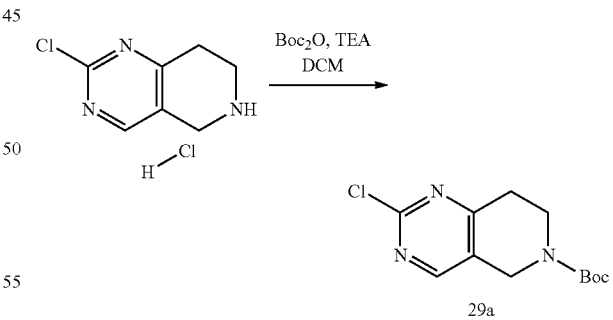

To a flask was added 2-chloro-5,6,7,8-tetrahydropyrido[4,3-d]pyrimidine hydrochloride (CAS: 1314723-39-1, Vendor: PharmaBlock, 206 mg, 1.00 mmol) and DCM (5 mL). Then TEA (303 mg, 418 μL, 3.00 mmol) and Boc$_2$O (327 mg, 348 μL, 1.50 mmol) was added dropwise and the mixture was stirred at rt for 2 hrs. After being diluted with DCM (30 mL), the mixture was washed with sat. NH$_4$Cl (20 mL) twice. The organic layer was dried over Na$_2$SO$_4$ and concentrated to give an oil which was purified by flash column (EA/PE=0 to 40%) to give compound 29a (250 mg) as a white solid. MS: calc'd 270 (MH⁺), measured 270 (MH⁺).

Example 30

5-[(2S,6R)-2-[[4-(6,7-dihydro-5H-pyrrolo[3,4-b]pyridin-2-yl)piperazin-1-yl]methyl]-6-methyl-morpholin-4-yl]quinoline-8-carbonitrile

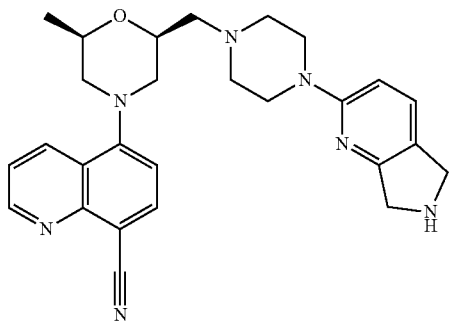 [SMILES: C[C@@H]1CN(c2ccc(C#N)c3ncccc23)C[C@H](CN2CCN(c3ccc4c(n3)CNC4)CC2)O1]

The title compound was prepared in analogy to the preparation of Example 7 by using 2-chloro-6,7-dihydro-5H-pyrrolo[3,4-b]pyridine hydrochloride (CAS: 1841081-37-5, Vendor: PharmaBlock) instead of 5-bromoisoindoline hydrochloride, replacing RuPhos Pd G2, Cs₂CO₃ and 1,4-dioxane with Pd₂(dba)₃, BINAP, t-BuONa, and toluene in the Buchwald-Hartwig amination reaction, replacing Pd/C with Pd(OH)₂/C in the hydrogenation reaction and replacing DIPEA with TEA in the Boc protection reaction. Example 30 (29 mg) was obtained as a light yellow powder. MS: calc'd 470 (MH⁺), measured 470 (MH⁺). ¹H NMR (400 MHz, METHANOL-d₄) δ=9.01 (dd, J=1.6, 4.3 Hz, 1H), 8.68 (dd, J=1.7, 8.6 Hz, 1H), 8.19 (d, J=8.1 Hz, 1H), 7.73-7.64 (m, 2H), 7.30 (d, J=8.1 Hz, 1H), 6.98 (d, J=8.8 Hz, 1H), 4.60 (s, 2H), 4.58-4.52 (m, 1H), 4.47 (s, 3H), 4.26-4.17 (m, 1H), 3.91-3.56 (m, 3H), 3.54-3.37 (m, 6H), 3.25 (br s, 2H), 2.86-2.78 (m, 1H), 2.78-2.70 (m, 1H), 1.34 (d, J=6.2 Hz, 3H).

Example 31

5-[(2R,6S)-2-methyl-6-[[4-(4,5,6,7-tetrahydrothiazolo[5,4-c]pyridin-2-yl)piperazin-1-yl]methyl]morpholin-4-yl]quinoline-8-carbonitrile

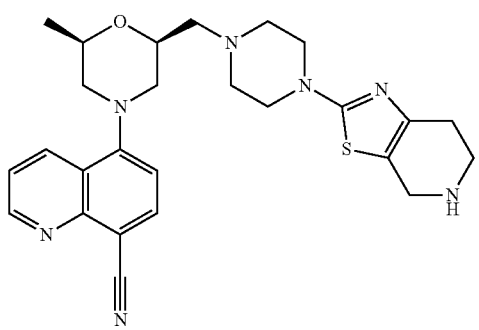 [SMILES: C[C@@H]1CN(c2ccc(C#N)c3ncccc23)C[C@H](CN2CCN(c3nc4c(s3)CNCC4)CC2)O1]

The title compound was prepared according to the following scheme:

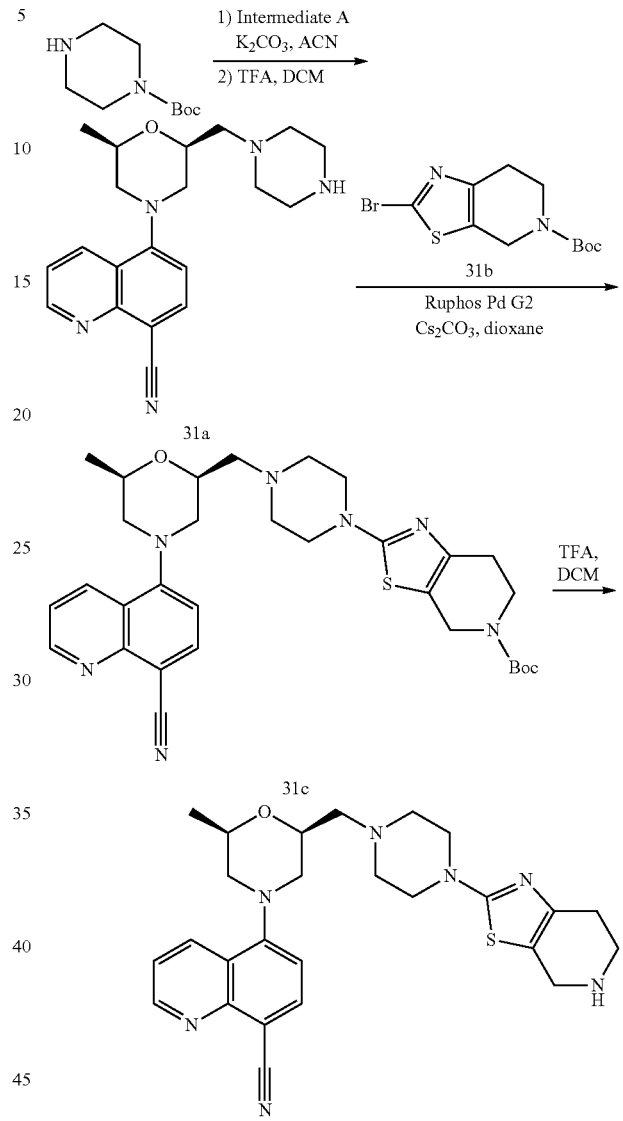

Step 1: Preparation of 5-[(2R,6S)-2-methyl-6-(piperazin-1-ylmethyl)morpholin-4-yl]quinoline-8-carbonitrile (Compound 31a)

To a flask was added [(2R,6R)-4-(8-cyano-5-quinolyl)-6-methyl-morpholin-2-yl]methyl trifluoromethanesulfonate (Intermediate A, 100 mg, 241 μmol), tert-butyl piperazine-1-carboxylate (54 mg, 289 μmol), potassium carbonate (100 mg, 722 μmol) and acetonitrile (4 mL). The reaction mixture was stirred at 85° C. for 2 hrs. After being cooled down, the mixture was filtered through celite and the filtrate was concentrated to give a brown oil which was purified by flash column (EA/PE=0 to 100%) to give a yellow oil. Then it was dissolved in DCM (2 mL) and TFA (1 mL). The mixture was stirred at rt for 1 h and concentrated directly to give compound 31a (100 mg) as an oil. MS: calc'd 352 (MH⁺), measured 352 (MH⁺).

Step 2: Preparation of tert-butyl 2-[4-[[(2S,6R)-4-(8-cyano-5-quinolyl)-6-methyl-morpholin-2-yl]methyl]piperazin-1-yl]-6,7-dihydro-4H-thiazolo[5,4-c]pyridine-5-carboxylate (Compound 31c)

To a flask was added tert-butyl 2-bromo-6,7-dihydrothiazolo[5,4-c]pyridine-5 (4H)-carboxylate (compound 31b, CAS: 365996-06-1, Vendor: PharmaBlock, 64 mg, 200 µmol), 5-[(2R,6S)-2-methyl-6-(piperazin-1-ylmethyl)morpholin-4-yl]quinoline-8-carbonitrile (compound 31a, 70 mg, 0.2 mmol), $Cs_2CO_3$ (261 mg, 800 µmol) and 1,4-dioxane (4 mL). The suspension was bubbled with $N_2$ for 5 mins and Ruphos Pd G2 (16 mg, 20 µmol) was added. The mixture was stirred at 90° C. for 16 hrs. After being cooled down, the mixture was diluted with EA (10 mL) and filtered through celite. The filtrate was concentrated to give compound 31c (150 mg) as a brown oil which was used in next step without further purification. MS: calc'd 590 ($MH^+$), measured 590 ($MH^+$).

Step 3: Preparation of 5-[(2R,6S)-2-methyl-6-[[4-(4,5,6,7-tetrahydrothiazolo[5,4-c]pyridin-2-yl)piperazin-1-yl]methyl]morpholin-4-yl]quinoline-8-carbonitrile (Example 31)

To a flask was added tert-butyl 2-[4-[[(2S,6R)-4-(8-cyano-5-quinolyl)-6-methyl-morpholin-2-yl]methyl]piperazin-1-yl]-6,7-dihydro-4H-thiazolo[5,4-c]pyridine-5-carboxylate (compound 31c, 150 mg), DCM (2 mL) and TFA (1 mL). The mixture was stirred at rt for 2 hrs and concentrated directly to give an oil which was purified via prep-HPLC to give Example 31 (16 mg) as a light brown solid. MS: calc'd 490 ($MH^+$), measured 490 ($MH^+$). $^1$H NMR (400 MHz, METHANOL-$d_4$) δ=8.99 (dd, J=1.6, 4.2 Hz, 1H), 8.66 (dd, J=1.7, 8.6 Hz, 1H), 8.16 (d, J=7.9 Hz, 1H), 7.65 (dd, J=4.2, 8.6 Hz, 1H), 7.28 (d, J=8.1 Hz, 1H), 4.55-4.45 (m, 1H), 4.32 (s, 2H), 4.24-4.13 (m, 1H), 4.03-3.71 (m, 4H), 3.71-3.49 (m, 6H), 3.47-3.37 (m, 4H), 3.00-2.88 (m, 2H), 2.82-2.68 (m, 2H), 1.32 (d, J=6.2 Hz, 3H).

Example 32

5-[(2S,6R)-2-[[3-(6,7-dihydro-5H-pyrrolo[3,4-d]pyrimidin-2-ylamino)pyrrolidin-1-yl]methyl]-6-methyl-morpholin-4-yl]quinoline-8-carbonitrile

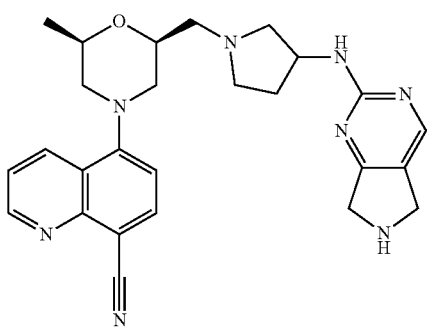 [SMILES: C[C@@H]1CN(c2ccc(C#N)c3ncccc23)C[C@H](CN2CCC(Nc3ncc4c(n3)CNC4)C2)O1]

The title compound was prepared according to the following scheme:

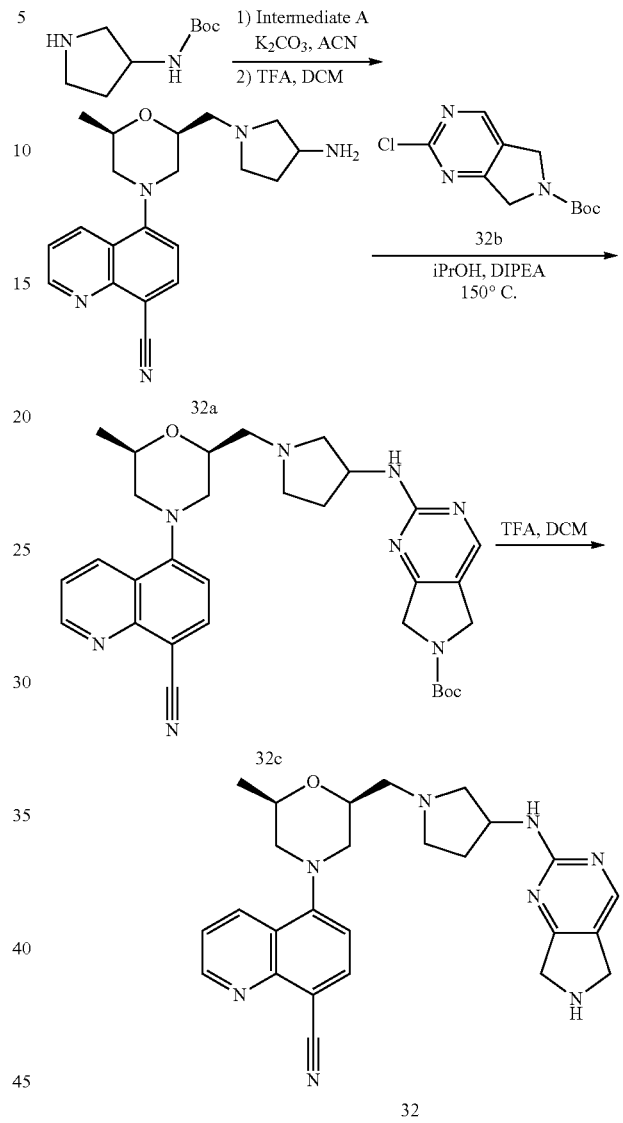

Step 1: Preparation of 5-[(2S,6R)-2-[(3-aminopyrrolidin-1-yl)methyl]-6-methyl-morpholin-4-yl]quinoline-8-carbonitrile (Compound 32a)

To a flask was added [(2R,6R)-4-(8-cyano-5-quinolyl)-6-methyl-morpholin-2-yl]methyl trifluoromethanesulfonate (Intermediate A, 100 mg, 241 µmol), tert-butyl pyrrolidin-3-ylcarbamate (CAS: 99724-19-3, Vendor: TCI, 67 mg, 361 µmol), $K_2CO_3$ (67 mg, 481 µmol) and acetonitrile (4 mL). The solution was stirred at 85° C. for 2 hrs. After being cooled down, the mixture was filtered through celite and concentrated to give an oil which was purified by flash column (EA/PE=0 to 100%) to give a yellow oil.

The oil was dissolved in DCM (2 ml) and TFA (1 mL), and stirred at rt for 2 hrs. The mixture was concentrated to give compound 32a (77 mg) as an oil. MS: calc'd 352 ($MH^+$), measured 352 ($MH^+$).

Step 2&3: Preparation of 5-[(2S,6R)-2-[[3-(6,7-dihydro-5H-pyrrolo[3,4-d]pyrimidin-2-ylamino)pyrrolidin-1-yl]methyl]-6-methyl-morpholin-4-yl]quinoline-8-carbonitrile Example 32

To a microwave tube was added 5-[(2S,6R)-2-[(3-aminopyrrolidin-1-yl)methyl]-6-methyl-morpholin-4-yl]quinoline-8-carbonitrile (compound 32a, 77 mg, 220 μmol), tert-butyl 2-chloro-5,7-dihydro-6H-pyrrolo[3,4-d]pyrimidine-6-carboxylate (compound 32b, CAS: 1211581-47-3, Vendor: PharmaBlock, 56 mg, 220 μmol), DIPEA (1.48 g, 2.00 mL, 11.50 mmol) and 2-propanol (4 mL). The tube was sealed and reacted under microwave at 150° C. for 2 hrs. After being cooled down, the mixture was concentrated to give an oil which was dissolved in DCM (2 mL) and TFA (1 mL) and stirred at rt for 2 hrs. The mixture was concentrated and purified by prep-HPLC to give Example 32 (39 mg) as a light yellow powder. MS: calc'd 471 (MH$^+$), measured 471 (MH$^+$). $^1$H NMR (400 MHz, METHANOL-d$_4$) δ=9.02 (dd, J=1.53, 4.22 Hz, 1H), 8.68 (br d, J=8.80 Hz, 1H), 8.47-8.40 (m, 1H), 8.19 (d, J=7.95 Hz, 1H), 7.67 (dd, J=4.40, 8.68 Hz, 1H), 7.30 (d, J=8.07 Hz, 1H), 4.71 (br s, 1H), 4.60 (s, 2H), 4.51-4.35 (m, 3H), 4.25-3.97 (m, 2H), 3.80 (br s, 1H), 3.63 (br s, 1H), 3.54-3.39 (m, 5H), 2.84-2.70 (m, 2H), 2.69-2.41 (m, 1H), 2.25 (br s, 1H), 1.36-1.24 (m, 3H).

Example 33

5-[(2R,6S)-2-methyl-6-[[4-(4,5,6,7-tetrahydrothiazolo[5,4-c]pyridin-2-yl)-1,4-diazepan-1-yl]methyl]morpholin-4-yl]quinoline-8-carbonitrile

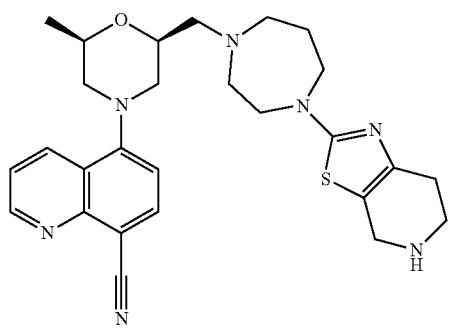 [SMILES: C[C@@H]1CN(c2ccc(C#N)c3ncccc23)C[C@H](CN2CCCN(c3nc4c(s3)CNCC4)CC2)O1]

The title compound was prepared in analogy to the preparation of Example 31 by using tert-butyl 1,4-diazepane-1-carboxylate (CAS: 112275-50-0, Vendor: Acros Organics) instead of tert-butyl piperazine-1-carboxylate. Example 33 (11 mg) was obtained as a light yellow solid. MS: calc'd 504 (MH$^+$), measured 504 (MH$^+$). $^1$H NMR (400 MHz, METHANOL-d$_4$) δ=9.02 (dd, J=1.59, 4.28 Hz, 1H), 8.68 (dd, J=1.59, 8.56 Hz, 1H), 8.19 (d, J=7.95 Hz, 1H), 7.67 (dd, J=4.28, 8.56 Hz, 1H), 7.30 (d, J=8.07 Hz, 1H), 4.49 (br t, J=9.48 Hz, 1H), 4.32 (s, 2H), 4.26-4.11 (m, 2H), 3.86-3.62 (m, 4H), 3.56 (br t, J=6.17 Hz, 3H), 3.49-3.35 (m, 6H), 2.94 (br t, J=6.17 Hz, 2H), 2.82-2.69 (m, 2H), 2.51-2.32 (m, 2H), 1.33 (d, J=6.24 Hz, 3H).

Example 34

5-[(2R,6S)-2-methyl-6-[[4-(6-methyl-7,8-dihydro-5H-1,6-naphthyridin-2-yl)piperazin-1-yl]methyl]morpholin-4-yl]quinoline-8-carbonitrile

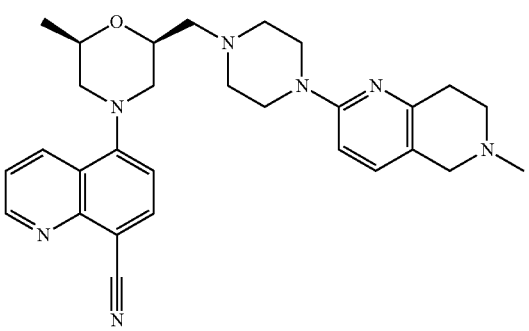 [SMILES: C[C@@H]1CN(c2ccc(C#N)c3ncccc23)C[C@H](CN2CCN(c3ccc4c(n3)CCN(C)C4)CC2)O1]

The title compound was prepared in analogy to the preparation of Example 1 by using 2-chloro-6-methyl-7,8-dihydro-5H-1,6-naphthyridine (compound 34a) instead of tert-butyl 2-bromo-6,7-dihydro-4H-pyrazolo[1,5-a]pyrazine-5-carboxylate and without step 4. Example 34 (2 mg) was obtained as a yellow oil. MS: calc'd 498 (MH$^+$), measured 498 (MH$^+$). $^1$H NMR (400 MHz, METHANOL-d$_4$) δ=9.00 (dd, J=1.65, 4.22 Hz, 1H), 8.67 (dd, J=1.65, 8.62 Hz, 1H), 8.17 (d, J=8.07 Hz, 1H), 7.66 (dd, J=4.28, 8.56 Hz, 1H), 7.47 (d, J=8.68 Hz, 1H), 7.29 (d, J=8.07 Hz, 1H), 6.90 (d, J=8.80 Hz, 1H), 4.58-4.33 (m, 3H), 4.33-3.97 (m, 3H), 3.96-3.33 (m, 12H), 3.26-3.12 (m, 2H), 3.06 (s, 3H), 2.83-2.71 (m, 2H), 1.38-1.27 (m, 3H).

The compound 34a was prepared according to the following scheme:

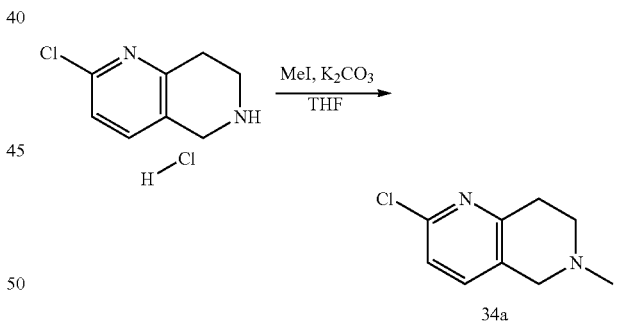

Preparation of 2-chloro-6-methyl-7,8-dihydro-5H-1,6-naphthyridine (Compound 34a)

To a flask was added 2-chloro-5,6,7,8-tetrahydro-1,6-naphthyridine hydrochloride (CAS: 766545-20-4, Vendor: PharmaBlock, 60 mg, 293 μmol), methyl iodide (62 mg, 27 μL, 439 μmol), K$_2$CO$_3$ (40 mg, 293 μmol) and THF (4 mL), the suspension was heated to 50° C. for 2 hrs. After being cooled down, the mixture was filtered through celite and concentrated to give compound 34a (55 mg) as a pale yellow solid. MS: calc'd 183 (MH$^+$), measured 183 (MH$^+$).

Example 35A and Example 35B

5-[(2S,6R)-2-[[(6R)-6-hydroxy-4-(5,6,7,8-tetrahydro-1,6-naphthyridin-2-yl)-1,4-diazepan-1-yl]methyl]-6-methyl-morpholin-4-yl]quinoline-8-carbonitrile and 5-[(2S,6R)-2-[[(6S)-6-hydroxy-4-(5,6,7,8-tetrahydro-1,6-naphthyridin-2-yl)-1,4-diazepan-1-yl]methyl]-6-methyl-morpholin-4-yl]quinoline-8-carbonitrile

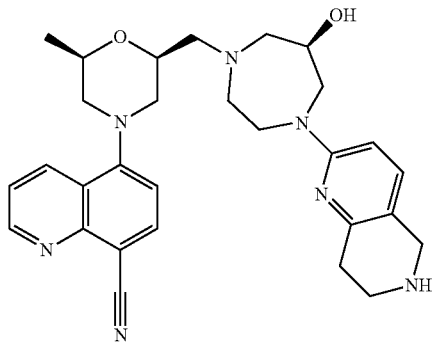

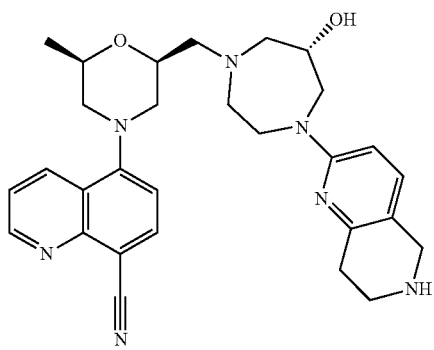

The title compounds were prepared in analogy to the preparation of Example 31 by using tert-butyl 6-hydroxy-1,4-diazepane-1-carboxylate (CAS: 956317-40-1, Vendor: WuXi Apptec) and tert-butyl 2-chloro-7,8-dihydro-5H-1,6-naphthyridine-6-carboxylate (CAS: 1151665-15-4, Vendor: PharmaBlock) instead of tert-butyl piperazine-1-carboxylate and tert-butyl 2-bromo-6,7-dihydrothiazolo[5,4-c]pyridine-5(4H)-carboxylate (compound 31b). The Example 35A (faster eluting) and Example 35B (slower eluting) were separated at step 3 by prep-HPLC (Gradient: 5-20% ACN in Water (0.05% TFA), Column: Sunfire C18, Diameter: 3 cm from Waters).

Example 35A (6 mg) was obtained as a light yellow solid. MS: calc'd 514 (MH$^+$), measured 514 (MH$^+$). $^1$H NMR (400 MHz, METHANOL-d$_4$) δ=8.99 (dd, J=1.59, 4.28 Hz, 1H), 8.65 (dd, J=1.71, 8.56 Hz, 1H), 8.16 (d, J=8.07 Hz, 1H), 7.65 (dd, J=4.16, 8.56 Hz, 1H), 7.42 (d, J=8.80 Hz, 1H), 7.27 (d, J=8.07 Hz, 1H), 6.79 (d, J=8.80 Hz, 1H), 4.54-4.31 (m, 2H), 4.25 (s, 2H), 4.19-4.05 (m, 2H), 3.99-3.68 (m, 3H), 3.63-3.52 (m, 3H), 3.51-3.33 (m, 5H), 3.28-3.15 (m, 2H), 3.06 (t, J=6.42 Hz, 2H), 2.83-2.66 (m, 2H), 1.34-1.19 (m, 3H).

Example 35B (6 mg) was obtained as a light yellow solid. MS: calc'd 514 (MH$^+$), measured 514 (MH$^+$). $^1$H NMR (400 MHz, METHANOL-d$_4$) δ=9.00 (dd, J=1.59, 4.16 Hz, 1H), 8.64 (dd, J=1.65, 8.50 Hz, 1H), 8.17 (d, J=7.95 Hz, 1H), 7.65 (dd, J=4.28, 8.56 Hz, 1H), 7.43 (d, J=8.80 Hz, 1H), 7.28 (d, J=8.07 Hz, 1H), 6.81 (d, J=8.80 Hz, 1H), 4.52-4.41 (m, 2H), 4.32-4.22 (m, 3H), 4.20-4.12 (m, 1H), 4.12-3.88 (m, 3H), 3.86-3.73 (m, 2H), 3.70-3.63 (m, 1H), 3.61-3.50 (m, 3H), 3.45-3.36 (m, 4H), 3.07 (br t, J=6.24 Hz, 2H), 2.85-2.67 (m, 2H), 1.29-1.14 (m, 3H).

Example 36

5-[(2R,6S)-2-methyl-6-[[1-(5,6,7,8-tetrahydro-1,6-naphthyridin-2-yl)-1,6-diazaspiro[3.3]heptan-6-yl]methyl]morpholin-4-yl]quinoline-8-carbonitrile

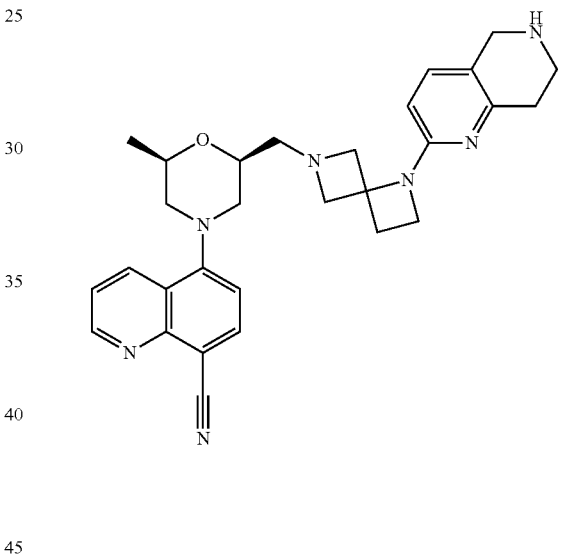

The title compound was prepared in analogy to the preparation of Example 31 by using tert-butyl 1,6-diazaspiro[3.3]heptane-1-carboxylate (CAS: 1330763-95-5, Vendor: PharmaBlock) and tert-butyl 2-chloro-7,8-dihydro-5H-1,6-naphthyridine-6-carboxylate (CAS: 1151665-15-4, Vendor: PharmaBlock) instead of tert-butyl piperazine-1-carboxylate and tert-butyl 2-bromo-6,7-dihydrothiazolo[5,4-c]pyridine-5(4H)-carboxylate (compound 31b). Example 36 (2 mg) was obtained as a light yellow solid. MS: calc'd 496 (MH$^+$), measured 496 (MH$^+$). $^1$H NMR (400 MHz, METHANOL-d$_4$) δ=9.02 (dd, J=1.59, 4.28 Hz, 1H), 8.69 (d, J=8.44 Hz, 1H), 8.19 (d, J=8.07 Hz, 1H), 7.68 (dd, J=4.22, 8.62 Hz, 1H), 7.57-7.43 (m, 1H), 7.32 (dd, J=4.58, 8.01 Hz, 1H), 6.49-6.30 (m, 1H), 5.20 (d, J=12.10 Hz, 1H), 4.59-4.45 (m, 2H), 4.40-4.23 (m, 3H), 4.22-4.09 (m, 1H), 4.00-3.90 (m, 2H), 3.90-3.70 (m, 1H), 3.65-3.49 (m, 3H), 3.48-3.37 (m, 3H), 3.29-3.21 (m, 1H), 3.19-3.13 (m, 1H), 2.91-2.81 (m, 1H), 2.81-2.72 (m, 2H), 2.71-2.63 (m, 1H), 1.31 (t, J=5.99 Hz, 3H).

Example 37

5-[(2S,6R)-2-[[9-(6,7-dihydro-5H-pyrrolo[3,4-b]pyridin-3-yl)-3-oxa-7,9-diazabicyclo[3.3.1]nonan-7-yl]methyl]-6-methyl-morpholin-4-yl]quinoline-8-carbonitrile

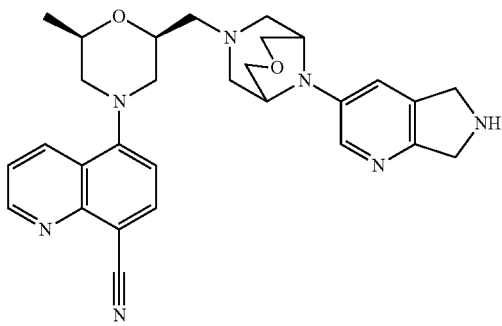 [SMILES: C[C@@H]1CN(c2ccc(C#N)c3ncccc23)C[C@H](CN2CC3COCC(C2)N3c2cnc3c(c2)CNC3)O1]

The title compound was prepared in analogy to the preparation of Example 10 by using 7-benzyl-3-oxa-7,9-diazabicyclo[3.3.1]nonane (CAS: 1357353-12-8, Vendor: Wuxi Apptec) instead of benzyl piperazine-1-carboxylate and replacing RuPhos Pd G2, $Cs_2CO_3$ and 1,4-dioxane with $Pd_2(dba)_3$, XantPhos, t-BuONa, and toluene in the Buchwald-Hartwig amination reaction. Example 37 (3 mg) was obtained as a yellow solid. MS: calc'd 512 (MH$^+$), measured 512 (MH$^+$). $^1$H NMR (400 MHz, METHANOL-d$_4$) δ=9.01 (dd, J=1.5, 4.3 Hz, 1H), 8.67 (dd, J=1.7, 8.6 Hz, 1H), 8.35 (d, J=2.4 Hz, 1H), 8.18 (d, J=8.1 Hz, 1H), 7.67 (dd, J=4.3, 8.6 Hz, 1H), 7.54 (d, J=2.2 Hz, 1H), 7.30 (d, J=8.1 Hz, 1H), 4.71 (s, 2H), 4.54 (s, 3H), 4.40-4.06 (m, 7H), 3.98 (br d, J=12.5 Hz, 2H), 3.61 (br t, J=12.9 Hz, 2H), 3.46 (br dd, J=6.2, 12.2 Hz, 2H), 3.35 (br s, 2H), 2.79 (q, J=11.2 Hz, 2H), 1.32 (d, J=6.4 Hz, 3H).

Example 38

5-[(2S,6R)-2-[[3-(isoindolin-5-ylamino)pyrrolidin-1-yl]methyl]-6-methyl-morpholin-4-yl]quinoline-8-carbonitrile

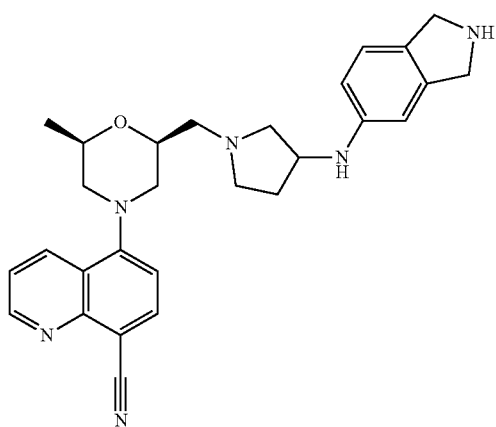 [SMILES: C[C@@H]1CN(c2ccc(C#N)c3ncccc23)C[C@H](CN2CCC(Nc3ccc4c(c3)CNC4)C2)O1]

The title compound was prepared in analogy to the preparation of Example 7 by using benzyl 3-aminopyrrolidine-1-carboxylate (CAS: 185057-50-5, Vendor: PharmaBlock) instead of benzyl piperazine-1-carboxylate, replacing RuPhos Pd G2 with $Pd_2(dba)_3$, (R)-BINAP in the Buchwald-Hartwig amination reaction and replacing MeOH by isopropanol in the hydrogenation reaction. Example 38 (12 mg) was obtained as a yellow solid. MS: calc'd 469 (MH$^+$), measured 469 (MH$^+$). $^1$H NMR (400 MHz, METHANOL-d$_4$) δ=8.97 (d, J=3.9 Hz, 1H), 8.64 (br d, J=8.6 Hz, 1H), 8.14 (d, J=8.1 Hz, 1H), 7.63 (br dd, J=4.4, 8.6 Hz, 1H), 7.25 (d, J=8.1 Hz, 1H), 7.20 (d, J=8.3 Hz, 1H), 6.75-6.67 (m, 2H), 4.51 (d, J=15.9 Hz, 4H), 4.44-4.25 (m, 2H), 4.22-3.54 (m, 4H), 3.54-3.35 (m, 5H), 2.81-2.67 (m, 2H), 2.48 (br s, 1H), 2.11 (br s, 1H), 1.29 (br d, J=5.4 Hz, 3H).

Example 39

5-[(2R,6S)-2-methyl-6-[[4-(5,6,7,8-tetrahydropyrido[4,3-d]pyrimidin-2-yl)-1,4-diazepan-1-yl]methyl]morpholin-4-yl]quinoline-8-carbonitrile

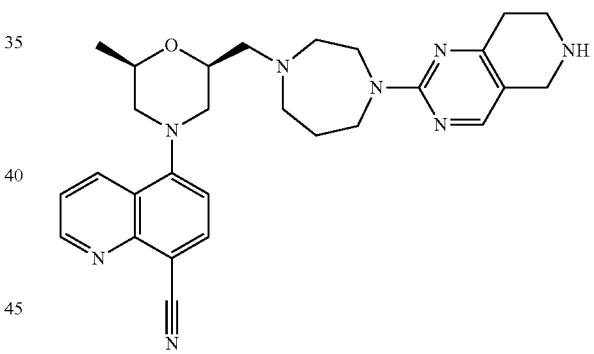

The title compound was prepared in analogy to the preparation of Example 32 by using tert-butyl 1,4-diazepane-1-carboxylate (CAS: 112275-50-0, Vendor: Acros Organics) and tert-butyl 2-chloro-7,8-dihydro-5H-pyrido[4,3-d]pyrimidine-6-carboxylate (compound 29a) instead of tert-butyl pyrrolidin-3-ylcarbamate and tert-butyl 2-chloro-5,7-dihydro-6H-pyrrolo[3,4-d]pyrimidine-6-carboxylate (compound 32b) and replacing 2-propanol by DMA in the S$_N$Ar reaction. Example 39 (11 mg) was obtained as a yellow solid. MS: calc'd 499 (MH$^+$), measured 499 (MH$^+$). $^1$H NMR (400 MHz, METHANOL-d$_4$) δ=9.00-8.95 (m, 1H), 8.65 (br d, J=8.6 Hz, 1H), 8.27 (s, 1H), 8.18-8.12 (dd, 1H), 7.64 (dd, J=4.4, 8.6 Hz, 1H), 7.26 (br d, J=8.1 Hz, 1H), 4.54-4.32 (m, 2H), 4.27 (s, 2H), 4.20-4.11 (m, 1H), 4.09-3.67 (m, 5H), 3.57 (t, J=6.5 Hz, 2H), 3.52-3.33 (m, 6H), 3.05 (t, J=6.5 Hz, 2H), 2.73 (q, J=10.8 Hz, 2H), 2.40-2.26 (m, 2H), 1.30 (br d, J=6.1 Hz, 3H).

Example 40

5-[(2R,6S)-2-methyl-6-[[4-(5,6,7,8-tetrahydropyrido[3,4-b]pyrazin-3-yl)piperazin-1-yl]methyl]morpholin-4-yl]quinoline-8-carbonitrile

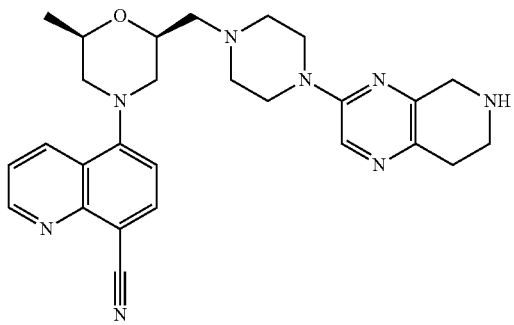

The title compound was prepared according to the following scheme:

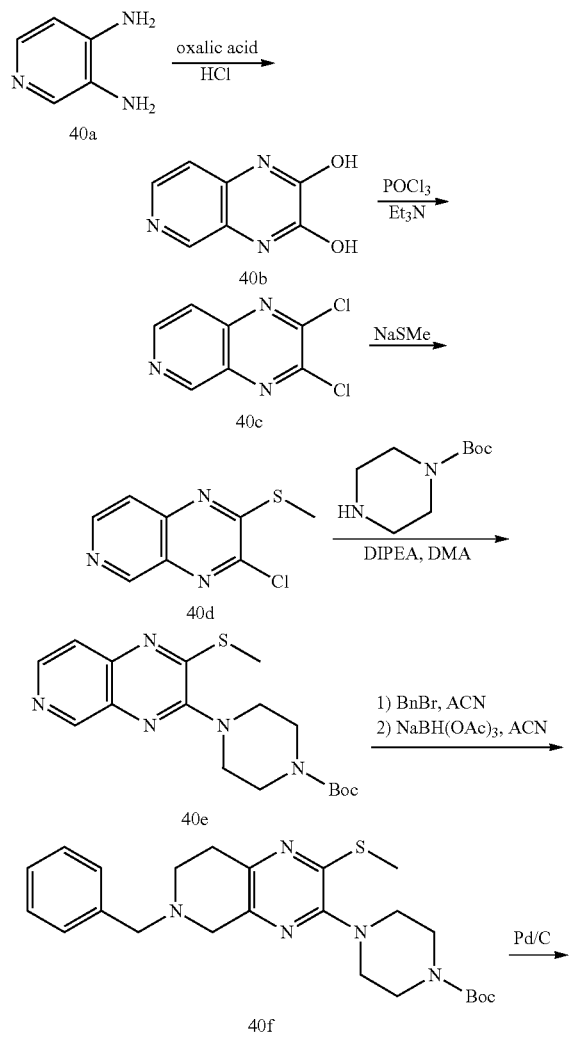

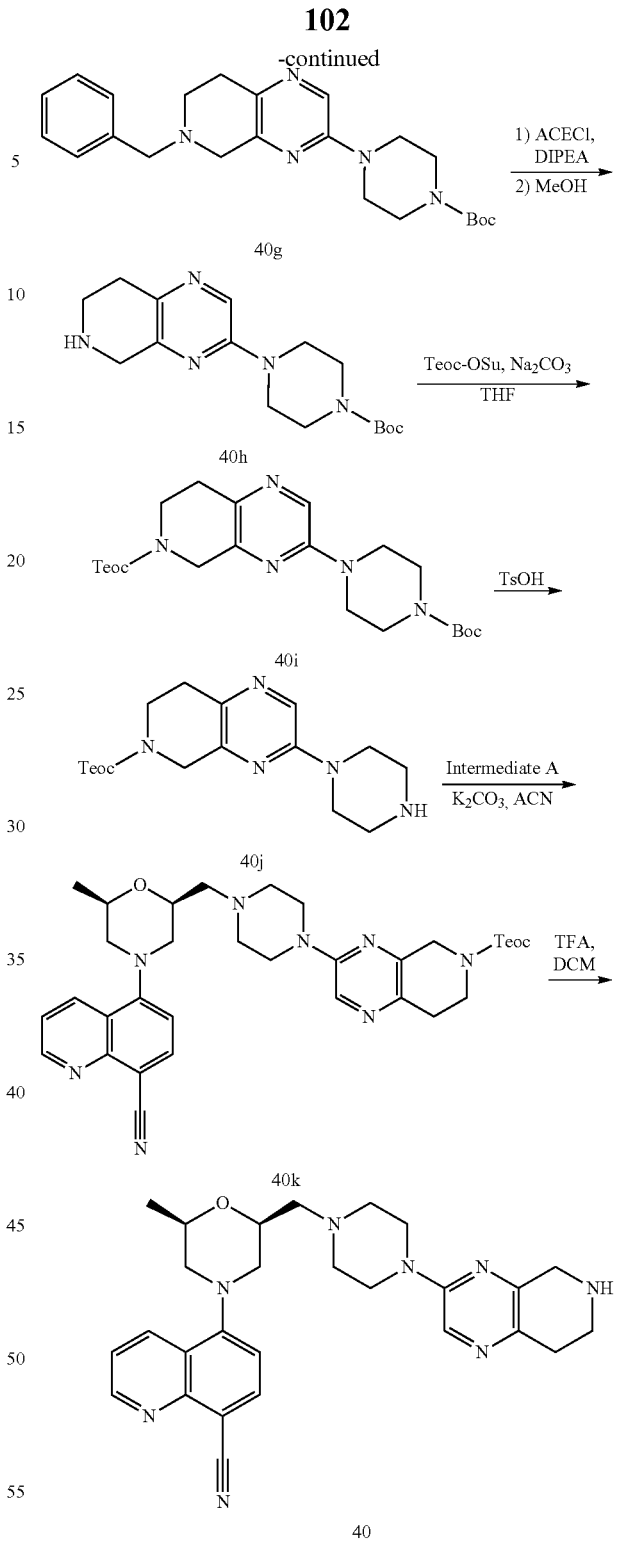

Step 1: Preparation of pyrido[3,4-b]pyrazine-2,3-diol (Compound 40b)

To a solution of 3,4-diaminopyridine (compound 40a, CAS: 54-96-6, Vendor: Alfa Aesar, 10.00 g, 91.63 mmol) in HCl (4 N, 100 mL) was added oxalic acid (9.90 g, 109.96 mmol). The reaction was stirred at 100° C. for 18 hrs. After being cooled down, the solid was collected by filtration, washed with EtOH (50 mL) and dried to give the compound 40b (12.00 g) as a yellow solid.

Step 2: Preparation of 2,3-dichloropyrido[3,4-b]pyrazine (Compound 40c)

To a solution of pyrido[3,4-b]pyrazine-2,3-diol (compound 40b, 12.00 g, 73.56 mmol) in trichlorophosphate (122.00 mL, 1.27 mol) was added triethylamine (10.25 mL, 73.56 mmol). The reaction mixture was heated at 130° C. for 48 hrs. Then the mixture was concentrated and quenched with aq.NaHCO$_3$. After filtration, the aqueous solution was extracted with EA (500 mL) twice. The organic layer was washed with brine (20 mL), dried over anhydrous Na$_2$SO$_4$, filtered and concentrated. The residue was purified by flash column (PE:EA=5:1) to give compound 40c (900 mg) as a white solid. MS: calc'd 200 (MH$^+$), measured 200 (MH$^+$).

Step 3: Preparation of 3-chloro-2-methylsulfanyl-pyrido[3,4-b]pyrazine (Compound 40d)

To a solution of 2,3-dichloropyrido[3,4-b]pyrazine (compound 40c, 800 mg, 4.00 mmol) in THF (60 mL) was added sodium thiomethoxide (308 mg, 4.40 mmol) at 0° C. After being stirred at 0° C. for 1 h, the reaction was quenched with aq. NH$_4$Cl (40 mL), and extracted with EA (40 mL). The organic layer was washed with brine (20 mL) twice, dried over anhydrous Na$_2$SO$_4$, filtered and concentrated. The residue was purified by flash column (PE:EA=5:1) to give compound 40d (750 mg) as a yellow gum. MS: calc'd 212 (MH$^+$), measured 212 (MH$^+$).

Step 4: Preparation of tert-butyl 4-(2-methylsulfanylpyrido[3,4-b]pyrazin-3-yl)piperazine-1-carboxylate (Compound 40e)

To a solution of 3-chloro-2-methylsulfanyl-pyrido[3,4-b]pyrazine (compound 40d, 750 mg, 3.54 mmol) in N,N-dimethylacetamide (36 mL) was added tert-butyl piperazine-1-carboxylate (726 mg, 3.90 mmol) and N,N-diisopropylethylamine (1.23 mL, 7.09 mmol). After being stirred at 50° C. for 4 hrs, the reaction mixture was diluted with EA (50 mL) and then washed with brine (20 mL). The organic layer was concentrated and purified by flash column (PE:EA=5:1) to give compound 40e (500 mg) as a yellow gum. MS: calc'd 362 (MH$^+$), measured 362 (MH$^+$).

Step 5: Preparation of tert-butyl 4-(6-benzyl-2-methylsulfanyl-7,8-dihydro-5H-pyrido[3,4-b]pyrazin-3-yl)piperazine-1-carboxylate (Compound 40f)

To a solution of tert-butyl 4-(2-methylsulfanylpyrido[3,4-b]pyrazin-3-yl)piperazine-1-carboxylate (compound 40e, 500 mg, 1.38 mmol) in acetonitrile (10 mL) was added benzyl bromide (0.17 mL, 1.46 mmol). After being stirred at 80° C. for 2 hrs, the reaction mixture was concentrated to give a yellow gum, which was dissolved in acetonitrile (30 mL) again. Sodium triacetoxyborohydride (1.45 g, 6.85 mmol) was added at 0° C., and the reaction was stirred at 20° C. for 4 hrs. After concentration, the residue was purified by flash column (DCM:MeOH=20:1) to give compound 40f (500 mg) as a yellow gum. MS: calc'd 456 (MH$^+$), measured 456 (MH$^+$).

Step 6: Preparation of tert-butyl 4-(6-benzyl-7,8-dihydro-5H-pyrido[3,4-b]pyrazin-3-yl)piperazine-1-carboxylate (Compound 40g)

To a solution of tert-butyl 4-(6-benzyl-2-methylsulfanyl-7,8-dihydro-5H-pyrido[3,4-b]pyrazin-3-yl)piperazine-1-carboxylate (compound 40f, 500 mg, 1.10 mmol) in THF (30 mL) was added Pd/C (10 wt. %, 300 mg, 1.10 mmol) and triethylsilane (3.00 g, 25.86 mmol) dropwise at 0° C. After being stirred at 20° C. for 18 hrs, the reaction mixture was filtered and concentrated. The residue was purified by flash column (PE:EA=5:1 to 1:1) to give compound 40g (250 mg) as a yellow solid. MS: calc'd 410 (MH$^+$), measured 410 (MH$^+$).

Step 7: Preparation of tert-butyl 4-(5,6,7,8-tetrahydropyrido[3,4-b]pyrazin-3-yl)piperazine-1-carboxylate (Compound 40h)

To a solution of tert-butyl 4-(6-benzyl-7,8-dihydro-5H-pyrido[3,4-b]pyrazin-3-yl)piperazine-1-carboxylate (compound 40g, 200 mg, 0.49 mmol) in 1,2-dichloroethane (4 mL) was added N,N-diisopropylethylamine (0.26 mL, 1.47 mmol) and 1-chloroethyl chloroformate (173 mg, 1.22 mmol) at 0° C. After being stirred at 25° C. for 2 hrs, the reaction mixture was concentrated and methanol (4 mL) was added. The mixture was further heated at 60° C. for 2 hrs. After concentration, the residue was purified by prep-TLC (DCM:MeOH=10:1) to give compound 40h (150 mg) as a white solid. MS: calc'd 320 (MH$^+$), measured 320 (MH$^+$).

Step 8: Preparation of 2-trimethylsilylethyl 3-(4-tert-butoxycarbonylpiperazin-1-yl)-7,8-dihydro-5H-pyrido[3,4-b]pyrazine-6-carboxylate (Compound 40i)

To a solution of tert-butyl 4-(5,6,7,8-tetrahydropyrido[3,4-b]pyrazin-3-yl)piperazine-1-carboxylate (compound 40h, 100 mg, 0.31 mmol) in THF (2 mL) was added sodium carbonate (83 mg, 0.78 mmol) and Teoc-OSu (162 mg, 0.63 mmol). After being stirred at 20° C. for 4 hrs, the reaction mixture was concentrated and dissolved in EA (20 ml). The organic layer was washed with water (20 mL) twice and brine (20 mL) once, dried over Na$_2$SO$_4$ and concentrated. The residue was purified by prep-TLC (PE:EA=1:1) to give compound 40i (60 mg) as a yellow gum. MS: calc'd 464 (MH$^+$), measured 464 (MH$^+$).

Step 9: Preparation of 2-trimethylsilylethyl 3-piperazin-1-yl-7,8-dihydro-5H-pyrido[3,4-b]pyrazine-6-carboxylate (Compound 40j)

To a solution of 2-trimethylsilylethyl 3-(4-tert-butoxycarbonylpiperazin-1-yl)-7,8-dihydro-5H-pyrido[3,4-b]pyrazine-6-carboxylate (compound 40i, 60 mg, 0.13 mmol) in methanol (2 mL) was added p-toluenesulfonic acid (33 mg, 0.19 mmol). After being stirred at 55° C. for 5 hrs, the reaction mixture was concentrated and purified by prep-TLC (DCM:MeOH=10:1) to give compound 40j (40 mg) as a yellow solid. MS: calc'd 364 (MH$^+$), measured 364 (MH$^+$).

Step 10: Preparation of 2-trimethylsilylethyl 3-[4-[[(2S,6R)-4-(8-cyano-5-quinolyl)-6-methyl-morpholin-2-yl]methyl]piperazin-1-yl]-7,8-dihydro-5H-pyrido[3,4-b]pyrazine-6-carboxylate (Compound 40k)

To a solution of [(2R,6R)-4-(8-cyano-5-quinolyl)-6-methyl-morpholin-2-yl]methyl trifluoromethanesulfonate (Intermediate A, 40 mg, 0.10 mmol) in acetonitrile (4 mL) was added potassium carbonate (40 mg, 0.29 mmol) and 2-trimethylsilylethyl 3-piperazin-1-yl-7,8-dihydro-5H-pyrido[3,4-b]pyrazine-6-carboxylate (compound 40j, 40 mg, 0.11 mmol). After being stirred at 55° C. for 2 hrs, the reaction mixture was filtered, concentrated and purified by prep-TLC (DCM:MeOH=20:1) to give compound 40k (40 mg) as a yellow gum. MS: calc'd 629 (MH$^+$), measured 629 (MH$^+$).

Step 11: Preparation of 5-[(2R,6S)-2-methyl-6-[[4-(5,6,7,8-tetrahydropyrido[3,4-b]pyrazin-3-yl)piperazin-1-yl]methyl]morpholin-4-yl]quinoline-8-carbonitrile (Example 40)

To a solution of 2-trimethylsilylethyl 3-[4-[[(2S,6R)-4-(8-cyano-5-quinolyl)-6-methyl-morpholin-2-yl]methyl]piperazin-1-yl]-7,8-dihydro-5H-pyrido[3,4-b]pyrazine-6-carboxylate (compound 40k, 40 mg, 0.06 mmol) in DCM (4 mL) was added trifluoroacetic acid (0.93 mL, 12.07 mmol). After being stirred at 20° C. for 1 h, the reaction mixture was concentrated and purified by prep-HPLC to give Example 40 (24 mg) as a white solid. MS: calc'd 485 (MH$^+$), measured 485 (MH$^+$). $^1$H NMR (400 MHz, METHANOL-d$_4$) δ=9.01 (dd, J=1.6, 4.4 Hz, 1H), 8.69 (d, J=8.4 Hz, 1H), 8.36 (s, 1H), 8.19 (d, J=8.0 Hz, 1H), 7.67 (dd, J=4.4, 8.4 Hz, 1H), 7.30 (d, J=8.0 Hz, 1H), 4.67-4.50 (m, 1H), 4.33 (s, 2H), 4.27-4.10 (m, 1H), 3.96-3.33 (m, 14H), 3.25-3.15 (m, 2H), 2.81-2.76 (m, 2H), 1.34 (d, J=6.0 Hz, 3H).

Example 41

5-[(2R,6S)-2-methyl-6-[[4-(5-methyl-6,7-dihydro-5H-pyrrolo[3,4-b]pyridin-3-yl)piperazin-1-yl]methyl]morpholin-4-yl]quinoline-8-carbonitrile

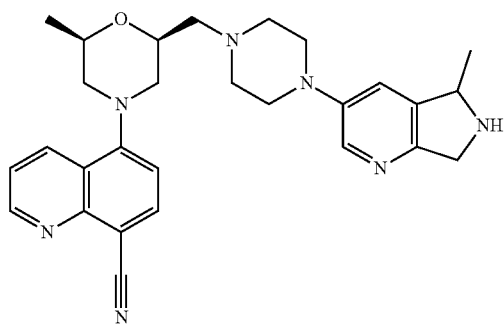 [SMILES: CC1NCc2ncc(N3CCN(C[C@H]4CN(c5ccc(C#N)c6ncccc56)C[C@@H](C)O4)CC3)cc21]

The title compound was prepared in analogy to the preparation of Example 40, step 8-11 by using tert-butyl 4-(5-methyl-6,7-dihydro-5H-pyrrolo[3,4-b]pyridin-3-yl)piperazine-1-carboxylate (compound 41i) instead of tert-butyl 4-(5,6,7,8-tetrahydropyrido[3,4-b]pyrazin-3-yl)piperazine-1-carboxylate (compound 40h). Example 41 (20 mg) was obtained as a brown solid. MS: calc'd 484 (MH$^+$), measured 484 (MH$^+$). $^1$H NMR (400 MHz, METHANOL-d$_4$) δ=8.98 (dd, J=1.6, 4.3 Hz, 1H), 8.66 (dd, J=1.6, 8.7 Hz, 1H), 8.37 (d, J=2.3 Hz, 1H), 8.15 (d, J=7.9 Hz, 1H), 7.65 (dd, J=4.2, 8.6 Hz, 1H), 7.57 (d, J=2.1 Hz, 1H), 7.28 (d, J=8.1 Hz, 1H), 5.11 (q, J=6.8 Hz, 1H), 4.61-4.51 (m, 3H), 4.26-4.18 (m, 1H), 4.15-3.39 (m, 12H), 2.86-2.71 (m, 2H), 1.75 (d, J=6.8 Hz, 3H), 1.33 (d, J=6.2 Hz, 3H).

The compound 41i was prepared according to the following scheme:

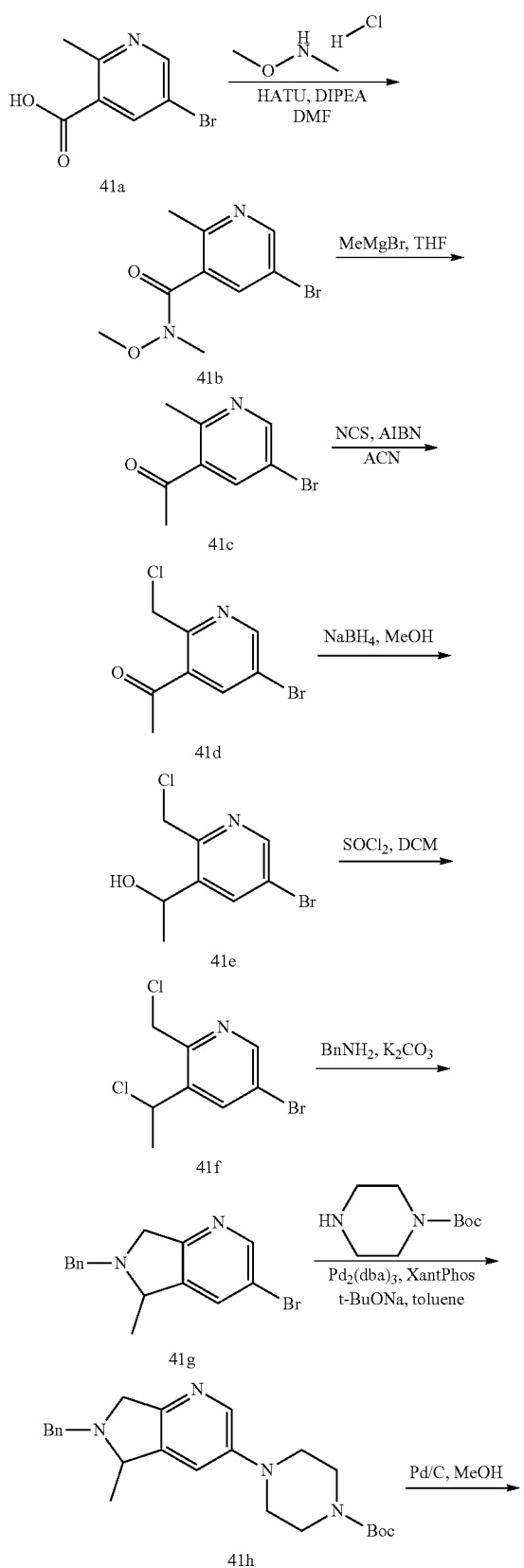

-continued

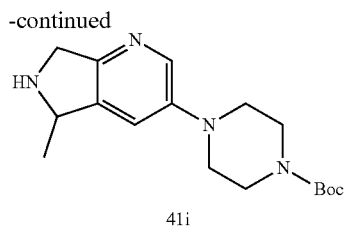

41i

Step 1: Preparation of 5-bromo-N-methoxy-N,2-dimethyl-pyridine-3-carboxamide (Compound 41b)

To a solution of 5-bromo-2-methyl-pyridine-3-carboxylic acid (compound 41a, 2.50 g, 11.57 mmol), DIPEA (5.98 g, 46.29 mmol) and HATU (5.28 g, 13.89 mmol) in DMF (40 mL) was added N-methoxymethanamine hydrochloride (2.26 g, 23.14 mmol) at 0° C. After being stirred at 40° C. for 18 hrs, the reaction was quenched by addition of aq. NH$_4$Cl (50 mL). The mixture was diluted with water (100 mL) and extracted with EtOAc (80 mL) three times. The combined organic layer was washed with water (60 mL) twice and brine (40 mL) once, dried over Na$_2$SO$_4$, concentrated and purified by flash column (PE:EtOAc=3:1) to give compound 40b (2.40 g) as a colorless oil. MS: calc'd 259 (MH$^+$), measured 259 (MH$^+$).

Step 2: Preparation of 1-(5-bromo-2-methyl-3-pyridyl)ethanone (Compound 41c)

To a solution of 5-bromo-N-methoxy-N,2-dimethyl-pyridine-3-carboxamide (compound 41b, 2.40 g, 9.26 mmol) in THF (40 mL) was added methylmagnesium bromide (3.0 M in diethyl ether, 4.63 mL, 13.89 mmol) at 0° C. After being stirred at 15° C. for 3 hrs, the reaction was quenched by addition of aq. NH$_4$Cl (40 mL), diluted with water (60 mL) and extracted with EtOAc (40 mL) three times. The combined organic layer was washed with water (50 mL) twice and brine (30 mL) once, dried over Na$_2$SO$_4$, concentrated and purified by flash column (PE:EtOAc=10:1) to give compound 41c (1.60 g) as a colorless oil. MS: calc'd 214 (MH$^+$), measured 214 (MH$^+$).

Step 3: Preparation of 1-[5-bromo-2-(chloromethyl)-3-pyridyl]ethanone (Compound 41d)

To a solution of 1-(5-bromo-2-methyl-3-pyridyl)ethanone (compound 41c, 1.50 g, 7.01 mmol) in acetonitrile (30 mL) was added NCS (1.50 g, 11.24 mmol) and AIBN (173 mg, 1.05 mmol). After being stirred at 80° C. for 16 hrs, the reaction was quenched by addition of aq. NH$_4$Cl (40 mL), diluted with water (60 mL) and extracted with EtOAc (50 mL) three times. The combined organic layer was washed with water (50 mL) twice and brine (30 mL) once, dried over Na$_2$SO$_4$, concentrated and purified by flash column to give compound 41d (700 mg) as a colorless oil. MS: calc'd 248 (MH$^+$), measured 248 (MH$^+$).

Step 4: Preparation of 1-[5-bromo-2-(chloromethyl)-3-pyridyl]ethanol (Compound 41e)

To a solution of 1-[5-bromo-2-(chloromethyl)-3-pyridyl]ethanone (compound 41d, 700 mg, 2.82 mmol) in methanol (20 mL) was added sodium borohydride (213 mg, 5.63 mmol) at 0° C. and stirred for 0.5 h. Then the reaction was quenched by addition of aq. NH$_4$Cl (10 mL), diluted with water (60 mL) and extracted with EtOAc (40 mL) three times. The combined organic layer was washed with water (30 mL) twice and brine (20 mL) once, dried over Na$_2$SO$_4$ and concentrated to give crude product compound 41e (600 mg) as a pink oil. MS: calc'd 250 (MH$^+$), measured 250 (MH$^+$).

Step 5: Preparation of 5-bromo-3-(1-chloroethyl)-2-(chloromethyl)pyridine (Compound 41f)

To a solution of 1-[5-bromo-2-(chloromethyl)-3-pyridyl]ethanol (compound 41e, 600 mg, 2.40 mmol) in DCM (15 mL) was added thionyl chloride (1.42 g, 11.98 mmol) at 0° C. After being stirred at 15° C. for 18 hrs, the reaction mixture was concentrated to give compound 41f (550 mg) as a yellow oil. MS: calc'd 268 (MH$^+$), measured 268 (MH$^+$).

Step 6: Preparation of 6-benzyl-3-bromo-5-methyl-5,7-dihydropyrrolo[3,4-b]pyridine (Compound 41g)

To a solution of 5-bromo-3-(1-chloroethyl)-2-(chloromethyl)pyridine (compound 41f, 550 mg, 2.05 mmol) in ethanol (5 mL) was added potassium carbonate (488 mg, 3.53 mmol) and benzylamine (0.19 mL, 1.76 mmol). After being stirred at 65° C. for 3 hrs, the reaction mixture was filtered, concentrated and purified by flash column (PE:EtOAc=5:1) to give compound 41g (300 mg) as a colorless oil. MS: calc'd 303 (MH$^+$), measured 303 (MH$^+$).

Step 7: Preparation of tert-butyl 4-(6-benzyl-5-methyl-5,7-dihydropyrrolo[3,4-b]pyridin-3-yl)piperazine-1-carboxylate (Compound 41h)

To a solution of 6-benzyl-3-bromo-5-methyl-5,7-dihydropyrrolo[3,4-b]pyridine (compound 41g) (300 mg, 0.99 mmol), tert-butyl piperazine-1-carboxylate (205 mg, 1.10 mmol), sodium tert-butoxide (192 mg, 2.00 mmol), 9,9-dimethyl-4,5-bis(diphenylphosphino)xanthene (116 mg, 0.20 mmol) in toluene (4 mL) was added tris(dibenzylideneacetone)dipalladium (0) (92 mg, 0.10 mmol). After being stirred at 110° C. under N$_2$ for 3 hrs, the reaction mixture was filtered, concentrated and purified by prep-TLC (PE:EtOAc=2:1) to give compound 41h (150 mg) as a yellow solid. MS: calc'd 409 (MH$^+$), measured 409 (MH$^+$).

Step 8: Preparation of tert-butyl 4-(5-methyl-6,7-dihydro-5H-pyrrolo[3,4-b]pyridin-3-yl)piperazine-1-carboxylate (Compound 41i)

To a solution of tert-butyl 4-(6-benzyl-5-methyl-5,7-dihydropyrrolo[3,4-b]pyridin-3-yl)piperazine-1-carboxylate (compound 41h, 130 mg, 0.32 mmol) in methanol (8 mL) was added Pd/C (10 wt. %, 130 mg). After being stirred at 50° C. under H$_2$ atmosphere for 18 hrs, the mixture was then filtered and concentrated to give compound 41i (80 mg) as a yellow oil. MS: calc'd 319 (MH$^+$), measured 319 (MH$^+$).

Example 42

5-[(2S,6R)-2-[[[1-(6,7-dihydro-5H-pyrrolo[3,4-d]pyrimidin-2-yl)azetidin-3-yl]amino]methyl]-6-methyl-morpholin-4-yl]quinoline-8-carbonitrile

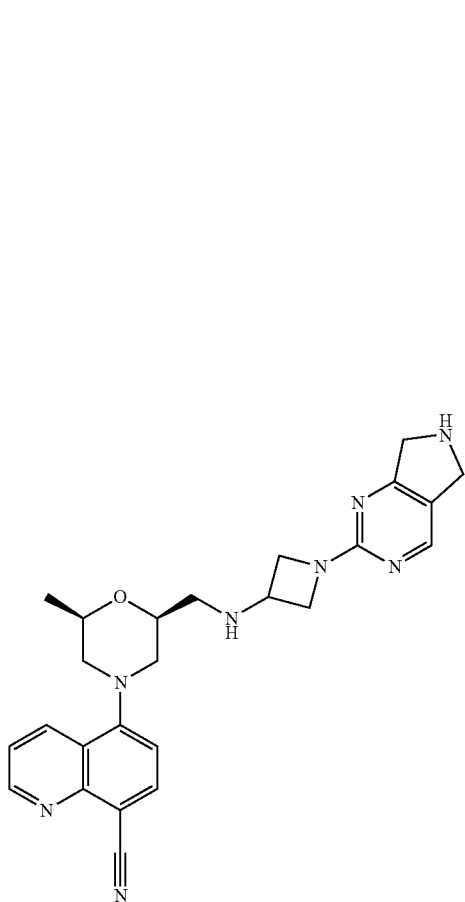 [SMILES: C[C@@H]1CN(c2ccc(C#N)c3ncccc23)C[C@H](CNC2CN(c3ncc4c(n3)CNC4)C2)O1]

The title compound was prepared in analogy to the preparation of Example 32 by using tert-butyl 3-aminoazetidine-1-carboxylate (CAS: 193269-78-2, Vendor: PharmaBlock) instead of tert-butyl pyrrolidin-3-ylcarbamate. Example 42 (13 mg) was obtained as a yellow solid. MS: calc'd 457 (MH$^+$), measured 457 (MH$^+$). $^1$H NMR (400 MHz, METHANOL-d$_4$) δ=9.01 (dd, J=1.6, 4.2 Hz, 1H), 8.68 (dd, J=1.6, 8.6 Hz, 1H), 8.45 (s, 1H), 8.18 (d, J=8.1 Hz, 1H), 7.67 (dd, J=4.3, 8.6 Hz, 1H), 7.30 (d, J=8.1 Hz, 1H), 4.61 (s, 2H), 4.57-4.44 (m, 4H), 4.40-4.26 (m, 4H), 4.25-4.11 (m, 1H), 3.53-3.37 (m, 3H), 3.23 (dd, J=9.9, 12.8 Hz, 1H), 2.86-2.70 (m, 2H), 1.34 (d, J=6.4 Hz, 3H).

Example 43

5-[(2S,6R)-2-[[[1-(6,7-dihydro-5H-pyrrolo[3,4-b]pyridin-3-yl)azetidin-3-yl]amino]methyl]-6-methyl-morpholin-4-yl]quinoline-8-carbonitrile The title compound was prepared in analogy to the preparation of Example 31 by using tert-butyl 3-aminoazetidine-1-carboxylate and tert-butyl 3-bromo-5,7-dihydropyrrolo[3,4-b]pyridine-6-carboxylate instead of tert-butyl piperazine-1-carboxylate and tert-butyl 2-bromo-6,7-dihydrothiazolo[5,4-c]pyridine-5 (4H)-carboxylate (compound 31b). Example 43 (22 mg) was obtained as a yellow solid. MS: calc'd 456 (MH$^+$), measured 456 (MH$^+$). $^1$H NMR (400 MHz, METHANOL-d$_4$) δ=9.02 (dd, J=1.6, 4.3 Hz, 1H), 8.68 (dd, J=1.7, 8.6 Hz, 1H), 8.19 (d, J=8.1 Hz, 1H), 7.86 (d, J=2.6 Hz, 1H), 7.67 (dd, J=4.2, 8.6 Hz, 1H), 7.30 (d, J=8.1 Hz, 1H), 7.06 (d, J=2.3 Hz, 1H), 4.66 (s, 2H), 4.50 (s, 2H), 4.43-4.29 (m, 4H), 4.24-4.09 (m, 3H), 3.53-3.36 (m, 3H), 3.23 (dd, J=9.8, 12.9 Hz, 1H), 2.88-2.68 (m, 2H), 1.34 (d, J=6.2 Hz, 3H).

Example 44

5-[(2R,6S)-2-methyl-6-[[8-(1,2,3,4-tetrahydroisoquinolin-6-yl)-5-oxa-2,8-diazaspiro[3.5]nonan-2-yl]methyl]morpholin-4-yl]quinoline-8-carbonitrile

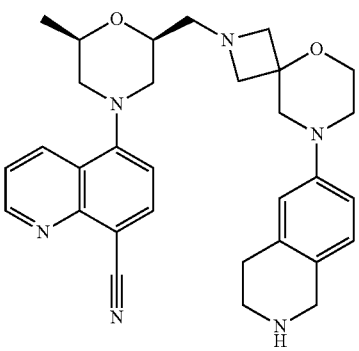 [SMILES: C[C@@H]1CN(c2ccc(C#N)c3ncccc23)C[C@H](CN2CC3(C2)CN(c2ccc4c(c2)CCNC4)CCO3)O1]

The title compound was prepared in analogy to the preparation of Example 31 by using tert-butyl 5-oxa-2,8-diazaspiro[3.5]nonane-8-carboxylate (CAS: 1251005-61-4, Vendor: PharmaBlock) and tert-butyl 6-bromo-3,4-dihydro-1H-isoquinoline-2-carboxylate (CAS: 893566-74-0, Vendor: Wuxi) instead of tert-butyl piperazine-1-carboxylate and tert-butyl 2-bromo-6,7-dihydrothiazolo[5,4-c]pyridine-5 (4H)-carboxylate (compound 31b). Example 44 (25 mg) was obtained as a light yellow powder. MS: calc'd 525 (MH+), measured 525 (MH+). $^1$H NMR (400 MHz, METHANOL-d$_4$) δ=9.01 (dd, J=1.6, 4.3 Hz, 1H), 8.67 (dd, J=1.3, 8.6 Hz, 1H), 8.18 (d, J=8.1 Hz, 1H), 7.67 (dd, J=4.2, 8.6 Hz, 1H), 7.29 (d, J=8.1 Hz, 1H), 7.16 (d, J=8.6 Hz, 1H), 7.00 (dd, J=2.4, 8.6 Hz, 1H), 6.91 (d, J=2.2 Hz, 1H), 4.58-4.38 (m, 2H), 4.38-4.20 (m, 5H), 4.19-4.09 (m, 1H), 4.03-3.87 (m, 2H), 3.63-3.56 (m, 1H), 3.63-3.56 (m, 1H), 3.55-3.46 (m, 3H), 3.46-3.39 (m, 3H), 3.22-3.06 (m, 4H), 2.80 (t, J=11.1 Hz, 1H), 2.72 (dd, J=10.3, 12.2 Hz, 1H), 1.31 (d, J=6.2 Hz, 3H).

Example 45

5-[(2R,6S)-2-methyl-6-[[8-(5,6,7,8-tetrahydro-1,7-naphthyridin-2-yl)-5-oxa-2,8-diazaspiro[3.5]nonan-2-yl]methyl]morpholin-4-yl]quinoline-8-carbonitrile

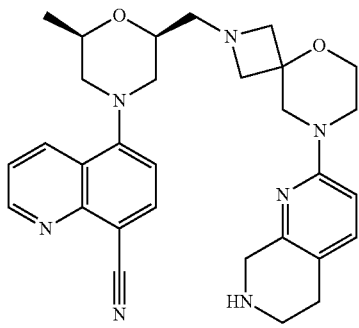 [SMILES: C[C@@H]1CN(c2ccc(C#N)c3ncccc23)C[C@H](CN2CC3(C2)CN(c2ccc4c(n2)CNCC4)CCO3)O1]

The title compound was prepared in analogy to the preparation of Example 31 by using tert-butyl 5-oxa-2,8-diazaspiro[3.5]nonane-8-carboxylate (CAS: 1251005-61-4, Vendor: PharmaBlock) and tert-butyl 2-chloro-6,8-dihydro-5H-1,7-naphthyridine-7-carboxylate (CAS: 1211581-54-2, Vendor: Bepharm) instead of tert-butyl piperazine-1-carboxylate and tert-butyl 2-bromo-6,7-dihydrothiazolo[5,4-c]pyridine-5 (4H)-carboxylate (compound 31b). Example 45 (12 mg) was obtained as a light yellow solid. MS: calc'd 526 (MH+), measured 526 (MH+). $^1$H NMR (400 MHz, METHANOL-d$_4$) δ=8.98 (dd, J=1.6, 4.3 Hz, 1H), 8.65 (dd, J=1.5, 8.6 Hz, 1H), 8.16 (d, J=8.1 Hz, 1H), 7.65 (dd, J=4.2, 8.6 Hz, 1H), 7.50 (d, J=8.8 Hz, 1H), 7.27 (d, J=8.1 Hz, 1H), 6.88 (d, J=8.8 Hz, 1H), 4.46-4.27 (m, 4H), 4.22 (s, 2H), 4.16-4.07 (m, 1H), 3.93-3.73 (m, 4H), 3.58-3.38 (m, 9H), 3.00 (t, J=6.1 Hz, 2H), 2.81-2.66 (m, 2H), 1.29 (d, J=6.4 Hz, 3H).

Example 46

5-[(2R,6S)-2-methyl-6-[[8-(5,6,7,8-tetrahydro-1,7-naphthyridin-3-yl)-5-oxa-2,8-diazaspiro[3.5]nonan-2-yl]methyl]morpholin-4-yl]quinoline-8-carbonitrile

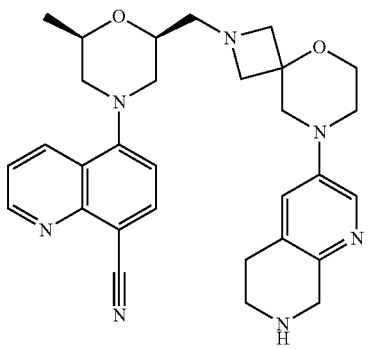 [SMILES: C[C@@H]1CN(c2ccc(C#N)c3ncccc23)C[C@H](CN2CC3(C2)CN(c2cnc4c(c2)CCNC4)CCO3)O1]

The title compound was prepared in analogy to the preparation of Example 31 by using tert-butyl 5-oxa-2,8-diazaspiro[3.5]nonane-8-carboxylate (CAS: 1251005-61-4, Vendor: PharmaBlock) and tert-butyl 3-bromo-6,8-dihydro-5H-1,7-naphthyridine-7-carboxylate (CAS: 1184950-48-8, Vendor: PharmaBlock) instead of tert-butyl piperazine-1-carboxylate and tert-butyl 2-bromo-6,7-dihydrothiazolo[5,4-c]pyridine-5 (4H)-carboxylate (compound 31b). Example 46 (14 mg) was obtained as a light yellow solid. MS: calc'd 526 (MH+), measured 526 (MH+). $^1$H NMR (400 MHz, METHANOL-d$_4$) δ=8.99 (dd, J=1.5, 4.2 Hz, 1H), 8.66 (d, J=8.4 Hz, 1H), 8.31 (d, J=2.4 Hz, 1H), 8.16 (d, J=7.9 Hz, 1H), 7.66 (dd, J=4.2, 8.6 Hz, 1H), 7.46 (d, J=2.2 Hz, 1H), 7.27 (d, J=8.1 Hz, 1H), 4.62-4.23 (m, 7H), 4.19-4.09 (m, 1H), 3.94 (br s, 2H), 3.65-3.48 (m, 6H), 3.42 (br d, J=12.2 Hz, 2H), 3.26 (br s, 2H), 3.18 (t, J=6.2 Hz, 2H), 2.85-2.65 (m, 2H), 1.31 (d, J=6.2 Hz, 3H).

Example 47

5-[(2R,6S)-2-methyl-6-[[8-(5,6,7,8-tetrahydro-1,6-naphthyridin-3-yl)-5-oxa-2,8-diazaspiro[3.5]nonan-2-yl]methyl]morpholin-4-yl]quinoline-8-carbonitrile

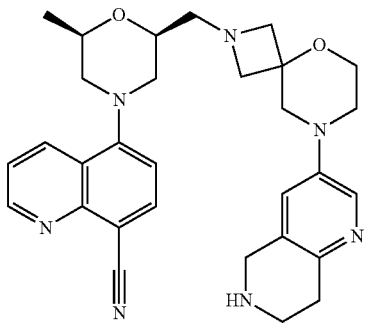 [SMILES: C[C@@H]1CN(c2ccc(C#N)c3ncccc23)C[C@H](CN2CC3(C2)CN(c2cnc4c(c2)CNCC4)CCO3)O1]

113

The title compound was prepared according to the following scheme:

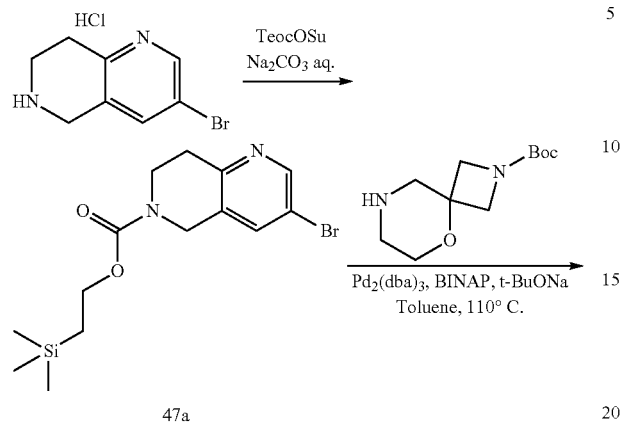

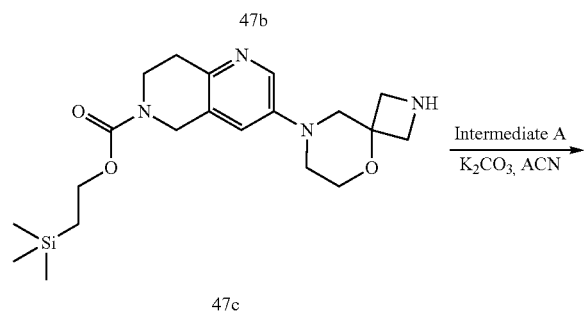

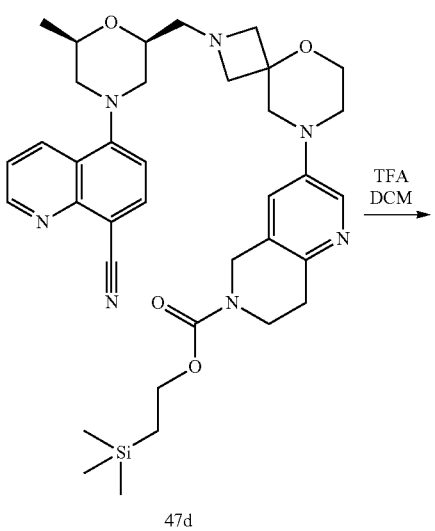

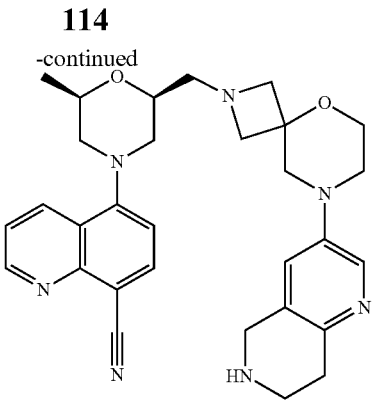

Step 1: Preparation of 2-trimethylsilylethyl 3-bromo-7,8-dihydro-5H-1,6-naphthyridine-6-carboxylate (Compound 47a)

To a solution of 3-bromo-5,6,7,8-tetrahydro-1,6-naphthyridine hydrochloride (CAS: 1159010-96-4, Vendor: PharmaBlock, 300 mg, 1.20 mmol), sodium carbonate (382 mg, 3.61 mmol) in THF (3 mL) and water (3 mL) was added N-[2-(trimethylsilyl)ethoxycarbonyloxy]succinimide (624 mg, 2.40 mmol). After being stirred at 25° C. for 5 hrs, the reaction was quenched by addition of saturated NH$_4$Cl (aq. 20 mL), diluted with 50 mL water, extracted with EA (30 mL) three times. The combined organic layer was washed with water (30 mL) twice and brine (20 mL) once, dried over Na$_2$SO$_4$ and concentrated to give crude product which was purified by flash column (PE/EA=10/1) to give compound 47a (400 mg) as a white solid. MS calc'd 357 (MH$^+$), measured 357 (MH$^+$).

Step 2: Preparation of tert-butyl 8-[6-(2-trimethylsilylethoxycarbonyl)-7,8-dihydro-5H-1,6-naphthyridin-3-yl]-5-oxa-2,8-diazaspiro[3.5]nonane-2-carboxylate (Compound 47b)

To a solution of 2-trimethylsilylethyl 3-bromo-7,8-dihydro-5H-1,6-naphthyridine-6-carboxylate (compound 47a, 150 mg, 0.42 mmol), tert-butyl 5-oxa-2,8-diazaspiro[3.5]nonane-2-carboxylate (CAS: 1251011-05-8, Vendor: PharmaBlock, 105 mg, 0.46 mmol), sodium tert-butoxide (101 mg, 1.05 mmol), R-BINAP (52 mg, 0.08 mmol) in toluene (4 mL) was added Pd$_2$(dba)$_3$ (38 mg, 0.04 mmol). The solution was stirred at 110° C. under N$_2$ atmosphere for 3 hrs. After being cooled down, the mixture was quenched by addition of saturated NH$_4$Cl (aq. 20 mL), diluted with 50 mL water, extracted with EA (30 mL) three times. The combined organic layer was washed with water (30 mL) twice and brine (20 mL) once, dried over Na$_2$SO$_4$ and concentrated to give crude product which was purified by flash column (PE/EA=1/1) to give compound 47b (140 mg) as a yellow oil. MS calc'd 419 (MH$^+$), measured 419 (MH$^+$).

Step 3: Preparation of 2-trimethylsilylethyl 3-(5-oxa-2,8-diazaspiro[3.5]nonan-8-yl)-7,8-dihydro-5H-1,6-naphthyridine-6-carboxylate (Compound 47c)

A solution of tert-butyl 8-[6-(2-trimethylsilylethoxycarbonyl)-7,8-dihydro-5H-1,6-naphthyridin-3-yl]-5-oxa-2,8-diazaspiro[3.5]nonane-2-carboxylate (compound 47b, 110 mg, 0.22 mmol) and TsOH (75 mg, 0.44 mmol) in methanol (3 mL) was stirred at 55° C. for 5 hrs. After being cooled down, the mixture was concentrated and purified by prep-TLC (DCM/MeOH=10/1) to give compound 47c (80 mg) as a yellow gum. MS calc'd 405 (MH$^+$), measured 405 (MH$^+$).

Step 4: Preparation of 2-trimethylsilylethyl 3-[2-[[(2S,6R)-4-(8-cyano-5-quinolyl)-6-methyl-morpholin-2-yl]methyl]-5-oxa-2,8-diazaspiro[3.5]nonan-8-yl]-7,8-dihydro-5H-1,6-naphthyridine-6-carboxylate (Compound 47d)

A solution of [(2R,6R)-4-(8-cyano-5-quinolyl)-6-methyl-morpholin-2-yl]methyl trifluoromethanesulfonate (Intermedia A, 40 mg, 0.10 mmol), 2-trimethylsilylethyl 3-(5-oxa-2,8-diazaspiro[3.5]nonan-8-yl)-7,8-dihydro-5H-1,6-naphthyridine-6-carboxylate (compound 47c, 58 mg, 0.14 mmol), potassium carbonate (33 mg, 0.24 mmol) in acetonitrile (2 mL) was stirred at 55° C. for 2 hrs. After being cooled down, the mixture was filtered, concentrated and purified by prep-TLC (DCM/MeOH=10/1) to give compound 47d (30 mg) as a yellow gum. MS calc'd 670 (MH$^+$), measured 670 (MH$^+$).

Step 5: Preparation of 5-[(2R,6S)-2-methyl-6-[[8-(5,6,7,8-tetrahydro-1,6-naphthyridin-3-yl)-5-oxa-2,8-diazaspiro[3.5]nonan-2-yl]methyl]morpholin-4-yl]quinoline-8-carbonitrile (Example 47)

To a solution of 2-trimethylsilylethyl 3-[2-[[(2S,6R)-4-(8-cyano-5-quinolyl)-6-methyl-morpholin-2-yl]methyl]-5-oxa-2,8-diazaspiro[3.5]nonan-8-yl]-7,8-dihydro-5H-1,6-naphthyridine-6-carboxylate (compound 47d, 30 mg, 0.04 mmol) in DCM (1 mL) was added trifluoroacetic acid (0.40 mL) at 0° C. After being stirred at 25° C. for 1 h, the mixture was concentrated and purified by prep-HPLC to give Example 47 (20 mg) as a yellow solid. MS calc'd 526 (MH$^+$), measured 526 (MH$^+$). $^1$H NMR (400 MHz, METHANOL-d$_4$) δ=8.98 (dd, J=1.6, 4.2 Hz, 1H), 8.64 (dd, J=1.5, 8.6 Hz, 1H), 8.40 (d, J=2.6 Hz, 1H), 8.15 (d, J=7.9 Hz, 1H), 7.76 (s, 1H), 7.65 (dd, J=4.2, 8.6 Hz, 1H), 7.26 (d, J=8.1 Hz, 1H), 4.62-4.25 (m, 7H), 4.18-4.08 (m, 1H), 3.96 (br s, 2H), 3.72-3.57 (m, 5H), 3.57-3.49 (m, 1H), 3.46-3.38 (m, 2H), 3.32-3.24 (m, 4H), 2.86-2.67 (m, 2H), 1.30 (d, J=6.2 Hz, 3H).

Example 48

5-[(2R,6S)-2-methyl-6-[[8-(5,6,7,8-tetrahydro-2,6-naphthyridin-3-yl)-5-oxa-2,8-diazaspiro[3.5]nonan-2-yl]methyl]morpholin-4-yl]quinoline-8-carbonitrile

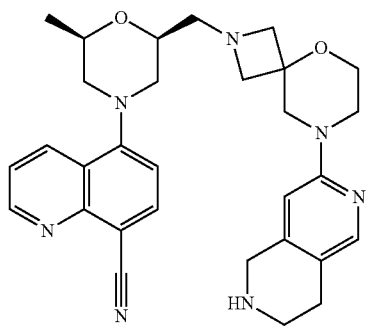 [SMILES: C[C@@H]1CN(c2ccc(C#N)c3ncccc23)C[C@H](CN2CC3(C2)CN(c2cc4c(cn2)CCNC4)CCO3)O1]

The title compound was prepared in analogy to the preparation of Example 31 by using tert-butyl 5-oxa-2,8-diazaspiro[3.5]nonane-8-carboxylate (CAS: 1251005-61-4, Vendor: PharmaBlock) and tert-butyl 7-chloro-3,4-dihydro-1H-2,6-naphthyridine-2-carboxylate (CAS: 1060816-50-3, Vendor: SCRC) instead of tert-butyl piperazine-1-carboxylate and tert-butyl 2-bromo-6,7-dihydrothiazolo[5,4-c]pyridine-5 (4H)-carboxylate (compound 31b). Example 48 (15 mg) was obtained as a light yellow solid. MS: calc'd 526 (MH$^+$), measured 526 (MH$^+$). $^1$H NMR (400 MHz, METHANOL-d$_4$) δ=8.89 (dd, J=1.7, 4.3 Hz, 1H), 8.55 (dd, J=1.6, 8.6 Hz, 1H), 8.07 (d, J=7.9 Hz, 1H), 8.02 (s, 1H), 7.55 (dd, J=4.3, 8.6 Hz, 1H), 7.18 (d, J=7.9 Hz, 1H), 6.67 (s, 1H), 4.42-4.10 (m, 7H), 4.06-3.96 (m, 1H), 3.85-3.64 (m, 4H), 3.48-3.37 (m, 4H), 3.36-3.28 (m, 4H), 2.93 (t, J=6.2 Hz, 2H), 2.72-2.65 (m, 1H), 2.61 (dd, J=10.4, 12.2 Hz, 1H), 1.19 (d, J=6.4 Hz, 3H).

Example 49

5-[(2R,6S)-2-methyl-6-[[8-(5,6,7,8-tetrahydro-1,6-naphthyridin-2-yl)-5-oxa-2,8-diazaspiro[3.5]nonan-2-yl]methyl]morpholin-4-yl]quinoline-8-carbonitrile

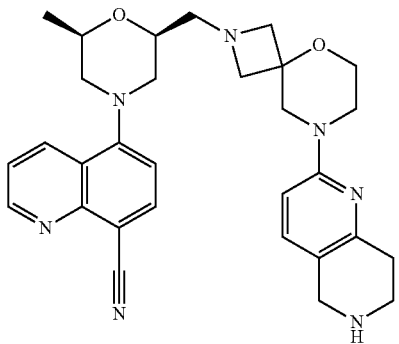 [SMILES: C[C@@H]1CN(c2ccc(C#N)c3ncccc23)C[C@H](CN2CC3(C2)CN(c2ccc4c(n2)CCNC4)CCO3)O1]

The title compound was prepared in analogy to the preparation of Example 31 by using tert-butyl 5-oxa-2,8-diazaspiro[3.5]nonane-8-carboxylate (CAS: 1251005-61-4, Vendor: PharmaBlock) and tert-butyl 2-chloro-7,8-dihydro-1,6-naphthyridine-6 (5H)-carboxylate (CAS: 1151665-15-4, Vendor: PharmaBlock) instead of tert-butyl piperazine-1-carboxylate and tert-butyl 2-bromo-6,7-dihydrothiazolo[5,4-c]pyridine-5 (4H)-carboxylate (compound 31b). Example 49 (11 mg) was obtained as a light yellow solid. MS: calc'd 526 (MH$^+$), measured 526 (MH$^+$). $^1$H NMR (400 MHz, METHANOL-d$_4$) δ=8.98 (dd, J=1.6, 4.3 Hz, 1H), 8.64 (dd, J=1.6, 8.6 Hz, 1H), 8.15 (d, J=7.9 Hz, 1H), 7.64 (dd, J=4.3, 8.6 Hz, 1H), 7.47 (d, J=8.7 Hz, 1H), 7.26 (d, J=8.1 Hz, 1H), 6.85 (d, J=8.8 Hz, 1H), 4.51-4.17 (m, 7H), 4.16-4.06 (m, 1H), 3.97-3.71 (m, 4H), 3.61-3.53 (m, 3H), 3.52-3.44 (m, 3H), 3.40 (br d, J=11.6 Hz, 2H), 3.08 (t, J=6.4 Hz, 2H), 2.82-2.74 (m, 1H), 2.70 (dd, J=10.4, 12.2 Hz, 1H), 1.29 (d, J=6.2 Hz, 3H).

Example 50

5-[(2R,6S)-2-methyl-6-[[8-(5,6,7,8-tetrahydropyrido[3,4-b]pyrazin-2-yl)-5-oxa-2,8-diazaspiro[3.5]nonan-2-yl]methyl]morpholin-4-yl]quinoline-8-carbonitrile

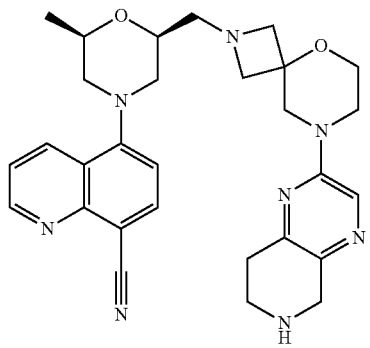 [SMILES: C[C@@H]1CN(c2ccc(C#N)c3ncccc23)C[C@H](CN2CC3(C2)CN(c2cnc4c(n2)CCNC4)CCO3)O1]

The title compound was prepared in analogy to the preparation of Example 47 by using tert-butyl-8-[6-(2-trimethylsilylethoxycarbonyl)-7,8-dihydro-5H-pyrido[3,4-b]pyrazin-2-yl]-5-oxa-2,8-diazaspiro[3.5]nonane-2-carboxylate (compound 50c) instead of tert-butyl 8-[6-(2-trimethylsilylethoxycarbonyl)-7,8-dihydro-5H-1,6-naphthyridin-3-yl]-5-oxa-2,8-diazaspiro[3.5]nonane-2-carboxylate (compound 47b). Example 50 (12 mg) was obtained as a yellow solid. MS calc'd 527 (MH$^+$), measured 527 (MH$^+$). $^1$H NMR (400 MHz, METHANOL-d$_4$) δ=8.97 (dd, J=1.2, 4.2 Hz, 1H), 8.63 (d, J=8.3 Hz, 1H), 8.23 (s, 1H), 8.13 (d, J=7.8 Hz, 1H), 7.63 (dd, J=4.2, 8.6 Hz, 1H), 7.25 (d, J=8.1 Hz, 1H), 4.33 (s, 7H), 4.16-4.05 (m, 1H), 3.90 (br s, 4H), 3.66-3.54 (m, 5H), 3.53-3.44 (m, 1H), 3.40 (br d, J=12.0 Hz, 2H), 3.11 (br t, J=6.2 Hz, 2H), 2.81-2.65 (m, 2H), 1.28 (d, J=6.1 Hz, 3H).

The compound 50c was prepared according to the following scheme:

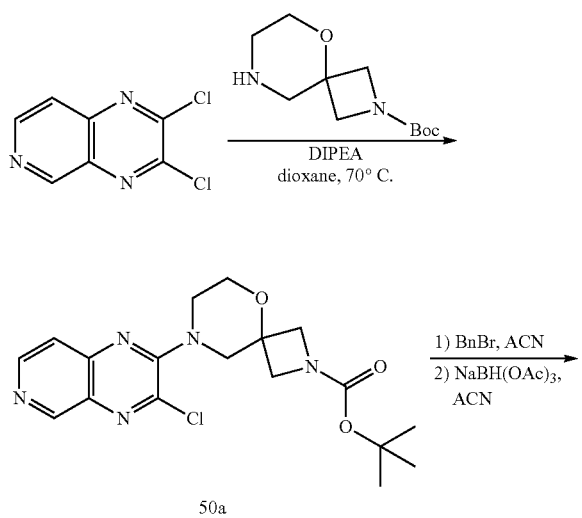

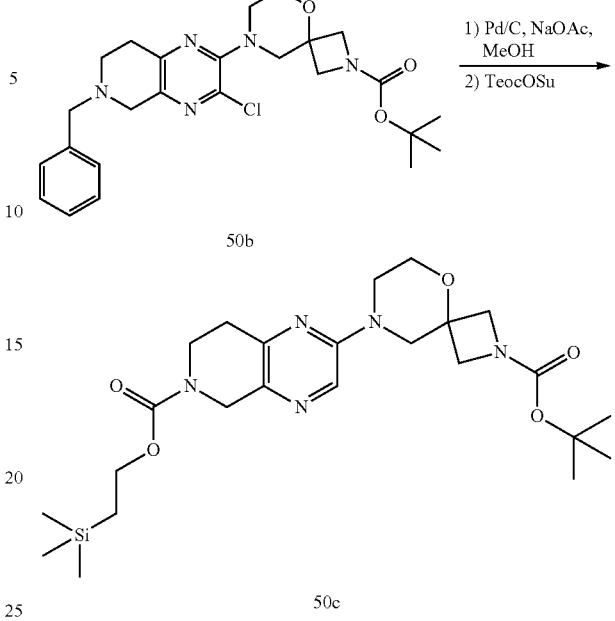

Step 1: Preparation of tert-butyl 8-(3-chloropyrido[3,4-b]pyrazin-2-yl)-5-oxa-2,8-diazaspiro[3.5]nonane-2-carboxylate (Compound 50a)

To the solution of 2,3-dichloropyrido[3,4-b]pyrazine (CAS: 35251-99-1, Vendor: Aldrich, 300 mg, 1.51 mmol) in 1,4-dioxane (10 mL) was added N,N-diisopropylethylamine (0.39 mL, 2.26 mmol) and tert-butyl 5-oxa-2,8-diazaspiro[3.5]nonane-2-carboxylate (CAS: 1251011-05-8, Vendor: PharmaBlock, 348 mg, 1.52 mmol). After being stirred at 40° C. for 2 hrs, the reaction mixture was concentrated to give compound 50a (550 mg) as a yellow oil. MS calc'd 392 (MH$^+$), measured 392 (MH$^+$).

Step 2: Preparation of tert-butyl 8-(6-benzyl-3-chloro-7,8-dihydro-5H-pyrido[3,4-b]pyrazin-2-yl)-5-oxa-2,8-diazaspiro[3.5]nonane-2-carboxylate (Compound 50b)

To the solution of tert-butyl 8-(3-chloropyrido[3,4-b]pyrazin-2-yl)-5-oxa-2,8-diazaspiro[3.5]nonane-2-carboxylate (compound 50a, 500 mg, 1.28 mmol) in ACN (10 mL) was added benzyl bromide (0.16 mL, 1.35 mmol). After being stirred at 70° C. for 2 hrs, the reaction mixture was concentrated to give the crude product which was dissolved in ACN (10 mL). Then sodium triacetoxyborohydride (1129 mg, 5.33 mmol) was added at 0° C. The reaction was stirred at rt for 16 hrs, and then ice-water (50 ml) was added. The mixture was extracted with EA (50 mL) for three times. The combined organic layer was dried over Na$_2$SO$_4$, filtered and the residue was purified by flash column (PE/EA=3/1) to give compound 50b (250 mg) as a colorless oil. MS calc'd 486 (MH$^+$), measured 486 (MH$^+$).

Step 3: Preparation of tert-butyl 8-[6-(2-trimethylsilylethoxycarbonyl)-7,8-dihydro-5H-pyrido[3,4-b]pyrazin-2-yl]-5-oxa-2,8-diazaspiro[3.5]nonane-2-carboxylate (Compound 50c)

The solution of tert-butyl 8-(6-benzyl-3-chloro-7,8-dihydro-5H-pyrido[3,4-b]pyrazin-2-yl)-5-oxa-2,8-diazaspiro

[3.5]nonane-2-carboxylate (compound 50b, 210 mg, 0.43 mmol), sodium acetate (106 mg, 1.30 mmol), Pd/C (10 wt. %, 55 mg, 0.52 mmol) in methanol (9 mL) was stirred at 25° C. for 3 hrs under $H_2$ atmosphere. After filtration, the mixture was concentrated to give tert-butyl 8-(5,6,7,8-tetrahydropyrido[3,4-b]pyrazin-2-yl)-5-oxa-2,8-diazaspiro[3.5]nonane-2-carboxylate (150 mg) as a colorless oil.

To the solution of tert-butyl 8-(5,6,7,8-tetrahydropyrido[3,4-b]pyrazin-2-yl)-5-oxa-2,8-diazaspiro[3.5]nonane-2-carboxylate (150 mg, 0.42 mmol) and sodium carbonate (132 mg, 1.25 mmol) in THF (5 mL) and water (5 mL) was added 2,5-dioxopyrrolidin-1-yl (2-(trimethylsilyl)ethyl) carbonate (215 mg, 0.83 mmol). After being stirred at 25° C. for 3 hrs, the reaction was quenched by addition of saturated $NH_4Cl$ (10 mL), diluted with water (30 mL), extracted with EA (50 mL) for three times. The combined organic layer was washed with brine (50 mL) twice, dried over $Na_2SO_4$ and concentrated to give the crude product which was purified by prep-TLC (PE/EA=2/1) to give compound 50c (150 mg) as a colorless oil. MS calc'd 506 ($MH^+$), measured 506 ($MH^+$).

Example 51

5-[(2R,6S)-2-methyl-6-[[8-(5,6,7,8-tetrahydropyrido[4,3-d]pyrimidin-2-yl)-5-oxa-2,8-diazaspiro[3.5]nonan-2-yl]methyl]morpholin-4-yl]quinoline-8-carbonitrile

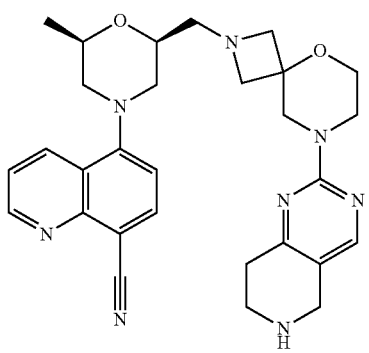 [SMILES: C[C@@H]1CN(c2ccc(C#N)c3ncccc23)C[C@H](CN2CC3(C2)CN(c2ncc4c(n2)CCNC4)CCO3)O1]

The title compound was prepared in analogy to the preparation of Example 47 by using tert-butyl 8-[6-(2-trimethylsilylethoxycarbonyl)-7,8-dihydro-5H-pyrido[4,3-d]pyrimidin-2-yl]-5-oxa-2,8-diazaspiro[3.5]nonane-2-carboxylate (compound 51c) instead of tert-butyl 8-[6-(2-trimethylsilylethoxycarbonyl)-7,8-dihydro-5H-1,6-naphthyridin-3-yl]-5-oxa-2,8-diazaspiro[3.5]nonane-2-carboxylate (compound 47b). Example 51 (12 mg) was obtained as a yellow solid. MS calc'd 527 ($MH^+$), measured 527 ($MH^+$). $^1$H NMR (400 MHz, METHANOL-$d_4$) δ=9.01-8.99 (m, 1H), 8.65 (dd, J=1.2, 8.4 Hz, 1H), 8.29 (s, 1H), 8.17 (d, J=7.6 Hz, 1H), 7.66 (dd, J=4.4, 8.4 Hz, 1H), 7.28 (d, J=8.0 Hz, 1H), 4.55-4.20 (m, 7H), 4.18-4.0 (m, 3H), 3.9-3.7 (m, 4H), 3.65-3.45 (m, 4H), 3.4-3.35 (m, 2H), 3.10-3.00 (m, 2H), 2.84-2.7 (m, 2H), 1.30 (d, J=6.4 Hz, 3H).

The compound 51c was prepared according to the following scheme:

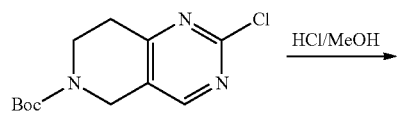

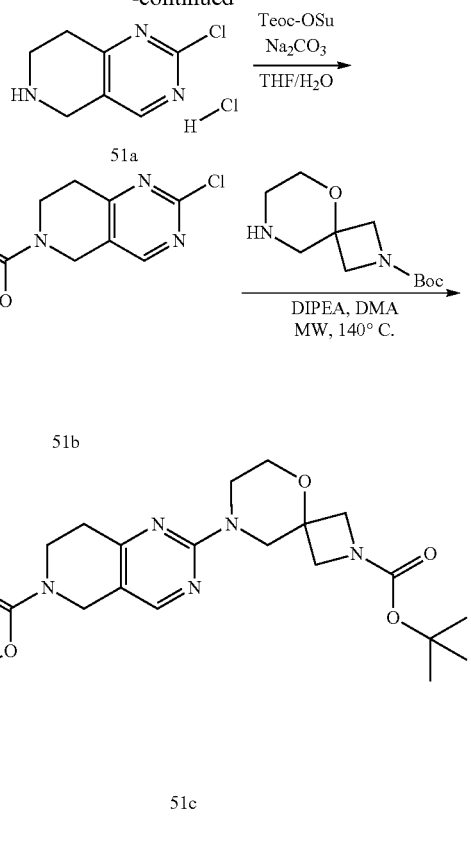

Step 1: Preparation of 2-chloro-5,6,7,8-tetrahydropyrido[4,3-d]pyrimidine hydrochloride (Compound 51a)

To the solution of tert-butyl 2-chloro-7,8-dihydro-5H-pyrido[4,3-d]pyrimidine-6-carboxylate (CAS: 1092352-55-0, Vendor: PharmaBlock, 250 mg, 0.93 mmol) in methanol (2 mL) was added HCl (1.25 M in MeOH 10 mL, 125.00 mmol). After being stirred at rt for 1 h, the mixture was concentrated to give compound 51a (190 mg) as a yellow solid which was used for the next step without further purification. MS calc'd 170 ($MH^+$), measured 170 ($MH^+$).

Step 2: Preparation of 2-trimethylsilylethyl 2-chloro-7,8-dihydro-5H-pyrido[4,3-d]pyrimidine-6-carboxylate (Compound 51b)

To the solution of 2-chloro-5,6,7,8-tetrahydropyrido[4,3-d]pyrimidine hydrochloride (compound 51a, 190 mg, 0.92 mmol) and sodium carbonate (293 mg, 2.77 mmol) in THF (3 mL) and water (3 mL) was added 2,5-dioxopyrrolidin-1-yl(2-(trimethylsilyl) ethyl) carbonate (478 mg, 1.84 mmol). After being stirred at rt for 3 hrs, the reaction was quenched by addition of saturated $NH_4Cl$ (10 mL), diluted with water (30 mL) and extracted with EA (20 mL) for three times. The combined organic layer was washed with water (20 mL) twice and brine (20 mL) once, dried over $Na_2SO_4$, concentrated and purified by prep-TLC (PE/EA=3/1) to give compound 51b (270 mg) as a yellow gum. MS calc'd 314 ($MH^+$), measured 314 ($MH^+$).

121

Step 3: Preparation of tert-butyl 8-[6-(2-trimethylsilylethoxycarbonyl)-7,8-dihydro-5H-pyrido[4,3-d]pyrimidin-2-yl]-5-oxa-2,8-diazaspiro[3.5]nonane-2-carboxylate (Compound 51c)

To the solution of 2-trimethylsilylethyl 2-chloro-7,8-dihydro-5H-pyrido[4,3-d]pyrimidine-6-carboxylate (compound 51b, 200 mg, 0.64 mmol) in 1-butanol (3 mL) was added N,N-diisopropylethylamine (0.22 mL, 1.27 mmol) and tert-butyl 5-oxa-2,8-diazaspiro[3.5]nonane-2-carboxylate (CAS: 1251011-05-8, Vendor: PharmaBlock; 218 mg, 0.96 mmol). The solution was reacted under microwave at 140° C. for 2 hrs. After concentration, the residue was purified by prep-TLC (PE/EA=2/1) to give compound 51c (140 mg) as a yellow gum. MS calc'd 506 (MH$^+$), measured 506 (MH$^+$).

Example 52

5-[(2S,6R)-2-[[(4aR,7aR)-4-(5,6,7,8-tetrahydro-1,7-naphthyridin-3-yl)-2,3,4a,5,7,7a-hexahydropyrrolo[3,4-b][1,4]oxazin-6-yl]methyl]-6-methylmorpholin-4-yl]quinoline-8-carbonitrile

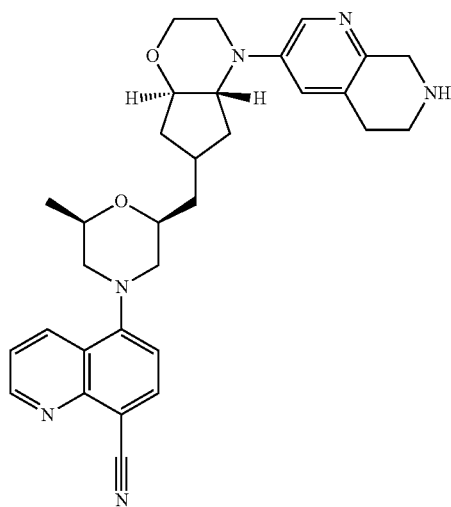 [SMILES: C[C@@H]1CN(c2ccc(C#N)c3ncccc23)C[C@H](CC2C[C@@H]3[C@@H](C2)OCCN3c2cnc3c(c2)CCNC3)O1]

The title compound was prepared in analogy to the preparation of Example 31 by using tert-butyl (4aR,7aR)-3,4a,5,6,7,7a-hexahydro-2H-pyrrolo[3,4-b][1,4]oxazine-4-carboxylate (CAS: 1932337-68-2, Vendor: PharmaBlock) and tert-butyl 3-bromo-5,8-dihydro-1,7-naphthyridine-7(6H)-carboxylate (CAS: 1823228-83-6, Vendor: Wuxi) instead of tert-butyl piperazine-1-carboxylate and tert-butyl 2-bromo-6,7-dihydrothiazolo[5,4-c]pyridine-5 (4H)-carboxylate (compound 31b). Example 52 (7 mg) was obtained as a light yellow powder. MS: calc'd 526 (MH$^+$), measured 526 (MH$^+$). $^1$H NMR (400 MHz, METHANOL-d$_4$) δ=8.99 (dd, J=1.7, 4.2 Hz, 1H), 8.66 (dd, J=1.7, 8.6 Hz, 1H), 8.29 (d, J=2.4 Hz, 1H), 8.16 (d, J=8.1 Hz, 1H), 7.65 (dd, J=4.3, 8.6 Hz, 1H), 7.48 (d, J=2.3 Hz, 1H), 7.27 (d, J=7.9 Hz, 1H), 4.45-4.38 (m, 1H), 4.35 (s, 2H), 4.21-4.12 (m, 2H), 4.10-3.90 (m, 4H), 3.65-3.47 (m, 5H), 3.46-3.34 (m, 5H), 3.21-3.13 (m, 2H), 2.99 (dt, J=3.7, 12.1 Hz, 1H), 2.81-2.66 (m, 2H), 1.29 (d, J=6.2 Hz, 3H).

Example 53 cis-5-[(2R,6S)-2-methyl-6-[[4-(5,6,7,8-tetrahydro-1,6-naphthyridin-2-yl)-2,3,4a,5,7,7a-hexahydropyrrolo[3,4-b][1,4]oxazin-6-yl]methyl]morpholin-4-yl]quinoline-8-carbonitrile

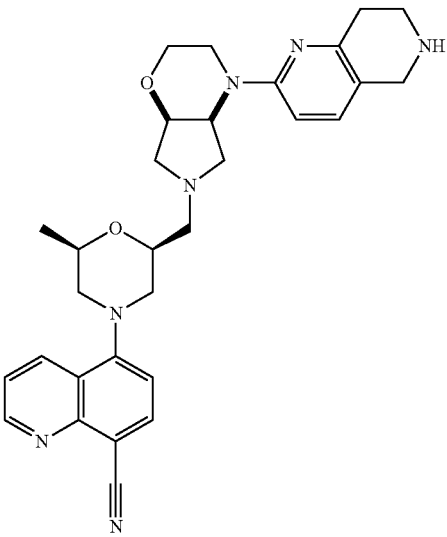

The title compound was prepared according to the following scheme:

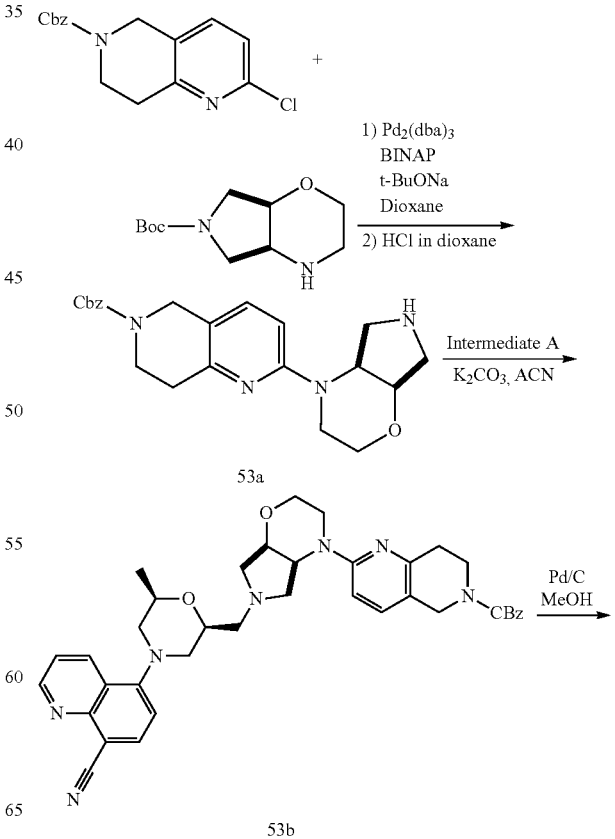

-continued

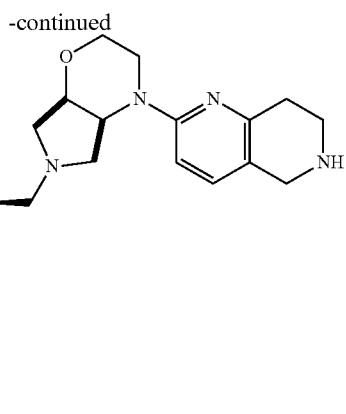

53

Step 1: Preparation of cis-benzyl 2-(3,4a,5,6,7,7a-hexahydro-2H-pyrrolo[3,4-b][1,4]oxazin-4-yl)-7,8-dihydro-5H-1,6-naphthyridine-6-carboxylate (Compound 53a)

To a microwave tube was added benzyl 2-chloro-7,8-dihydro-1,6-naphthyridine-6 (5H)-carboxylate (116 mg, 383 µmol), cis-tert-butyl (4a,7a)-hexahydropyrrolo[3,4-b][1,4]oxazine-6 (2H)-carboxylate (CAS: 159991-15-8, Vendor: Pharmablock, 96 mg, 421 µmol), sodium 2-methylpropan-2-olate (74 mg, 766 µmol), Pd$_2$(dba)$_3$ (35 mg, 38 µmol), BINAP (48 mg, 77 µmol) and 1,4-dioxane (4 mL). The mixture was heated to 100° C. for 16 hrs. After being cooled down, the mixture was diluted with EA (10 mL) and filtered. The filtrate was concentrated and purified via flash column (EA/PE=0 to 60%) to give an oil which was treated with HCl in dioxane (2 N, 10 mL) for 2 hrs. The mixture was concentrated to give compound 53a as a white solid. MS: calc'd 395 (MH$^+$), measured 395 (MH$^+$).

Step 2: Preparation of cis-benzyl 2-[6-[[(2S,6R)-4-(8-cyano-5-quinolyl)-6-methyl-morpholin-2-yl]methyl]-2,3,4a,5,7,7a-hexahydropyrrolo[3,4-b][1,4]oxazin-4-yl]-7,8-dihydro-5H-1,6-naphthyridine-6-carboxylate (Compound 53b)

To a flask was added [(2R,6R)-4-(8-cyanoquinolin-5-yl)-6-methylmorpholin-2-yl]methyl trifluoromethanesulfonate (100 mg, 241 µmol), cis-benzyl 2-(3,4a,5,6,7,7a-hexahydro-2H-pyrrolo[3,4-b][1,4]oxazin-4-yl)-7,8-dihydro-5H-1,6-naphthyridine-6-carboxylate (compound 53a, 104 mg, 265 µmol), potassium carbonate (100 mg, 722 µmol) and acetonitrile (4 mL), the mixture was heated to 85° C. for 1 h. After being cooled down, the mixture was filtered, the filtrate was concentrated and purified via flash column (EA/PE=0 to 100%) to give compound 53b as an oil. MS: calc'd 660 (MH$^+$), measured 660 (MH$^+$).

Step 3: Preparation of cis-5-[(2R,6S)-2-methyl-6-[[4-(5,6,7,8-tetrahydro-1,6-naphthyridin-2-yl)-2,3,4a,5,7,7a-hexahydropyrrolo[3,4-b][1,4]oxazin-6-yl]methyl]morpholin-4-yl]quinoline-8-carbonitrile (Compound 53)

To the mixture of cis-benzyl 2-[6-[[(2S,6R)-4-(8-cyano-5-quinolyl)-6-methyl-morpholin-2-yl]methyl]-2,3,4a,5,7,7a-hexahydropyrrolo[3,4-b][1,4]oxazin-4-yl]-7,8-dihydro-5H-1,6-naphthyridine-6-carboxylate (compound 53b) in MeOH (2 mL) was added Pd/C (10 wt. %, 26 mg, 241 µmol). The mixture was stirred at r.t. with H$_2$ balloon overnight. After filtration, the mixture was concentrated and purified via prep-HPLC to give Example 53 (13 mg) as a light yellow powder. MS: calc'd 526 (MH$^+$), measured 526 (MH$^+$). $^1$H NMR (400 MHz, METHANOL-d$_4$) δ=8.99 (dd, J=1.6, 4.3 Hz, 1H), 8.65 (br d, J=8.1 Hz, 1H), 8.16 (d, J=7.9 Hz, 1H), 7.65 (br dd, J=4.3, 8.6 Hz, 1H), 7.51-7.43 (m, 1H), 7.28 (d, J=7.9 Hz, 1H), 6.82 (br d, J=8.8 Hz, 1H), 4.45-4.30 (m, 2H), 4.27 (s, 2H), 4.19-4.10 (m, 2H), 4.06-3.80 (m, 3H), 3.80-3.67 (m, 2H), 3.63-3.48 (m, 5H), 3.46-3.35 (m, 3H), 3.27-3.15 (m, 1H), 3.08 (br t, J=6.5 Hz, 2H), 2.84-2.65 (m, 2H), 1.30 (d, J=6.2 Hz, 3H).

Example 54 trans-5-[(2R,6S)-2-methyl-6-[[3-(5,6,7,8-tetrahydro-1,6-naphthyridin-2-yl)-3,7-diazabicyclo[4.2.0]octan-7-yl]methyl]morpholin-4-yl]quinoline-8-carbonitrile

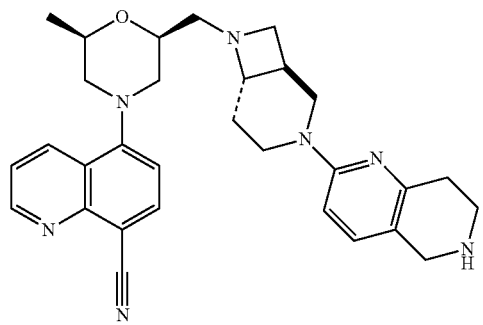

Example 55 cis-5-[(2R,6S)-2-methyl-6-[[3-(5,6,7,8-tetrahydro-1,6-naphthyridin-2-yl)-3,7-diazabicyclo[4.2.0]octan-7-yl]methyl]morpholin-4-yl]quinoline-8-carbonitrile

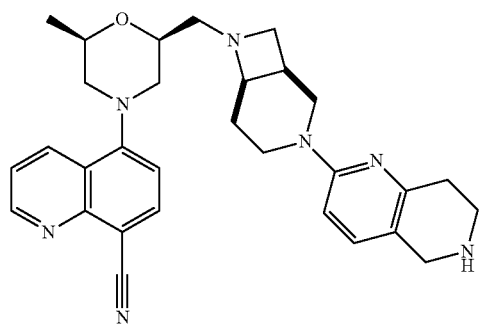

The mixture of Example 54 and 55 were prepared in analogy to the preparation of Example 31 by using tert-butyl 3,7-diazabicyclo[4.2.0]octane-3-carboxylate (CAS: 885271-67-0, Vendor: PharmaBlock) and tert-butyl 2-chloro-7,8-dihydro-1,6-naphthyridine-6 (5H)-carboxylate (CAS: 1151665-15-4, Vendor: PharmaBlock) instead of tert-butyl piperazine-1-carboxylate and tert-butyl 2-bromo-6,7-dihydrothiazolo[5,4-c]pyridine-5 (4H)-carboxylate (compound 31b). Example 54 (slower eluting) and 55 (faster eluting) were separated by prep-HPLC (Gradient: 10%-25% ACN in water (0.05% TFA), Column: Waters Atlantis T3 C18, 30×100 mm, 5 μm).

Example 54 (3 mg) was obtained as a light yellow solid. MS: calc'd 510 (MH$^+$), measured 510 (MH$^+$). $^1$H NMR (400 MHz, METHANOL-d$_4$) δ=8.99 (dd, J=1.7, 4.2 Hz, 1H), 8.62 (dd, J=1.6, 8.6 Hz, 1H), 8.16 (d, J=8.1 Hz, 1H), 7.64 (dd, J=4.3, 8.6 Hz, 1H), 7.48 (d, J=8.9 Hz, 1H), 7.27 (d, J=7.9 Hz, 1H), 6.78 (d, J=8.7 Hz, 1H), 4.42-4.22 (m, 4H), 4.22-4.03 (m, 3H), 4.02-3.89 (m, 1H), 3.81-3.62 (m, 2H), 3.61-3.50 (m, 3H), 3.48-3.35 (m, 4H), 3.27-3.16 (m, 1H), 3.08 (t, J=6.4 Hz, 2H), 2.82-2.66 (m, 2H), 2.59-2.47 (m, 1H), 2.44-2.31 (m, 1H), 1.35-1.25 (m, 3H).

Example 55 (6 mg) was obtained as a light yellow solid. MS: calc'd 510 (MH$^+$), measured 510 (MH$^+$). $^1$H NMR (400 MHz, METHANOL-d$_4$) δ=9.02-8.93 (m, 1H), 8.66-8.57 (m, 1H), 8.15 (d, J=7.9 Hz, 1H), 7.67-7.59 (m, 1H), 7.51 (d, J=8.9 Hz, 1H), 7.26 (d, J=8.1 Hz, 1H), 6.82 (br d, J=8.8 Hz, 1H), 4.44-4.32 (m, 1H), 4.32-4.21 (m, 3H), 4.21-3.94 (m, 3H), 3.94-3.81 (m, 1H), 3.80-3.62 (m, 1H), 3.61-3.47 (m, 3H), 3.46-3.36 (m, 3H), 3.36-3.32 (m, 2H), 3.27-3.16 (m, 1H), 3.16-3.04 (m, 2H), 2.83-2.65 (m, 2H), 2.62-2.26 (m, 2H), 1.34-1.25 (m, 3H).

Example 56

5-[(2S,6R)-2-[[3,3-dimethyl-4-(5,6,7,8-tetrahydro-1,6-naphthyridin-3-yl)piperazin-1-yl]methyl]-6-methyl-morpholin-4-yl]quinoline-8-carbonitrile

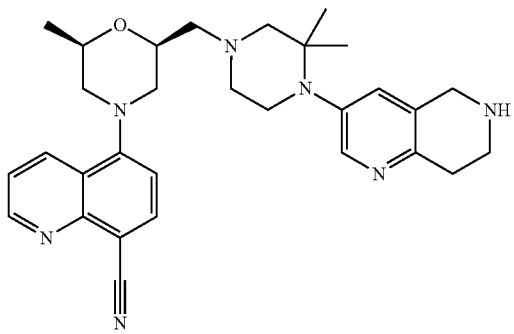 [SMILES: C[C@@H]1CN(c2ccc(C#N)c3ncccc23)C[C@H](CN2CCN(c3cnc4c(c3)CNCC4)C(C)(C)C2)O1]

The title compound was prepared in analogy to the preparation of Example 47 by using tert-butyl 3,3-dimethylpiperazine-1-carboxylate (CAS: 259808-67-8, Vendor: PharmaBlock) instead of tert-butyl 5-oxa-2,8-diazaspiro[3.5]nonane-2-carboxylate (CAS: 1251011-05-8, Vendor: PharmaBlock). Example 56 (24 mg) was obtained as a light yellow gum. MS: calc'd 512 (MH$^+$), measured 512 (MH$^+$). $^1$H NMR (400 MHz, METHANOL-d$_4$) δ=9.01-8.94 (m, 1H), 8.68-8.60 (m, 1H), 8.39 (br s, 1H), 8.19-8.10 (m, 1H), 7.79-7.60 (m, 2H), 7.30-7.23 (m, 1H), 4.57 (br t, J=8.82 Hz, 1H), 4.47 (br s, 2H), 4.26-4.15 (m, 1H), 4.02-3.52 (m, 5H), 3.50-3.34 (m, 5H), 3.29-3.01 (m, 4H), 2.77 (q, J=12.05 Hz, 2H), 1.37-1.19 (m, 9H).

Example 57

5-[(2R,6S)-2-methyl-6-[[3-(5,6,7,8-tetrahydropyrido[4,3-d]pyrimidin-2-ylamino)pyrrolidin-1-yl]methyl]morpholin-4-yl]quinoline-8-carbonitrile

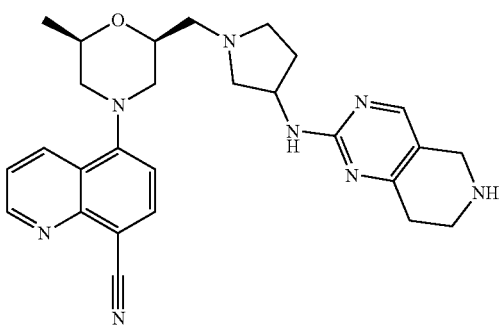 [SMILES: C[C@@H]1CN(c2ccc(C#N)c3ncccc23)C[C@H](CN2CCC(Nc3ncc4c(n3)CCNC4)C2)O1]

The title compound was prepared in analogy to the preparation of Example 6 by using tert-butyl 2-chloro-7,8-dihydro-5H-pyrido[4,3-d]pyrimidine-6-carboxylate (CAS: 1092352-55-0, Vendor: PharmaBlock) and benzyl 3-aminopyrrolidine-1-carboxylate (CAS: 185057-50-5, Vendor: PharmaBlock) instead of tert-butyl 4-chloro-5,7-dihydropyrrolo[3,4-d]pyrimidine-6-carboxylate and benzyl piperazine-1-carboxylate. Example 57 (26 mg) was obtained as a yellow solid. MS: calc'd 485 (MH$^+$), measured 485 (MH$^+$). $^1$H NMR (400 MHz, METHANOL-d$_4$) δ=8.95 (dd, J=1.5, 4.4 Hz, 1H), 8.62 (br d, J=8.6 Hz, 1H), 8.27-8.22 (m, 1H), 8.11 (d, J=8.1 Hz, 1H), 7.61 (dd, J=4.2, 8.6 Hz, 1H), 7.23 (d, J=8.1 Hz, 1H), 4.73-4.61 (m, 1H), 4.40 (br s, 1H), 4.27 (s, 2H), 4.22-3.95 (m, 2H), 3.80 (br s, 1H), 3.58 (br t, J=6.5 Hz, 3H), 3.54-3.35 (m, 5H), 3.12-2.98 (m, 2H), 2.81-2.50 (m, 3H), 2.22 (br s, 1H), 1.34-1.20 (m, 3H).

Example 58

5-[(2S,6R)-2-[[4-(4-methoxy-1,2,3,4-tetrahydroisoquinolin-6-yl)piperazin-1-yl]methyl]-6-methyl-morpholin-4-yl]quinoline-8-carbonitrile

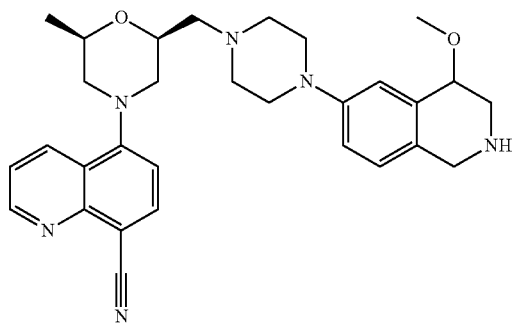 [SMILES: COC1CNCc2ccc(N3CCN(C[C@H]4CN(c5ccc(C#N)c6ncccc56)C[C@@H](C)O4)CC3)cc21]

The title compound was prepared in analogy to the preparation of Example 31 by using tert-butyl 6-bromo-4-methoxy-3,4-dihydro-1H-isoquinoline-2-carboxylate (compound 58b) instead of tert-butyl 2-bromo-6,7-dihydrothiazolo[5,4-c]pyridine-5 (4H)-carboxylate (compound 31b). Example 58 (14 mg) was obtained as a yellow solid. MS: calc'd 513 (MH$^+$), measured 513 (MH$^+$). $^1$H NMR (400

MHz, METHANOL-d₄) δ=8.99 (dd, J=1.5, 4.2 Hz, 1H), 8.66 (dd, J=1.5, 8.6 Hz, 1H), 8.16 (d, J=8.1 Hz, 1H), 7.65 (dd, J=4.3, 8.6 Hz, 1H), 7.31-7.22 (m, 2H), 7.19-7.09 (m, 2H), 4.61-4.48 (m, 2H), 4.38-4.26 (m, 2H), 4.25-4.16 (m, 1H), 4.11-3.34 (m, 17H), 2.86-2.70 (m, 2H), 1.34 (d, J=6.2 Hz, 3H).

The compound 58b was prepared according to the following scheme:

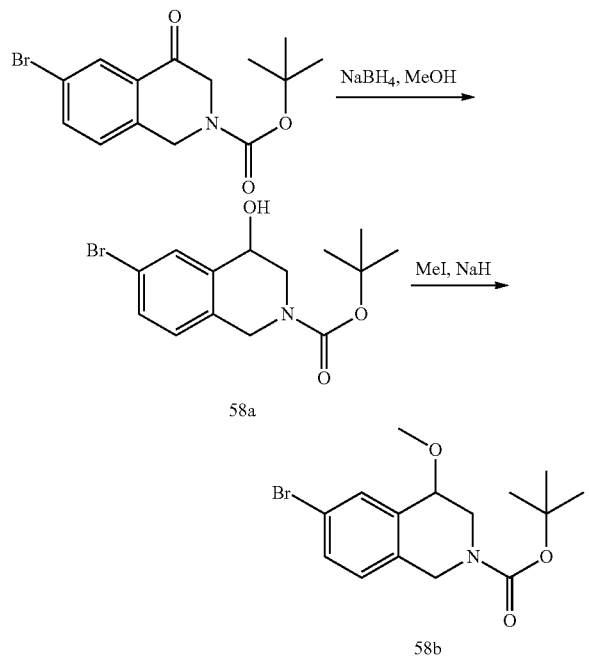

Step 1: Preparation of tert-butyl 6-bromo-4-hydroxy-3,4-dihydro-1H-isoquinoline-2-carboxylate (Compound 58a)

To the solution of tert-butyl 6-bromo-4-oxo-1,3-dihydroisoquinoline-2-carboxylate (CAS: 1935005-74-5, Vendor: Aldrich, 200 mg, 0.61 mmol) in methanol (4 mL) was added sodium borohydride (47 mg, 1.23 mmol) at 0° C. After being stirred at 0° C. for 1 h, the reaction was quenched by addition of saturated NH₄Cl (20 mL), diluted with water (50 mL), and extracted with EA (30 mL) for three times. The combined organic layer was washed with water (40 mL) twice and brine (30 ml) once, dried over Na₂SO₄ and concentrated to give the crude product 58a (210 mg) as a yellow gum. MS: calc'd 328 (MH⁺), measured 328 (MH⁺).

Step 2: Preparation of tert-butyl 6-bromo-4-methoxy-3,4-dihydro-1H-isoquinoline-2-carboxylate (Compound 58b)

To the solution of tert-butyl 6-bromo-4-hydroxy-3,4-dihydro-1H-isoquinoline-2-carboxylate (compound 58a, 210 mg, 0.41 mmol) in THF (5 mL) was added sodium hydride (60% in oil, 32 mg, 0.81 mmol) at 0° C. After being stirred for 10 mins, iodomethane (86 mg, 0.61 mmol) was added to the mixture at 0° C. After being stirred at rt for 2 hrs, the reaction was quenched by addition of saturated NH₄Cl (20 mL), diluted with water (50 mL) and extracted with EA (20 mL) for three times. The combined organic layer was washed with water (20 mL) twice and brine (20 mL) once, dried over Na₂SO₄, concentrated and purified by prep-TLC (PE/EA=5/1) to give compound 58b (100 mg) as a white solid. MS: calc'd 342 (MH⁺), measured 342 (MH⁺).

Example 59

5-[(2S,6R)-2-[[4-(4-hydroxy-2-methyl-3,4-dihydro-1H-isoquinolin-6-yl)piperazin-1-yl]methyl]-6-methyl-morpholin-4-yl]quinoline-8-carbonitrile

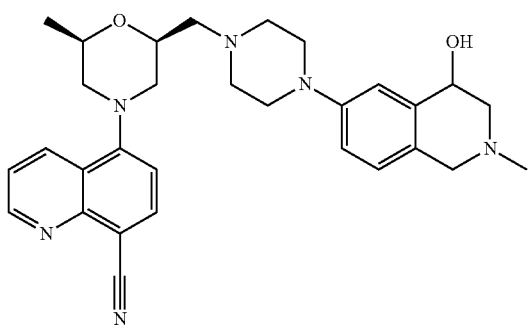 [SMILES: C[C@@H]1CN(c2ccc(C#N)c3ncccc23)C[C@H](CN2CCN(c3ccc4c(c3)C(O)CN(C)C4)CC2)O1]

The title compound was prepared according to the following scheme:

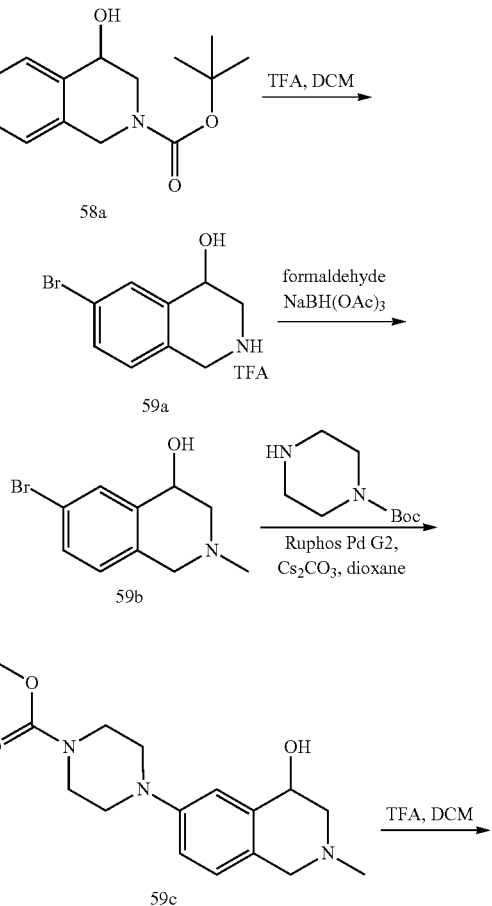

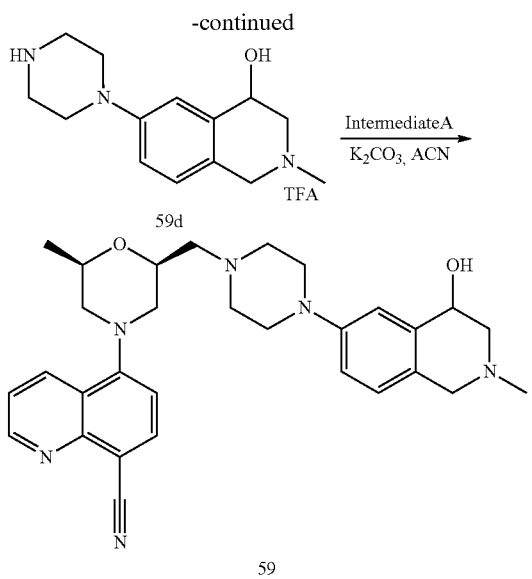

Step 1: Preparation of 6-bromo-1,2,3,4-tetrahydroisoquinolin-4-ol 2,2,2-trifluoroacetic acid (Compound 59a)

To the solution of tert-butyl 6-bromo-4-hydroxy-3,4-dihydro-1H-isoquinoline-2-carboxylate (compound 58a, 260 mg, 0.79 mmol) in DCM (2 mL) was added trifluoroacetic acid (600 μL) at 0° C. After being stirred at rt for 2 hrs, the mixture was concentrated to give compound 59a (260 mg) as a yellow oil which was used in the next step directly. MS: calc'd 228 (MH$^+$), measured 228 (MH$^+$).

Step 2: Preparation of 6-bromo-2-methyl-3,4-dihydro-1H-isoquinolin-4-ol (Compound 59b)

The solution of 6-bromo-1,2,3,4-tetrahydroisoquinolin-4-ol 2,2,2-trifluoroacetic acid (compound 59a, 230 mg, 0.67 mmol), formaldehyde (164 mg, 2.02 mmol) in methanol (3 mL) was stirred at 50° C. for 2 hrs. Then sodium triacetoxyborohydride (427 mg, 2.02 mmol) was added and the mixture was stirred at 50° C. for 16 hrs. The mixture was concentrated and purified by prep-TLC (DCM/MeOH=10/1) to give compound 59b (120 mg) as a yellow oil. MS: calc'd 242 (MH$^+$), measured 242 (MH$^+$).

Step 3: Preparation of tert-butyl 4-(4-hydroxy-2-methyl-3,4-dihydro-1H-isoquinolin-6-yl)piperazine-1-carboxylate (Compound 59c)

To the solution of 6-bromo-2-methyl-3,4-dihydro-1H-isoquinolin-4-ol (compound 59b, 100 mg, 0.29 mmol), 1-Boc-piperazine (108 mg, 0.58 mmol), cesium carbonate (235 mg, 0.72 mmol) in 1,4-dioxane (5 mL) was added Ruphos Pd G2 (22 mg, 0.03 mmol). After being stirred at 90° C. for 2 hrs under N$_2$ atmosphere, the mixture was concentrated and purified by prep-TLC (DCM/MeOH=10/1) to give compound 59c (30 mg) as a colorless oil. MS: calc'd 348 (MH$^+$), measured 348 (MH$^+$).

Step 4: Preparation of 2-methyl-6-piperazin-1-yl-3,4-dihydro-1H-isoquinolin-4-ol 2,2,2-trifluoroacetic acid (Compound 59d)

To the solution of tert-butyl 4-(4-hydroxy-2-methyl-3,4-dihydro-1H-isoquinolin-6-yl)piperazine-1-carboxylate (compound 59c, 30 mg, 0.07 mmol) in DCM (1 mL) was added trifluoroacetic acid (400 μL) at 0° C., and the mixture was stirred at rt for 2 hrs. Then the mixture was concentrated to give compound 59d (20 mg) as a brown oil and used in the next step directly. MS: calc'd 248 (MH$^+$), measured 248 (MH$^+$).

Step 5: Preparation of 5-[(2S,6R)-2-[[4-(4-hydroxy-2-methyl-3,4-dihydro-1H-isoquinolin-6-yl)piperazin-1-yl]methyl]-6-methyl-morpholin-4-yl]quinoline-8-carbonitrile (Compound 59)

The solution of [(2R,6R)-4-(8-cyano-5-quinolyl)-6-methyl-morpholin-2-yl]methyl trifluoromethanesulfonate (Intermediate A, 15 mg, 0.04 mmol), potassium carbonate (12 mg, 0.09 mmol), 2-methyl-6-piperazin-1-yl-3,4-dihydro-1H-isoquinolin-4-ol (compound 59d, 17 mg, 0.05 mmol) in acetonitrile (1 mL) was stirred at 55° C. for 2 hrs. After filtration, the mixture was concentrated and purified by prep-HPLC to give Example 59 (2 mg) as a yellow gum. MS: calc'd 513 (MH$^+$), measured 513 (MH$^+$). $^1$H NMR (400 MHz, METHANOL-d$_4$) δ=9.02 (dd, J=1.6, 4.3 Hz, 1H), 8.69 (dd, J=1.6, 8.6 Hz, 1H), 8.20 (d, J=7.9 Hz, 1H), 7.68 (dd, J=4.2, 8.6 Hz, 1H), 7.32 (d, J=8.1 Hz, 1H), 7.24-7.11 (m, 3H), 4.83-4.74 (m, 1H), 4.51 (br d, J=18.6 Hz, 2H), 4.32-4.16 (m, 2H), 4.00-3.39 (m, 13H), 3.29-3.17 (m, 1H), 3.09 (s, 3H), 2.86-2.70 (m, 2H), 1.34 (d, J=6.2 Hz, 3H).

Example 60

5-[(2R,6S)-2-methyl-6-[[4-(3-methyl-5,6,7,8-tetrahydropyrido[3,4-b]pyrazin-2-yl)piperazin-1-yl]methyl]morpholin-4-yl]quinoline-8-carbonitrile

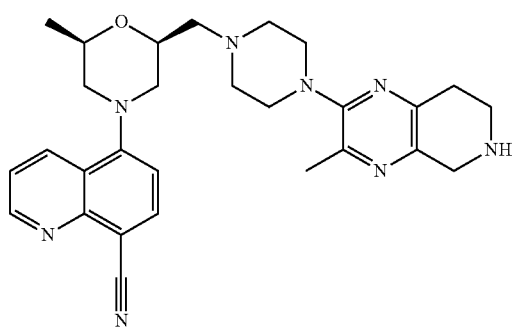 [SMILES: Cc1nc2c(nc1N1CCN(C[C@H]3CN(c4ccc(C#N)c5ncccc45)C[C@@H](C)O3)CC1)CCNC2]

The title compound was prepared in analogy to the preparation of Example 47 by using 2-trimethylsilylethyl 2-(4-tert-butoxycarbonylpiperazin-1-yl)-3-methyl-7,8-dihydro-5H-pyrido[3,4-b]pyrazine-6-carboxylate (compound 60h) instead of tert-butyl 8-[6-(2-trimethylsilyl ethoxycarbonyl)-7,8-dihydro-5H-1,6-naphthyridin-3-yl]-5-oxa-2,8-diazaspiro[3.5]nonane-2-carboxylate (compound 47b). Example 60 (12 mg) was obtained as a yellow solid. MS calc'd 499 (MH$^+$), measured 499 (MH$^+$). $^1$H NMR (400 MHz, METHANOL-d$_4$) δ=8.95 (dd, J=1.6, 4.3 Hz, 1H), 8.63 (dd, J=1.6, 8.6 Hz, 1H), 8.11 (d, J=7.9 Hz, 1H), 7.62 (dd, J=4.2, 8.6 Hz, 1H), 7.24 (d, J=8.1 Hz, 1H), 4.57 (br t, J=9.9 Hz, 1H), 4.36 (s, 2H), 4.25-4.12 (m, 1H), 3.82 (br s, 4H), 3.63 (t, J=6.4 Hz, 2H), 3.58-3.34 (m, 8H), 3.17 (br t, J=6.2 Hz, 2H), 2.82-2.67 (m, 2H), 2.54 (s, 3H), 1.31 (d, J=6.2 Hz, 3H).

The compound 60h was prepared according to the following scheme:

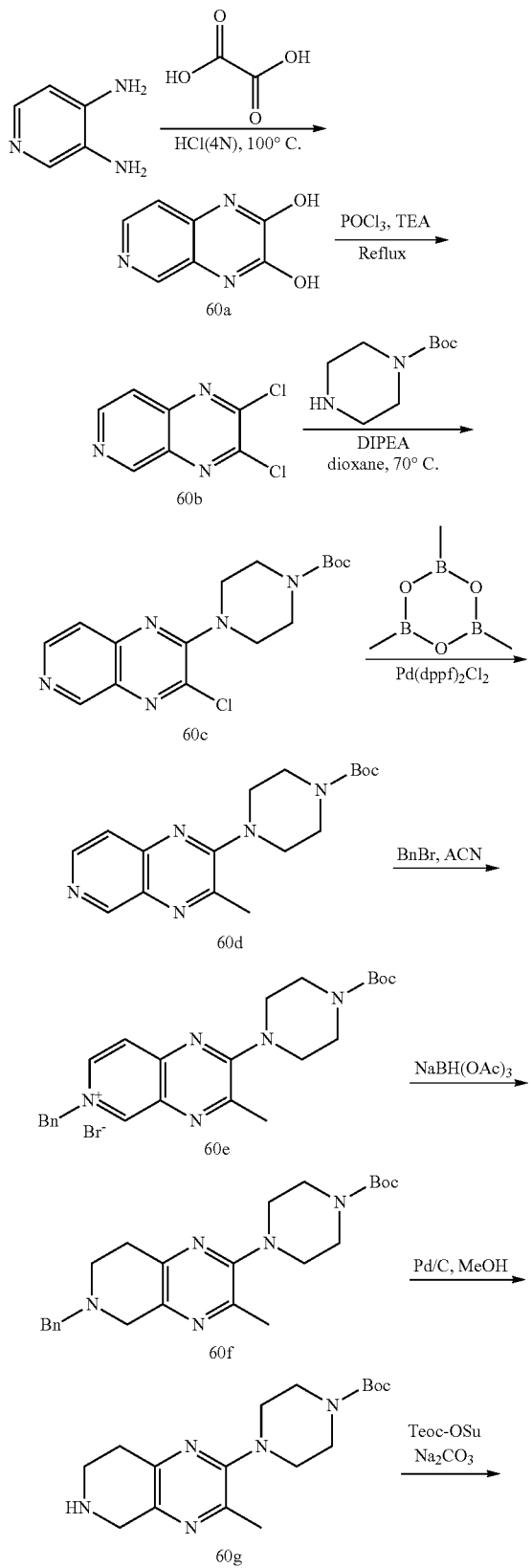

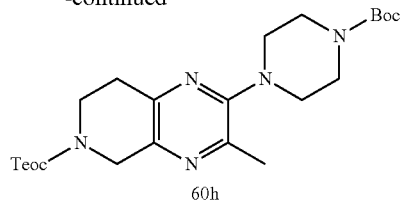

Step 1: Preparation of pyrido[3,4-b]pyrazine-2,3-diol (Compound 60a)

To the solution of 3,4-diaminopyridine (CAS: 54-96-6, Vendor: Alfa Aesar, 20.00 g, 183.27 mmol) in aqueous hydrogenchloride (4 N, 200 mL, 800.00 mmol) was added oxalic acid (19.80 g, 219.92 mmol). The reaction was stirred at 100° C. for 18 hrs. After being cooled down, the mixture was filtered, and the wet cake was washed with EtOH (200 mL) and dried to give the compound 60a (33.00 g) as a white solid. $^1$H NMR (400 MHz, METHANOL-$d_4$) δ=13.01 (br s, 1H), 12.60 (br s, 1H), 8.50 (s, 1H), 8.42 (d, J=6.2 Hz, 1H), 7.52 (d, J=6.2 Hz, 1H).

Step 2: Preparation of 2,3-dichloropyrido[3,4-b]pyrazine (Compound 60b)

To the solution of pyrido[3,4-b]pyrazine-2,3-diol (compound 60a, 10.00 g, 61.30 mmol) in trichlorophosphate (102 mL, 1.06 mol) was added triethylamine (8 mL, 61.30 mmol). The reaction was heated to 130° C. for 18 hrs. After being cooled down, the mixture was concentrated and the residue was quenched with aq. solution of NaHCO$_3$. After filtration, the mixture was extracted with EA (500 mL) twice. The organic layer was washed with brine (200 mL), and dried over anhydrous Na$_2$SO$_4$. After filtration, the mixture was concentrated to give the crude product which was purified by flash column (PE/EA=5:1) to give compound 60b (400 mg) as a white solid. MS: calc'd 200 (MH$^+$), measured 200 (MH$^+$).

Step 3: Preparation of tert-butyl 4-(3-chloropyrido[3,4-b]pyrazin-2-yl)piperazine-1-carboxylate (Compound 60c)

To the solution of 2,3-dichloropyrido[3,4-b]pyrazine (compound 60b, 400 mg, 2.00 mmol) in 1,4-dioxane (14 mL) was added N,N-diisopropylethylamine (0.52 mL, 3.00 mmol) and 1-Boc-piperazine (376 mg, 2.02 mmol). The mixture was stirred at 40° C. for 2 hrs. After being cooled down, the reaction mixture was concentrated and purified by flash column (PE/EA=3/1) to give compound 60c (620 mg) as a yellow solid. MS: calc'd 350 (MH$^+$), measured 350 (MH$^+$).

Step 4: Preparation of tert-butyl 4-(3-methylpyrido[3,4-b]pyrazin-2-yl)piperazine-1-carboxylate (Compound 60d)

To the solution of trimethylboroxine (CAS: 823-96-1, Vendor: sigma-aldrich, 9329 mg, 74.32 mmol) and tert-butyl 4-(3-chloropyrido[3,4-b]pyrazin-2-yl)piperazine-1-carboxylate (compound 60c, 520 mg, 1.49 mmol) in 1,4-dioxane (12 mL) and water (2 mL) was added Pd(dppf)$_2$Cl$_2$ (108 mg, 0.15 mmol) and potassium carbonate (308 mg, 2.23 mmol). The mixture was stirred at 100° C. under nitrogen for 5 hrs. After being cooled down, the reaction mixture was concentrated and purified by flash column (PE/EA=5/1 to 3/1) to give compound 60d (495 mg) as a yellow oil. MS: calc'd 330 (MH$^+$), measured 330 (MH$^+$).

Step 5: Preparation of tert-butyl 4-(6-benzyl-3-methyl-pyrido[3,4-b]pyrazin-6-ium-2-yl)piperazine-1-carboxylate; bromide (Compound 60e)

To the solution of tert-butyl 4-(3-methylpyrido[3,4-b]pyrazin-2-yl)piperazine-1-carboxylate (compound 60d, 495 mg, 1.50 mmol) in ACN (12 mL) was added benzyl bromide (0.18 mL, 1.50 mmol). The reaction was heated to 70° C. for 2 hrs. After being cooled down, the mixture was concentrated to give the crude product 60e (735 mg) as a brown solid, which was used for the next step without purification. MS: calc'd 420 (MH$^+$), measured 420 (MH$^+$).

Step 6: Preparation of tert-butyl 4-(6-benzyl-3-methyl-7,8-dihydro-5H-pyrido[3,4-b]pyrazin-2-yl)piperazine-1-carboxylate (Compound 60f)

To the solution of tert-butyl 4-(6-benzyl-3-methyl-pyrido[3,4-b]pyrazin-6-ium-2-yl) piperazine-1-carboxylate bromide (compound 60e, 730 mg, 1.46 mmol) in ACN (14 mL) was added sodium triacetoxyborohydride (3091 mg, 14.59 mmol) at 0° C. After being stirred at 40° C. for 3 hrs, the reaction was quenched by addition of water (50 mL) and extracted with EA (80 mL) for three times. The combined organic layer was washed with brine (100 mL), dried over Na$_2$SO$_4$, concentrated and purified by flash column (PE/EA=1/1) to give compound 60f (360 mg) as a yellow solid. MS: calc'd 424 (MH$^+$), measured 424 (MH$^+$).

Step 7: Preparation of tert-butyl 4-(3-methyl-5,6,7,8-tetrahydropyrido[3,4-b]pyrazin-2-yl)piperazine-1-carboxylate (Compound 60g)

To the solution of tert-butyl 4-(6-benzyl-3-methyl-7,8-dihydro-5H-pyrido[3,4-b]pyrazin-2-yl)piperazine-1-carboxylate (compound 60f, 360 mg, 0.85 mmol) in methanol (5 mL) was added Pd/C (10 wt. %, 36 mg, 0.19 mmol). The mixture was stirred at rt for 2 hrs under H$_2$ atmosphere. After filtration, the mixture was concentrated to give compound 60g (250 mg) as a yellow gum. MS: calc'd 334 (MH$^+$), measured 334 (MH$^+$).

Step 8: Preparation of 2-trimethylsilylethyl 2-(4-tert-butoxycarbonylpiperazin-1-yl)-3-methyl-7,8-dihydro-5H-pyrido[3,4-b]pyrazine-6-carboxylate (Compound 60h)

To the solution of tert-butyl 4-(3-methyl-5,6,7,8-tetrahydropyrido[3,4-b]pyrazin-2-yl)piperazine-1-carboxylate (compound 60g, 250 mg, 0.75 mmol), sodium carbonate (159 mg, 1.50 mmol) in 1,4-dioxane (6 mL) and water (1 mL) was added 2,5-dioxopyrrolidin-1-yl (2-(trimethylsilyl)ethyl) carbonate (583 mg, 2.25 mmol). After being stirred at rt for 1 h, the reaction mixture was concentrated and purified by flash column (PE/EA=5/1) to give compound 60h (290 mg) as a yellow oil. MS: calc'd 478 (MH$^+$), measured 478 (MH$^+$).

Example 61

5-[(2R,6S)-2-methyl-6-[[4-(5,6,7,8-tetrahydropyrido[4,3-d]pyrimidin-4-yl)piperazin-1-yl]methyl]morpholin-4-yl]quinoline-8-carbonitrile

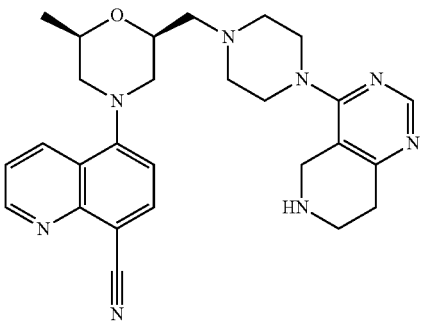 [SMILES: C[C@@H]1CN(c2ccc(C#N)c3ncccc23)C[C@H](CN2CCN(c3ncnc4c3CNCC4)CC2)O1]

The title compound was prepared in analogy to the preparation of Example 6 by using tert-butyl 4-chloro-7,8-dihydropyrido[4,3-d]pyrimidine-6 (5H)-carboxylate (CAS: 1056934-87-2, Vendor: Bepharm) instead of tert-butyl 4-chloro-5,7-dihydropyrrolo[3,4-d]pyrimidine-6-carboxylate. Example 61 (45 mg) was obtained as a yellow solid. MS: calc'd 485 (MH$^+$), measured 485 (MH$^+$). $^1$H NMR (400 MHz, METHANOL-d$_4$) δ=9.00 (dd, J=1.6, 4.3 Hz, 1H), 8.74 (s, 1H), 8.66 (dd, J=1.6, 8.7 Hz, 1H), 8.16 (d, J=8.1 Hz, 1H), 7.66 (dd, J=4.3, 8.6 Hz, 1H), 7.28 (d, J=8.1 Hz, 1H), 4.6-4.5 (m, 1H), 4.43 (s, 2H), 4.3-4.1 (m, 1H), 3.95 (br s, 4H), 3.8-3.5 (m, 6H), 3.5-3.4 (m, 4H), 3.24 (t, J=6.5 Hz, 2H), 2.8-2.7 (m, 2H), 1.33 (d, J=6.2 Hz, 3H).

Example 62

5-[(2R,6S)-2-methyl-6-[[4-(5,6,7,8-tetrahydro-2,6-naphthyridin-1-yl)piperazin-1-yl]methyl]morpholin-4-yl]quinoline-8-carbonitrile

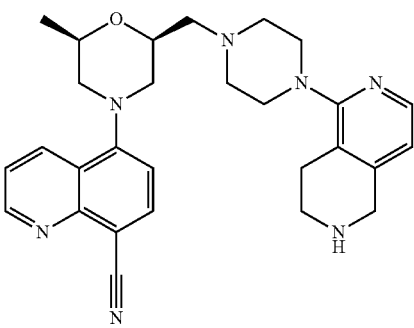 [SMILES: C[C@@H]1CN(c2ccc(C#N)c3ncccc23)C[C@H](CN2CCN(c3nccc4c3CCNC4)CC2)O1]

The title compound was prepared in analogy to the preparation of Example 47 by using 2-trimethylsilylethyl 5-(4-tert-butoxycarbonylpiperazin-1-yl)-3,4-dihydro-1H-2,6-naphthyridine-2-carboxylate (compound 62b) instead of tert-butyl 8-[6-(2-trimethylsilylethoxycarbonyl)-7,8-dihydro-5H-1,6-naphthyridin-3-yl]-5-oxa-2,8-diazaspiro[3.5]nonane-2-carboxylate (compound 47b). Example 62 (2 mg) was obtained as a yellow solid. MS: calc'd 484 (MH$^+$), measured 484 (MH$^+$). $^1$H NMR (400 MHz, METHANOL-d4) δ=9.02 (dd, J=1.5, 4.2 Hz, 1H), 8.70 (dd, J=1.6, 8.4 Hz, 1H), 8.25 (d, J=5.1 Hz, 1H), 8.20 (d, J=8.1 Hz, 1H), 7.68 (dd, J=4.4, 8.6 Hz, 1H), 7.32 (d, J=8.3 Hz, 1H), 7.04 (d, J=5.4 Hz, 1H), 4.54 (br s, 1H), 4.43 (s, 2H), 4.22 (br d, J=8.1 Hz, 1H), 3.80 (br s, 2H), 3.60 (br s, 2H), 3.56-3.49 (m, 3H), 3.49-3.40 (m, 5H), 3.08 (br t, J=6.1 Hz, 2H), 2.87-2.69 (m, 4H), 1.35 (d, J=6.1 Hz, 3H).

The compound 62b was prepared according to the following scheme:

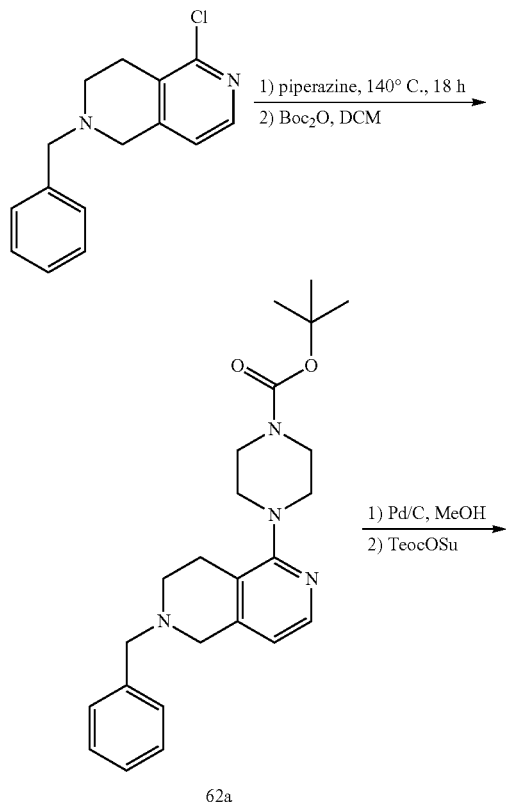

Step 1: Preparation of tert-butyl 4-(6-benzyl-7,8-dihydro-5H-2,6-naphthyridin-1-yl)piperazine-1-carboxylate (Compound 62a)

The mixture of piperazine (6.00 g, 69.65 mmol) and 2-benzyl-5-chloro-3,4-dihydro-1H-2,6-naphthyridine (CAS: 1104027-46-4, Vendor: Bepharm, 300 mg, 1.16 mmol) was stirred at 140° C. for 8 hrs. After being cooled down, the mixture was dissolved in water (50 mL) and extracted with EA (50 mL) twice. The combined organic layer was dried over $Na_2SO_4$, filtered and concentrated to give an oil. Then it was dissolved in DCM (5 mL) and N,N-diisopropylethylamine (0.36 mL, 2.08 mmol) and di-t-butyldicarbonate (339 mg, 1.56 mmol) were added. After being stirred at rt for 2 hrs, the mixture was quenched by addition of water (50 mL) and aq. $NaHCO_3$ (30 mL), extracted with EA (50 mL) for three times. The combined organic layer was dried over $Na_2SO_4$, filtered and concentrated, the residue was purified by pre-TLC (EA/PE=1/3) to give compound 62a (100 mg) as a yellow oil. MS: calc'd 409 ($MH^+$), measured 409 ($MH^+$).

Step 2: Preparation of 2-trimethylsilylethyl 5-(4-tert-butoxycarbonylpiperazin-1-yl)-3,4-dihydro-1H-2,6-naphthyridine-2-carboxylate (Compound 62b)

To the solution of tert-butyl 4-(6-benzyl-7,8-dihydro-5H-2,6-naphthyridin-1-yl)piperazine-1-carboxylate (compound 62a, 90 mg, 0.22 mmol) in methanol (3 mL) was added Pd/C (10 wt. %, 50 mg, 0.22 mmol). After being stirred at 50° C. for 3 hrs, the reaction mixture was filtered and concentrated to give the residue (90 mg) as a yellow oil.

To the solution of the above residue (90 mg, 0.28 mmol) and sodium carbonate (89 mg, 0.85 mmol) in THF (2 mL) and water (2 mL) was added 2,5-dioxopyrrolidin-1-yl (2-(trimethyl silyl)ethyl) carbonate (146 mg, 0.57 mmol). After being stirred at rt for 3 hrs, the reaction was quenched by addition of saturated $NH_4Cl$ (10 mL), diluted with water (30 mL) and extracted with EA (20 mL) for three times. The combined organic layer was washed with water (20 mL) twice and brine (20 mL) once, dried over $Na_2SO_4$, concentrated and purified by prep-TLC (PE/EA=2/1) to give compound 62b (50 mg) as a colorless oil. MS: calc'd 463 ($MH^+$), measured 463 ($MH^+$).

Example 63

5-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoline-8-carbonitrile

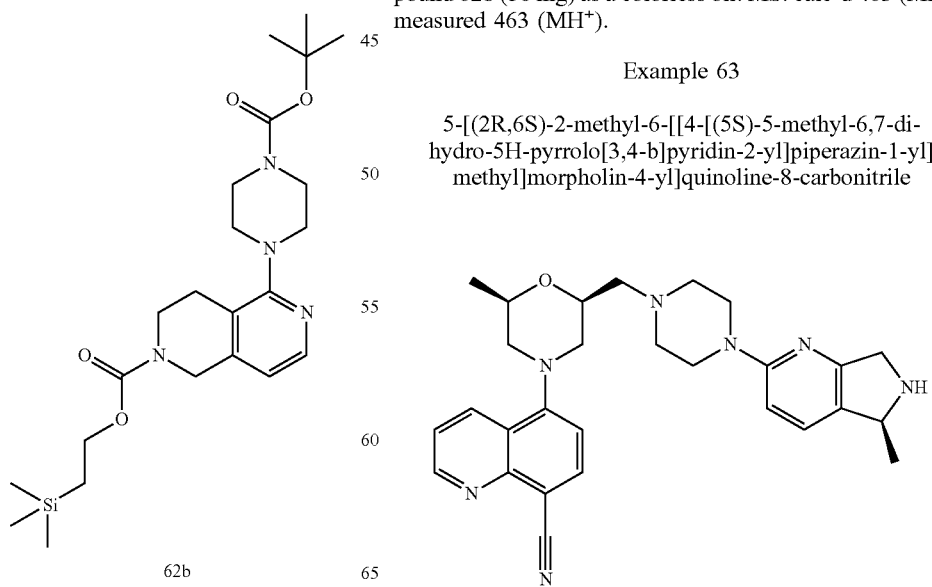

Example 64
5-[(2R,6S)-2-methyl-6-[[4-[(5R)-5-methyl-6,7-di-hydro-5H-pyrrolo[3,4-b]pyridin-2-yl]piperazin-1-yl]methyl]morpholin-4-yl]quinoline-8-carbonitrile
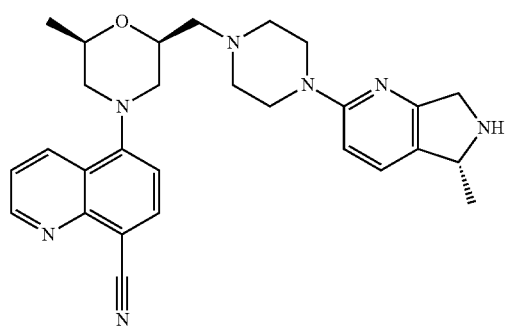 [SMILES: C[C@@H]1CN(c2ccc(C#N)c3ncccc23)C[C@H](CN2CCN(c3ccc4c(n3)CN[C@@H]4C)CC2)O1]
The title compounds were prepared according to the following scheme:
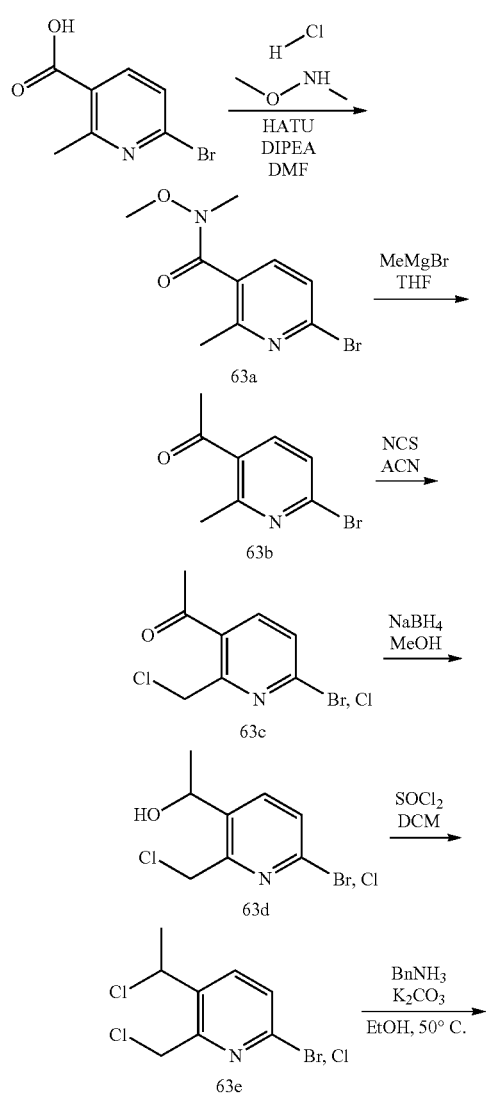
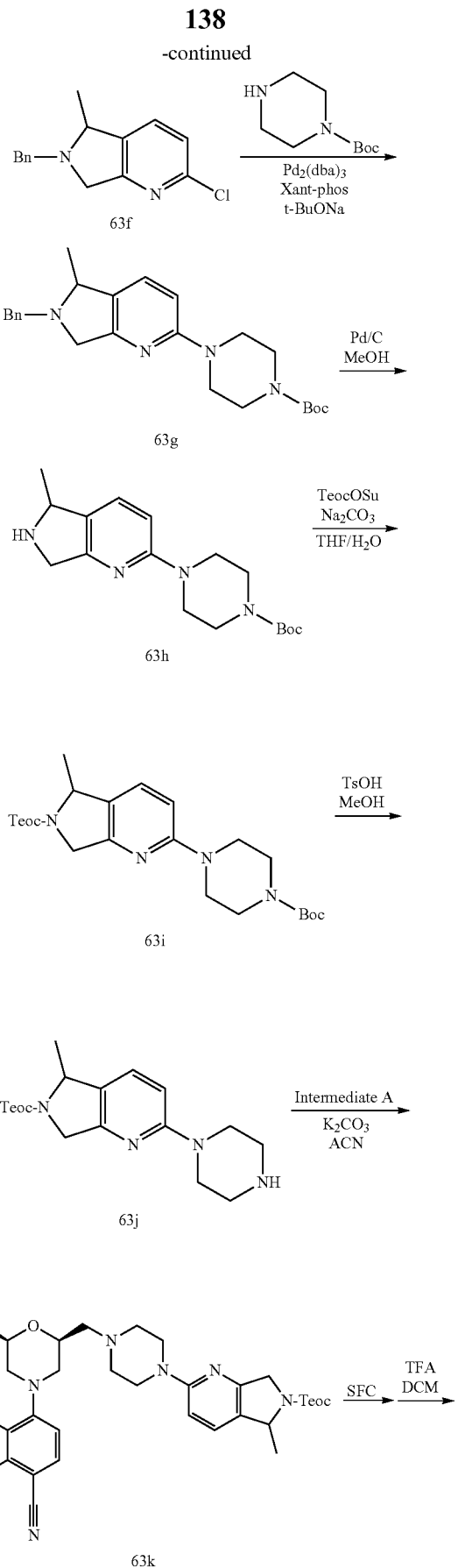

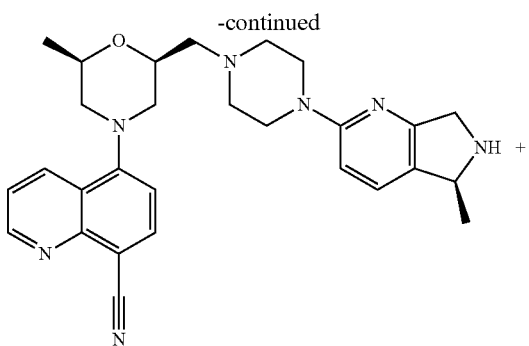

63

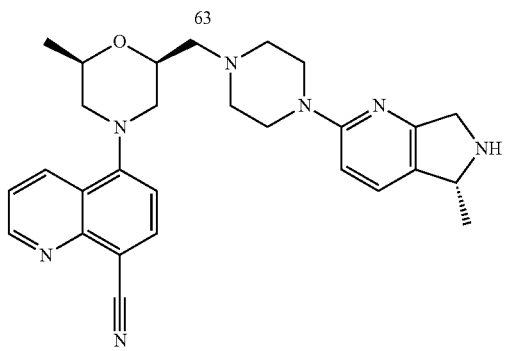

64

Step 1: Preparation of 6-bromo-N-methoxy-N,2-dimethyl-pyridine-3-carboxamide (Compound 63a)

To the solution of 6-bromo-2-methyl-pyridine-3-carboxylic acid (CAS: 1060805-97-1, Vendor: Bepharm, 7.00 g, 32.40 mmol), DIPEA (16.75 g, 129.60 mmol) and O-(7-azabenzotriazol-1-yl)-N,N,N',N'-tetramethyluronium hexafluorophosphate (15.00 g, 38.90 mmol) in DMF (140 mL) was added O,N-dimethylhydroxylamine hydrochloride (CAS: 6638-79-5, Vendor: TCI, 6.32 g, 64.81 mmol). After being stirred at rt for 4 hrs, the reaction was quenched by addition of saturated NH$_4$Cl (100 mL), diluted with water (500 mL) and extracted with EA (400 mL) for three times. The combined organic layer was washed with water (300 mL) twice and brine (100 mL) once, dried over Na$_2$SO$_4$, concentrated and purified by flash column (PE/EA=5/1) to give the compound 63a (7.50 g) as a yellow oil. MS: calc'd 259 (MH$^+$), measured 259 (MH$^+$).

Step 2: Preparation of 1-(6-bromo-2-methyl-3-pyridyl)ethanone (Compound 63b)

To the solution of 6-bromo-N-methoxy-N,2-dimethyl-pyridine-3-carboxamide (compound 63a, 7.50 g, 28.95 mmol) in THF (130 mL) was added methylmagnesium bromide (3.0 M in THF, 19 mL, 57.89 mmol) at 0° C. After being stirred at rt for 2 hrs, the reaction was quenched by addition of saturated NH$_4$Cl (80 mL), diluted with water (200 mL) and extracted with EA (80 mL) for three times. The combined organic layer was washed with water (100 mL) twice and brine (60 mL) dried over Na$_2$SO$_4$, concentrated and purified by flash column (PE/EA=10/1) to give compound 63b (5.70 g) as a yellow oil. MS: calc'd 214 (MH$^+$), measured 214 (MH$^+$).

Step 3: Preparation of the mixture of 1-[6-bromo-2-(chloromethyl)-3-pyridyl]ethanone and 1-[6-chloro-2-(chloromethyl)-3-pyridyl]ethanone (Compound 63c)

The solution of 1-(6-bromo-2-methyl-3-pyridyl)ethanone (compound 63b, 3.00 g, 14.01 mmol), 2,2'-azobis(2-methylpropionitrile) (345 mg, 2.10 mmol) and NCS (3.74 g, 28.03 mmol) in acetonitrile (100 mL) was stirred at 80° C. for 16 hrs. The reaction was quenched by 40 mL saturated NH$_4$Cl, diluted with 100 mL water, and extracted with 60 mL EA for three times. The combined organic layer was washed with 60 mL water twice and 40 mL brine once, dried over Na$_2$SO$_4$, concentrated and purified by prep-HPLC to give compound 63c (1.70 g) as a yellow oil. MS: calc'd 248/204 (MH$^+$), measured 248/204 (MH$^+$).

Step 4: Preparation of the mixture of 1-[6-bromo-2-(chloromethyl)-3-pyridyl]ethanol and 1-[6-chloro-2-(chloromethyl)-3-pyridyl]ethanol (Compound 63d)

To the solution of 1-[6-bromo-2-(chloromethyl)-3-pyridyl]ethanone and 1-[6-chloro-2-(chloromethyl)-3-pyridyl]ethanone (compound 63c, 1.70 g, 5.91 mmol) in methanol (40 mL) was added sodium borohydride (447 mg, 11.83 mmol) at 0° C. After being stirred at 0° C. for 1 h, the reaction was quenched by 20 mL saturated NH$_4$Cl, diluted with 100 mL water and extracted with 60 mL EA for three times. The combined organic layer was washed with 60 mL water twice and 40 mL brine once, dried over Na$_2$SO$_4$ and concentrated to give the crude product compound 63d (1.60 g) as a colorless oil. MS: calc'd 250/206 (MH$^+$), measured 250/206 (MH$^+$).

Step 5: Preparation of the mixture of 6-bromo-3-(1-chloroethyl)-2-(chloromethyl)pyridine and 6-chloro-3-(1-chloroethyl)-2-(chloromethyl)pyridine (Compound 63e)

To the solution of 1-[6-bromo-2-(chloromethyl)-3-pyridyl]ethanol and 1-[6-chloro-2-(chloromethyl)-3-pyridyl]ethanol (compound 63d, 1.60 g, 5.57 mmol) in DCM (30 mL) was added thionyl chloride (3.31 g, 27.83 mmol) at 0° C. After being stirred at rt for 3 hrs, the mixture was concentrated directly and purified by flash column (PE/EA=10/1) to give compound 63e (1.20 g) as a colorless oil. MS: calc'd 268/224 (MH$^+$), measured 268/224 (MH$^+$).

Step 6: Preparation of 6-benzyl-2-chloro-5-methyl-5,7-dihydropyrrolo[3,4-b]pyridine (Compound 63f)

To the solution of 6-bromo-3-(1-chloroethyl)-2-(chloromethyl)pyridine and 6-chloro-3-(1-chloroethyl)-2-(chloromethyl)pyridine (compound 63e, 1.20 g, 4.00 mmol) in ethanol (15 mL) was added potassium carbonate (1.11 g, 8.00 mmol) and benzylamine (0.48 mL, 4.40 mmol). After being stirred at 65° C. for 3 hrs, the mixture was quenched by 20 mL saturated NH$_4$Cl, diluted with 100 mL water, extracted with 50 mL EA for three times. The combined organic layer was washed with 60 mL water twice and 40 mL brine once, dried over Na$_2$SO$_4$, concentrated and purified by flash column (PE/EA=10/1) to give compound 63f (1.10 g) as a yellow solid. MS: calc'd 259 (MH$^+$), measured 259 (MH$^+$).

Step 7: Preparation of tert-butyl 4-(6-benzyl-5-methyl-5,7-dihydropyrrolo[3,4-b]pyridin-2-yl)piperazine-1-carboxylate (Compound 63g)

To the solution of 1-Boc-piperazine (874 mg, 4.69 mmol), 6-benzyl-2-chloro-5-methyl-5,7-dihydropyrrolo[3,4-b]pyridine (compound 63f, 900 mg, 3.13 mmol), sodium tert-butoxide (601 mg, 6.25 mmol), Xantphos (362 mg, 0.63 mmol) in toluene (25 mL) was added Pd$_2$(dba)$_3$ (286 mg, 0.31 mmol). After being stirred at 110° C. for 18 hrs under N$_2$ atmosphere, the mixture was concentrated and purified by flash column (PE/EA=5/1) to give compound 63g (1.20 g) as a yellow solid. MS: calc'd 409 (MH$^+$), measured 409 (MH$^+$).

Step 8: Preparation of tert-butyl 4-(5-methyl-6,7-dihydro-5H-pyrrolo[3,4-b]pyridin-2-yl)piperazine-1-carboxylate (Compound 63h)

To the solution of tert-butyl 4-(6-benzyl-5-methyl-5,7-dihydropyrrolo[3,4-b]pyridin-2-yl)piperazine-1-carboxylate (compound 63g, 1.20 g, 2.54 mmol) in methanol (30 mL) was added Pd/C (10 wt. %, 300 mg, 1.32 mmol). After being stirred at 40° C. for 18 hrs under H$_2$ atmosphere, the mixture was filtered, and concentrated to give compound 63h (800 mg) as a black oil. MS: calc'd 319 (MH$^+$), measured 319 (MH$^+$).

Step 9: Preparation of 2-trimethylsilylethyl 2-(4-tert-butoxycarbonylpiperazin-1-yl)-5-methyl-5,7-dihydropyrrolo[3,4-b]pyridine-6-carboxylate (Compound 63i)

To the solution of tert-butyl 4-(5-methyl-6,7-dihydro-5H-pyrrolo[3,4-b]pyridin-2-yl)piperazine-1-carboxylate (compound 63h, 800 mg, 2.01 mmol) and sodium carbonate (639 mg, 6.03 mmol) in THF (10 mL) and water (10 mL) was added 2,5-dioxopyrrolidin-1-yl (2-(trimethylsilyl)ethyl) carbonate (1042 mg, 4.02 mmol). After being stirred at rt for 3 hrs, the reaction was quenched by addition of 20 mL saturated NH$_4$Cl, diluted with 60 mL water, extracted with 40 mL EA for three times. The combined organic layer was washed with 50 mL water twice and 20 mL brine once, dried over Na$_2$SO$_4$, concentrated and purified by flash column (PE/EA=3/1) to give compound 63i (900 mg) as a yellow oil. MS: calc'd 463 (MH$^+$), measured 463 (MH$^+$).

Step 10: Preparation of 2-trimethylsilylethyl 5-methyl-2-piperazin-1-yl-5,7-dihydropyrrolo[3,4-b]pyridine-6-carboxylate (Compound 63j)

The solution of 2-trimethylsilylethyl 2-(4-tert-butoxycarbonylpiperazin-1-yl)-5-methyl-5,7-dihydropyrrolo[3,4-b]pyridine-6-carboxylate (compound 63i, 900 mg, 1.62 mmol) and p-toluenesulfonic acid (557 mg, 3.24 mmol) in methanol (14 mL) was stirred at 55° C. for 5 hrs. After concentration, the mixture was purified by prep-TLC (DCM/MeOH=20/1) to give compound 63j (600 mg) as a white solid. MS: calc'd 363 (MH$^+$), measured 363 (MH$^+$).

Step 11: Preparation of 2-trimethylsilylethyl 2-[4-[[(2S,6R)-4-(8-cyano-5-quinolyl)-6-methyl-morpholin-2-yl]methyl]piperazin-1-yl]-5-methyl-5,7-dihydropyrrolo[3,4-b]pyridine-6-carboxylate (Compound 63k)

The solution of [(2R,6R)-4-(8-cyano-5-quinolyl)-6-methyl-morpholin-2-yl]methyl trifluoromethanesulfonate (Intermediate A, 500 mg, 1.20 mmol), potassium carbonate (416 mg, 3.0 mmol) and 2-trimethylsilylethyl 5-methyl-2-piperazin-1-yl-5,7-dihydropyrrolo[3,4-b]pyridine-6-carboxylate (compound 63j, 567 mg, 1.56 mmol) in acetonitrile (20 mL) was stirred at 60° C. for 2 hrs. After being cooled down, the mixture was concentrated and purified by flash column (PE/EA=1/1) to give compound 63k (420 mg) as a yellow gum. MS: calc'd 628 (MH$^+$), measured 628 (MH$^+$).

Step 12: Preparation of 5-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoline-8-carbonitrile (Example 63) and 5-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoline-8-carbonitrile (Example 64)

2-trimethylsilylethyl 2-[4-[[(2S,6R)-4-(8-cyano-5-quinolyl)-6-methylmorpholin-2-yl]methyl]piperazin-1-yl]-5-methyl-5,7-dihydropyrrolo[3,4-b]pyridine-6-carboxylate (compound 63k) was separated by chiral SFC (Gradient: 50% Ethanol (0.1% NH$_3$H$_2$O) in CO$_2$, Column: «Column_3») to give two isomers: A (slower eluting, 200 mg) as a yellow gum and B (faster eluting, 190 mg) as a yellow gum.

The two isomers were treated with TFA (1 mL) in DCM (5 mL) overnight to give the corresponding Example 63 and Example 64.

Example 63 (135 mg) was obtained as a red solid. MS: calc'd 484 (MH$^+$), measured 484 (MH$^+$). $^1$H NMR (400 MHz, DMSO-d$_6$) δ=9.07 (dd, J=1.5, 4.2 Hz, 1H), 8.64 (dd, J=1.5, 8.6 Hz, 1H), 8.28 (d, J=8.1 Hz, 1H), 7.74-7.62 (m, 2H), 7.27 (d, J=8.1 Hz, 1H), 6.97 (d, J=8.8 Hz, 1H), 4.94-4.80 (m, 1H), 4.66-4.54 (m, 1H), 4.46-4.31 (m, 4H), 4.07-4.02 (m, 1H), 3.77 (br d, J=12.3 Hz, 1H), 3.59-3.36 (m, 6H), 3.30-3.11 (m, 3H), 2.79-2.63 (m, 2H), 1.57 (d, J=6.7 Hz, 3H), 1.21 (d, J=6.2 Hz, 3H).

Example 64 (121 mg) was obtained as a red solid. MS calc'd 484 (MH$^+$), measured 484 (MH$^+$). $^1$H NMR (400 MHz, DMSO-d$_6$) δ=9.07 (dd, J=1.5, 4.2 Hz, 1H), 8.63 (dd, J=1.5, 8.5 Hz, 1H), 8.29 (d, J=7.9 Hz, 1H), 7.74-7.64 (m, 2H), 7.27 (d, J=8.1 Hz, 1H), 6.97 (d, J=8.7 Hz, 1H), 4.93-4.82 (m, 1H), 4.57 (br t, J=9.0 Hz, 1H), 4.45-4.28 (m, 4H), 4.14-4.03 (m, 1H), 3.68-3.64 (m, 1H), 3.56 (br d, J=11.7 Hz, 1H), 3.50-3.33 (m, 5H), 3.30-3.10 (m, 3H), 2.79-2.63 (m, 2H), 1.57 (d, J=6.7 Hz, 3H), 1.21 (d, J=6.2 Hz, 3H).

The structures of Example 63 and 64 were confirmed by their NMR of corresponding MTPA amides. (Ref: The Assignment of Absolute Configuration by NMR. José Manuel Seco, Emilio Quiiioi, and Ricardo Riguera, Chem. Rev. 2004, 104, 17-117.)

143                                   144

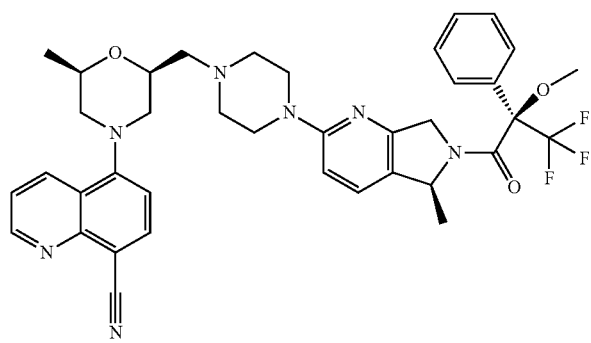
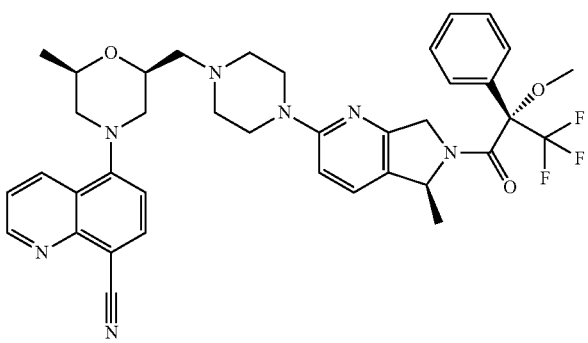

63-MTPA amides

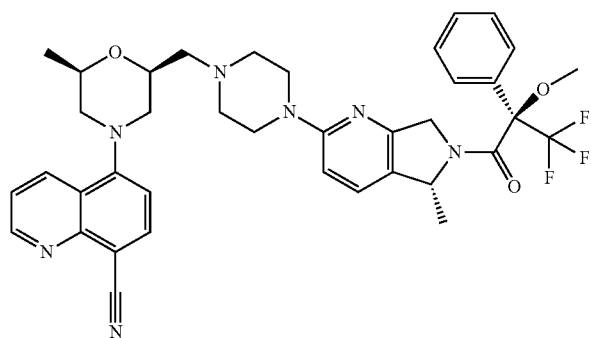

64-MTPA amides

Example 65 and Example 66

5-[(2R,6S)-2-methyl-6-[[4-[(7R)-7-methyl-6,7-di-
hydro-5H-pyrrolo[3,4-b]pyridin-2-yl]piperazin-1-yl]
methyl]morpholin-4-yl]quinoline-8-carbonitrile and
5-[(2R,6S)-2-methyl-6-[[4-[(7S)-7-methyl-6,7-di-
hydro-5H-pyrrolo[3,4-b]pyridin-2-yl]piperazin-1-yl]
methyl]morpholin-4-yl]quinoline-8-carbonitrile

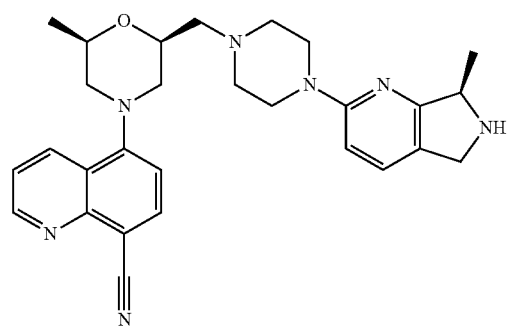

-continued

The title compounds were prepared in analogy to the preparation of Example 63 and 64 by using 1-[6-bromo-3-(hydroxymethyl)-2-pyridyl]ethanone (compound 65d) instead of the mixture of 1-[6-bromo-2-(chloromethyl)-3-pyridyl]ethanone and 1-[6-chloro-2-(chloromethyl)-3-pyridyl]ethanone (compound 63c). The intermediates of Teoc protected Example 65 (faster eluting) and 66 (slower eluting) were separated by chiral SFC (Gradient: 60% Isopropanol (0.1% $NH_3H_2O$) in $CO_2$, Column: Daicel chiralcel OD 250×30 mm, 10 μm).

Example 65 (7 mg) was obtained as a yellow solid. MS: calc'd 484 (MH$^+$), measured 484 (MH$^+$). $^1$H NMR (400

MHz, DMSO-d$_6$) δ=9.02 (dd, J=1.6, 4.4 Hz, 1H), 8.69 (dd, J=1.2, 8.4 Hz, 1H), 8.2 (d, J=7.6 Hz, 1H), 7.71-7.66 (m, 2H), 7.31 (d, J=8.4 Hz, 1H), 6.98 (d, J=8.8 Hz, 1H), 4.87-4.78 (m, 1H), 4.65-4.40 (m, 3H), 4.30-4.16 (m, 1H), 4.12-3.30 (m, 12H), 2.81-2.76 (m, 2H), 1.69 (d, J=6.8 Hz, 3H), 1.34 (d, J=6.4 Hz, 3H).

Example 66 (6 mg) was obtained as a yellow solid. MS: calc'd 484 (MH$^+$), measured 484 (MH$^+$). $^1$H NMR (400 MHz, DMSO-d$_6$) δ=9.02 (dd, J=2.0, 4.4 Hz, 1H), 8.69 (dd, J=1.6, 8.4 Hz, 1H), 8.2 (d, J=8.0 Hz, 1H), 7.71-7.66 (m, 2H), 7.31 (d, J=8.4 Hz, 1H), 6.98 (d, J=9.2 Hz, 1H), 4.80-4.75 (m, 1H), 4.60-4.45 (m, 3H), 4.30-4.16 (m, 1H), 4.12-3.4 (m, 12H), 2.80-2.70 (m, 2H), 1.67 (d, J=6.4 Hz, 3H), 1.35 (d, J=6.4 Hz, 3H).

The compound 65d was prepared according to the following scheme:

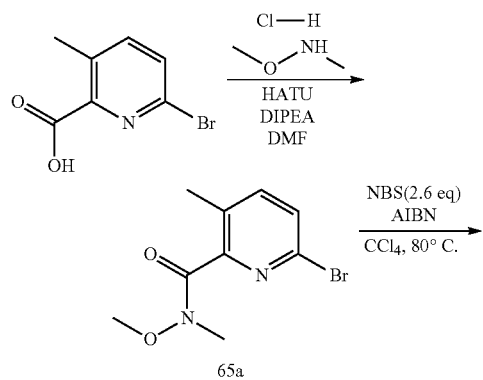

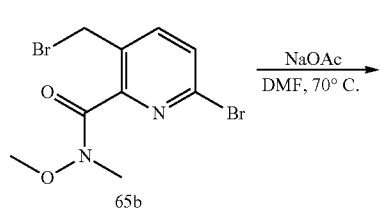

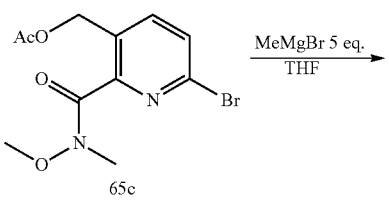

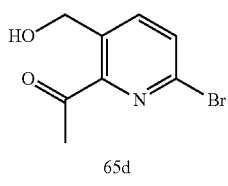

Step 1: Preparation of 6-bromo-N-methoxy-N,3-dimethyl-pyridine-2-carboxamide (Compound 65a)

To the solution of 6-bromo-3-methyl-pyridine-2-carboxylic acid (CAS: 1211516-18-5, Vendor: PharmaBlock; 7.36 g, 34.07 mmol) in DMF (110 mL) was added DIPEA (17.61 g, 136.28 mmol), HATU (15.55 g, 40.88 mmol) and O,N-dimethylhydroxylamine hydrochloride (CAS: 6638-79-5, Vendor: TCI, 6.65 g, 68.14 mmol) at 0° C. After being stirred at rt for 18 hrs, the reaction was quenched by addition of 500 mL water and extracted with 400 mL EA for three times. The combined organic layer was washed with 100 mL water twice and 100 mL brine once, dried over Na$_2$SO$_4$, concentrated and purified by flash column (PE/EA=5/1) to give compound 65a (9.20 g) as a yellow solid. MS: calc'd 259 (MH$^+$), measured 259 (MH$^+$).

Step 2: Preparation of 6-bromo-3-(bromomethyl)-N-methoxy-N-methyl-pyridine-2-carboxamide (Compound 65b)

To the solution of 6-bromo-N-methoxy-N,3-dimethyl-pyridine-2-carboxamide (compound 65a, 7.40 g, 28.56 mmol) in carbon tetrachloride (296 mL) was added 2,2'-azobis(2-methylpropionitrile) (938 mg, 5.71 mmol) and 1-bromopyrrolidine-2,5-dione (12.24 g, 68.54 mmol). After being stirred at 80° C. for 5 hrs, the mixture was concentrated and purified by flash column (EA/PE=1/10) to give compound 65b (3.00 g) as a colorless oil. MS: calc'd 337 (MH$^+$), measured 337 (MH$^+$).

Step 3: Preparation of [6-bromo-2-[methoxy(methyl)carbamoyl]-3-pyridyl]methyl acetate (Compound 65c)

To the solution of 6-bromo-3-(bromomethyl)-N-methoxy-N-methyl-pyridine-2-carboxamide (compound 65b, 4.00 g, 11.83 mmol) in DMF (80 mL) was added sodium acetate (4.48 mL, 59.17 mmol). The reaction was stirred at 70° C. for 2 hrs. After being cooled down, the mixture was poured into EA (200 mL) and washed with 50 mL water twice and 50 ml saturated brine once. The organic phase was dried over Na$_2$SO$_4$, concentrated and purified by flash column (PE/EA=10/1) to give compound 65c (2.00 g) as a yellow oil. MS: calc'd 273 (MH$^+$), measured 273 (MH$^+$).

Step 4: Preparation of 1-[6-bromo-3-(hydroxymethyl)-2-pyridyl]ethanone (Compound 65d)

To the solution of [6-bromo-2-[methoxy(methyl)carbamoyl]-3-pyridyl]methyl acetate (compound 65c, 1.90 g, 5.99 mmol) in THF (46 mL) was added methylmagnesium bromide (3.0 M in THF, 9.5 mL, 28.5 mmol) dropwise at 0° C. After being stirred at 0° C. for 2.5 hrs, the reaction was quenched by addition of MeOH (10 mL). The mixture was concentrated to give the crude product compound 65d (1.38 g) as a yellow gum, which was used in the next step without further purification. MS: calc'd 230 (MH$^+$), measured 230 (MH$^+$).

Example 67 and Example 68

5-[(2R,6S)-2-methyl-6-[[4-[(7S)-7-methyl-6,7-di-hydro-5H-pyrrolo[3,4-b]pyridin-3-yl]piperazin-1-yl]methyl]morpholin-4-yl]quinoline-8-carbonitrile and
5-[(2R,6S)-2-methyl-6-[[4-[(7R)-7-methyl-6,7-di-hydro-5H-pyrrolo[3,4-b]pyridin-3-yl]piperazin-1-yl]methyl]morpholin-4-yl]quinoline-8-carbonitrile

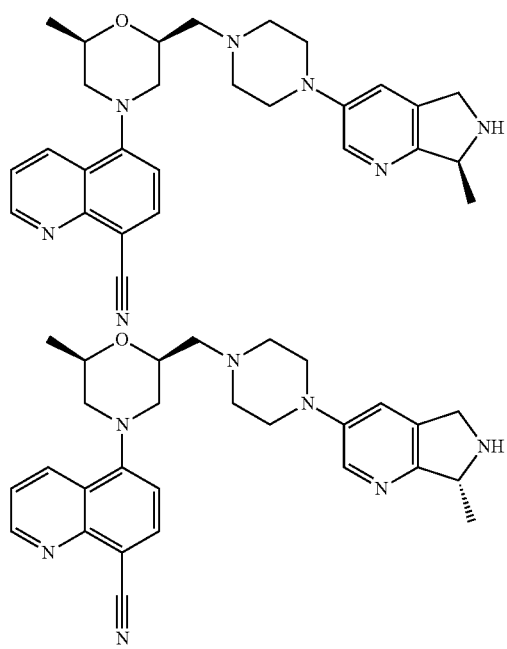

The title compounds were prepared in analogy to the preparation of Example 31 by using tert-butyl 3-bromo-7-methyl-5,7-dihydropyrrolo[3,4-b]pyridine-6-carboxylate (compound 67h) instead of tert-butyl 2-bromo-6,7-dihydro-4H-thiazolo[5,4-c]pyridine-5-carboxylate (compound 31b). The Boc protected Example 67 (faster eluting) and 68 (slower eluting) were separated by chiral SFC (Gradient: 55% Ethanol (0.1% NH₃H₂O) in CO₂, Column: Daicel chiralpak AD 250×30 mm, 10 μm).

Example 67 (29 mg) was obtained as a brown solid. MS: calc'd 484 (MH⁺), measured 484 (MH⁺). $^1$H NMR (400 MHz, DMSO-$d_6$) δ=8.97 (dd, J=1.6, 4.3 Hz, 1H), 8.65 (dd, J=1.7, 8.6 Hz, 1H), 8.37 (d, J=2.6 Hz, 1H), 8.14 (d, J=7.9 Hz, 1H), 7.64 (dd, J=4.3, 8.7 Hz, 1H), 7.58 (d, J=2.4 Hz, 1H), 7.26 (d, J=8.1 Hz, 1H), 4.89-4.86 (m, 1H), 4.71-4.52 (m, 3H), 4.26-4.17 (m, 1H), 4.15-3.36 (m, 12H), 2.85-2.69 (m, 2H), 1.71 (d, J=6.8 Hz, 3H), 1.33 (d, J=6.2 Hz, 3H).

Example 68 (27 mg) was obtained as a brown solid. MS: calc'd 484 (MH⁺), measured 484 (MH⁺). $^1$H NMR (400 MHz, DMSO-$d_6$) δ=8.98 (dd, J=1.5, 4.3 Hz, 1H), 8.65 (dd, J=1.5, 8.6 Hz, 1H), 8.37 (d, J=2.6 Hz, 1H), 8.14 (d, J=7.9 Hz, 1H), 7.65 (dd, J=4.3, 8.6 Hz, 1H), 7.58 (d, J=2.4 Hz, 1H), 7.27 (d, J=8.1 Hz, 1H), 4.89-4.84 (m, 1H), 4.71-4.53 (m, 3H), 4.26-4.17 (m, 1H), 4.15-3.35 (m, 12H), 2.86-2.69 (m, 2H), 1.71 (d, J=6.8 Hz, 3H), 1.33 (d, J=6.2 Hz, 3H).

The compound 67h was prepared according to the following scheme:

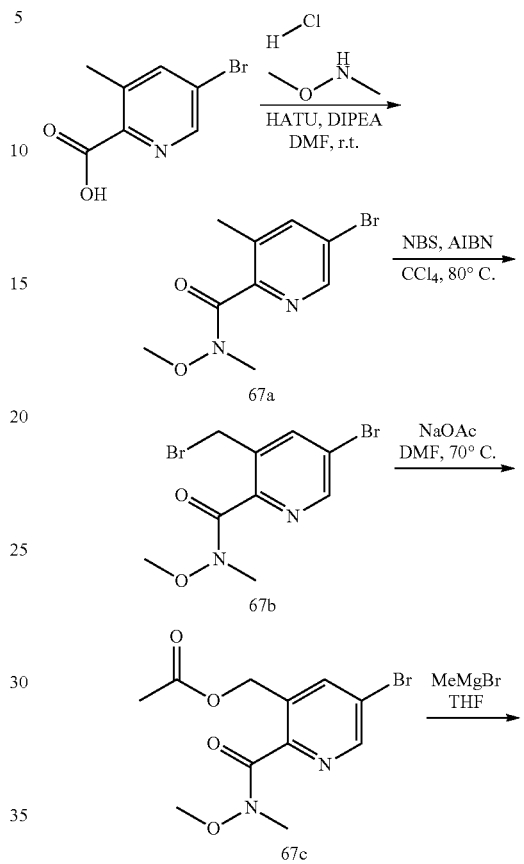

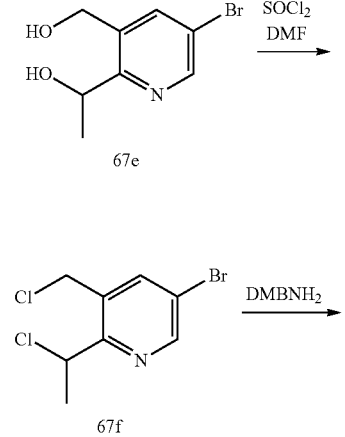

-continued

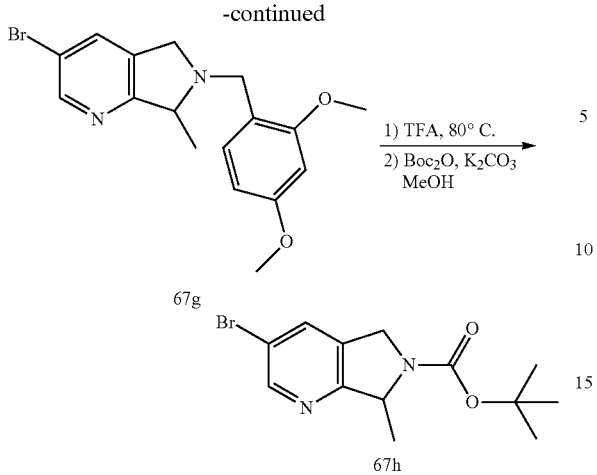

Step 1: Preparation of 5-bromo-N-methoxy-N,3-dimethyl-pyridine-2-carboxamide (Compound 67a)

To the mixture of HATU (21 g, 55.55 mmol) and 5-bromo-2-carboxy-3-methylpyridine (CAS: 886365-43-1, Vendor: PharmaBlock, 23.14 mL, 46.29 mmol) was added a solution of DIPEA (24 mL, 138.87 mmol) in DMF (97 mL) and O,N-dimethylhydroxylamine HCl (5 g, 50.92 mmol) at 0° C. After being stirred at 20° C. for 18 hrs, the reaction mixture was diluted with 2000 mL water and extracted with EA (1000 mL) for three times. The combined organic layer was washed with brine (2000 mL) twice, dried over $Na_2SO_4$, and concentrated to give a residue which was purified by flash column (PE/EA=2/1) to give compound 67a (16 g) as a yellow oil. MS calc'd 259 ($MH^+$), measured 259 ($MH^+$).

Step 2: Preparation of 5-bromo-3-(bromomethyl)-N-methoxy-N-methyl-pyridine-2-carboxamide (Compound 67b)

To a solution of 5-bromo-N-methoxy-N,3-dimethyl-pyridine-2-carboxamide (compound 67a, 14 g, 54.03 mmol) in carbon tetrachloride (420 mL) was added 2,2'-azobis(2-methylpropionitrile) (2660 mg, 16.21 mmol) and 1-bromopyrrolidine-2,5-dione (23 g, 129.68 mmol). After being stirred at 80° C. for 6 hrs, the reaction mixture was concentrated to give a residue which was purified by flash column (PE/EA=10/1) to give compound 67b (3800 g). MS calc'd 337 ($MH^+$), measured 337 ($MH^+$).

Step 3: Preparation of [5-bromo-2-[methoxy(methyl)carbamoyl]-3-pyridyl]methyl acetate (Compound 67c)

To a solution of 5-bromo-3-(bromomethyl)-N-methoxy-N-methyl-pyridine-2-carboxamide (compound 67b, 1500 mg, 4.44 mmol) in DMF (15 mL) was added sodium acetate (1 mL, 13.31 mmol). After being stirred at 70° C. for 1 h, the reaction mixture was diluted with 500 mL water and extracted with EA (400 mL) for three times. The combined organic layer was washed with brine (300 mL) for three times, dried over $Na_2SO_4$, and concentrated to give a residue which was purified by flash column (PE/EA=5/1) to give compound 67c (1220 mg) as a yellow oil. MS calc'd 317 ($MH^+$), measured 317 ($MH^+$).

Step 4: Preparation of 1-[5-bromo-3-(hydroxymethyl)-2-pyridyl]ethanone (Compound 67d)

To the solution of [5-bromo-2-[methoxy(methyl)carbamoyl]-3-pyridyl]methyl acetate (compound 67c, 1000 mg, 3.15 mmol) in THF (24 mL) was added methylmagnesium bromide (3M in THF, 4.2 mL, 12.61 mmol) dropwise at 0° C. The mixture was stirred at 0° C. for 2.5 hrs and then quenched with MeOH (50 mL). The mixture was concentrated directly to give compound 67d (700 mg) which was used in next step without further purification. MS cal'd 230 ($MH^+$), measured 230 ($MH^+$).

Step 5: Preparation of 1-[5-bromo-3-(hydroxymethyl)-2-pyridyl]ethanol (Compound 67e)

To the solution of 1-[5-bromo-3-(hydroxymethyl)-2-pyridyl]ethanone (compound 67d, 700 mg, 3.04 mmol) in methanol (19.3 mL) was added sodium borohydride (345 mg, 9.13 mmol) at 0° C. After being stirred at 0° C. for 1 h, the reaction mixture was concentrated to give a residue. The residue was quenched with $H_2O$ (50 mL) and extracted with EA (50 mL) for six times. The combined organic layer was washed with brine (150 mL) twice, dried over $Na_2SO_4$, and concentrated to give a crude product which was purified by flash column (PE/EA=3/1) to give compound 67e (420 mg) as a yellow oil. MS calc'd 232 ($MH^+$), measured 232 ($MH^+$).

Step 6: Preparation of 5-bromo-2-(1-chloroethyl)-3-(chloromethyl)pyridine (Compound 67f)

To the solution of 1-[5-bromo-3-(hydroxymethyl)-2-pyridyl]ethanol (compound 76e, 420 mg, 1.81 mmol) in DCE (7 mL) was added thionyl chloride (1.4 mL, 18.83 mmol) at 0° C. After being stirred at 25° C. for 18 hrs, the reaction mixture was concentrated to give a residue which was diluted with DCM (20 mL) and ice-water (20 mL). The mixture was adjusted to pH 6 with sat. $NaHCO_3$ (2 mL) and extracted with DCM (20 mL) for three times. The combined organic layer was washed with brine (50 mL) twice, dried over $Na_2SO_4$, and concentrated to give a residue which was purified by flash column (PE/EA=100:1) to give compound 67f (380 mg) as a colorless oil. MS calc'd 268 ($MH^+$), measured 268 ($MH^+$).

Step 7: Preparation of 3-bromo-6-[(2,4-dimethoxyphenyl)methyl]-7-methyl-5,7-dihydropyrrolo[3,4-b]pyridine (Compound 67g)

To the solution of 5-bromo-2-(1-chloroethyl)-3-(chloromethyl)pyridine (compound 67f, 380 mg, 1.41 mmol) in ethanol (5.65 mL) was added potassium carbonate (390 mg, 2.83 mmol) and 2,4-dimethoxybenzylamine (0.23 mL, 1.55 mmol). After being stirred at 65° C. for 2 hrs, the mixture was filtered and concentrated to give crude product which was purified by flash column (PE/EA=10/1) to give compound 67g (420 mg) as a light yellow solid. MS calc'd 363 ($MH^+$), measured 363 ($MH^+$).

Step 8: Preparation of tert-butyl 3-bromo-7-methyl-5,7-dihydropyrrolo[3,4-b]pyridine-6-carboxylate (Compound 67h)

The solution of 3-bromo-6-[(2,4-dimethoxyphenyl)methyl]-7-methyl-5,7-dihydropyrrolo[3,4-b]pyridine (compound 67g, 400 mg, 1.10 mmol) in trifluoroacetic acid (7 mL, 91.13 mmol) was heated to 80° C. and stirred for 2 hrs.

After being cooled down, the reaction mixture was concentrated to give 3-bromo-7-methyl-6,7-dihydro-5H-pyrrolo[3,4-b]pyridine; 2,2,2-trifluoroacetic acid (350 mg) as a purple oil which was dissolved in methanol (8 mL), and potassium carbonate (443 mg, 3.21 mmol) and di-t-butyldicarbonate (467 mg, 2.14 mmol) were added. After being stirred at 25° C. for 18 hrs, the mixture was concentrated to give a crude product which was purified by flash column (PE/EA=10/1) to give compound 67h (280 mg) as a yellow oil. MS calc'd 313 (MH+), measured 313 (MH+).

Example 69

5-[(2R,6S)-2-methyl-6-[[4-(5,6,7,8-tetrahydro-1,7-naphthyridin-2-yl)piperazin-1-yl]methyl]morpholin-4-yl]quinoline-8-carbonitrile

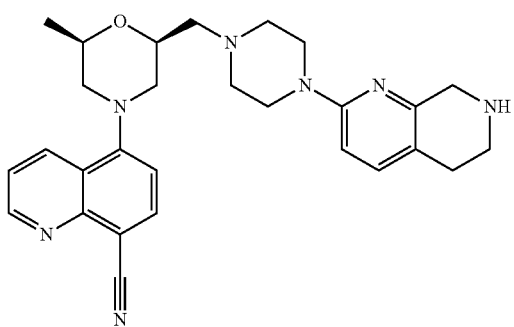 [SMILES: C[C@@H]1CN(c2ccc(C#N)c3ncccc23)C[C@H](CN2CCN(c3ccc4c(n3)CNCC4)CC2)O1]

The title compound was prepared in analogy to the preparation of Example 1 by using tert-butyl 2-chloro-6,8-dihydro-5H-1,7-naphthyridine-7-carboxylate (CAS: 1211581-54-2, Vendor: PharmaBlock) instead of tert-butyl 2-bromo-6,7-dihydro-4H-pyrazolo[1,5-a]pyrazine-5-carboxylate. Example 69 (46 mg) was obtained as a yellow solid. MS: calc'd 484 (MH+), measured 484 (MH+). $^1$H NMR (400 MHz, METHANOL-$d_4$) δ=8.95 (dd, J=1.5, 4.2 Hz, 1H), 8.62 (dd, J=1.7, 8.6 Hz, 1H), 8.11 (d, J=8.1 Hz, 1H), 7.61 (dd, J=4.2, 8.6 Hz, 1H), 7.51 (d, J=8.8 Hz, 1H), 7.23 (d, J=8.1 Hz, 1H), 6.91 (d, J=8.8 Hz, 1H), 4.80-4.30 (m, 3H), 4.24 (s, 2H), 4.22-4.13 (m, 1H), 4.07-3.54 (m, 3H), 3.54-3.45 (m, 3H), 3.44-3.34 (m, 5H), 3.30-3.14 (m, 1H), 3.01 (br t, J=6.1 Hz, 2H), 2.80-2.67 (m, 2H), 1.31 (d, J=6.1 Hz, 3H).

Example 70 and Example 71

5-[(2R,6S)-2-methyl-6-[[4-[(6R)-6-methyl-5,6,7,8-tetrahydro-2,7-naphthyridin-3-yl]piperazin-1-yl]methyl]morpholin-4-yl]quinoline-8-carbonitrile and
5-[(2R,6S)-2-methyl-6-[[4-[(6S)-6-methyl-5,6,7,8-tetrahydro-2,7-naphthyridin-3-yl]piperazin-1-yl]methyl]morpholin-4-yl]quinoline-8-carbonitrile

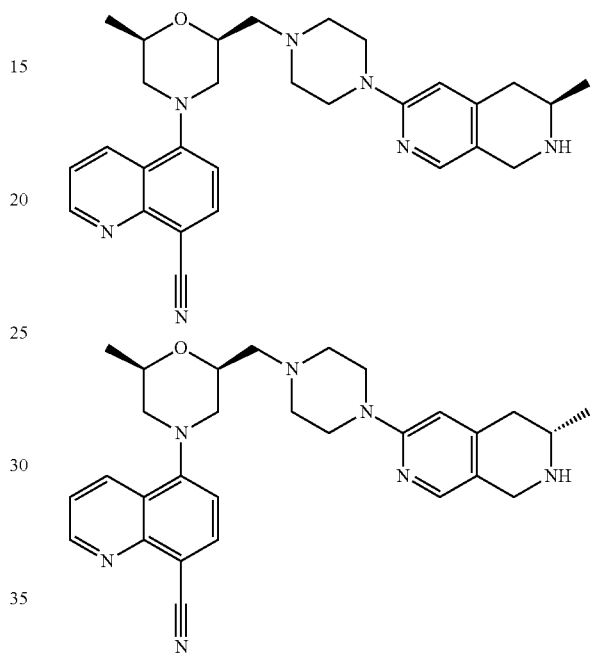

The title compounds were prepared according to the following scheme:

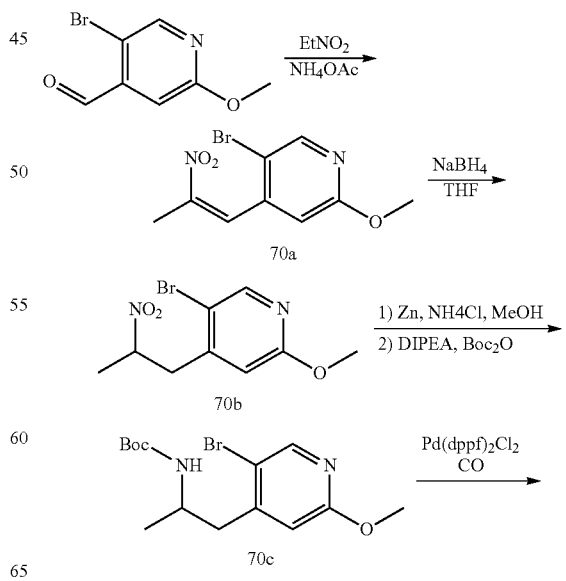

153
-continued

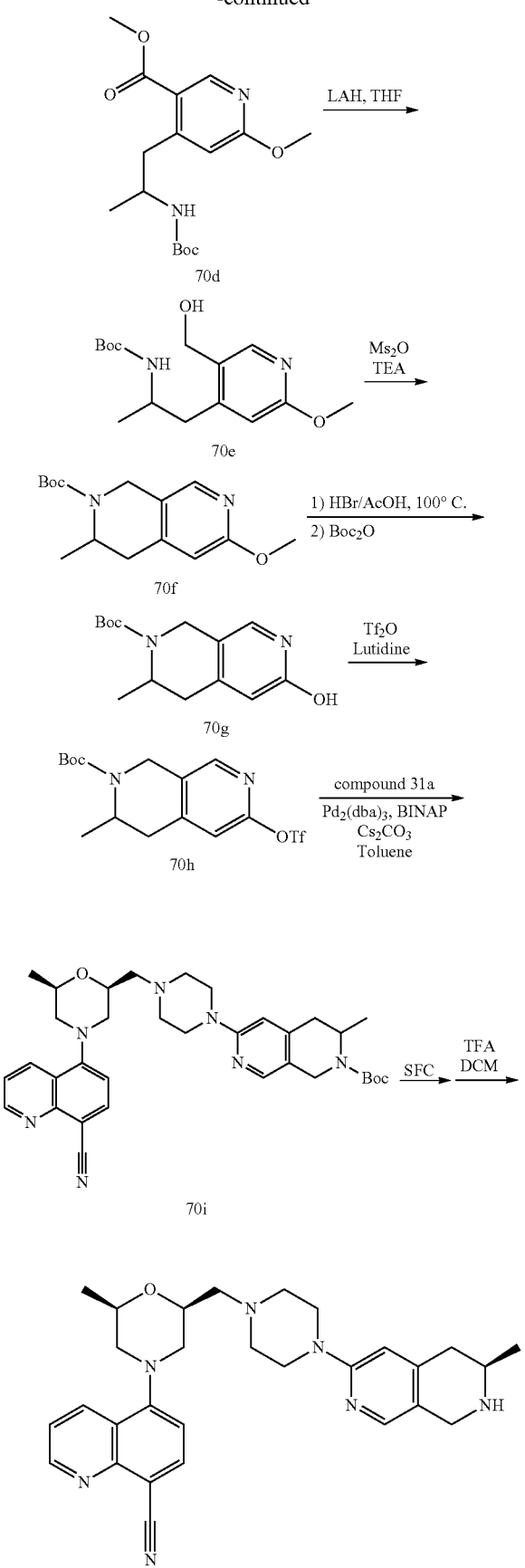

154
-continued

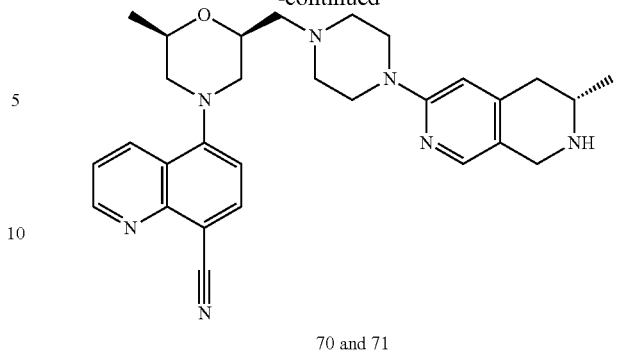

70 and 71

Step 1: Preparation of 5-bromo-2-methoxy-4-[(Z)-2-nitroprop-1-enyl]pyridine (Compound 70a)

The solution of 5-bromo-2-methoxy-pyridine-4-carbaldehyde (CAS: 936011-17-5, Vendor: Bide, 25.00 g, 115.72 mmol) and ammonium acetate (4.46 g, 57.86 mmol) in nitroethane (150 mL) was stirred at 100° C. for 16 hrs. After being cooled down, the mixture was concentrated and purified by flash column (PE/EA=10/1) to give compound 70a (23.00 g) as a green solid. MS: calc'd 273 (MH$^+$), measured 273 (MH$^+$).

Step 2: Preparation of 5-bromo-2-methoxy-4-(2-nitropropyl)pyridine (Compound 70b)

To the solution of 5-bromo-2-methoxy-4-[(Z)-2-nitroprop-1-enyl]pyridine (compound 70a, 23.00 g, 75.80 mmol) in THF (300 mL) was added sodium borohydride (4.30 g, 113.70 mmol) at 0° C. After being stirred at 0° C. for 1 h, the mixture was quenched by addition of 200 mL saturated NH$_4$Cl, diluted with 500 mL water, and extracted with 200 mL EA for three times. The combined organic layer was washed with 200 mL water twice and 80 mL brine once, dried over Na$_2$SO$_4$, concentrated and purified by flash column (PE/EA=5/1) to give compound 70b (12.60 g) as a yellow solid. MS: calc'd 275 (MH$^+$), measured 275 (MH$^+$).

Step 3: Preparation of tert-butyl N-[2-(5-bromo-2-methoxy-4-pyridyl)-1-methyl-ethyl]carbamate (Compound 70c)

To the solution of 5-bromo-2-methoxy-4-(2-nitropropyl)pyridine (compound 70b, 12.60 g, 42.00 mmol), ammonium chloride (26.96 g, 504.00 mmol) in methanol (300 mL) and water (15 mL) was added zinc (16.48 g, 252.00 mmol) for 3 times. After being stirred at rt for 18 hrs, the mixture was filtered and to the filtrate was added DIPEA (15 mL, 84.00 mmol) and di-t-butyldicarbonate (13.75 g, 63.00 mmol). After being stirred at rt for another 4 hrs, the reaction was quenched by addition of 60 mL saturated NH$_4$Cl, diluted with 200 mL water and extracted with 100 mL EA for three times. The combined organic layer was washed with 100 mL water twice and 50 mL brine once, dried over Na$_2$SO$_4$, concentrated and purified by flash column (PE/EA=5/1) to give compound 70c (8.50 g) as a yellow solid. MS: calc'd 345 (MH$^+$), measured 345 (MH$^+$).

Step 4: Preparation of methyl 4-[2-(tert-butoxycarbonylamino)propyl]-6-methoxy-pyridine-3-carboxylate (Compound 70d)

The solution of tert-butyl N-[2-(5-bromo-2-methoxy-4-pyridyl)-1-methyl-ethyl]carbamate (compound 70c, 8.50 g, 19.52 mmol), 1,3-bis(diphenylphosphino)propane (3.22 g, 7.81 mmol), TEA (141 mL, 97.62 mmol) in methanol (170 mL) was stirred at 100° C. for 20 hrs under CO atmosphere. After being cooled down, the reaction was quenched by addition of 50 mL saturated NH$_4$Cl, diluted with 400 mL water and extracted with 100 mL EA for three times. The combined organic layer was washed with 50 mL water twice and 100 mL brine once, dried over Na$_2$SO$_4$, concentrated and purified by flash column (PE/EA=10/1) to give compound 70d (7.10 g) as a white solid. MS: calc'd 325 (MH$^+$), measured 325 (MH$^+$).

Step 5: Preparation of tert-butyl N-[2-[5-(hydroxymethyl)-2-methoxy-4-pyridyl]-1-methyl-ethyl]carbamate (Compound 70e)

To the solution of methyl 4-[2-(tert-butoxycarbonylamino)propyl]-6-methoxy-pyridine-3-carboxylate (compound 70d, 7.10 g, 17.4 mmol) in THF (150 mL) was added lithium aluminum hydride (1.32 g, 34.80 mmol) at 0° C. After being stirred at 0° C. for 2 hrs, the reaction was quenched by addition of 60 mL saturated NH$_4$Cl, diluted with 300 mL water and extracted with 100 mL EA for three times. The combined organic layer was washed with 100 mL water twice and 60 mL brine once, dried over Na$_2$SO$_4$, concentrated and purified by flash column (PE/EA=3/1) to give compound 70e (3.10 g) as a white solid. MS: calc'd 297 (MH$^+$), measured 297 (MH$^+$).

Step 6: Preparation of tert-butyl 6-methoxy-3-methyl-3,4-dihydro-1H-2,7-naphthyridine-2-carboxylate (Compound 70f)

To the solution of tert-butyl N-[2-[5-(hydroxymethyl)-2-methoxy-4-pyridyl]-1-methyl-ethyl]carbamate (compound 70e, 3.10 g, 9.94 mmol), DIPEA (5 mL, 29.81 mmol) in DCM (70 mL) was added methanesulfonic anhydride (3.46 g, 19.87 mmol) at 0° C. After being stirred at rt for 18 hrs, the reaction was quenched by addition of 40 mL saturated NH$_4$Cl, diluted with 150 mL water and extracted with 60 mL DCM for three times. The combined organic layer was washed with 60 mL water twice and 40 mL brine once, dried over Na$_2$SO$_4$, concentrated and purified by flash column (PE/EA=10/1) to give compound 70f (2.00 g) as a white solid. MS: calc'd 279 (MH$^+$), measured 279 (MH$^+$).

Step 7: Preparation of tert-butyl 6-hydroxy-3-methyl-3,4-dihydro-1H-2,7-naphthyridine-2-carboxylate (Compound 70g)

The solution of tert-butyl 6-methoxy-3-methyl-3,4-dihydro-1H-2,7-naphthyridine-2-carboxylate (compound 70f, 2.00 g, 7.19 mmol) in hydrobromic acid (20 mL) was stirred at 100° C. for 18 hrs. After being cooled down, the mixture was concentrated and re-dissolved in methanol (30 mL). After basified to pH=8 with K$_2$CO$_3$, di-t-butyldicarbonate (2.35 g, 10.78 mmol) was added. The solution was stirred at rt for another 2 hrs. Then it was concentrated and purified by prep-TLC (DCM/MeOH=10/1) to give compound 70g (1.10 g) as a yellow solid. MS: calc'd 265 (MH$^+$), measured 265 (MH$^+$).

Step 8: Preparation of tert-butyl 3-methyl-6-(trifluoromethylsulfonyloxy)-3,4-dihydro-1H-2,7-naphthyridine-2-carboxylate (Compound 70h)

To the solution of tert-butyl 6-hydroxy-3-methyl-3,4-dihydro-1H-2,7-naphthyridine-2-carboxylate (compound 70g, 300 mg, 0.99 mmol) in DCM (10 mL) was added 2,6-dimethylpyridine (424 mg, 3.96 mmol) and trifluoromethanesulfonic anhydride (558 mg, 1.98 mmol) dropwise at 0° C. After being stirred at 0° C. for 1 h, the reaction was quenched by addition of ice water (30 mL), and extracted with DCM (20 mL) for three times. The combined organic layer was washed with 20 mL water twice, dried over Na$_2$SO$_4$, concentrated and purified by prep-TLC (PE/EA=1/1) to give compound 70h (310 mg) as a white solid. MS: calc'd 398 (MH$^+$), measured 398 (MH$^+$).

Step 9: Preparation of tert-butyl 3-methyl-6-[4-[[(2S,6R)-4-(8-cyano-5-quinolyl)-6-methyl-morpholin-2-yl]methyl]piperazin-1-yl]-3,4-dihydro-1H-2,7-naphthyridine-2-carboxylate (Compound 70i)

To the solution of tert-butyl 3-methyl-6-(trifluoromethylsulfonyloxy)-3,4-dihydro-1H-2,7-naphthyridine-2-carboxylate (compound 70h, 276 mg, 0.63 mmol), 5-[(2R,6S)-2-methyl-6-(piperazin-1-ylmethyl)morpholin-4-yl]quinoline-8-carbonitrile (compound 31a, 110 mg, 0.31 mmol), BINAP (39 mg, 0.06 mmol), cesium carbonate (255 mg, 0.78 mmol) in toluene (3 mL) was added Pd$_2$(dba)$_3$ (28 mg, 0.03 mmol). After being stirred at 100° C. for 18 hrs under N$_2$ atmosphere, the mixture was concentrated and purified by prep-TLC (DCM/MeOH=20/1) three times to give compound 70i (30 mg) as a yellow gum. MS: calc'd 598 (MH$^+$), measured 598 (MH$^+$).

Step 10: preparation of 5-[(2R,6S)-2-methyl-6-[[4-[(6R)-6-methyl-5,6,7,8-tetrahydro-2,7-naphthyridin-3-yl]piperazin-1-yl]methyl]morpholin-4-yl]quinoline-8-carbonitrile and 5-[(2R,6S)-2-methyl-6-[[4-[(6S)-6-methyl-5,6,7,8-tetrahydro-2,7-naphthyridin-3-yl]piperazin-1-yl]methyl]morpholin-4-yl]quinoline-8-carbonitrile (Example 70 and 71)

tert-Butyl 3-methyl-6-[4-[[(2S,6R)-4-(8-cyano-5-quinolyl)-6-methyl-morpholin-2-yl]methyl]piperazin-1-yl]-3,4-dihydro-1H-2,7-naphthyridine-2-carboxylate (compound 70i) was separated by chiral SFC (Gradient: 35% Ethanol (0.1% NH$_3$H$_2$O) in CO$_2$, Column: Daicel chiralpak AS-H 250×30 mm, 5 μm) to give two isomers: A (faster eluting, 13 mg) as a yellow gum and B (slower eluting, 14 mg) as a yellow gum. MS: calc'd 598 (MH$^+$), measured 598 (MH$^+$).

The two isomers were treated with TFA (1 mL) in DCM (5 mL) overnight to give the corresponding Example 70 and Example 71.

Example 70 (8 mg) was obtained as a brown solid. MS: calc'd 498 (MH$^+$), measured 498 (MH$^+$). $^1$H NMR (400 MHz, DMSO-d$_6$) δ=9.00 (dd, J=1.5, 4.2 Hz, 1H), 8.68 (dd, J=1.6, 8.6 Hz, 1H), 8.17 (d, J=8.1 Hz, 1H), 8.12 (s, 1H), 7.67 (dd, J=4.3, 8.6 Hz, 1H), 7.29 (d, J=8.1 Hz, 1H), 6.87 (s, 1H), 4.61-4.50 (m, 1H), 4.47-4.15 (m, 4H), 4.14-3.34 (m, 12H), 3.20 (dd, J=4.6, 18.2 Hz, 1H), 2.90 (dd, J=10.9, 17.9 Hz, 1H), 2.78 (td, J=11.2, 18.1 Hz, 2H), 1.50 (d, J=6.5 Hz, 3H), 1.34 (d, J=6.2 Hz, 3H).

Example 71 (7 mg) was obtained as a brown solid. MS: calc'd 498 (MH$^+$), measured 498 (MH$^+$). $^1$H NMR (400 MHz, DMSO-d$_6$) δ=9.00 (dd, J=1.6, 4.2 Hz, 1H), 8.68 (dd, J=1.6, 8.7 Hz, 1H), 8.18 (d, J=7.9 Hz, 1H), 8.12 (s, 1H), 7.67 (dd, J=4.2, 8.6 Hz, 1H), 7.30 (d, J=7.9 Hz, 1H), 6.87 (s, 1H), 4.60-4.50 (m, 1H), 4.46-4.16 (m, 4H), 4.15-3.36 (m, 12H), 3.24-3.14 (m, 1H), 2.90 (dd, J=10.9, 18.0 Hz, 1H), 2.85-2.71 (m, 2H), 1.50 (d, J=6.5 Hz, 3H), 1.34 (d, J=6.2 Hz, 3H).

Example 72 and Example 73

5-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoline-8-carbonitrile and 5-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoline-8-carbonitrile

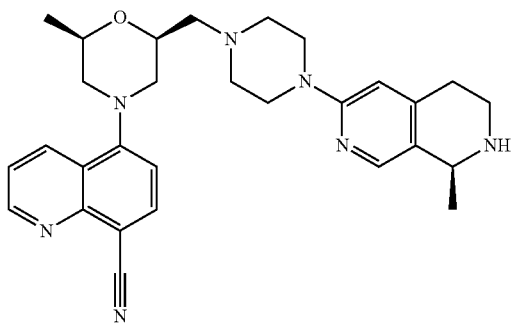

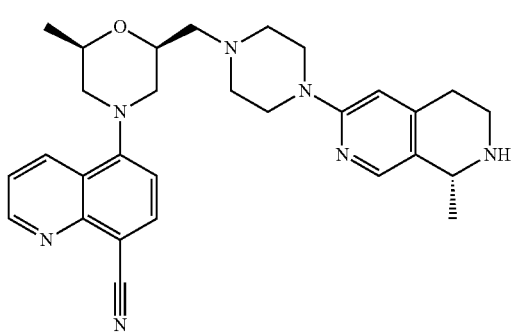

The title compounds were prepared in analogy to the preparation of Example 70 and 71 by using tert-butyl N-[2-[5-(1-hydroxyethyl)-2-methoxy-4-pyridyl]ethyl] carbamate (compound 72g) instead of tert-butyl N-[2-[5-(hydroxymethyl)-2-methoxy-4-pyridyl]-1-methyl-ethyl]carbamate (compound 70e). The Boc protected Example 72 (faster eluting) and 73 (slower eluting) were separated by chiral SFC (Gradient: 55% Methanol (0.1% $NH_3H_2O$) in $CO_2$, Column: Daicel chiralcel OD 250×30 mm, 10 μm).

Example 72 (17 mg) was obtained as a yellow solid. MS: calc'd 498 ($MH^+$), measured 498 ($MH^+$). $^1H$ NMR (400 MHz, DMSO-$d_6$) δ=9.02 (dd, J=2.0, 6.4 Hz, 1H), 8.70 (dd, J=2.0, 11.6 Hz, 1H), 8.20-8.17 (m, 2H), 7.67 (dd, J=6.0, 11.6 Hz, 1H), 7.31 (d, J=10.4 Hz, 1H), 6.84 (s, 1H), 4.70-4.45 (m, 2H), 4.35-3.35 (m, 16H), 3.25-3.00 (m, 2H), 2.80-2.70 (m, 1H), 1.71 (d, J=8.8 Hz, 3H), 1.34 (d, J=8.0 Hz, 3H).

Example 73 (18 mg) was obtained as a yellow solid. MS: calc'd 498 ($MH^+$), measured 498 ($MH^+$). $^1H$ NMR (400 MHz, DMSO-$d_6$) δ=9.03-9.01 (m, 1H), 8.68 (dd, J=2.0, 11.6 Hz, 1H), 8.21-8.18 (m, 2H), 7.67 (dd, J=5.2, 11.2 Hz, 1H), 7.31 (d, J=10.8 Hz, 1H), 6.84 (s, 1H), 4.75-4.45 (m, 2H), 4.35-3.35 (m, 16H), 3.15-3.05 (m, 2H), 2.80-2.70 (m, 1H), 1.71 (d, J=8.8 Hz, 3H), 1.34 (d, J=8.4 Hz, 3H).

The compound 72g was prepared according to the following scheme:

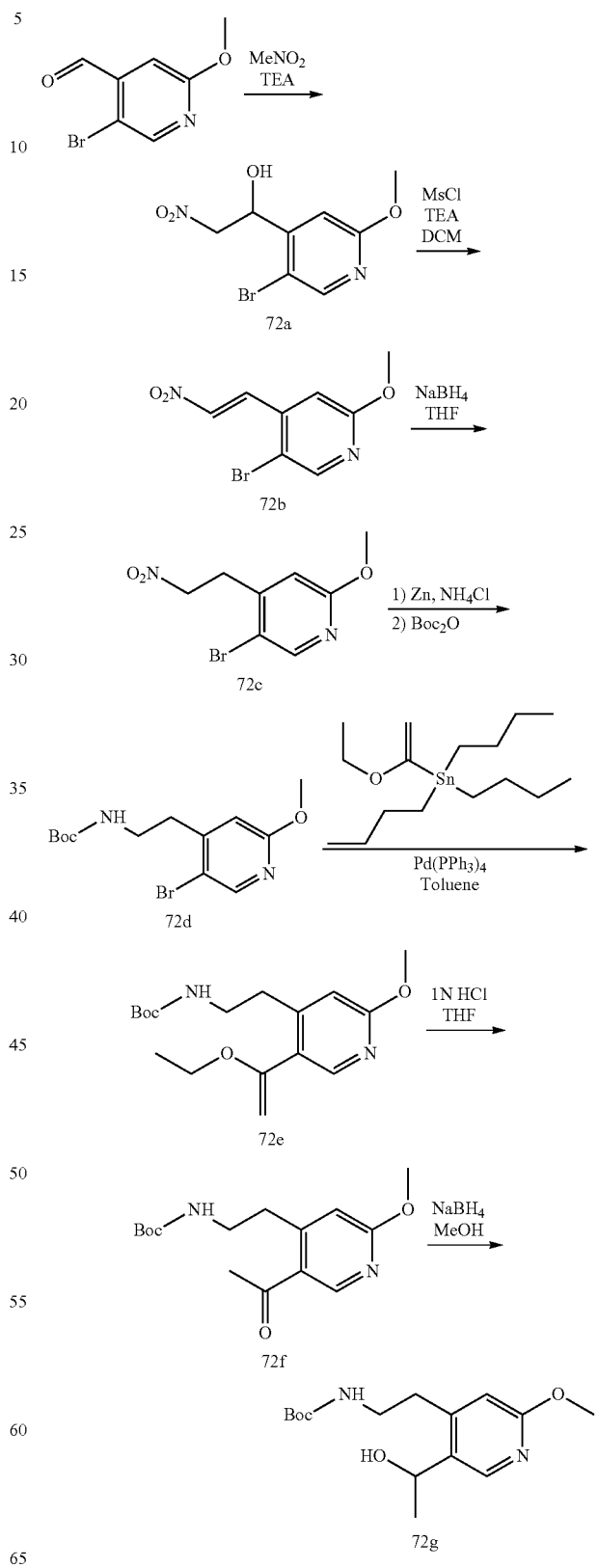

Step 1 and 2: Preparation of 5-bromo-2-methoxy-4-[(E)-2-nitrovinyl]pyridine (Compound 72b)

To the solution of 5-bromo-2-methoxy-pyridine-4-carbaldehyde (CAS: 936011-17-5, Vendor: Bide, 25.00 g, 115.72 mmol) in DCM (500 mL) was added nitromethane (7.52 mL, 138.87 mmol) and TEA (33 mL, 231.45 mmol). After being stirred at rt for 1 h, the reaction mixture was concentrated to give the crude product which was dissolved in DCM (500 mL) and TEA (50.81 mL, 364.53 mmol) was added. The mixture was cooled with ice bath and methanesulfonyl chloride (27 mL, 347.17 mmol) was added drop-wise. After being stirred at rt for 0.5 h, the reaction mixture was quenched by addition of H$_2$O (400 mL) and saturated NaHCO$_3$ (100 mL). The organic layer was separated and the water layer was extracted with DCM (150 mL) for three times. The combined organic layer was washed with H$_2$O (400 mL) and saturated NaHCO$_3$ (100 mL) and brine (100 mL), dried over Na$_2$SO$_4$, filtered and concentrated to give an oil which was purified by flash column (PE/EA=25/1) to give compound 72b (15.00 g) as a light yellow solid. MS: calc'd 259 (MH$^+$), measured 259 (MH$^+$).

Step 3: Preparation of 5-bromo-2-methoxy-4-(2-nitroethyl)pyridine (Compound 72c)

To the solution of 5-bromo-2-methoxy-4-[(E)-2-nitrovinyl]pyridine (compound 72b, 13.80 g, 53.27 mmol) in THF (140 mL) was added sodium borohydride (6.00 g, 159.81 mmol) at 0° C. After being stirred at 0° C. for 2 hrs, the reaction was quenched by addition of saturated NH$_4$Cl (30 mL) and diluted with H$_2$O (70 mL). The mixture was extracted with EA (150 mL) for four times. The combined organic layer was dried over Na$_2$SO$_4$, filtered and concentrated to give a crude product which was purified by flash column (PE/EA=9/1) to give compound 72c (6.00 g) as a light yellow oil. MS: calc'd 261 (MH$^+$), measured 261 (MH$^+$).

Step 4: Preparation of tert-butyl N-[2-(5-bromo-2-methoxy-4-pyridyl)ethyl]carbamate (Compound 72d)

The mixture of 5-bromo-2-methoxy-4-(2-nitroethyl)pyridine (compound 72c, 6.00 g, 21.61 mmol), ammonium chloride (9.30 g, 173.86 mmol), zinc (8.50 g, 130.01 mmol) in THF (150 mL) and methanol (150 mL) was stirred at rt for 18 hrs. The mixture was filtered and the wet-cake was washed with DCM/MeOH=2/1 (V/V, 1200 mL). The combined organic layer was concentrated to give a crude product which was dissolved in DCM (100 mL) and methanol (100 mL). To the solution, DIPEA (15 mL, 86.12 mmol) and di-t-butyldicarbonate (9.50 g, 43.53 mmol) was added and the mixture was stirred at rt for 18 hrs. After concentration, the mixture was diluted with H$_2$O (300 mL) and saturated NaHCO$_3$ (50 mL). The mixture was extracted with EA (100 mL) for four times. The combined organic layer was washed with brine (30 mL), dried over Na$_2$SO$_4$ and concentrated to give a crude product which was purified by flash column (PE/EA=9/1) to give compound 72d (6.10 g) as a white solid. MS: calc'd 331 (MH$^+$), measured 331 (MH$^+$).

Step 5: Preparation of tert-butyl N-[2-[5-(1-ethoxyvinyl)-2-methoxy-4-pyridyl]ethyl]carbamate (Compound 72e)

The mixture of tert-butyl N-[2-(5-bromo-2-methoxy-4-pyridyl)ethyl]carbamate (compound 72d, 5.70 g, 17.21 mmol), Pd(PPh$_3$)$_4$ (2.00 g, 1.73 mmol), tributyl(1-ethoxyvinyl) tin (12.43 g, 34.42 mmol) in toluene (120 mL) was degassed and purged with N$_2$ for 3 times, and then stirred at 110° C. under N$_2$ atmosphere for 18 hrs. After being cooled down, the reaction was quenched by addition of KF aqueous solution (50 mL), and extracted with EA (100 mL) twice. The organic layer was washed with brine (50 mL), dried over Na$_2$SO$_4$ and concentrated to give the crude product which was purified by HPLC to give compound 72e (4.70 g) as a white solid. MS: calc'd 323 (MH$^+$), measured 323 (MH$^+$).

Step 6: Preparation of tert-butyl N-[2-(5-acetyl-2-methoxy-4-pyridyl)ethyl]carbamate (Compound 72f)

To the solution of tert-butyl N-[2-[5-(1-ethoxyvinyl)-2-methoxy-4-pyridyl]ethyl]carbamate (compound 72e, 4.50 g, 13.96 mmol) in THF (61 mL) was added hydrogenchloride (1M in H$_2$O 6.14 mL, 6.14 mmol) drop-wise at 0° C. After being stirred at rt for 1.5 hrs, the reaction mixture was added into 100 mL saturated NaHCO$_3$ below 5° C. Then it was diluted with H$_2$O (50 mL) and extracted with EA (100 mL) twice. The combined organic layer was dried over Na$_2$SO$_4$ and concentrated to give compound 72f (3.50 g) as a white solid, which was used in next step without further purification. MS: calc'd 295 (MH$^+$), measured 295 (MH$^+$).

Step 7: Preparation of tert-butyl N-[2-[5-(1-hydroxyethyl)-2-methoxy-4-pyridyl]ethyl]carbamate (Compound 72g)

To the solution of tert-butyl N-[2-(5-acetyl-2-methoxy-4-pyridyl)ethyl]carbamate (compound 72f, 3.50 g, 11.89 mmol) in methanol (70 mL) was added sodium borohydride (675 mg, 17.84 mmol) at 0° C. After being stirred at 0° C. for 2 hrs, the mixture was concentrated and purified by HPLC to give compound 72g (3.40 g) as a white solid. MS: calc'd 297 (MH$^+$), measured 297 (MH$^+$).

Example 74 and Example 75

5-[(2R,6S)-2-methyl-6-[[4-[(5R)-5-methyl-5,6,7,8-tetrahydro-2,6-naphthyridin-3-yl]piperazin-1-yl]methyl]morpholin-4-yl]quinoline-8-carbonitrile and 5-[(2R,6S)-2-methyl-6-[[4-[(5S)-5-methyl-5,6,7,8-tetrahydro-2,6-naphthyridin-3-yl]piperazin-1-yl]methyl]morpholin-4-yl]quinoline-8-carbonitrile

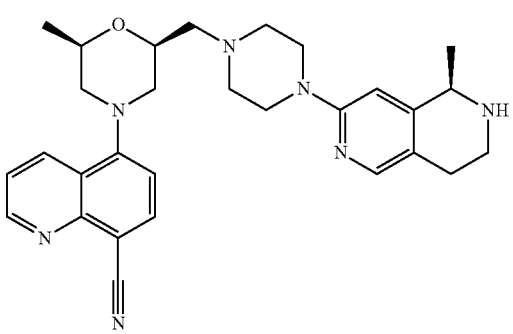

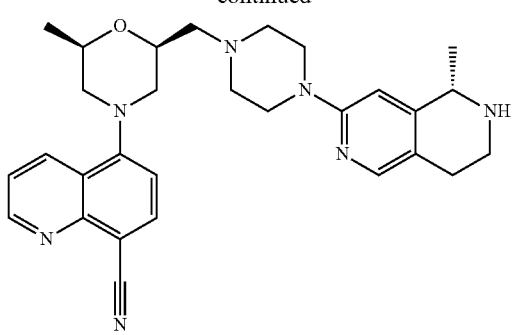
The title compounds were prepared according to the following scheme:
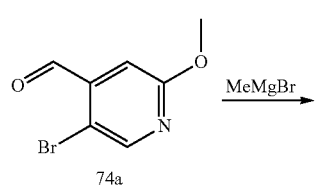
74a
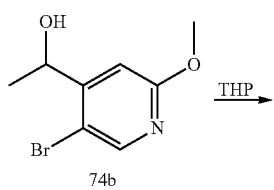
74b
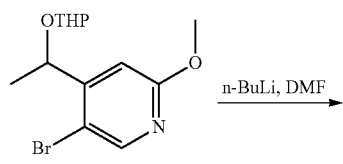
74c
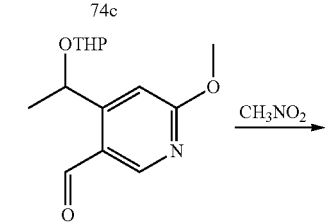
74d
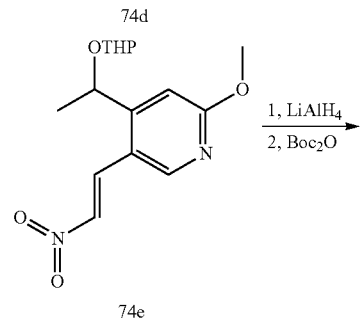
74e
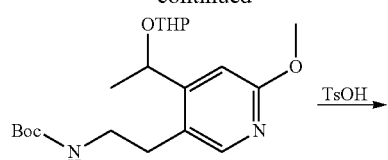
74f
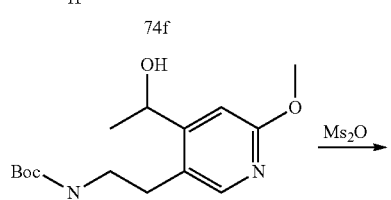
74g
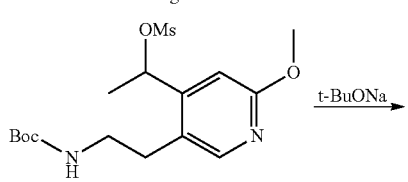
74h
74i
74j
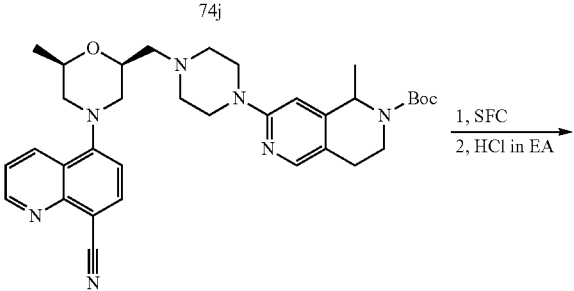
74k
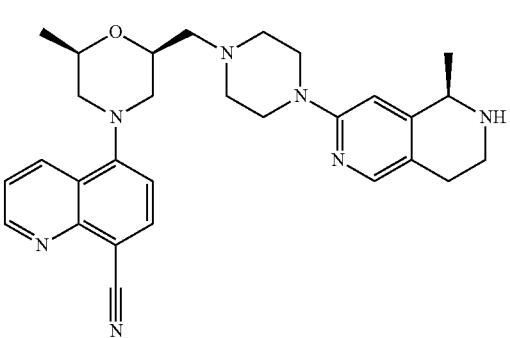

-continued

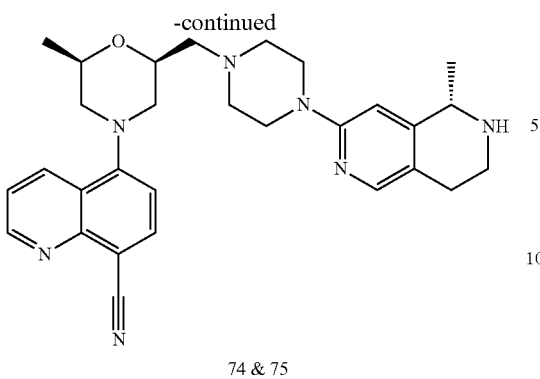

74 & 75

Step 1: Preparation of 1-(5-bromo-2-methoxy-4-pyridyl)ethanol (Compound 74b)

To the solution of 5-bromo-2-methoxy-pyridine-4-carbaldehyde (compound 74a, 25.00 g, 115.70 mmol) in THF (250 mL) was added MeMgBr (3M in 2-Me-THF, 50.20 mL, 150.40 mmol) drop wise at −78° C. over 30 mins. After being stirred at −78° C. for 0.5 h, the mixture was warmed to rt slowly and then quenched with 100 mL saturated $NH_4Cl$, diluted with 400 mL water and extracted with 150 mL EA twice. The combined organic layer was washed with 180 mL water and 100 mL brine, dried over $Na_2SO_4$ and concentrated to give the crude product compound 74b (27.00 g) as a yellow oil. MS calc'd 232 ($MH^+$), measured 232 ($MH^+$).

Step 2: Preparation of 5-bromo-2-methoxy-4-(1-tetrahydropyran-2-yloxyethyl) pyridine (Compound 74c)

To the solution of 1-(5-bromo-2-methoxy-4-pyridyl)ethanol (compound 74b, 27.00 g, 103.31 mmol), dihydropyran (12.25 mL, 134.31 mmol) in DCM (300 mL) was added p-TsOH (1.78 g, 10.30 mmol). After being stirred at rt for 18 hrs, the reaction was quenched with 20 mL saturated $NaHCO_3$, diluted with 500 mL water and extracted with 150 mL DCM twice. The combined organic layer was washed with 150 mL water and 100 mL brine, dried over $Na_2SO_4$, concentrated and purified by flash column (PE/EA=10/1) to give compound 74c (30.00 g) as a yellow oil. MS calc'd 316 ($MH^+$), measured 316 ($MH^+$).

Step 3: Preparation of 6-methoxy-4-(1-tetrahydropyran-2-yloxyethyl)pyridine-3-carbaldehyde (Compound 74d)

To the solution of 5-bromo-2-methoxy-4-(1-tetrahydropyran-2-yloxyethyl)pyridine (compound 74c, 30.00 g, 86.34 mmol) in THF (300 mL) was added n-BuLi (51.80 mL, 129.51 mmol) at −60° C. over 30 mins. Then it was stirred at −60° C. for 0.5 h and DMF (20.06 mL, 259.02 mmol) was added. After being stirred at this temperature for another 1 h, the solution was warmed to rt and quenched with 50 mL saturated $NH_4Cl$, diluted with 500 mL water and extracted with 200 mL EA twice. The combined organic layer was washed with water and brine, dried over $Na_2SO_4$ and concentrated to give the crude product which was purified by flash column (PE/EA=10/1) to give compound 74d (16.00 g) as a yellow oil. MS calc'd 266 ($MH^+$), measured 266 ($MH^+$).

Step 4: Preparation of 2-methoxy-5-[(E)-2-nitrovinyl]-4-(1-tetrahydropyran-2-yloxyethyl)pyridine (Compound 74e)

The mixture of 6-methoxy-4-(1-tetrahydropyran-2-yloxyethyl)pyridine-3-carbaldehyde (compound 74d, 15.50 g, 58.42 mmol), ammonium acetated (2.25 g, 29.20 mmol) in nitromethane (300 mL) was stirred at 70° C. for 12 hrs. After being cooled down, the mixture was concentrated and purified by flash column (PE/EA=20/1) to give compound 74e (10.00 g) as a green solid. MS calc'd 309 ($MH^+$), measured 309 ($MH^+$).

Step 5: Preparation of tert-butyl N-[2-[6-methoxy-4-(1-tetrahydropyran-2-yloxyethyl)-3-pyridyl]ethyl]carbamate (Compound 74f)

To the solution of 2-methoxy-5-[(E)-2-nitrovinyl]-4-(1-tetrahydropyran-2-yloxyethyl)pyridine (compound 74e, 9.00 g, 25.00 mmol) in THF (225 mL) was added $LiAlH_4$ (2.85 g, 74.96 mmol) at 0° C. The mixture was stirred at rt for 2 hrs and then 20 mL $K_2CO_3$ (1 N, aq.) was added to the mixture at 0° C., and it was stirred for 10 mins. The mixture was filtered and the wet-cake was washed with 300 mL DCM/MeOH (V/V=20/1). The filtrate was concentrated and re-dissolved in DCM (270 mL), and then DIPEA (13.06 mL, 74.96 mmol) and di-t-butyldicarbonate (11.00 g, 49.97 mmol) were added. The mixture was stirred at rt for another 2 hrs. The reaction was quenched with 50 mL saturated $NH_4Cl$, diluted with water and extracted with 50 mL DCM. The combined organic layer was washed with water (50 mL) and brine (50 mL), dried over $Na_2SO_4$ and concentrated to give the crude product which was purified by flash column (PE/EA=10/1) to give compound 74f (4.00 g) as a yellow oil. MS calc'd 381 ($MH^+$), measured 381 ($MH^+$).

Step 6: Preparation of tert-butyl N-[2-[4-(1-hydroxyethyl)-6-methoxy-3-pyridyl]ethyl]carbamate (Compound 74g)

To the solution of tert-butyl N-[2-[6-methoxy-4-(1-tetrahydropyran-2-yloxyethyl)-3-pyridyl]ethyl]carbamate (compound 74f, 4.50 g, 10.05 mmol) (two batches) in methanol (80 mL) was added p-TsOH (2.87 g, 15.08 mmol). After being stirred at rt for 2 hrs, the mixture was adjusted to pH=7 with 1N aqueous solution of $K_2CO_3$ and then most methanol was removed in vacuo and the residue was re-dissolved in EA (50 mL). The solution was washed with water (50 mL) and brine (50 mL), dried over $Na_2SO_4$ and concentrated to give crude compound 74g (3.50 g) as a yellow oil. MS calc'd 297 ($MH^+$), measured 297 ($MH^+$).

Step 7: Preparation of 1-[5-[2-(tert-butoxycarbonylamino)ethyl]-2-methoxy-4-pyridyl]ethyl methanesulfonate (Compound 74h)

To the solution of tert-butyl N-[2-[4-(1-hydroxyethyl)-6-methoxy-3-pyridyl]ethyl]carbamate (compound 74g, 3.50 g, 10.39 mmol), DIPEA (5.43 mL, 31.18 mmol) in DCM (70 mL) was added methanesulfonic anhydride (3.60 g, 20.79 mmol) at 0° C. After being stirred at rt for 2 hrs, the reaction was quenched with saturated $NH_4Cl$. The organic layer was dried over $Na_2SO_4$ and concentrated to give crude compound 74h (4.30 g) as a yellow oil. MS calc'd 375 ($MH^+$), measured 375 ($MH^+$).

Step 8: Preparation of tert-butyl 7-methoxy-1-methyl-3,4-dihydro-1H-2,6-naphthyridine-2-carboxylate (Compound 74i)

The mixture of 1-[5-[2-(tert-butoxycarbonylamino)ethyl]-2-methoxy-4-pyridyl]ethyl methanesulfonate (compound 74h, 4.30 g, 9.65 mmol), sodium tert-butoxide (2.78 g, 28.94 mmol), KI (157 mg, 4.82 mmol) in DMF (60 mL) was stirred at 100° C. for 20 mins. The reaction was quenched with water (100 mL) and extracted with EA (60 mL) for three times. The organic layers were dried over $Na_2SO_4$ and concentrated to give the crude product which was purified by flash column (PE/EA=5/1) to give compound 74i (2.40 g) as a yellow oil. MS calc'd 279 ($MH^+$), measured 279 ($MH^+$).

Step 9: Preparation of tert-butyl 7-bromo-1-methyl-3,4-dihydro-1H-2,6-naphthyridine-2-carboxylate (Compound 74j)

To the mixture of tert-butyl 7-methoxy-1-methyl-3,4-dihydro-1H-2,6-naphthyridine-2-carboxylate (compound 74i, 700 mg, 2.51 mmol) in toluene (5 mL) was added phosphorus oxybromide (2.88 g, 10.10 mmol) at rt. The vial was capped and stirred at 120° C. for 2 hrs. Then the second batch of phosphorus oxybromide (2.88 g, 10.10 mmol) was added and the mixture was stirred at 125° C. for another 2 hrs. After being cooled down, the mixture was diluted with THF (50 mL) and quenched with 10 mL $K_2CO_3$ (2 M, aq.). Then DIPEA (8.78 ml, 50.3 mmol) and $Boc_2O$ (1.75 mL, 7.54 mmol) were added to the mixture and stirred at rt for 1 h. The reaction was concentrated and purified by flash column (EA/hexane=0% to 30%) to give compound 74j (170 mg) as a colorless oil. MS calc'd 327 ($MH^+$), measured 327 ($MH^+$).

Step 10: Preparation of tert-butyl 1-methyl-7-[4-[[(2S,6R)-4-(8-cyano-5-quinolyl)-6-methyl-morpholin-2-yl]methyl]piperazin-1-yl]-3,4-dihydro-1H-2,6-naphthyridine-2-carboxylate (Compound 74k)

A mixture of 5-[(2R,6S)-2-methyl-6-(piperazin-1-ylmethyl)morpholin-4-yl]quinoline-8-carbonitrile (compound 31a, 100 mg, 285 μmol), tert-butyl 7-bromo-1-methyl-3,4-dihydro-1H-2,6-naphthyridine-2-carboxylate (compound 74j, 93 mg, 285 μmol), sodium tert-butoxide (137 mg, 1.42 mmol), BINAP (35 mg, 57 μmol) and $Pd_2(dba)_3$ (26 mg, 29 μmol) in toluene (5 mL) was stirred at 100° C. for 16 hrs. The reaction was concentrated and purified by flash column to give compound 74k (80 mg) as a light yellow solid. MS calc'd 598 ($MH^+$), measured 598 ($MH^+$).

Step 11: Preparation of 5-[(2R,6S)-2-methyl-6-[[4-[(5R)-5-methyl-5,6,7,8-tetrahydro-2,6-naphthyridin-3-yl]piperazin-1-yl]methyl]morpholin-4-yl]quinoline-8-carbonitrile and 5-[(2R,6S)-2-methyl-6-[[4-[(5S)-5-methyl-5,6,7,8-tetrahydro-2,6-naphthyridin-3-yl]piperazin-1-yl]methyl]morpholin-4-yl]quinoline-8-carbonitrile (Example 74 and 75)

tert-butyl 1-methyl-7-[4-[[(2S,6R)-4-(8-cyano-5-quinolyl)-6-methyl-morpholin-2-yl]methyl]piperazin-1-yl]-3,4-dihydro-1H-2,6-naphthyridine-2-carboxylate (compound 74k, 80 mg) was separated by chiral SFC (Gradient: 50% Isopropanol (0.1% $NH_3H_2O$) in $CO_2$, Column: «Column_3») to give two isomers: A (faster eluting, 30 mg) as a yellow gum and B (slower eluting, 30 mg) as a yellow gum.

MS: calc'd 598 ($MH^+$), measured 598 ($MH^+$). The two isomers were stirred in 1 M HCl in EA (5 mL) at rt for 16 hrs. Then the reaction mixture was concentrated and the residue was dissolved in NaOH (1 M, 5 mL) and extracted with EA (10 mL). The organic layer was dried over $Na_2SO_4$ and concentrated to give corresponding Example 74 and 75.

Example 74 (25 mg) was obtained as a yellow solid. MS calc'd 498 ($MH^+$), measured 498 ($MH^+$). $^1$H NMR (400 MHz, METHANOL-d4) δ=8.97 (dd, J=1.7, 4.2 Hz, 1H), 8.66 (dd, J=1.6, 8.6 Hz, 1H), 8.15 (d, J=7.9 Hz, 1H), 7.88 (s, 1H), 7.64 (dd, J=4.2, 8.6 Hz, 1H), 7.25 (d, J=7.9 Hz, 1H), 6.62 (s, 1H), 4.27-4.15 (m, 1H), 4.14-4.00 (m, 2H), 3.46 (t, J=5.3 Hz, 5H), 3.39 (br d, J=11.9 Hz, 1H), 3.26-3.18 (m, 1H), 2.95 (ddd, J=5.0, 8.3, 12.9 Hz, 1H), 2.84-2.50 (m, 10H), 1.48 (d, J=6.7 Hz, 3H), 1.26 (d, J=6.2 Hz, 3H).

Example 75 (25 mg) was obtained as a yellow solid. MS calc'd 498 ($MH^+$), measured 498 ($MH^+$). $^1$H NMR (400 MHz, METHANOL-d4) δ=8.88 (dd, J=1.7, 4.3 Hz, 1H), 8.56 (dd, J=1.7, 8.6 Hz, 1H), 8.05 (d, J=7.9 Hz, 1H), 7.78 (s, 1H), 7.54 (dd, J=4.3, 8.6 Hz, 1H), 7.15 (d, J=8.1 Hz, 1H), 6.53 (s, 1H), 4.16-4.06 (m, 1H), 4.04-3.88 (m, 2H), 3.37 (t, J=5.3 Hz, 5H), 3.29 (br d, J=11.9 Hz, 1H), 3.17-3.08 (m, 1H), 2.91-2.80 (m, 1H), 2.70-2.41 (m, 10H), 1.43-1.31 (m, 3H), 1.20-1.11 (m, 3H).

Example 76 and Example 77

5-[(2R,6S)-2-methyl-6-[[4-[(7S)-7-methyl-5,6,7,8-tetrahydro-2,6-naphthyridin-3-yl]piperazin-1-yl]methyl]morpholin-4-yl]quinoline-8-carbonitrile and 5-[(2R,6S)-2-methyl-6-[[4-[(7R)-7-methyl-5,6,7,8-tetrahydro-2,6-naphthyridin-3-yl]piperazin-1-yl]methyl]morpholin-4-yl]quinoline-8-carbonitrile

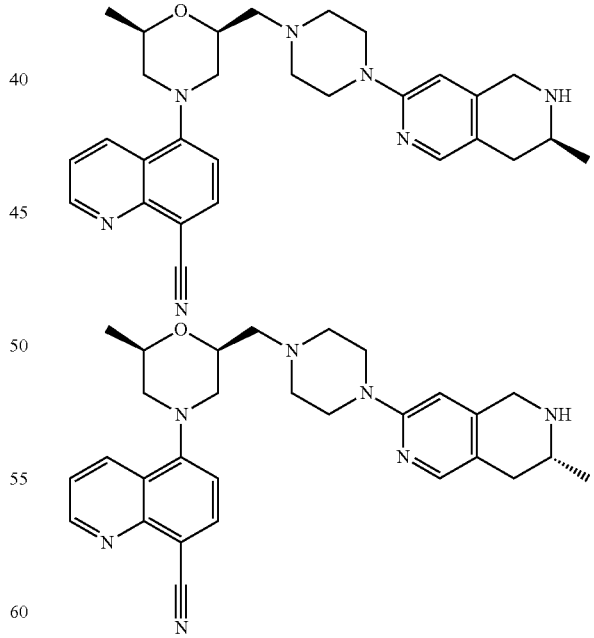

The title compounds were prepared in analogy to the preparation of Example 70 and 71 by using tert-butyl 7-methoxy-3-methyl-3,4-dihydro-1H-2,6-naphthyridine-2-carboxylate (compound 76f) instead of tert-butyl 6-methoxy-3-methyl-3,4-dihydro-1H-2,7-naphthyridine-2- carboxylate (compound 70f). The Boc protected Example 76 (faster eluting) and 77 (slower eluting) were separated by chiral SFC (Gradient: 35% Ethanol (0.1% NH₃H₂O) in CO₂, Column: Daicel chiralpak AS-H 250×30 mm, 5 μm).

Example 76 (24 mg) was obtained as a yellow solid. MS: calc'd 498 (MH⁺), measured 498 (MH⁺), ¹H NMR (400 MHz, METHANOL-d4) δ=9.02 (dd, J=1.6, 4.4 Hz, 1H), 8.70-8.67 (m, 1H), 8.19 (d, J=7.6 Hz, 1H), 8.14 (s, 1H), 7.68 (dd, J=2.4, 4.4 Hz, 1H), 7.31 (d, J=8.0 Hz, 1H), 6.84 (s, 1H), 4.53-4.50 (m, 1H), 4.42 (s, 2H), 4.25-4.18 (m, 1H), 3.80-3.30 (m, 11H), 3.20-3.10 (m, 1H), 2.81-2.76 (m, 5H), 1.51 (d, J=6.8 Hz, 3H), 1.34 (d, J=6.4 Hz, 3H).

Example 77 (22 mg) was obtained as a yellow solid. MS: calc'd 498 (MH⁺), measured 498 (MH⁺), ¹H NMR (400 MHz, METHANOL-d4) δ=9.02 (dd, J=1.6, 4.4 Hz, 1H), 8.68 (dd, J=1.6, 8.4 Hz, 1H), 8.19 (d, J=8.0 Hz, 1H), 8.14 (s, 1H), 7.68 (dd, J=4.4, 8.8 Hz, 1H), 7.31 (d, J=8.4 Hz, 1H), 6.84 (s, 1H), 4.53-4.50 (m, 1H), 4.42 (s, 2H), 4.25-4.18 (m, 1H), 3.85-3.30 (m, 13H), 3.20-3.10 (m, 1H), 2.84-2.76 (m, 3H), 1.51 (d, J=6.4 Hz, 3H), 1.34 (d, J=6.4 Hz, 3H).

The compound 76f was prepared according to the following scheme:

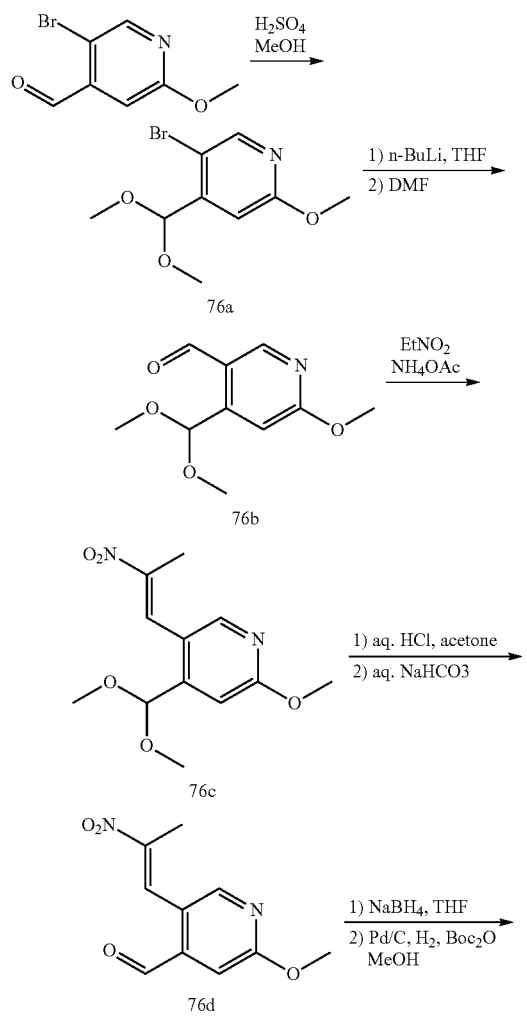

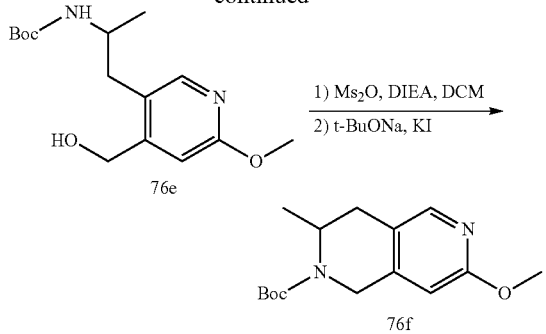

Step 1: Preparation of 5-bromo-4-(dimethoxymethyl)-2-methoxy-pyridine (Compound 76a)

To the solution of 5-bromo-2-methoxy-pyridine-4-carbaldehyde (CAS: 936011-17-5, Vendor: Bidepharm, 25.0 g, 115.72 mmol) in methanol (500 mL) was added sulfuric acid (14.19 mL, 231.5 mmol). After being stirred at rt for 18 hrs, the mixture was concentrated and added to the mixture solvent of aq. Na₂CO₃ (150 mL) and EA (150 mL). The mixture was separated, the organic layer was washed with brine (50 mL), dried over Na₂SO₄ and concentrated to give compound 76a (28.0 g) as a yellow oil. MS: calc'd 262 (MH⁺), measured 262 (MH⁺).

Step 2: Preparation of 4-(dimethoxymethyl)-6-methoxy-pyridine-3-carbaldehyde (Compound 76b)

To the solution of 5-bromo-4-(dimethoxymethyl)-2-methoxy-pyridine (compound 76a, 23.00 g, 87.75 mmol) in THF (230 mL) was added n-butyllithium (42.12 mL, 105.30 mmol) at −58° C. The mixture was stirred at −58° C. for 0.5 h and DMF (19.22 g, 263.3 mmol) was added at this temperature. After 15 mins, the reaction mixture was warm to −30° C. and stirred for 15 mins. Then it was quenched by addition of cold aq. NH₄Cl (100 mL), and extracted with EA (150 mL) twice. The combined organic layer was washed with brine (100 ml) twice, dried over Na₂SO₄, and concentrated to give the crude product compound 76b (24.0 g) as a black oil, which was used for the next step without further purification. MS: calc'd 212 (MH⁺), measured 212 (MH⁺).

Step 3: Preparation of 4-(dimethoxymethyl)-2-methoxy-5-[(E)-2-nitroprop-1-enyl]pyridine (Compound 76c)

The solution of 4-(dimethoxymethyl)-6-methoxy-pyridine-3-carbaldehyde (compound 76b, 23.00 g, 108.90 mmol) and ammonium acetate (6.72 g, 87.12 mmol) in nitroethane (230 mL) was stirred at 100° C. for 18 hrs. The mixture was concentrated and purified by flash column (PE/EA=10/1) to give compound 76c (16.00 g) as a yellow gum. MS: calc'd 269 (MH⁺), measured 269 (MH⁺).

Step 4: Preparation of 2-methoxy-5-[(E)-2-nitroprop-1-enyl]pyridine-4-carbaldehyde (Compound 76d)

To the solution of 4-(dimethoxymethyl)-2-methoxy-5-[(E)-2-nitroprop-1-enyl]pyridine (compound 76c, 16.00 g, 59.64 mmol) in acetone (160 mL) was added hydrogen chloride (6N, 100 mL, 600 mmol) at 0° C. After the mixture was stirred at rt for 18 hrs, water (250 mL) and EA (25 mL) was added, and the mixture was adjusted to pH=7-8. The mixture was extracted with EA (200 mL) twice and the organic layer was washed with brine (100 mL), dried over Na$_2$SO$_4$ and concentrated to give compound 76d (11.00 g) as a yellow solid. MS: calc'd 223 (MH$^+$), measured 223 (MH$^+$).

Step 5: Preparation of tert-butyl N-[2-[4-(hydroxymethyl)-6-methoxy-3-pyridyl]-1-methyl-ethyl]carbamate (Compound 76e)

To the solution of 2-methoxy-5-[(E)-2-nitroprop-1-enyl]pyridine-4-carbaldehyde (compound 76d, 5.00 g, 22.50 mmol) in THF (250 mL) was added sodium borohydride (3.00 g, 79.30 mmol) at 0° C. After being stirred at 0° C. for 3 hrs, the mixture was filtered. To the filtrate was added MeOH (50 mL), Pd/C (10 wt. %, 1.00 g) and di-t-butyldicarbonate (9.65 g, 44.20 mmol). The reaction mixture was stirred at rt for 18 hrs under H$_2$ atmosphere. After filtration, the mixture was concentrated to give the crude product which was purified by flash column (PE/EA=10/1 to 2/1) to give compound 76e (2.00 g) as a white solid. MS: calc'd 297 (MH$^+$), measured 297 (MH$^+$).

Step 6: Preparation of tert-butyl 7-methoxy-3-methyl-3,4-dihydro-1H-2,6-naphthyridine-2-carboxylate (Compound 76f)

To the solution of tert-butyl N-[2-[4-(hydroxymethyl)-6-methoxy-3-pyridyl]-1-methyl-ethyl]carbamate (compound 76e, 2.00 g, 6.75 mmol), DIPEA (3.53 mL, 20.25 mmol) in DCM (40 mL) was added methanesulfonic anhydride (2.35 g, 13.5 mmol) at 0° C. The mixture was stirred at rt for 2 hrs and quenched with 40 mL saturated NH$_4$Cl. The mixture was diluted with 150 mL water and extracted with 80 mL DCM for three times. The combined organic layer was washed with 80 mL water twice and 60 mL brine once, dried over Na$_2$SO$_4$ and concentrated to give the crude product (2.53 g) which was dissolved in DMF (35 mL). KI (0.56 g, 3.37 mmol) and sodium tert-butoxide (1.95 g, 20.25 mmol) was added to the mixture. After being stirred at 10° C. for 0.5 h, the reaction was quenched with 50 mL saturated NH$_4$Cl. The mixture was diluted with 200 mL water and extracted with 80 mL EA for three times. The combined organic layer was washed with 80 mL water twice and 40 mL brine once, dried over Na$_2$SO$_4$, concentrated and purified by flash column (PE/EA=5/1) to give compound 76f (1.30 g) as a yellow solid. MS calc'd 279 (MH$^+$), measured 279 (MH$^+$).

Example 78 and Example 79

8-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoxaline-5-carbonitrile and 8-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoxaline-5-carbonitrile

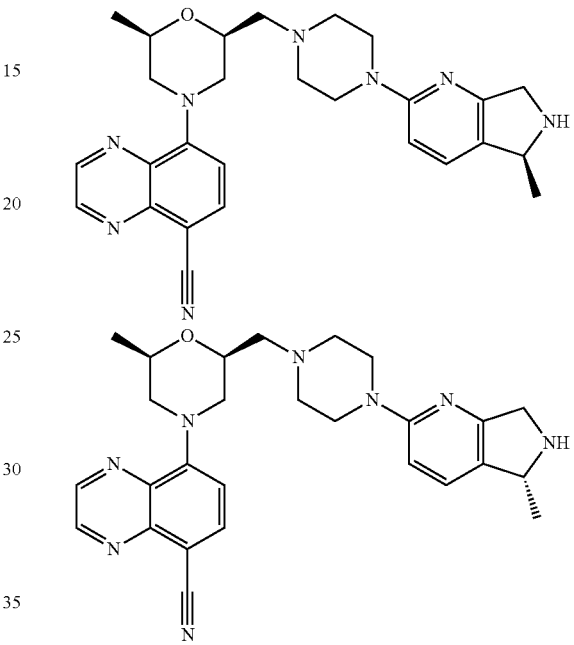

The title compounds were prepared in analogy to the preparation of Example 1 by using tert-butyl 2-chloro-5-methyl-5,7-dihydropyrrolo[3,4-b]pyridine-6-carboxylate (compound 78a) and Intermediate C instead of tert-butyl 2-bromo-6,7-dihydro-4H-pyrazolo[1,5-a]pyrazine-5-carboxylate and Intermediate A. The Boc protected Example 78 (faster eluting) and 79 (slower eluting) were separated by chiral SFC (Gradient: 60% Methanol (0.1% NH$_3$H$_2$O) in CO$_2$, Column: Daicel chiralcel OD 250×30 mm, 10 μm).

Example 78 (15 mg) was obtained as a yellow solid. MS: calc'd 485 (MH$^+$), measured 485 (MH$^+$). $^1$H NMR (400 MHz, DMSO-d$_6$) δ=9.05-8.88 (m, 2H), 8.17 (d, J=8.3 Hz, 1H), 7.67 (d, J=8.8 Hz, 1H), 7.28 (d, J=8.3 Hz, 1H), 6.99 (d, J=8.8 Hz, 1H), 5.01 (q, J=6.6 Hz, 1H), 4.86-4.76 (m, 1H), 4.70-4.38 (m, 4H), 4.30 (br d, J=12.0 Hz, 1H), 4.22-4.10 (m, 2H), 3.63 (q, J=7.0 Hz, 3H), 3.54-3.36 (m, 4H), 3.15 (br d, J=1.8 Hz, 1H), 2.93-2.81 (m, 2H), 1.68 (d, J=6.7 Hz, 3H), 1.35 (d, J=6.1 Hz, 3H).

Example 79 (15 mg) was obtained as a yellow solid. MS: calc'd 485 (MH$^+$), measured 485 (MH$^+$), $^1$H NMR (400 MHz, DMSO-d$_6$) δ=9.04-8.88 (m, 2H), 8.18 (d, J=8.3 Hz, 1H), 7.67 (d, J=8.7 Hz, 1H), 7.28 (d, J=8.4 Hz, 1H), 6.98 (d, J=8.8 Hz, 1H), 5.01 (q, J=6.8 Hz, 1H), 4.85-4.72 (m, 1H), 4.64-4.41 (m, 4H), 4.31 (br d, J=12.1 Hz, 1H), 4.22-4.10 (m, 2H), 3.63 (q, J=7.1 Hz, 3H), 3.52-3.36 (m, 4H), 2.95-2.62 (m, 3H), 1.68 (d, J=6.7 Hz, 3H), 1.35 (d, J=6.1 Hz, 3H).

The compound 78a was prepared according to the following scheme:

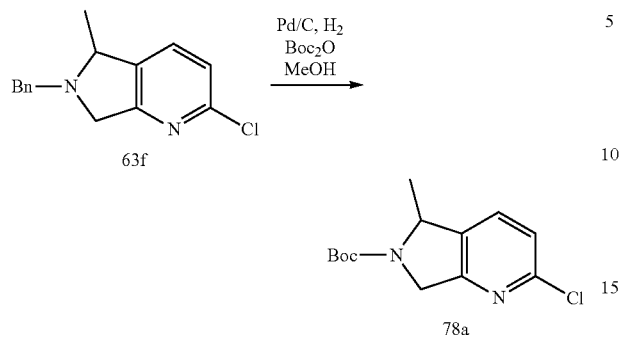

Step 1: Preparation of tert-butyl 2-chloro-5-methyl-5,7-dihydropyrrolo[3,4-b]pyridine-6-carboxylate (Compound 78a)

To a flask was added 6-benzyl-2-chloro-5-methyl-5,7-dihydropyrrolo[3,4-b]pyridine (compound 63f, 500 mg, 1.93 mmol), MeOH (5 ml), Boc-Anhydride (670 mg, 3.07 mmol) and Pd/C (10% wt. %, 100 mg, 940 μmol). The mixture was stirred at rt with hydrogen balloon for 2 hrs. After filtration, the mixture was concentrated to give compound 78a (500 mg) as an oil and used in the next step directly. MS: calc'd 269 (MH$^+$), measured 269 (MH$^+$).

Example 80

8-[(2R,6S)-2-methyl-6-[[4-(5,6,7,8-tetrahydro-2,6-naphthyridin-3-yl)piperazin-1-yl]methyl]morpholin-4-yl]quinoxaline-5-carbonitrile

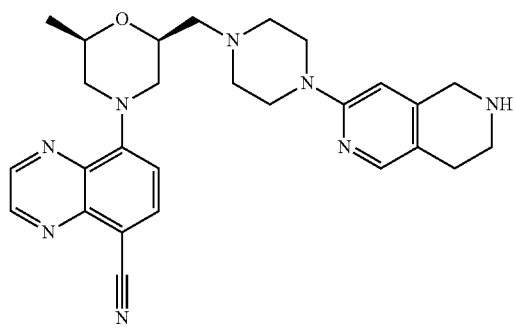 [SMILES: C[C@@H]1CN(c2ccc(C#N)c3nccnc23)C[C@H](CN2CCN(c3cc4c(cn3)CCNC4)CC2)O1]

The title compound was prepared in analogy to the preparation of Example 1 by using tert-butyl 7-chloro-3,4-dihydro-2,6-naphthyridine-2 (1H)-carboxylate (CAS: 1060816-50-3, Vendor: Shanghai Hong-chuang Pharma Tech Co., Ltd.) and Intermediate C instead of tert-butyl 2-bromo-6,7-dihydro-4H-pyrazolo[1,5-a]pyrazine-5-carboxylate and Intermediate A, replacing RuPhos Pd G2, Cs$_2$CO$_3$ with Pd$_2$(dba)$_3$, BINAP, t-BuONa in the Buchwald-Hartwig amination reaction. Example 80 (42 mg) was obtained as a yellow solid. MS: calc'd 485 (MH$^+$), measured 485 (MH$^+$). $^1$H NMR (400 MHz, METHANOL-d$_4$) δ=9.00 (d, J=1.8 Hz, 1H), 8.91 (d, J=1.8 Hz, 1H), 8.24-8.12 (m, 2H), 7.29 (d, J=8.3 Hz, 1H), 6.83 (s, 1H), 5.00-4.88 (m, 3H), 4.87-4.77 (m, 3H), 4.47 (br d, J=8.8 Hz, 1H), 4.37 (s, 2H), 4.31 (br d, J=11.7 Hz, 1H), 4.21-4.13 (m, 2H), 3.53 (t, J=6.3 Hz, 3H), 3.47-3.37 (m, 3H), 3.05 (t, J=6.2 Hz, 2H), 2.92-2.81 (m, 2H), 1.36 (d, J=6.1 Hz, 3H).

Example 81 and Example 82

8-[(2R,6S)-2-methyl-6-[[4-[(7S)-7-methyl-5,6,7,8-tetrahydro-2,6-naphthyridin-3-yl]piperazin-1-yl]methyl]morpholin-4-yl]quinoxaline-5-carbonitrile and 8-[(2R,6S)-2-methyl-6-[[4-[(7R)-7-methyl-5,6,7,8-tetrahydro-2,6-naphthyridin-3-yl]piperazin-1-yl]methyl]morpholin-4-yl]quinoxaline-5-carbonitrile

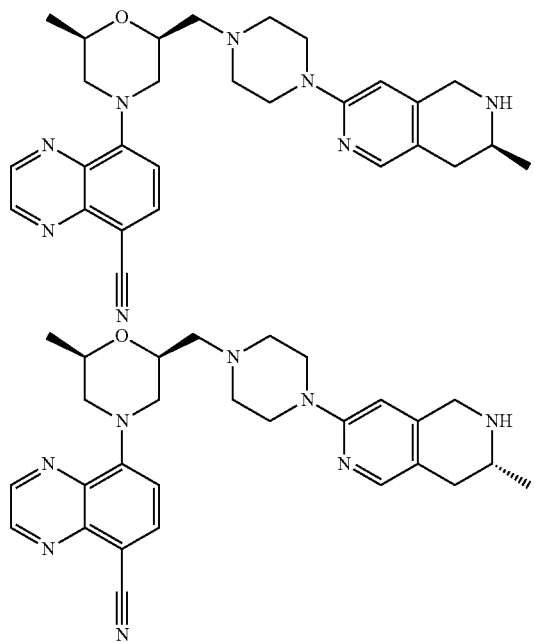

The title compounds were prepared according to the following scheme:

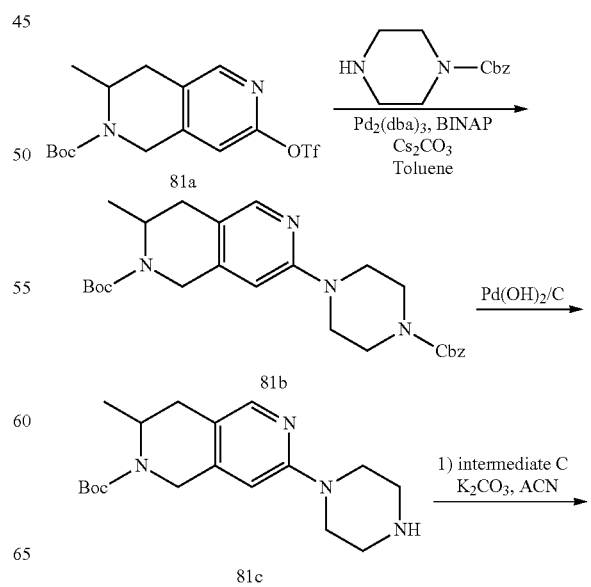

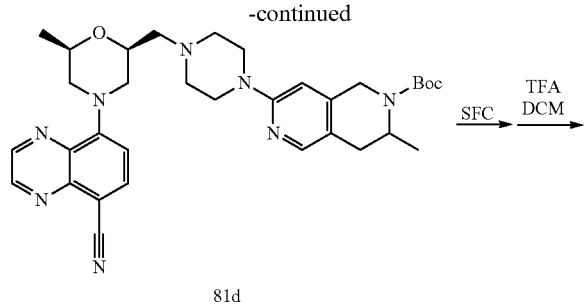

81d

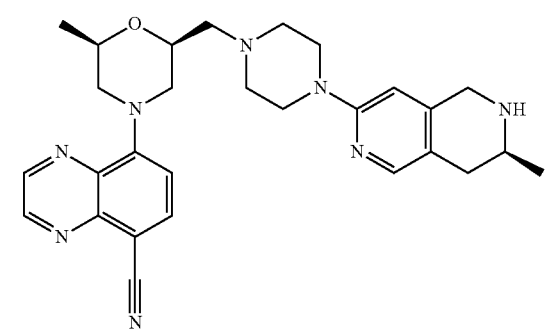

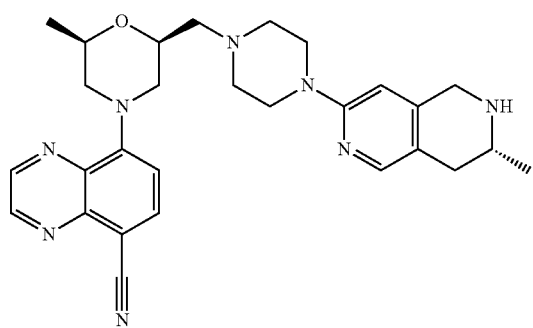

81 and 82

Step 1: Preparation of tert-butyl 7-(4-benzyloxycarbonylpiperazin-1-yl)-3-methyl-3,4-dihydro-1H-2,6-naphthyridine-2-carboxylate (Compound 81b)

To the solution of (R)-BINAP (20 mg, 0.03 mmol), cesium carbonate (103 mg, 0.32 mmol), Pd$_2$(dba)$_3$ (16 mg, 0.02 mmol), 1-Cbz-piperazine (56 mg, 0.25 mmol) in toluene (2 mL) was added tert-butyl 3-methyl-7-(trifluoromethylsulfonyloxy)-3,4-dihydro-1H-2,6-naphthyridine-2-carboxylate (compound 81a, the synthesis of compound 81a is refer to the synthesis of compound 70h, 50 mg, 0.13 mmol) and stirred at 100° C. under N$_2$ atmosphere for 18 hrs. After being cooled down, the reaction mixture was filtered. The filtrate was concentrated and purified by prep-TLC (PE/EA=2/1) to give compound 81b (50 mg) as a yellow gum. MS: calc'd 467 (MH$^+$), measured 467 (MH$^+$).

Step 2: Preparation of tert-butyl 3-methyl-7-piperazin-1-yl-3,4-dihydro-1H-2,6-naphthyridine-2-carboxylate (Compound 81c)

To the solution of tert-butyl 7-(4-benzyloxycarbonylpiperazin-1-yl)-3-methyl-3,4-dihydro-1H-2,6-naphthyridine-2-carboxylate (compound 81b, 130 mg, 0.28 mmol) in methanol (5 mL) was added Pd/C (10 wt. %, 20 mg, 0.28 mmol). After being stirred at 20° C. under H$_2$ atmosphere for 2 hrs, the mixture was filtered, and the filtrate was concentrated to give compound 81c (80 mg) as a yellow gum. MS: calc'd 333 (MH$^+$), measured 333 (MH$^+$).

Step 3: Preparation of tert-butyl 7-[4-[[(2S,6R)-4-(8-cyanoquinoxalin-5-yl)-6-methyl-morpholin-2-yl]methyl]piperazin-1-yl]-3-methyl-3,4-dihydro-1H-2,6-naphthyridine-2-carboxylate (Compound 81d)

To the solution of tert-butyl 3-methyl-7-piperazin-1-yl-3,4-dihydro-1H-2,6-naphthyridine-2-carboxylate (compound 81c, 76 mg, 0.23 mmol), potassium carbonate (79 mg, 0.57 mmol) in acetonitrile (4 mL) was added [(2R,6R)-4-(8-cyanoquinoxalin-5-yl)-6-methyl-morpholin-2-yl]methyl trifluoromethanesulfonate (Intermediate C, 95 mg, 0.23 mmol). After being stirred at 55° C. for 2 hrs, the mixture was filtered, concentrated and purified by prep-TLC (PE/EA=1/1) to give the compound 81d (70 mg) as a yellow solid. MS: calc'd 599 (MH$^+$), measured 599 (MH$^+$).

Step 4: Preparation of 8-[(2R,6S)-2-methyl-6-[[4-[(7S)-7-methyl-5,6,7,8-tetrahydro-2,6-naphthyridin-3-yl]piperazin-1-yl]methyl]morpholin-4-yl]quinoxaline-5-carbonitrile and 8-[(2R,6S)-2-methyl-6-[[4-[(7R)-7-methyl-5,6,7,8-tetrahydro-2,6-naphthyridin-3-yl]piperazin-1-yl]methyl]morpholin-4-yl]quinoxaline-5-carbonitrile (Example 81 and 82)

The racemic compound 81d was separated by chiral SFC (Gradient: 35% Methanol (0.1% NH$_3$H$_2$O) in CO$_2$, Column: Daicel chiralpak AS-H 250×30 mm, 5 μm) to give the two isomers: A (faster eluting, 30 mg) as a yellow gum and B (slower eluting, 38 mg) as a yellow gum. The two isomers were stirred in TFA (2 mL) and DCM (5 mL) at rt for 16 hrs. Then the reaction mixture was concentrated to give the corresponding Example 81 and 82.

Example 81 (23 mg) was obtained as a yellow solid. MS: calc'd 499 (MH$^+$), measured 499 (MH$^+$). $^1$H NMR (400 MHz, DMSO-d$_6$) δ=8.99 (d, J=2.4 Hz, 1H), 8.91 (d, J=2.4 Hz, 1H), 8.17 (d, J=10.8 Hz, 1H), 8.13 (s, 1H), 7.28 (d, J=11.2 Hz, 1H), 6.83 (s, 1H), 4.55-4.25 (m, 5H), 4.20-4.10 (m, 2H), 3.85-3.30 (m, 10H), 3.20-3.10 (m, 1H), 2.87-2.70 (m, 3H), 1.51 (d, J=8.8 Hz, 3H), 1.35 (d, J=8.0 Hz, 3H).

Example 82 (18 mg) was obtained as a yellow solid. MS: calc'd 499 (MH$^+$), measured 499 (MH$^+$). $^1$H NMR (400 MHz, DMSO-d$_6$) δ=8.99 (d, J=2.4 Hz, 1H), 8.91 (d, J=2.4 Hz, 1H), 8.17 (d, J=10.8 Hz, 1H), 8.13 (s, 1H), 7.28 (d, J=11.2 Hz, 1H), 6.84 (s, 1H), 4.55-4.20 (m, 5H), 4.18-4.04 (m, 2H), 3.80-3.30 (m, 10H), 3.20-3.10 (m, 1H), 2.95-2.75 (m, 3H), 1.51 (d, J=8.8 Hz, 3H), 1.35 (d, J=8.4 Hz, 3H).

Example 83 and Example 84

8-[(2R,6S)-2-methyl-6-[[4-[(6R)-6-methyl-5,6,7,8-tetrahydro-2,7-naphthyridin-3-yl]piperazin-1-yl]methyl]morpholin-4-yl]quinoxaline-5-carbonitrile and 8-[(2R,6S)-2-methyl-6-[[4-[(6S)-6-methyl-5,6,7,8-tetrahydro-2,7-naphthyridin-3-yl]piperazin-1-yl]methyl]morpholin-4-yl]quinoxaline-5-carbonitrile

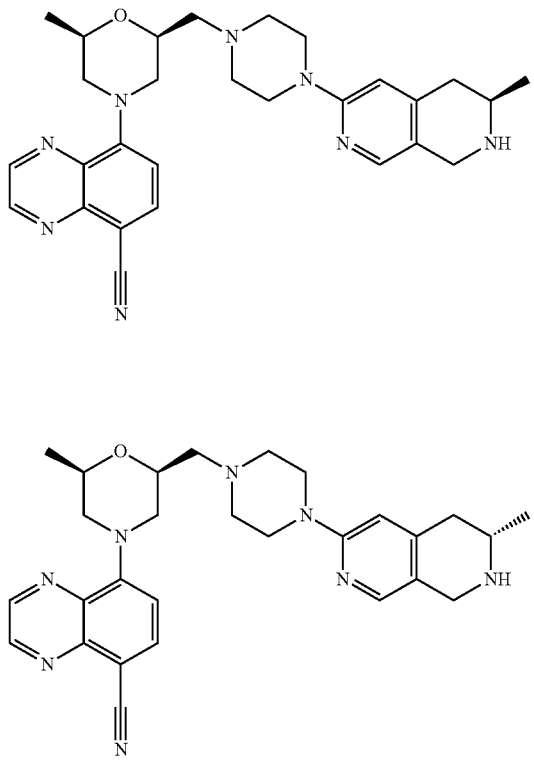

The title compounds were prepared in analogy to the preparation of Example 81 and 82 by using tert-butyl-3-methyl-6-(trifluoromethylsulfonyloxy)-3,4-dihydro-1H-2,7-naphthyridine-2-carboxylate (compound 70h) instead of tert-butyl 3-methyl-7-(trifluoromethylsulfonyloxy)-3,4-dihydro-1H-2,6-naphthyridine-2-carboxylate (compound 81a). The Boc protected Example 83 (faster eluting) and 84 (slower eluting) were separated by chiral SFC (Gradient: 55% Ethanol (0.1% NH$_3$H$_2$O) in CO$_2$, Column: Daicel chiralpak AY 250×50 mm, 10 μm).

Example 83 (30 mg) was obtained as a brown solid. MS: calc'd 499 (MH$^+$), measured 499 (MH$^+$). $^1$H NMR (400 MHz, DMSO-d$_6$) δ=8.99 (d, J=1.6 Hz, 1H), 8.91 (d, J=1.6 Hz, 1H), 8.17 (d, J=8.3 Hz, 1H), 8.12 (s, 1H), 7.28 (d, J=8.3 Hz, 1H), 6.85 (s, 1H), 4.60-4.08 (m, 8H), 4.06-3.37 (m, 9H), 3.19 (br dd, J=4.6, 18.1 Hz, 1H), 2.96-2.79 (m, 3H), 1.50 (d, J=6.5 Hz, 3H), 1.35 (d, J=6.1 Hz, 3H).

Example 84 (32 mg) was obtained as a brown solid. MS: calc'd 499 (MH$^+$), measured 499 (MH$^+$). $^1$H NMR (400 MHz, DMSO-d$_6$) δ=8.99 (d, J=1.7 Hz, 1H), 8.91 (d, J=1.7 Hz, 1H), 8.16 (d, J=8.3 Hz, 1H), 8.12 (s, 1H), 7.27 (d, J=8.3 Hz, 1H), 6.86 (s, 1H), 4.58-4.08 (m, 8H), 4.07-3.38 (m, 9H), 3.19 (dd, J=4.7, 18.0 Hz, 1H), 2.96-2.80 (m, 3H), 1.50 (d, J=6.5 Hz, 3H), 1.35 (d, J=6.2 Hz, 3H).

Example 85 and Example 86

8-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoxaline-5-carbonitrile and 8-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoxaline-5-carbonitrile

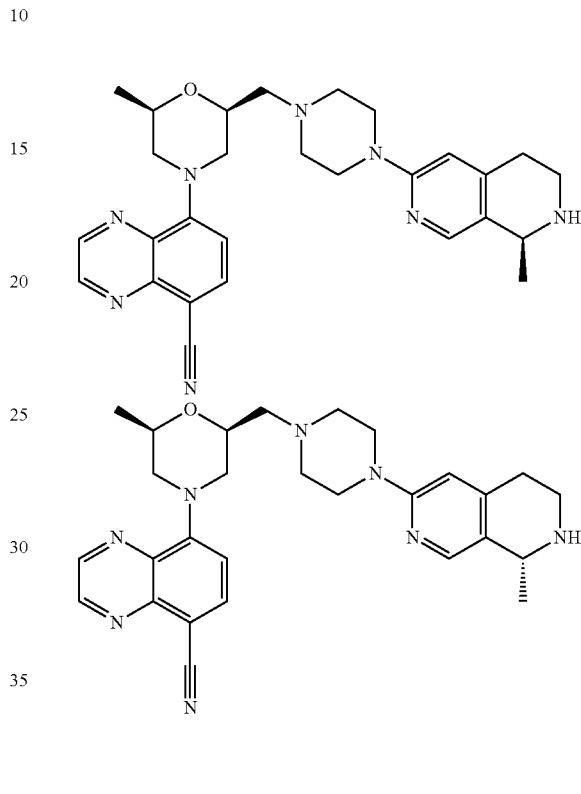

The title compounds were prepared in analogy to the preparation of Example 81 and 82 by using tert-butyl 1-methyl-6-(trifluoromethylsulfonyloxy)-3,4-dihydro-1H-2,7-naphthyridine-2-carboxylate (compound 85c) instead of tert-butyl 3-methyl-7-(trifluoromethylsulfonyloxy)-3,4-dihydro-1H-2,6-naphthyridine-2-carboxylate (compound 81a). The Boc protected Example 85 (faster eluting) and 86 (slower eluting) were separated by chiral SFC (Gradient: 60% Isopropanol (0.1% NH$_3$H$_2$O) in CO$_2$, Column: Daicel chiralpak AD 250×50 mm, 10 μm).

Example 85 (49 mg) was obtained as a yellow gum. MS: calc'd 499 (MH$^+$), measured 499 (MH$^+$). $^1$H NMR (400 MHz, DMSO-d$_6$) δ=9.01-8.85 (m, 2H), 8.20-8.11 (m, 2H), 7.26 (d, J=8.3 Hz, 1H), 6.83 (s, 1H), 4.61 (q, J=6.7 Hz, 1H), 4.55-4.24 (m, 3H), 4.21-3.91 (m, 3H), 3.80-3.35 (m, 9H), 3.30-3.23 (m, 1H), 3.20-3.00 (m, 2H), 2.91-2.77 (m, 2H), 1.70 (d, J=6.8 Hz, 3H), 1.34 (d, J=6.1 Hz, 3H).

Example 86 (50 mg) was obtained as a yellow gum. MS: calc'd 499 (MH$^+$), measured 499 (MH$^+$). $^1$H NMR (400 MHz, DMSO-d$_6$) δ=8.98 (d, J=1.8 Hz, 1H), 8.89 (d, J=1.8 Hz, 1H), 8.19-8.13 (m, 2H), 7.26 (d, J=8.4 Hz, 1H), 6.83 (s, 1H), 4.61 (q, J=6.6 Hz, 1H), 4.52-4.41 (m, 1H), 4.28 (br d, J=12.0 Hz, 2H), 4.24-3.92 (m, 3H), 3.82-3.34 (m, 9H), 3.30-3.24 (m, 1H), 3.18-3.02 (m, 2H), 2.91-2.78 (m, 2H), 1.70 (d, J=6.8 Hz, 3H), 1.34 (d, J=6.1 Hz, 3H).

The compound 85c was prepared according to the following scheme:

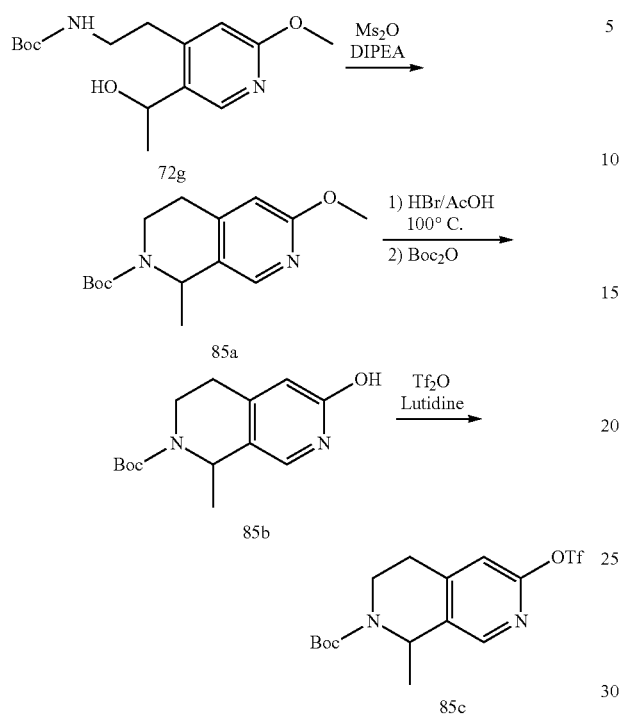

Step 1: Preparation of tert-butyl 6-methoxy-1-methyl-3,4-dihydro-1H-2,7-naphthyridine-2-carboxylate (Compound 85a)

To the solution of tert-butyl N-[2-[5-(1-hydroxyethyl)-2-methoxy-4-pyridyl]ethyl]carbamate (compound 72g, 3.40 g, 11.47 mmol), DIPEA (5.99 mL, 34.42 mmol) in DCM (68 mL) was added methanesulfonic anhydride (4.00 g, 22.95 mmol) at 0° C. After being stirred at rt for 18 hrs, the reaction was quenched with 50 mL water, extracted with 100 mL DCM for three times. The combined organic layer was washed with 80 mL water twice and 60 mL brine once, dried over $Na_2SO_4$ and concentrated to give the crude product which was purified by flash column to give compound 85a (2.30 mg) as a white solid. MS: calc'd 279 ($MH^+$), measured 279 ($MH^+$).

Step 2: Preparation of tert-butyl 6-hydroxy-1-methyl-3,4-dihydro-1H-2,7-naphthyridine-2-carboxylate (Compound 85b)

A solution of tert-butyl 6-methoxy-1-methyl-3,4-dihydro-1H-2,7-naphthyridine-2-carboxylate (compound 85a, 2.30 g, 8.26 mmol) in hydrobromic acid (33% in AcOH, 24 mL) was heated to 100° C. for 16 hrs. After concentration, the residue was re-dissolved in MeOH (36 mL), and adjusted to pH=8-9 with aq. $K_2CO_3$. Then di-t-butyldicarbonate (2.65 g, 12.16 mmol) was added and the reaction mixture was stirred at rt for 2 hrs. After concentration, the residue was purified via flash column (DCM/MeOH=20/1) to give compound 85b (1.80 g) as a yellow solid. MS: calc'd 265 ($MH^+$), measured 265 ($MH^+$).

Step 3: Preparation of tert-butyl 1-methyl-6-(trifluoromethylsulfonyloxy)-3,4-dihydro-1H-2,7-naphthyridine-2-carboxylate (Compound 85c)

To the solution of tert-butyl 6-hydroxy-1-methyl-3,4-dihydro-1H-2,7-naphthyridine-2-carboxylate (compound 85b, 200 mg, 0.76 mmol) in DCM (5 mL) was added 2,6-dimethylpyridine (324 mg, 3.03 mmol) and trifluoromethane sulfonic anhydride (427 mg, 1.51 mmol) dropwise at 0° C. After being stirred at 0° C. for 1 h, the reaction was quenched with ice water (20 mL), and extracted with DCM (20 mL) twice. The organic layer was washed with 10 ml 5% citric acid (aq.) twice and brine (10 mL) once, dried over $Na_2SO_4$ and concentrated to give the crude product compound 85c (300 mg) as a yellow gum, which was used for the next step without purification. MS: calc'd 397 ($MH^+$), measured 397 ($MH^+$).

Example 87 and Example 88

8-[(2R,6S)-2-methyl-6-[[4-[(5R)-5-methyl-5,6,7,8-tetrahydro-2,6-naphthyridin-3-yl]piperazin-1-yl]methyl]morpholin-4-yl]quinoxaline-5-carbonitrile and 8-[(2R,6S)-2-methyl-6-[[4-[(5S)-5-methyl-5,6,7,8-tetrahydro-2,6-naphthyridin-3-yl]piperazin-1-yl]methyl]morpholin-4-yl]quinoxaline-5-carbonitrile

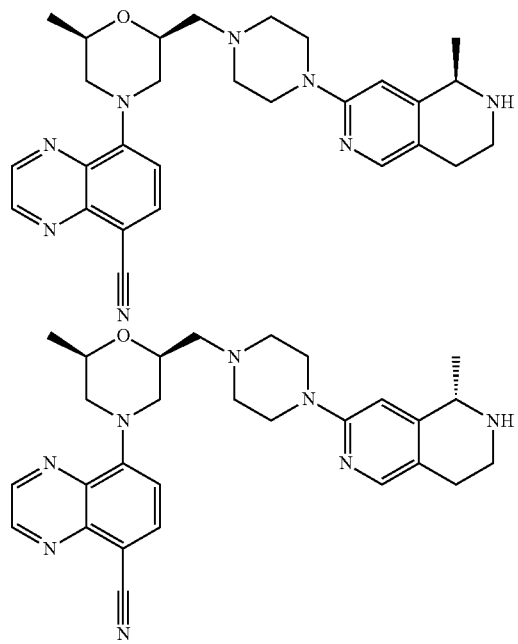

The title compounds were prepared in analogy to the preparation of Example 74 and 75 by using Intermediate C instead of Intermediate A. The Boc protected Example 87 (faster eluting) and 88 (slower eluting) were separated by chiral SFC (Gradient: 40% Isopropanol (0.1% $NH_3H_2O$) in $CO_2$, Column: «Column_3»).

Example 87 (21 mg) was obtained as a dark brown solid. MS: calc'd 499 ($MH^+$), measured 499 ($MH^+$). $^1H$ NMR (400 MHz, METHANOL-d4) δ=8.99 (d, J=1.7 Hz, 1H), 8.92 (d, J=1.8 Hz, 1H), 8.22-8.09 (m, 2H), 7.50 (s, 1H), 7.29 (d, J=8.4 Hz, 1H), 4.87-4.80 (m, 1H), 4.62-4.42 (m, 3H), 4.38-4.28 (m, 1H), 4.26-4.14 (m, 2H), 4.04-3.76 (m, 4H), 3.71-3.44 (m, 6H), 3.22-3.15 (m, 2H), 2.98-2.81 (m, 2H), 1.84 (d, J=7.1 Hz, 3H), 1.36 (d, J=6.1 Hz, 3H).

Example 88 (22 mg) was obtained as a dark brown solid. MS: calc'd 499 (MH+), measured 499 (MH+). ¹H NMR (400 MHz, METHANOL-d4) δ=8.99 (d, J=1.8 Hz, 1H), 8.92 (d, J=1.7 Hz, 1H), 8.26-8.07 (m, 2H), 7.48 (s, 1H), 7.29 (d, J=8.4 Hz, 1H), 4.84 (q, J=7.0 Hz, 1H), 4.59-4.38 (m, 3H), 4.37-4.27 (m, 1H), 4.23-4.12 (m, 2H), 4.04-3.76 (m, 4H), 3.71-3.47 (m, 6H), 3.22-3.11 (m, 2H), 2.95-2.78 (m, 2H), 1.84 (d, J=7.0 Hz, 3H), 1.36 (d, J=6.2 Hz, 3H).

Example 89

(2R,6S)-4-(8-methoxyquinoxalin-5-yl)-2-methyl-6-[[4-(5,6,7,8-tetrahydro-2,6-naphthyridin-3-yl)piperazin-1-yl]methyl]morpholine

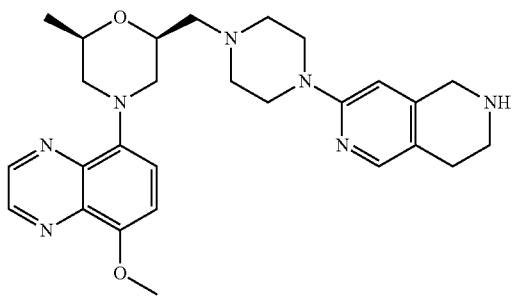 [SMILES: COc1ccc(N2C[C@H](CN3CCN(c4cc5c(cn4)CCNC5)CC3)O[C@H](C)C2)c2nccnc12]

The title compound was prepared in analogy to the preparation of Example 1 by using tert-butyl 7-chloro-3,4-dihydro-2,6-naphthyridine-2 (1H)-carboxylate (CAS: 1060816-50-3, Vendor: Shanghai Hong-chuang Pharma Tech Co., Ltd.) and Intermediate H instead of tert-butyl 2-bromo-6,7-dihydro-4H-pyrazolo[1,5-a]pyrazine-5-carboxylate and Intermediate A, replacing RuPhos Pd G2, Cs₂CO₃ with Pd₂(dba)₃, BINAP, t-BuONa in the Buchwald-Hartwig amination reaction. Example 89 (16 mg) was obtained as a yellow gum. MS: calc'd 490 (MH+), measured 490 (MH+). ¹H NMR (400 MHz, METHANOL-d₄) δ=8.94 (d, J=1.8 Hz, 1H), 8.86 (d, J=1.8 Hz, 1H), 8.14 (s, 1H), 7.36 (d, J=8.6 Hz, 1H), 7.26 (d, J=8.6 Hz, 1H), 6.95-6.85 (m, 1H), 4.57-4.47 (m, 1H), 4.38 (s, 2H), 4.24-4.14 (m, 1H), 4.07 (s, 3H), 3.96-3.46 (m, 10H), 3.45-3.34 (m, 3H), 3.32-3.17 (m, 1H), 3.06 (t, J=6.2 Hz, 2H), 2.66 (dt, J=4.0, 10.8 Hz, 2H), 1.33 (d, J=6.2 Hz, 3H).

Example 90

2-methyl-8-[(2R,6S)-2-methyl-6-[[4-(5,6,7,8-tetrahydro-2,6-naphthyridin-3-yl)piperazin-1-yl]methyl]morpholin-4-yl]quinoxaline-5-carbonitrile

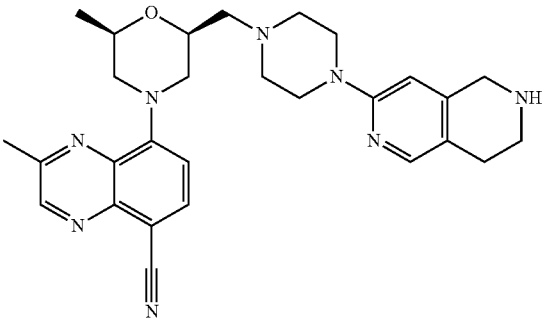 [SMILES: Cc1cnc2c(C#N)ccc(N3C[C@H](CN4CCN(c5cc6c(cn5)CCNC6)CC4)O[C@H](C)C3)c2n1]

The title compound was prepared in analogy to the preparation of Example 1 by using tert-butyl 7-chloro-3,4-dihydro-2,6-naphthyridine-2 (1H)-carboxylate (CAS: 1060816-50-3, Vendor: Shanghai Hong-chuang Pharma Tech Co., Ltd.) and Intermediate I instead of tert-butyl 2-bromo-6,7-dihydro-4H-pyrazolo[1,5-a]pyrazine-5-carboxylate and Intermediate A, replacing RuPhos Pd G2, Cs₂CO₃ with Pd₂(dba)₃, BINAP, t-BuONa in the Buchwald-Hartwig amination reaction. Example 90 (22 mg) was obtained as a yellow gum. MS: calc'd 499 (MH+), measured 499 (MH+). ¹H NMR (400 MHz, METHANOL-d₄) δ=8.81 (s, 1H), 8.11 (s, 1H), 8.01 (d, J=8.31 Hz, 1H), 7.17 (d, J=8.31 Hz, 1H), 6.87 (s, 1H), 4.48 (br t, J=9.90 Hz, 1H), 4.38 (s, 2H), 4.25 (br d, J=11.74 Hz, 1H), 4.15 (br dd, J=10.51, 1.71 Hz, 2H), 3.89 (br s, 3H), 3.68-3.35 (m, 9H), 3.04 (t, J=6.24 Hz, 2H), 2.89-2.78 (m, 2H), 2.76 (s, 3H), 1.33 (d, J=6.11 Hz, 3H).

Example 91

(2R,6S)-2-methyl-6-[[4-(5,6,7,8-tetrahydro-2,6-naphthyridin-3-yl)piperazin-1-yl]methyl]-4-[8-(trifluoromethyl)quinoxalin-5-yl]morpholine

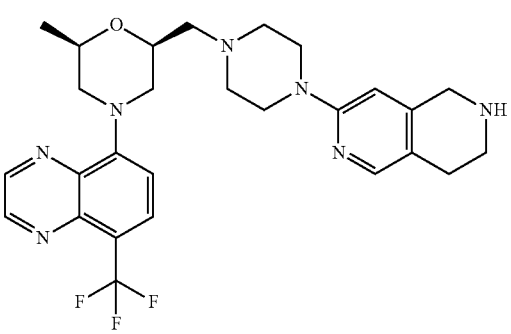 [SMILES: C[C@@H]1CN(c2ccc(C(F)(F)F)c3nccnc23)C[C@H](CN2CCN(c3cc4c(cn3)CCNC4)CC2)O1]

The title compound was prepared in analogy to the preparation of Example 1 by using tert-butyl 7-chloro-3,4-dihydro-2,6-naphthyridine-2 (1H)-carboxylate (CAS: 1060816-50-3, Vendor: Shanghai Hong-chuang Pharma Tech Co., Ltd.) and Intermediate J instead of tert-butyl 2-bromo-6,7-dihydro-4H-pyrazolo[1,5-a]pyrazine-5-carboxylate and Intermediate A, replacing RuPhos Pd G2, Cs₂CO₃ with Pd₂(dba)₃, BINAP, t-BuONa in the Buchwald-Hartwig amination reaction. Example 91 (17 mg) was obtained as a yellow gum. MS: calc'd 528 (MH⁺), measured 528 (MH⁺). ¹H NMR (400 MHz, METHANOL-d₄) δ=9.02-8.86 (m, 2H), 8.19-8.05 (m, 2H), 7.29 (d, J=8.3 Hz, 1H), 6.88 (s, 1H), 5.05 (s, 2H), 4.75 (br s, 2H), 4.57-4.44 (m, 1H), 4.39 (s, 2H), 4.22-3.97 (m, 4H), 3.64-3.50 (m, 5H), 3.47-3.40 (m, 2H), 3.06 (t, J=6.2 Hz, 2H), 2.78 (dt, J=6.7, 11.1 Hz, 2H), 1.35 (d, J=6.2 Hz, 3H).

Example 92 and Example 93

(2R,6S)-2-methyl-4-(8-methylquinoxalin-5-yl)-6-[[4-[(5R)-5-methyl-5,6,7,8-tetrahydro-2,6-naphthyridin-3-yl]piperazin-1-yl]methyl]morpholine and (2R,6S)-2-methyl-4-(8-methylquinoxalin-5-yl)-6-[[4-[(5S)-5-methyl-5,6,7,8-tetrahydro-2,6-naphthyridin-3-yl]piperazin-1-yl]methyl]morpholine

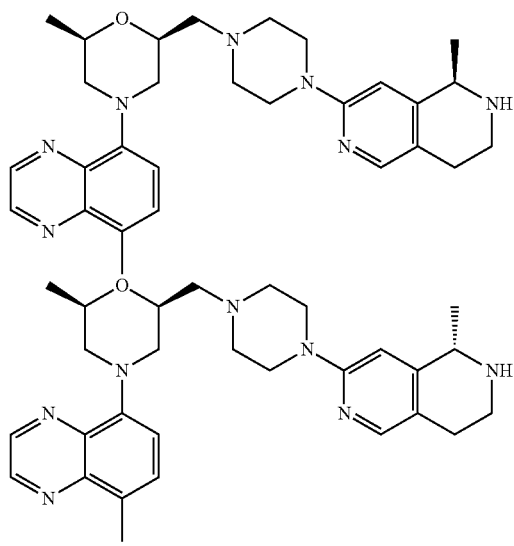

The title compounds were prepared in analogy to the preparation of Example 74 and 75 by using (2R,6S)-2-methyl-4-(8-methylquinoxalin-5-yl)-6-(piperazin-1-ylmethyl)morpholine (compound 92a) instead of 5-[(2R,6S)-2-methyl-6-(piperazin-1-ylmethyl)morpholin-4-yl]quinoline-8-carbonitrile (compound 31a). The Boc protected Example 92 (faster eluting) and 93 (slower eluting) were separated by chiral SFC (Gradient: 35% Ethanol (0.1% NH₃H₂O) in CO₂, Column: Daicel chiralcel OJ-H 250×30 mm, 5 µm).

Example 92 (9 mg) was obtained as a yellow gum. MS: calc'd 488 (MH⁺), measured 488 (MH⁺). ¹H NMR (400 MHz, METHANOL-d₄) δ=8.93-8.79 (m, 2H), 8.12 (s, 1H), 7.60 (d, J=7.8 Hz, 1H), 7.23 (d, J=7.8 Hz, 1H), 6.87 (s, 1H), 4.68-4.46 (m, 2H), 4.38-4.09 (m, 2H), 4.04-3.66 (m, 4H), 3.66-3.45 (m, 4H), 3.44-3.35 (m, 4H), 3.30-3.24 (m, 1H), 3.10-2.97 (m, 2H), 2.69 (s, 3H), 2.64 (t, J=10.8 Hz, 2H), 1.72 (d, J=7.0 Hz, 3H), 1.31 (d, J=6.2 Hz, 3H).

Example 93 (8 mg) was obtained as a yellow gum. MS: calc'd 488 (MH⁺), measured 488 (MH⁺). ¹H NMR (400 MHz, METHANOL-d₄) δ=8.89 (s, 1H), 8.83 (d, J=1.6 Hz, 1H), 8.12 (s, 1H), 7.60 (d, J=7.8 Hz, 1H), 7.23 (d, J=7.8 Hz, 1H), 6.87 (s, 1H), 4.74-4.48 (m, 2H), 4.40-4.13 (m, 2H), 4.02-3.66 (m, 4H), 3.66-3.46 (m, 4H), 3.45-3.34 (m, 4H), 3.30-3.15 (m, 1H), 3.08-3.00 (m, 2H), 2.69 (s, 3H), 2.64 (t, J=10.9 Hz, 2H), 1.72 (d, J=6.8 Hz, 3H), 1.31 (d, J=6.2 Hz, 3H).

The compound 92a was prepared according to the following scheme:

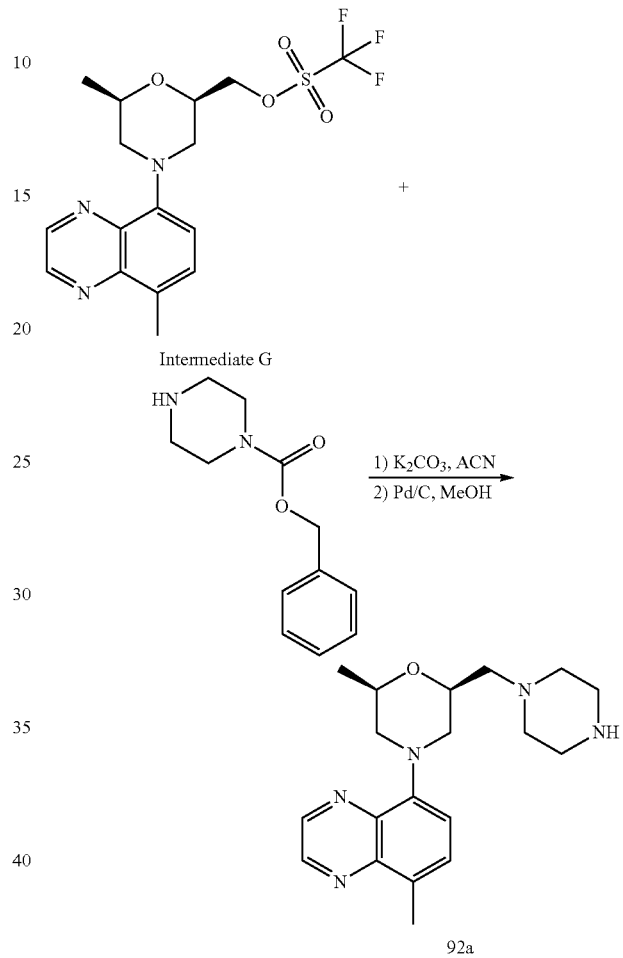

Step 1: Preparation of (2R,6S)-2-methyl-4-(8-methylquinoxalin-5-yl)-6-(piperazin-1-ylmethyl)morpholine (Compound 92a)

To the solution of benzyl piperazine-1-carboxylate (33 mg, 0.15 mmol) and potassium carbonate (35 mg, 0.25 mmol) in ACN (3 mL) was added [(2R,6R)-6-methyl-4-(8-methylquinoxalin-5-yl)morpholin-2-yl]methyl trifluoromethanesulfonate (Intermediate G, 50 mg, 0.12 mmol). After being stirred at 85° C. for 1 h, the reaction mixture was filtered and concentrated to give a crude product which was purified via flash column (EA/PE=0 to 75%) to give benzyl 4-[[(2S,6R)-6-methyl-4-(8-methylquinoxalin-5-yl)morpholin-2-yl]methyl]piperazine-1-carboxylate (50 mg) as a yellow solid which was re-dissolved in MeOH (3 mL) and Pd/C (10 wt. %, 20 mg) was added. After being stirred at rt under H₂ atmosphere for 2 hrs, the mixture was filtered and concentrated to give compound 92a (50 mg) as a gum which was used into next step without further purification. MS: calc'd 342 (MH⁺), measured 342 (MH⁺).

Example 94 and Example 95

2,3-dideuterio-8-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoxaline-5-carbonitrile and 2,3-dideuterio-8-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoxaline-5-carbonitrile

Example 96 and Example 97

2,3-dideuterio-8-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoxaline-5-carbonitrile and 2,3-dideuterio-8-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoxaline-5-carbonitrile

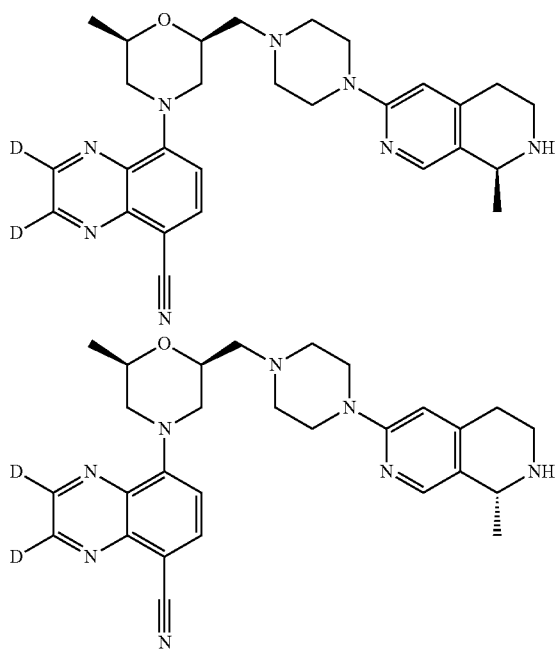

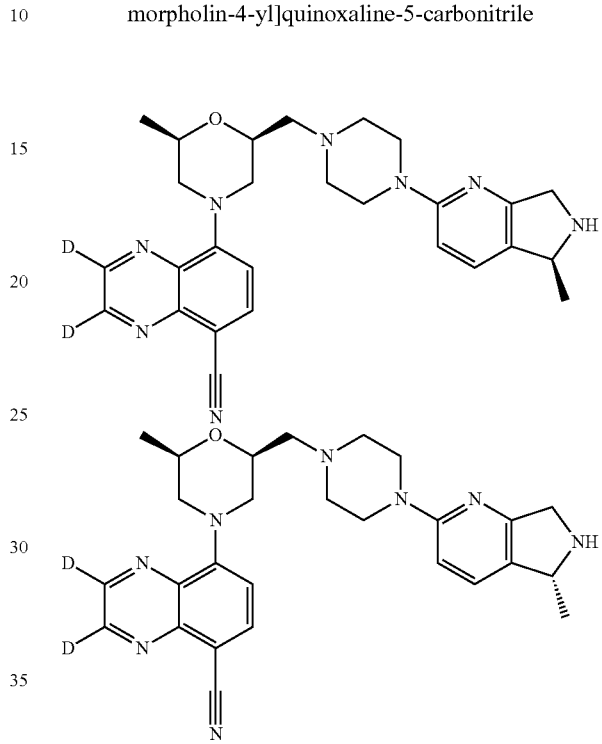

The title compounds were prepared in analogy to the preparation of Example 81 and 82 by using tert-butyl 1-methyl-6-(trifluoromethylsulfonyloxy)-3,4-dihydro-1H-2,7-naphthyridine-2-carboxylate (compound 85c) and Intermediate K instead of tert-butyl 3-methyl-7-(trifluoromethylsulfonyloxy)-3,4-dihydro-1H-2,6-naphthyridine-2-carboxylate (compound 81a) and Intermediate C. The Boc protected Example 94 (faster eluting) and 95 (slower eluting) were separated by chiral SFC (Gradient: 40% Isopropanol (0.1% NH$_3$H$_2$O) in CO$_2$, Column: «Column_3»).

Example 94 (25 mg) was obtained as a yellow gum. MS: calc'd 501 (MH$^+$), measured 501 (MH$^+$). $^1$H NMR (400 MHz, METHANOL-d$_4$) δ=8.22-8.14 (m, 2H), 7.30 (d, J=8.4 Hz, 1H), 7.24 (s, 1H), 4.68 (q, J=6.5 Hz, 1H), 4.58-4.36 (m, 3H), 4.35-4.27 (m, 1H), 4.23-4.13 (m, 2H), 4.05-3.73 (m, 3H), 3.72-3.62 (m, 3H), 3.56-3.42 (m, 5H), 3.30-3.24 (m, 1H), 2.88 (dt, J=10.7, 12.7 Hz, 2H), 1.75 (d, J=6.8 Hz, 3H), 1.36 (d, J=6.2 Hz, 3H).

Example 95 (26 mg) was obtained as a yellow gum. MS: calc'd 501 (MH$^+$), measured 501 (MH$^+$). $^1$H NMR (400 MHz, METHANOL-d$_4$) δ=8.22-8.14 (m, 2H), 7.35-7.27 (m, 2H), 4.69 (q, J=6.6 Hz, 1H), 4.60-4.36 (m, 3H), 4.35-4.28 (m, 1H), 4.23-4.13 (m, 2H), 4.03-3.75 (m, 3H), 3.72-3.62 (m, 3H), 3.57-3.42 (m, 5H), 3.30-3.25 (m, 1H), 2.94-2.82 (m, 2H), 1.76 (d, J=6.8 Hz, 3H), 1.37 (d, J=6.1 Hz, 3H).

The title compounds were prepared in analogy to the preparation of Example 1 by using tert-butyl 2-chloro-5-methyl-5,7-dihydropyrrolo[3,4-b]pyridine-6-carboxylate (compound 78a) and Intermediate K instead of tert-butyl 2-bromo-6,7-dihydro-4H-pyrazolo[1,5-a]pyrazine-5-carboxylate and Intermediate A. The Boc protected Example 96 (faster eluting) and 97 (slower eluting) were separated by chiral SFC (Gradient: 45% Ethanol in CO$_2$, Column: «Column_3»).

Example 96 (40 mg) was obtained as a brown solid. MS: calc'd 487 (MH$^+$), measured 487 (MH$^+$). $^1$H NMR (400 MHz, METHANOL-d$_4$) δ=8.16 (d, J=8.3 Hz, 1H), 7.73 (d, J=8.8 Hz, 1H), 7.29 (d, J=8.3 Hz, 1H), 7.06 (d, J=8.8 Hz, 1H), 5.04 (q, J=6.7 Hz, 1H), 4.61-4.46 (m, 5H), 4.34-4.28 (m, 1H), 4.23-4.12 (m, 2H), 3.93-3.84 (m, 1H), 3.84-3.74 (m, 1H), 3.59-3.42 (m, 4H), 3.42-3.35 (m, 2H), 2.95-2.88 (m, 1H), 2.88-2.81 (m, 1H), 1.70 (d, J=6.7 Hz, 3H), 1.36 (d, J=6.2 Hz, 3H).

Example 97 (41 mg) was obtained as a brown solid. MS: calc'd 487 (MH$^+$), measured 487 (MH$^+$). $^1$H NMR (400 MHz, METHANOL-d$_4$) δ=8.17 (d, J=8.3 Hz, 1H), 7.71 (d, J=8.8 Hz, 1H), 7.29 (d, J=8.3 Hz, 1H), 7.03 (d, J=8.8 Hz, 1H), 5.03 (q, J=6.8 Hz, 1H), 4.63-4.46 (m, 5H), 4.35-4.28 (m, 1H), 4.24-4.13 (m, 2H), 3.87 (br d, J=11.2 Hz, 1H), 3.80 (br d, J=12.0 Hz, 1H), 3.55-3.41 (m, 4H), 3.40-3.34 (m, 2H), 2.94-2.88 (m, 1H), 2.87-2.80 (m, 1H), 1.69 (d, J=6.7 Hz, 3H), 1.36 (d, J=6.1 Hz, 3H).

Example 98

2-deuterio-5-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoline-8-carbonitrile

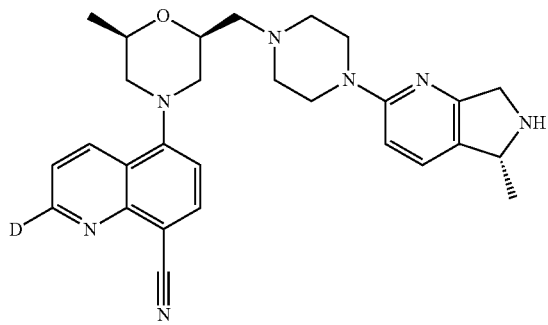 [SMILES: [2H]c1ccc2c(N3C[C@H](CN4CCN(c5ccc6c(n5)CN[C@@H]6C)CC4)O[C@H](C)C3)ccc(C#N)c2n1]

Example 99

2-deuterio-5-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoline-8-carbonitrile

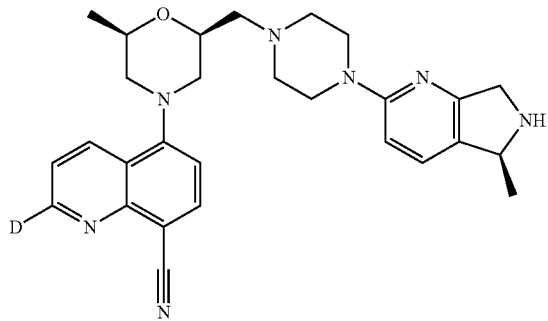 [SMILES: [2H]c1ccc2c(N3C[C@H](CN4CCN(c5ccc6c(n5)CN[C@H]6C)CC4)O[C@H](C)C3)ccc(C#N)c2n1]

The title compounds were prepared in analogy to the preparation of Example 1 by using tert-butyl 2-chloro-5-methyl-5,7-dihydropyrrolo[3,4-b]pyridine-6-carboxylate (compound 78a) and Intermediate L instead of tert-butyl 2-bromo-6,7-dihydro-4H-pyrazolo[1,5-a]pyrazine-5-carboxylate and Intermediate A. The Boc protected Example 98 (faster eluting) and 99 (slower eluting) were separated by chiral SFC (Gradient: 45% Ethanol in $CO_2$, Column: «Column_3»).

Example 98 (22 mg) was obtained as an orange solid. MS: calc'd 485 (MH$^+$), measured 485 (MH$^+$). $^1$H NMR (400 MHz, METHANOL-d$_4$) δ=8.96 (d, J=8.7 Hz, 1H), 8.30 (d, J=8.1 Hz, 1H), 7.85 (d, J=8.6 Hz, 1H), 7.69 (d, J=8.7 Hz, 1H), 7.40 (d, J=8.2 Hz, 1H), 7.01 (d, J=8.8 Hz, 1H), 5.02 (q, J=7.0 Hz, 1H), 4.65-4.60 (m, 1H), 4.60-4.49 (m, 2H), 4.47 (s, 2H), 4.29-4.19 (m, 1H), 3.90-3.77 (m, 2H), 3.56-3.40 (m, 6H), 3.39-3.34 (m, 2H), 2.91-2.85 (m, 1H), 2.84-2.78 (m, 1H), 1.69 (d, J=6.7 Hz, 3H), 1.35 (d, J=6.4 Hz, 3H).

Example 99 (27 mg) was obtained as an orange solid. MS: calc'd 485 (MH$^+$), measured 485 (MH$^+$). $^1$H NMR (400 MHz, METHANOL-d$_4$) δ=9.06 (d, J=8.7 Hz, 1H), 8.34 (d, J=8.1 Hz, 1H), 7.92 (d, J=8.7 Hz, 1H), 7.70 (d, J=8.8 Hz, 1H), 7.44 (d, J=8.2 Hz, 1H), 7.02 (d, J=8.8 Hz, 1H), 5.03 (q, J=6.4 Hz, 1H), 4.69-4.49 (m, 3H), 4.48 (s, 2H), 4.30-4.20 (m, 1H), 3.91-3.76 (m, 2H), 3.60-3.40 (m, 6H), 3.40-3.34 (m, 2H), 2.93-2.80 (m, 2H), 1.69 (d, J=6.7 Hz, 3H), 1.35 (d, J=6.2 Hz, 3H).

Example 100

1-methyl-4-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]-1,8-naphthyridin-2-one

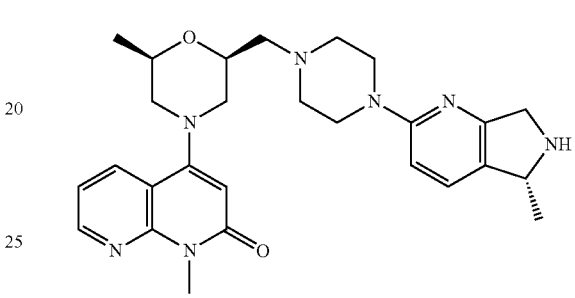

The title compound was prepared in analogy to the preparation of Example 1 by using tert-butyl (5R)-2-chloro-5-methyl-5,7-dihydropyrrolo[3,4-b]pyridine-6-carboxylate (compound 100a) and Intermediate M instead of tert-butyl 2-bromo-6,7-dihydro-4H-pyrazolo[1,5-a]pyrazine-5-carboxylate and Intermediate A. Example 100 (41 mg) was obtained as a light yellow solid. MS: calc'd 490 (MH$^+$), measured 490 (MH$^+$). $^1$H NMR (400 MHz, METHANOL-d$_4$) δ=8.59-8.52 (m, 1H), 8.16 (dd, J=1.7, 8.1 Hz, 1H), 7.54 (d, J=8.7 Hz, 1H), 7.22 (dd, J=4.6, 8.1 Hz, 1H), 6.86 (d, J=8.7 Hz, 1H), 6.08 (s, 1H), 4.92-4.83 (m, 1H), 4.47-4.27 (m, 4H), 4.03 (ddd, J=2.0, 6.3, 10.2 Hz, 1H), 3.66 (s, 3H), 3.59-3.18 (m, 11H), 2.62-2.47 (m, 2H), 1.56 (d, J=6.7 Hz, 3H), 1.20 (d, J=6.2 Hz, 3H).

The compound 100a (slower eluting) and 100b (faster eluting) were separated from compound 78a by chiral SFC (Gradient: 20% Methanol (0.1% NH$_3$H$_2$O) in $CO_2$, Column: Daicel «Column_3»). The structures of compound 100a and 100b were confirmed by their NMR of corresponding MTPA amide of the de-Boc amine similar to Example 63 and 64. (The Assignment of Absolute Configuration by NMR. José Manuel Seco, Emilio Quiiioi, and Ricardo Riguera, Chem. Rev. 2004, 104, 17-117.)

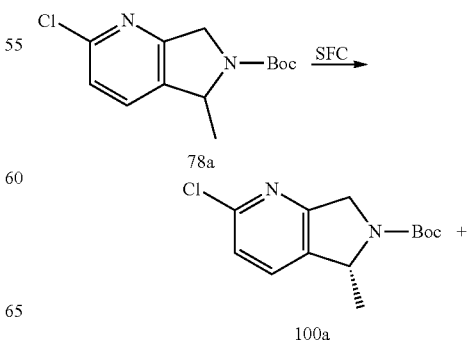

-continued

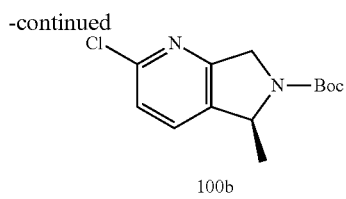

100b

Example 101

1-ethyl-4-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]-1,8-naphthyridin-2-one

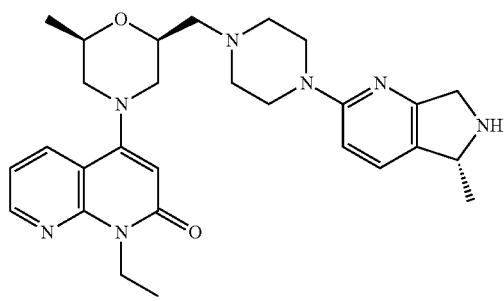 [SMILES: CCn1c(=O)cc(N2C[C@H](CN3CCN(c4ccc5c(n4)CN[C@@H]5C)CC3)O[C@H](C)C2)c2cccnc21]

The title compound was prepared in analogy to the preparation of Example 100 by using Intermediate N instead of Intermediate M. Example 101 (25 mg) was obtained as a light yellow solid. MS: calc'd 504 (MH$^+$), measured 504 (MH$^+$). $^1$H NMR (400 MHz, METHANOL-d$_4$) δ=8.68 (dd, J=1.7, 4.6 Hz, 1H), 8.29 (dd, J=1.7, 8.1 Hz, 1H), 7.67 (d, J=8.8 Hz, 1H), 7.34 (dd, J=4.6, 8.0 Hz, 1H), 6.98 (d, J=8.8 Hz, 1H), 6.20 (s, 1H), 5.01 (q, J=6.7 Hz, 1H), 4.57 (q, J=7.0 Hz, 2H), 4.51-4.41 (m, 3H), 4.15 (ddd, J=2.1, 6.3, 10.2 Hz, 1H), 3.91-3.34 (m, 12H), 2.76-2.58 (m, 2H), 1.68 (d, J=6.7 Hz, 3H), 1.36-1.26 (m, 6H).

Example 102

1-isopropyl-4-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]-1,8-naphthyridin-2-one

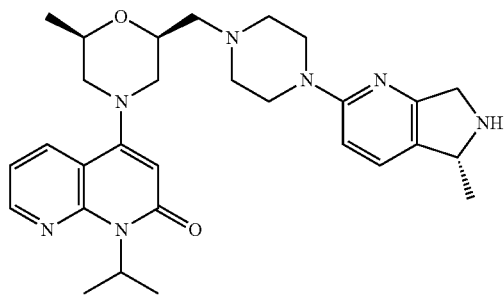 [SMILES: CC(C)n1c(=O)cc(N2C[C@H](CN3CCN(c4ccc5c(n4)CN[C@@H]5C)CC3)O[C@H](C)C2)c2cccnc21]

The title compound was prepared in analogy to the preparation of Example 100 by using Intermediate O instead of Intermediate M. Example 102 (36 mg) was obtained as a light yellow solid. MS: calc'd 518 (MH$^+$), measured 518 (MH$^+$). $^1$H NMR (400 MHz, METHANOL-d$_4$) δ=8.65 (dd, J=1.8, 4.6 Hz, 1H), 8.26 (dd, J=1.8, 8.0 Hz, 1H), 7.67 (d, J=8.8 Hz, 1H), 7.31 (dd, J=4.6, 8.0 Hz, 1H), 6.99 (d, J=8.7 Hz, 1H), 6.13 (s, 1H), 6.09-5.93 (m, 1H), 5.01 (q, J=6.6 Hz, 1H), 4.49-4.43 (m, 3H), 4.14 (ddd, J=2.3, 6.2, 10.2 Hz, 1H), 3.92-3.34 (m, 12H), 2.74-2.55 (m, 2H), 1.68 (d, J=6.8 Hz, 3H), 1.62 (d, J=7.0 Hz, 6H), 1.36-1.30 (m, 3H).

Example 103

1-methyl-4-[(2R,6S)-2-methyl-6-[[4-(5,6,7,8-tetrahydro-2,6-naphthyridin-3-yl)piperazin-1-yl]methyl]morpholin-4-yl]-1,8-naphthyridin-2-one

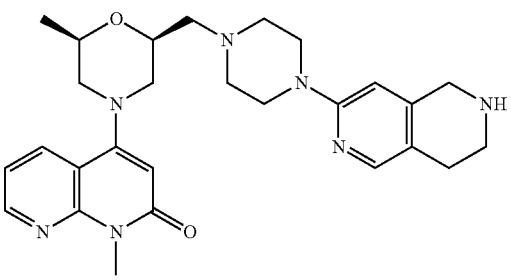 [SMILES: C[C@@H]1CN(c2cc(=O)n(C)c3ncccc23)C[C@H](CN2CCN(c3cc4c(cn3)CCNC4)CC2)O1]

The title compound was prepared in analogy to the preparation of Example 20 by using Intermediate M instead of Intermediate A. Example 103 (6.5 mg) was obtained as a light yellow solid. MS: calc'd 490 (MH$^+$), measured 490 (MH$^+$). $^1$H NMR (400 MHz, METHANOL-d$_4$) δ=8.54 (dd, J=1.7, 4.6 Hz, 1H), 8.17 (dd, J=1.8, 8.0 Hz, 1H), 7.78 (s, 1H), 7.21 (dd, J=4.6, 7.9 Hz, 1H), 6.44 (s, 1H), 6.05 (s, 1H), 4.09-4.00 (m, 1H), 3.97-3.87 (m, 1H), 3.81 (s, 2H), 3.66 (s, 3H), 3.40-3.27 (m, 6H), 2.97 (t, J=6.0 Hz, 2H), 2.69-2.59 (m, 4H), 2.57-2.38 (m, 6H), 1.14 (d, J=6.2 Hz, 3H).

Example 104

The following tests were carried out in order to determine the activity of the compounds of formula (I) and (Ia) in HEK293-Blue-hTLR-7/8/9 cells assay.

HEK293-Blue-hTLR-7 Cells Assay:

A stable HEK293-Blue-hTLR-7 cell line was purchased from InvivoGen (Cat. #: hkb-htlr7, San Diego, Calif., USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore, the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR7 cells were incubated at a density of 250,000-450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM R848 in above DMEM, perform incubation under 37° C. in a $CO_2$ incubator for 20 hrs. Then 20 μL of the supernatant from each well was incubated with 180 μL Quanti-blue substrate solution at 37° C. for 2 hrs and the absorbance was read at 620-655 nm using a spectrophotometer. The signaling pathway that TLR7 activation leads to downstream NF-κB activation has been widely accepted, and therefore similar reporter assay was modified for evaluating TLR7 antagonist.

HEK293-Blue-hTLR-8 Cells Assay:

A stable HEK293-Blue-hTLR-8 cell line was purchased from InvivoGen (Cat. #: hkb-htlr8, San Diego, Calif., USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore, the reporter expression was declined by TLR8 antagonist under the stimulation of a ligand, such as R848, for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR8 cells were incubated at a density of 250,000-450,000 cells/mL in a volume of 170 μL in a 96-well plate in Dulbecco's Modified Eagle's medium (DMEM) containing 4.5 g/L glucose, 50 U/nl penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 60 uM R848 in above DMEM, perform incubation under 37° C. in a $CO_2$ incubator for 20 hrs. Then 20 μL of the supernatant from each well was incubated with 180 μL Quanti-blue substrate solution at 37° C. for 2 hrs and the absorbance was read at 620-655 nm using a spectrophotometer. The signaling pathway that TLR8 activation leads to downstream NF-κB activation has been widely accepted, and therefore similar reporter assay was modified for evaluating TLR8 antagonist.

HEK293-Blue-hTLR-9 Cells Assay:

A stable HEK293-Blue-hTLR-9 cell line was purchased from InvivoGen (Cat. #: hkb-htlr9, San Diego, Calif., USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore, the reporter expression was declined by TLR9 antagonist under the stimulation of a ligand, such as ODN2006 (Cat. #: tlr1-2006-1, Invivogen, San Diego, Calif., USA), for incubation of 20 hrs. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR9 cells were incubated at a density of 250,000-450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM ODN2006 in above DMEM, perform incubation under 37° C. in a $CO_2$ incubator for 20 hrs. Then 20 μL of the supernatant from each well was incubated with 180 μL Quanti-blue substrate solution at 37° C. for 2 hrs and the absorbance was read at 620-655 nm using a spectrophotometer. The signaling pathway that TLR9 activation leads to downstream NF-κB activation has been widely accepted, and therefore similar reporter assay was modified for evaluating TLR9 antagonist.

The compounds of formula (I) or (Ia) have human TLR7 and/or TLR8 inhibitory activities ($IC_{50}$ value)<0.5 μM. Moreover, some compounds also have human TLR9 inhibitory activity <0.5 μM. Activity data of the compounds of the present invention were shown in Table 2.

TABLE 2

The activity of the compounds of present invention in HEK293-Blue-hTLR-7/8/9 cells assays

| Example No | HEK/hTLR7 $IC_{50}$ (μM) | HEK/hTLR8 $IC_{50}$ (μM) | HEK/hTLR9 $IC_{50}$ (μM) |
| --- | --- | --- | --- |
| R1 (reference compound) | 0.095 | 0.142 | 6.623 |
| R2 (reference compound) | 0.210 | 0.342 | 7.034 |
| 2 | 0.004 | 0.008 | 0.058 |
| 4 | 0.064 | 0.027 | 0.148 |
| 5 | 0.031 | 0.020 | 0.064 |
| 7 | 0.039 | 0.030 | 0.089 |
| 8 | 0.010 | <0.003 | 0.048 |
| 9 | 0.042 | 0.015 | 0.077 |
| 10 | 0.035 | 0.023 | 0.053 |
| 11 | 0.011 | 0.008 | 0.252 |
| 12 | 0.011 | 0.005 | 0.143 |
| 13 | 0.057 | 0.022 | 0.109 |
| 14 | 0.011 | 0.004 | 0.058 |
| 15 | 0.073 | 0.011 | 0.097 |
| 16 | 0.020 | 0.010 | 0.091 |
| 17 | 0.011 | 0.004 | 0.098 |
| 18 | 0.009 | 0.009 | 0.098 |
| 19 | 0.009 | 0.004 | 0.063 |
| 20 | 0.008 | 0.006 | 0.072 |
| 21 | 0.011 | 0.009 | 0.052 |
| 22 | 0.039 | 0.019 | 0.045 |
| 23 | 0.059 | 0.011 | 0.059 |
| 24 | 0.032 | 0.022 | 0.046 |
| 25 | 0.019 | 0.017 | 0.090 |
| 26 | 0.039 | 0.049 | 0.119 |
| 28 | 0.011 | 0.013 | 0.052 |
| 29 | 0.011 | <0.003 | 0.122 |
| 30 | 0.012 | 0.007 | 0.041 |
| 31 | 0.011 | <0.003 | 0.140 |
| 32 | 0.069 | 0.107 | 0.099 |
| 33 | 0.017 | 0.011 | 0.090 |
| 34 | 0.018 | 0.006 | 0.086 |
| 35A | 0.060 | 0.024 | 0.147 |
| 35B | 0.061 | 0.023 | 0.117 |
| 36 | 0.026 | 0.043 | 0.045 |
| 38 | 0.065 | 0.050 | 0.034 |
| 39 | 0.008 | 0.012 | 0.090 |
| 40 | 0.007 | 0.004 | 0.123 |
| 41 | 0.028 | 0.017 | 0.060 |
| 43 | 0.130 | 0.054 | 0.111 |
| 44 | 0.011 | 0.004 | 0.085 |
| 45 | 0.009 | 0.010 | 0.113 |
| 46 | 0.012 | 0.009 | 0.114 |
| 47 | 0.012 | 0.020 | 0.072 |
| 48 | 0.005 | 0.008 | 0.056 |

TABLE 2-continued

The activity of the compounds of present invention in HEK293-Blue-hTLR-7/8/9 cells assays

| Example No | HEK/hTLR7 $IC_{50}$ (μM) | HEK/hTLR8 $IC_{50}$ (μM) | HEK/hTLR9 $IC_{50}$ (μM) |
|---|---|---|---|
| 49 | 0.005 | <0.003 | 0.048 |
| 50 | 0.004 | <0.003 | 0.069 |
| 51 | 0.012 | 0.005 | 0.134 |
| 52 | <0.003 | 0.026 | 0.044 |
| 53 | 0.003 | 0.021 | 0.069 |
| 54 | 0.006 | 0.022 | <0.032 |
| 55 | 0.004 | 0.016 | <0.032 |
| 56 | 0.012 | 0.012 | 0.168 |
| 57 | 0.020 | 0.037 | 0.036 |
| 58 | 0.016 | 0.015 | 0.092 |
| 59 | 0.041 | 0.011 | 0.133 |
| 60 | 0.011 | 0.014 | 0.156 |
| 61 | 0.005 | 0.010 | 0.229 |
| 62 | <0.003 | 0.014 | 0.151 |
| 63 | 0.011 | 0.003 | 0.067 |
| 64 | 0.012 | 0.006 | 0.092 |
| 65 | 0.007 | 0.009 | 0.081 |
| 66 | 0.014 | 0.009 | 0.112 |
| 67 | 0.013 | 0.020 | 0.143 |
| 68 | 0.013 | 0.016 | 0.084 |
| 69 | 0.012 | 0.005 | 0.083 |
| 70 | 0.026 | 0.004 | 0.083 |
| 71 | 0.024 | 0.004 | 0.091 |
| 72 | 0.013 | 0.005 | 0.066 |
| 73 | 0.017 | 0.007 | 0.082 |
| 74 | 0.007 | 0.004 | 0.089 |
| 75 | 0.008 | 0.004 | 0.068 |
| 76 | 0.014 | 0.005 | 0.097 |
| 77 | 0.011 | 0.007 | 0.115 |
| 78 | 0.005 | 0.002 | 0.131 |
| 79 | 0.008 | 0.002 | 0.108 |
| 80 | 0.008 | 0.007 | 0.100 |
| 81 | 0.005 | 0.003 | 0.096 |
| 82 | 0.011 | 0.003 | 0.192 |
| 83 | 0.006 | 0.002 | 0.124 |
| 84 | 0.007 | 0.002 | 0.090 |
| 85 | 0.005 | 0.002 | 0.087 |
| 86 | 0.006 | 0.002 | 0.117 |
| 87 | 0.004 | 0.002 | 0.097 |
| 88 | 0.006 | 0.002 | 0.073 |
| 94 | 0.004 | 0.002 | 0.071 |
| 95 | 0.005 | 0.003 | 0.103 |
| 96 | 0.004 | 0.003 | 0.116 |
| 97 | 0.007 | 0.004 | 0.110 |
| 98 | 0.008 | 0.005 | 0.091 |
| 99 | 0.011 | 0.005 | 0.069 |

Example 105 hERG Channel Inhibition Assay:

The hERG channel inhibition assay is a highly sensitive measurement that identifies compounds exhibiting hERG inhibition related to cardiotoxicity in vivo. The hERG K$^+$ channels were cloned in humans and stably expressed in a CHO (Chinese hamster ovary) cell line. CHO$_{hERG}$ cells were used for patch-clamp (voltage-clamp, whole-cell) experiments. Cells were stimulated by a voltage pattern to activate hERG channels and conduct $I_{KhERG}$ currents (rapid delayed outward rectifier potassium current of the hERG channel). After the cells were stabilized for a few minutes, the amplitude and kinetics of $I_{KhERG}$ were recorded at a stimulation frequency of 0.1 Hz (6 bpm). Thereafter, the test compound was added to the preparation at increasing concentrations. For each concentration, an attempt was made to reach a steady-state effect, usually, this was achieved within 3-10 min at which time the next highest concentration was applied. The amplitude and kinetics of $I_{KhERG}$ are recorded in each concentration of the drug which were compared to the control values (taken as 100%). (references: Redfern W S, Carlsson L, Davis A S, Lynch W G, MacKenzie I, Palethorpe S, Siegl P K, Strang I, Sullivan A T, Wallis R, Camm A J, Hammond T G. 2003; Relationships between preclinical cardiac electrophysiology, clinical QT interval prolongation and torsade de pointes for a broad range of drugs: evidence for a provisional safety margin in drug development. Cardiovasc. Res. 58:32-45, Sanguinetti M C, Tristani-Firouzi M. 2006; hERG potassium channels and cardiac arrhythmia. Nature 440:463-469, Webster R, Leishman D, Walker D. 2002; Towards a drug concentration effect relationship for QT prolongation and torsades de pointes. Curr. Opin. Drug Discov. Devel. 5:116-26).

Results of hERG are given in Table 3. A safety ratio (hERG $IC_{20}/EC_{50}$)>30 suggests a sufficient window to differentiate the pharmacology by inhibiting TLR7/8/9 pathways from the potential hERG related cardiotoxicity. According to the calculation of hERG $IC_{20}$/TLR7/8/9 $IC_{50}$ below which serves as early selectivity index to assess hERG liability, obviously reference compounds ER-887258, ER-888285, ER-888286, R1 and R2 have much narrower safety window compared to the compounds of this invention.

TABLE 3 hERG and safety ratio results

| Example No | hERG $IC_{20}$ (μM) | hERG $IC_{50}$ (μM) | hERG $IC_{20}$/TLR7 $IC_{50}$ | hERG $IC_{20}$/TLR8 $IC_{50}$ | hERG $IC_{20}$/TLR9 $IC_{50}$ |
|---|---|---|---|---|---|
| ER-887258 | 0.687 | 2.784 | 8.1 | N.A. | 0.3 |
| ER-888285 | 1.006 | 3.105 | 8.4 | N.A. | 0.5 |
| ER-888286 | 0.348 | 1.297 | 0.3 | N.A. | 0.2 |
| R1 | 0.879 | 2.745 | 9.3 | 6.2 | 0.1 |
| R2 | 0.280 | 0.770 | 1.3 | 0.8 | 0.04 |
| 5 | >10 | >20 | >320.5 | >497.5 | >156.0 |
| 7 | 5.742 | >20 | 146.5 | 194.6 | 64.5 |
| 8 | >10 | >20 | >1020.4 | >3333.3 | >207.5 |
| 9 | 6.157 | >20 | 148.0 | 410.5 | 80.4 |
| 10 | >10 | >20 | >289.9 | >442.5 | >187.3 |
| 14 | 7.074 | >20 | 673.7 | 1725.4 | 122.8 |
| 16 | >10 | >20 | >490.2 | >1000.0 | >110.4 |
| 19 | >10 | >20 | >1118.6 | >2283.1 | >158.3 |
| 20 | >10 | >20 | >1298.7 | >1666.7 | >139.1 |
| 21 | >10 | >20 | >900.9 | >1098.9 | >193.8 |
| 22 | >10 | >20 | >259.7 | >520.8 | >222.7 |
| 23 | >10 | >20 | >170.6 | >934.6 | >170.1 |
| 25 | >10 | >20 | >520.8 | >584.8 | >111.7 |
| 30 | >10 | >20 | >840.3 | >1515.2 | >246.3 |
| 41 | >10 | >20 | >354.6 | >574.7 | >166.7 |
| 50 | >10 | >20 | >2702.7 | >3125.0 | >144.9 |
| 69 | 8.647 | >20 | 697.4 | 1879.8 | 104.3 |
| 70 | >10 | >20 | >390.6 | >2439.0 | >120.91 |
| 74 | >10 | >20 | >1470.6 | >2857.1 | >112.1 |
| 76 | >10 | >20 | >714.3 | >1960.8 | >102.7 |
| 77 | >10 | >20 | >885.0 | >1515.2 | >86.9 |

Example 106

The compounds would be desirable to have minimal DDI liabilities. Therefore, the effects of compounds of formula (I) or (Ia) on CYP2D6 are determined.

CYP Inhibition Assay

This is a high throughput screening assay used for assessment of reversible inhibition of CYP2D6 activity of test compounds in human liver microsome (HLM) in early discovery stage.

TABLE 4

Chemicals and materials used in the CYP inhibition assay

| Substances | Description | Source | Cat. No. | Final Concentration in incubation |
|---|---|---|---|---|
| Human Liver Microsomes | | BD-Gentest | 452117 | 0.2 mg/mL |
| Dextromethorphan | CYP2D6 substrate | Sigma | D-2531 | 5 µM |
| Dextrorphan | CYP2D6 product | | | |
| Dextrorphan-D3 | CYP2D6 internal standard | Promochem | CERD-041 | |
| Quinidine | CYP2D6 inhibitor | | | 0.5 µM |

Procedure 10 mM DMSO stock solutions of test compounds were diluted in DMSO to generate 2 mM intermediate stock solution. 250 nL of intermediate stock solution were transferred in duplicate into 3 separate 384 well microtitre plates (assay-ready plates). A mixture of HLM and each substrate was made up. 45 µL of HLM substrate mix was then transferred to each well of an assay ready plate and mixed. The negative (solvent) and positive control (standard inhibitor for CYP 2D6) were included in each assay ready plate. The assay ready plate was warmed to 37° C. in an incubator over 10 minutes. 5 µL pre-warmed NADPH regenerating system was added to each incubation well to start the reaction. Final incubation volume was 50 µL. The assay plate then was placed back in the 37° C. incubator. After 10-minute incubation, incubates were quenched by addition of 50 µL 100% acetonitrile containing internal standards (20 ng/mL D3-Dextrorphan). The supernatants were collected for RapidFire/MS/MS analysis.

RapidFire online solid phase extraction/sample injection system (Agilent) coupled with API4000 triple quadrupole mass spectrometer (AB Sciex) were used for sample analysis. The mobile phase composed of acetonitrile and water supplemented with 0.1% formic acid. A C4 solid phase extraction cartridge is used for sample separation. MS detection is achieved in positive ion MRM mode.

Data Analysis

Peak areas for substrate, metabolite and internal standard are determined using the RapidFire integrator software (version 3.6.12009.12296). Peak area ratios (PAR) of metabolite and internal standard (stable-labelled metabolite) are then calculated. The measurement window for each experiment is then defined:

PAR (0% activity)=average PAR for all incubations containing concentrated inhibitor;

Par (100% activity)=average PAR for all incubations containing no inhibitor (DMSO controls);

% Activity (test inhibitor)=[PAR (test inhibitor)−PAR (0% activity)]/[PAR (100% activity)−PAR (0% activity)];

% Inhibition (test inhibitor)=100−% Activity (test inhibitor).

The compounds of present invention were found to have low CYP inhibition for CYP2D6 determined in the assays described above.

TABLE 5

CYP inhibition of the compounds of this invention for CYP2D6

| Example No | CYP 2D6 inhibition % @ 10 µM |
|---|---|
| ER-888286 | 52.5 |
| 2 | −5 |
| 5 | 0.5 |
| 7 | 15 |
| 8 | 13 |
| 9 | −2.5 |
| 10 | 2.5 |
| 11 | 19 |
| 14 | −6 |
| 16 | 2.5 |
| 17 | 4.5 |
| 18 | 13 |
| 19 | 7.5 |
| 20 | −5.5 |
| 21 | −4.5 |
| 22 | 6 |
| 23 | 3.5 |
| 24 | −9.5 |
| 25 | −8 |
| 29 | 16.5 |
| 30 | 17.5 |
| 32 | 17.5 |
| 33 | −10.5 |
| 34 | 4 |
| 36 | 13.5 |
| 39 | 8.5 |
| 40 | 8 |
| 41 | −2 |
| 44 | 4 |
| 45 | 9 |
| 46 | 12 |
| 47 | −21.5 |
| 48 | −12 |
| 49 | 22 |
| 50 | 10.5 |
| 52 | 5 |
| 53 | 24 |
| 55 | 10.5 |
| 56 | −2.5 |
| 57 | −8 |
| 58 | 13 |
| 68 | 6 |
| 69 | 8.5 |
| 73 | 6 |
| 74 | 6 |
| 76 | 6 |
| 78 | 0.5 |
| 79 | 5.5 |
| 80 | 7 |
| 81 | 3.5 |
| 83 | −8 |
| 84 | −1.5 |
| 87 | −2.5 |
| 88 | 9.5 |
| 90 | 5 |
| 91 | 14 |

ND: not detected; percentage inhibition <0: not or weak inhibitor

Example 107

Human Microsome Stability Assay

The human microsomal stability assay is used for early assessment of metabolic stability of a test compound in human liver microsomes.

Human liver microsomes (Cat. NO.: 452117, Corning, USA; Cat. NO.: H2610, Xenotech, USA) were preincubated with test compound for 10 minutes at 37° C. in 100 mM potassium phosphate buffer, pH 7.4. The reactions were initiated by adding NADPH regenerating system. The final incubation mixtures contained 1 µM test compound, 0.5 mg/mL liver microsomal protein, 1 mM $MgCl_2$, 1 mM NADP, 1 unit/mL isocitric dehydrogenase and 6 mM isocitric acid in 100 mM potassium phosphate buffer, pH 7.4. After incubation times of 0, 3, 6, 9, 15 and 30 minutes at 37° C., 300 μL of cold acetonitrile (including internal standard) was added to 100 μL incubation mixture to terminate the reaction. Following precipitation and centrifugation, the amount of compound remaining in the samples were determined by LC-MS/MS. Controls of no NADPH regenerating system at zero and 30 minutes were also prepared and analyzed. The compounds of present invention showed good human liver microsome stability determined in the above assay, results are shown in Table 6 below.

TABLE 6

Human liver microsome stability of the compounds of present invention

| Example No | Clearance of Human microsome (mL/min/kg) |
| --- | --- |
| ER-887258 | 17.86 |
| ER-888285 | 17.15 |
| R2 | 15.43 |
| 7 | 8.75 |
| 9 | 6.74 |
| 10 | 8.61 |
| 13 | 8.00 |
| 20 | 6.43 |
| 22 | 6.82 |
| 23 | 6.15 |
| 24 | 6.15 |
| 27 | 7.28 |
| 28 | 6.15 |
| 37 | 6.72 |
| 63 | 6.15 |
| 67 | 6.15 |
| 69 | 6.23 |
| 70 | 7.55 |
| 74 | 7.39 |
| 76 | 6.15 |
| 77 | 6.34 |
| 78 | 7.50 |
| 80 | 6.15 |
| 81 | 6.15 |
| 82 | 8.84 |
| 83 | 8.31 |
| 85 | 7.83 |
| 86 | 7.69 |
| 87 | 8.91 |
| 89 | 6.54 |
| 95 | 7.13 |
| 96 | 6.23 |
| 97 | 6.15 |
| 98 | 8.02 |
| 99 | 6.32 |
| 100 | 8.54 |
| 101 | 6.67 |
| 103 | 6.15 |

The invention claimed is:

1. A compound of formula (I),

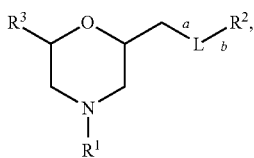

(I)

wherein:

$R^1$ is

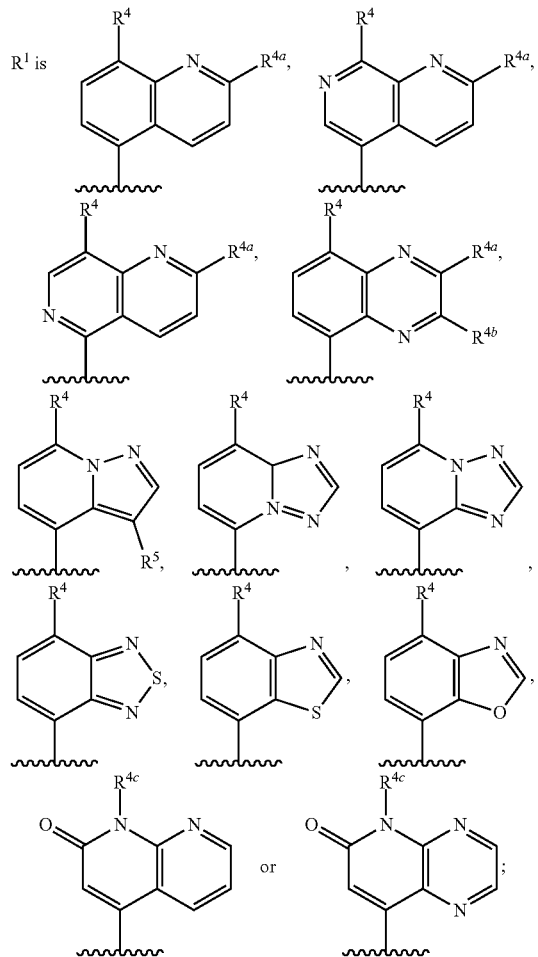

wherein $R^4$ is $C_{1-6}$alkyl, $C_{1-6}$alkoxy, halo$C_{1-6}$alkyl, halogen, nitro or cyano; $R^{4a}$ is H or deuterium; $R^{4b}$ is H, deuterium or $C_{1-6}$alkyl; $R^{4c}$ is $C_{1-6}$alkyl or $C_{3-7}$cycloalkyl; and $R^5$ is H or halogen;

$R^2$ is:
1,2,3,4-tetrahydroisoquinolinyl which is unsubstituted or substituted by $C_{1-6}$alkoxy, hydroxy or hydroxy$C_{1-6}$alkyl;
2,3-dihydro-1H-pyrrolo[3,4-c]pyridinyl;
3,4-dihydro-1H-isoquinolinyl di-substituted by hydroxy and $C_{1-6}$alkyl;
4,5,6,7-tetrahydropyrazolo[1,5-a]pyrazinyl;
4,5,6,7-tetrahydrothiazolo[5,4-c]pyridinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl which is unsubstituted or substituted by $C_{1-6}$alkyl;
5,6,7,8-tetrahydro-2,7-naphthyridinyl which is unsubstituted or substituted by $C_{1-6}$alkyl;
5,6,7,8-tetrahydropyrido[3,4-b]pyrazinyl which is unsubstituted or substituted by $C_{1-6}$alkyl;
5,6,7,8-tetrahydropyrido[3,4-d]pyrimidinyl;
5,6,7,8-tetrahydropyrido[4,3-d]pyrimidinyl;
6,7-dihydro-5H-pyrrolo[3,4-b]pyridinyl which is unsubstituted or substituted by $C_{1-6}$alkyl;
6,7-dihydro-5H-pyrrolo[3,4-d]pyrimidinyl;

7,8-dihydro-5H-1,6-naphthyridinyl substituted by $C_{1-6}$alkyl; or isoindolinyl which is unsubstituted or substituted by hydroxy$C_{1-6}$alkyl or $C_{1-6}$alkyl;

$R^3$ is $C_{1-6}$alkyl;

L is 1,4-diazepanyl; hydroxy-1,4-diazepanyl; piperazinyl; (hydroxy$C_{1-6}$alkyl)piperazinyl; 1,6-diazaspiro[3.3]heptanyl; aminoazetidinyl; pyrrolidinylamino; 3-oxa-7,9-diazabicyclo[3.3.1]nonanyl; 2,3,4a,5,7,7a-hexahydropyrrolo[3,4-b][1,4]oxazinyl; 3,3-dimethylpiperazinyl; 3,7-diazabicyclo[4.2.0]octanyl; or 5-oxa-2,8-diazaspiro[3.5]nonanyl; and a and b are reference labels to which instances of L are aligned;

or a pharmaceutically acceptable salt thereof.

2. A compound of claim 1, wherein:

$R^1$ is

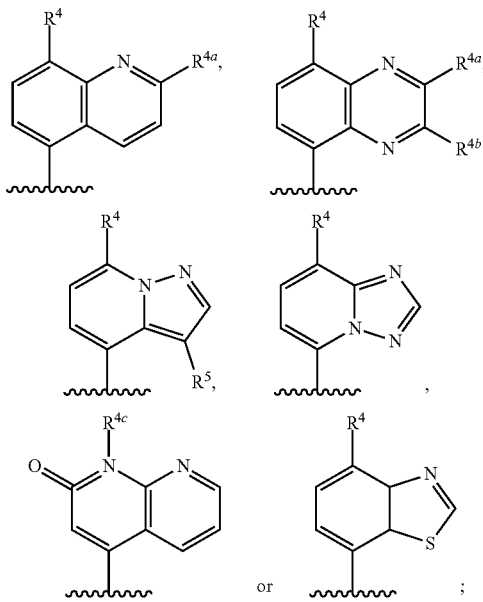

wherein:

$R^4$ is $C_{1-6}$alkyl, $C_{1-6}$alkoxy, halo$C_{1-6}$alkyl or cyano; $R^{4a}$ is H or deuterium; $R^{4b}$ is H, deuterium or $C_{1-6}$alkyl; $R^{4c}$ is $C_{1-6}$alkyl or $C_{3-7}$cycloalkyl; and $R^5$ is halogen;

or a pharmaceutically acceptable salt thereof.

3. A compound of claim 1, wherein the compound of formula (I) is a compound of formula (Ia),

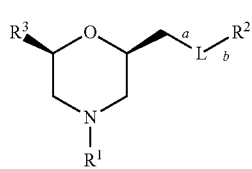

(Ia)

wherein:

$R^1$ is

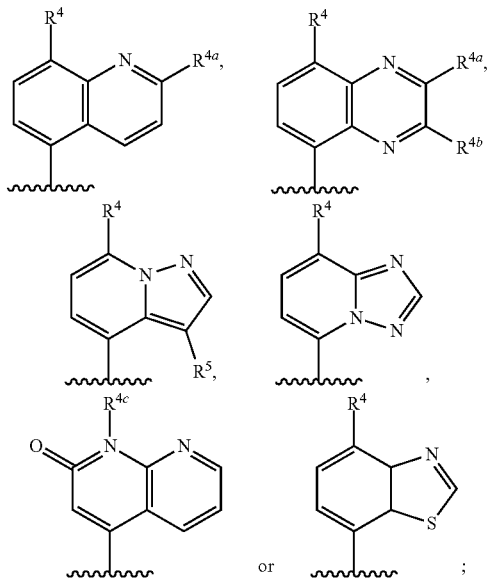

wherein:

$R^4$ is $C_{1-6}$alkyl, $C_{1-6}$alkoxy, halo$C_{1-6}$alkyl or cyano; $R^{4a}$ is H or deuterium; $R^{4b}$ is H, deuterium or $C_{1-6}$alkyl; $R^{4c}$ is $C_{1-6}$alkyl or $C_{3-7}$cycloalkyl;

$R^5$ is halogen; and a and b are reference labels to which instances of L are aligned;

or a pharmaceutically acceptable salt thereof.

4. A compound according to claim 2, wherein:

$R^4$ is methyl, trifluoromethyl, methoxy or cyano; $R^{4b}$ is H, deuterium or methyl; $R^{4c}$ is methyl, ethyl or isopropyl; $R^5$ is fluoro; and $R^2$ is 1-(hydroxymethyl)-1,2,3,4-tetrahydroisoquinolin-6-yl;
1,2,3,4-tetrahydroisoquinolin-7-yl;
1-methylisoindolin-5-yl;
2-(2-hydroxyethyl)isoindolin-5-yl;
2,3-dihydro-1H-pyrrolo[3,4-c]pyridin-6-yl;
2-methyl-6,7-dihydro-5H-pyrrolo[3,4-b]pyridin-3-yl;
3-methyl-5,6,7,8-tetrahydropyrido[3,4-b]pyrazin-2-yl;
4,5,6,7-tetrahydropyrazolo[1,5-a]pyrazin-1-yl;
4,5,6,7-tetrahydrothiazolo[5,4-c]pyridin-2-yl;
4-hydroxy-1,2,3,4-tetrahydroisoquinolin-6-yl;
4-hydroxy-2-methyl-3,4-dihydro-1H-isoquinolin-6-yl;
4-methoxy-1,2,3,4-tetrahydroisoquinolin-6-yl;
5,6,7,8-tetrahydro-1,6-naphthyridin-2-yl;
5,6,7,8-tetrahydro-1,6-naphthyridin-3-yl;
5,6,7,8-tetrahydro-1,7-naphthyridin-2-yl;
5,6,7,8-tetrahydro-1,7-naphthyridin-3-yl;
5,6,7,8-tetrahydro-2,6-naphthyridin-1-yl;
5,6,7,8-tetrahydro-2,6-naphthyridin-3-yl;
5,6,7,8-tetrahydro-2,7-naphthyridin-3-yl;
5,6,7,8-tetrahydropyrido[3,4-b]pyrazin-2-yl;
5,6,7,8-tetrahydropyrido[3,4-b]pyrazin-3-yl;
5,6,7,8-tetrahydropyrido[3,4-d]pyrimidin-2-yl;
5,6,7,8-tetrahydropyrido[4,3-d]pyrimidin-2-yl;
5,6,7,8-tetrahydropyrido[4,3-d]pyrimidin-4-yl;
5-methyl-5,6,7,8-tetrahydro-2,6-naphthyridin-3-yl;
5-methyl-6,7-dihydro-5H-pyrrolo[3,4-b]pyridin-2-yl;

6,7-dihydro-5H-pyrrolo[3,4-b]pyridin-2-yl;
6,7-dihydro-5H-pyrrolo[3,4-b]pyridin-3-yl;
6,7-dihydro-5H-pyrrolo[3,4-d]pyrimidin-2-yl;
6,7-dihydro-5H-pyrrolo[3,4-d]pyrimidin-4-yl;
6-methyl-5,6,7,8-tetrahydro-2,7-naphthyridin-3-yl;
6-methyl-7,8-dihydro-5H-1,6-naphthyridin-2-yl;
7-methyl-5,6,7,8-tetrahydro-2,6-naphthyridin-3-yl;
7-methyl-6,7-dihydro-5H-pyrrolo[3,4-b]pyridin-2-yl;
7-methyl-6,7-dihydro-5H-pyrrolo[3,4-b]pyridin-3-yl;
8-methyl-5,6,7,8-tetrahydro-2,7-naphthyridin-3-yl;
isoindolin-4-yl; or
isoindolin-5-yl;

R³ is methyl; and

L is 1,4-diazepanyl, hydroxy-1,4-diazepanyl, piperazinyl, (hydroxymethyl)piperazinyl, 1,6-diazaspiro[3.3]heptanyl, aminoazetidinyl, pyrrolidinylamino, 3-oxa-7,9-diazabicyclo[3.3.1]nonanyl, 2,3,4a,5,7,7a-hexahydropyrrolo[3,4-b][1,4]oxazinyl, 3,3-dimethyl-piperazinyl, 3,7-diazabicyclo[4.2.0]octanyl, or 5-oxa-2,8-diazaspiro[3.5]nonanyl, or a pharmaceutically acceptable salt thereof.

5. A compound according to claim 2, wherein:
R¹ is

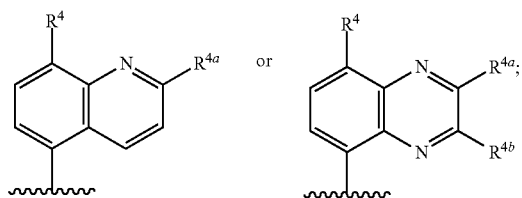

wherein R⁴ is cyano; and R⁴ᵇ is H or deuterium;
or a pharmaceutically acceptable salt thereof.

6. A compound according to claim 2, or a pharmaceutically acceptable salt thereof, wherein L is

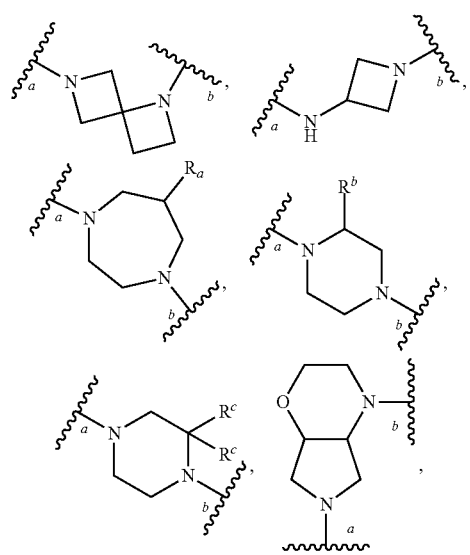

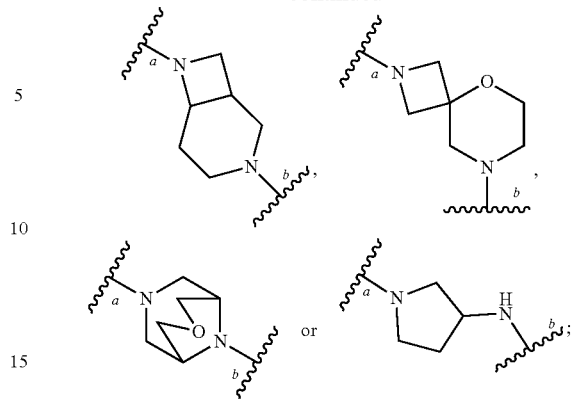

wherein Rᵃ is H or hydroxy; Rᵇ is H or hydroxyC₁₋₆alkyl; and Rᶜ is C₁₋₆alkyl, and a and b align with the reference labels in (I).

7. A compound according to claim 6, or a pharmaceutically acceptable salt thereof, wherein L is

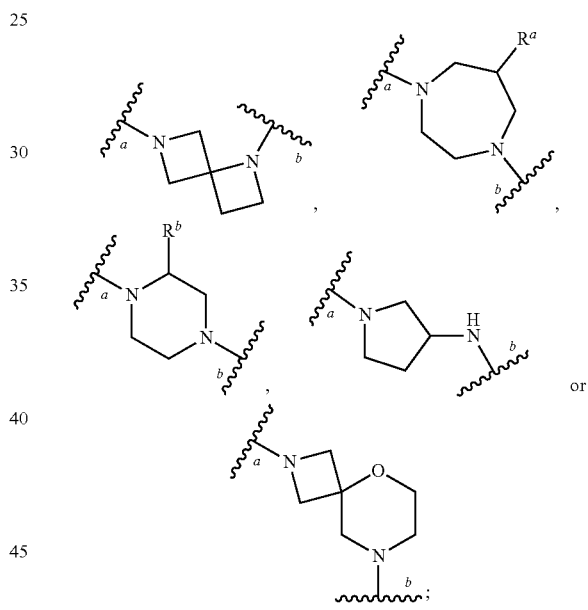

wherein Rᵃ is H; and a and b align with the reference labels in (I).

8. A compound according to claim 7, or a pharmaceutically acceptable salt thereof, wherein L is

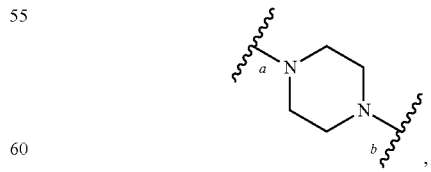

and a and b align with the reference labels in (I).

9. A compound according to claim 8, or a pharmaceutically acceptable salt thereof, wherein R² is 1,2,3,4-tetrahydroisoquinolinyl which is unsubstituted or substituted by hydroxy; 5,6,7,8-tetrahydro-1,6-naphthyridinyl; 5,6,7,8-tetrahydro-2,6-naphthyridinyl which is unsubstituted or substituted by $C_{1-6}$alkyl; 5,6,7,8-tetrahydro-2,7-naphthyridinyl; or 6,7-dihydro-5H-pyrrolo[3,4-b]pyridinyl which is unsubstituted or substituted by $C_{1-6}$alkyl.

10. A compound according to claim 9, or a pharmaceutically acceptable salt thereof, wherein $R^2$ is 1,2,3,4-tetrahydroisoquinolin-6-yl; 4-hydroxy-1,2,3,4-tetrahydroisoquinolin-6-yl; 5,6,7,8-tetrahydro-1,6-naphthyridin-2-yl; 5,6,7,8-tetrahydro-1,6-naphthyridin-3-yl; 5,6,7,8-tetrahydro-2,6-naphthyridin-3-yl; 5,6,7,8-tetrahydro-2,7-naphthyridin-3-yl; 5-methyl-5,6,7,8-tetrahydro-2,6-naphthyridin-3-yl; 5-methyl-6,7-dihydro-5H-pyrrolo[3,4-b]pyridin-2-yl; 6,7-dihydro-5H-pyrrolo[3,4-b]pyridin-2-yl; 6,7-dihydro-5H-pyrrolo[3,4-b]pyridin-3-yl; or 7-methyl-5,6,7,8-tetrahydro-2,6-naphthyridin-3-yl.

11. A compound according to claim 1, wherein:
R$^1$ is

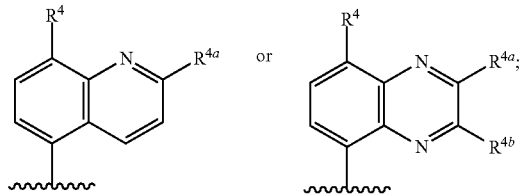

wherein $R^4$ is cyano; $R^{4a}$ is H or deuterium; $R^{4b}$ is H or deuterium;
$R^2$ is 1,2,3,4-tetrahydroisoquinolinyl which is unsubstituted or substituted by hydroxy; 5,6,7,8-tetrahydro-1,6-naphthyridinyl; 5,6,7,8-tetrahydro-2,6-naphthyridinyl which is unsubstituted or substituted by $C_{1-6}$alkyl; 5,6,7,8-tetrahydro-2,7-naphthyridinyl; or 6,7-dihydro-5H-pyrrolo[3,4-b]pyridinyl which is unsubstituted or substituted by $C_{1-6}$alkyl; and
L is

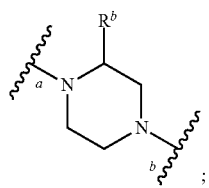

or a pharmaceutically acceptable salt thereof.

12. A compound according to claim 11, wherein:
$R^2$ is 1,2,3,4-tetrahydroisoquinolin-6-yl; 4-hydroxy-1,2,3,4-tetrahydroisoquinolin-6-yl; 5,6,7,8-tetrahydro-1,6-naphthyridin-2-yl; 5,6,7,8-tetrahydro-1,6-naphthyridin-3-yl; 5,6,7,8-tetrahydro-2,6-naphthyridin-3-yl; 5,6,7,8-tetrahydro-2,7-naphthyridin-3-yl; 5-methyl-5,6,7,8-tetrahydro-2,6-naphthyridin-3-yl; 5-methyl-6,7-dihydro-5H-pyrrolo[3,4-b]pyridin-2-yl; 6,7-dihydro-5H-pyrrolo[3,4-b]pyridin-2-yl; 6,7-dihydro-5H-pyrrolo[3,4-b]pyridin-3-yl; or 7-methyl-5,6,7,8-tetrahydro-2,6-naphthyridin-3-yl; and
$R^3$ is methyl; or a pharmaceutically acceptable salt thereof.

13. A compound selected from:
5-[(2R,6S)-2-methyl-6-[[4-(4,5,6,7-tetrahydropyrazolo[1,5-a]pyrazin-2-yl)piperazin-1-yl]methyl]morpholin-4-yl]quinoline-8-carbonitrile;
5-[(2S,6R)-2-[(4-isoindolin-4-ylpiperazin-1-yl)methyl]-6-methyl-morpholin-4-yl]quinoline-8-carbonitrile;
5-[(2S,6R)-2-[[(3S)-3-(hydroxymethyl)-4-isoindolin-5-yl-piperazin-1-yl]methyl]-6-methyl-morpholin-4-yl]quinoline-8-carbonitrile;
5-[(2S,6R)-2-[[(3R)-3-(hydroxymethyl)-4-isoindolin-5-yl-piperazin-1-yl]methyl]-6-methyl-morpholin-4-yl]quinoline-8-carbonitrile;
5-[(2R,6S)-2-methyl-6-[[4-(1,2,3,4-tetrahydroisoquinolin-6-yl)piperazin-1-yl]methyl]morpholin-4-yl]quinoline-8-carbonitrile;
5-[(2S,6R)-2-[[4-(6,7-dihydro-5H-pyrrolo[3,4-d]pyrimidin-4-yl)piperazin-1-yl]methyl]-6-methyl-morpholin-4-yl]quinoline-8-carbonitrile;
5-[(2S,6R)-2-[(4-isoindolin-5-ylpiperazin-1-yl)methyl]-6-methyl-morpholin-4-yl]quinoline-8-carbonitrile;
7-[(2S,6R)-2-[[4-(6,7-dihydro-5H-pyrrolo[3,4-b]pyridin-3-yl)piperazin-1-yl]methyl]-6-methyl-morpholin-4-yl]-1,3-benzothiazole-4-carbonitrile;
5-[(2R,6S)-2-methyl-6-[[4-(1,2,3,4-tetrahydroisoquinolin-7-yl)piperazin-1-yl]methyl]morpholin-4-yl]quinoline-8-carbonitrile;
5-[(2S,6R)-2-[[4-(6,7-dihydro-5H-pyrrolo[3,4-b]pyridin-3-yl)piperazin-1-yl]methyl]-6-methyl-morpholin-4-yl]quinoline-8-carbonitrile;
5-[(2S,6R)-2-[[4-(6,7-dihydro-5H-pyrrolo[3,4-d]pyrimidin-2-yl)piperazin-1-yl]methyl]-6-methyl-morpholin-4-yl]quinoline-8-carbonitrile;
5-[(2R,6S)-2-methyl-6-[[4-(5,6,7,8-tetrahydropyrido[3,4-d]pyrimidin-2-yl)piperazin yl]methyl]morpholin-4-yl]quinoline-8-carbonitrile;
5-[(2S,6R)-2-[[3-(hydroxymethyl)-4-isoindolin-5-yl-piperazin-1-yl]methyl]-6-methyl-morpholin-4-yl]quinoline-8-carbonitrile;
5-[(2R,6S)-2-methyl-6-[[4-(5,6,7,8-tetrahydro-1,6-naphthyridin-2-yl)piperazin-1-yl]methyl]morpholin-4-yl]quinoline-8-carbonitrile;
5-[(2S,6R)-2-[[2-(hydroxymethyl)-4-isoindolin-5-yl-piperazin-1-yl]methyl]-6-methyl-morpholin-4-yl]quinoline-8-carbonitrile;
5-[(2S,6R)-2-[[4-[2-(2-hydroxyethyl)isoindolin-5-yl]piperazin-1-yl]methyl]-6-methyl-morpholin-4-yl]quinoline-8-carbonitrile;
5-[(2R,6S)-2-methyl-6-[[4-(5,6,7,8-tetrahydropyrido[3,4-b]pyrazin-2-yl)piperazin-1-yl]methyl]morpholin-4-yl]quinoline-8-carbonitrile;
5-[(2S,6R)-2-[[4-(2,3-dihydro-1H-pyrrolo[3,4-c]pyridin-6-yl)piperazin-1-yl]methyl]-6-methyl-morpholin-4-yl]quinoline-8-carbonitrile;
5-[(2R,6S)-2-methyl-6-[[4-(5,6,7,8-tetrahydro-2,7-naphthyridin-3-yl)piperazin-1-yl]methyl]morpholin-4-yl]quinoline-8-carbonitrile;
5-[(2R,6S)-2-methyl-6-[[4-(5,6,7,8-tetrahydro-2,6-naphthyridin-3-yl)piperazin-1-yl]methyl]morpholin-4-yl]quinoline-8-carbonitrile;
5-[(2R,6S)-2-methyl-6-[[4-(5,6,7,8-tetrahydro-1,6-naphthyridin-3-yl)piperazin-1-yl]methyl]morpholin-4-yl]quinoline-8-carbonitrile;
5-[(2S,6R)-2-[[4-(4-hydroxy-1,2,3,4-tetrahydroisoquinolin-6-yl)piperazin-1-yl]methyl]-6-methyl-morpholin-4-yl]quinoline-8-carbonitrile;
5-[(2R,6S)-2-methyl-6-[[4-(5,6,7,8-tetrahydro-1,7-naphthyridin-3-yl)piperazin-1-yl]methyl]morpholin-4-yl]quinoline-8-carbonitrile;
5-[(2S,6R)-2-[[4-[1-(hydroxymethyl)-1,2,3,4-tetrahydroisoquinolin-6-yl]piperazin-1-yl]methyl]-6-methyl-morpholin-4-yl]quinoline-8-carbonitrile;

8-[(2S,6R)-2-[[4-(6,7-dihydro-5H-pyrrolo[3,4-b]pyridin-3-yl)piperazin-1-yl]methyl]-6-methyl-morpholin-4-yl]quinoxaline-5-carbonitrile;

4-[(2S,6R)-2-[[4-(6,7-dihydro-5H-pyrrolo[3,4-b]pyridin-3-yl)piperazin-1-yl]methyl]-6-methyl-morpholin-4-yl]-3-fluoro-pyrazolo[1,5-a]pyridine-7-carbonitrile;

5-[(2R,6S)-2-methyl-6-[[4-(5,6,7,8-tetrahydro-1,6-naphthyridin-3-yl)piperazin yl]methyl]morpholin-4-yl]-[1,2,4]triazolo[1,5-a]pyridine-8-carbonitrile;

5-[(2R,6S)-2-methyl-6-[[4-(1-methylisoindolin-5-yl)piperazin-1-yl]methyl]morpholin-4-yl]quinoline-8-carbonitrile;

5-[(2R,6S)-2-methyl-6-[[4-(5,6,7,8-tetrahydropyrido[4,3-d]pyrimidin-2-yl)piperazin-1-yl]methyl]morpholin-4-yl]quinoline-8-carbonitrile;

5-[(2S,6R)-2-[[4-(6,7-dihydro-5H-pyrrolo[3,4-b]pyridin-2-yl)piperazin-1-yl]methyl]-6-methyl-morpholin-4-yl]quinoline-8-carbonitrile;

5-[(2R,6S)-2-methyl-6-[[4-(4,5,6,7-tetrahydrothiazolo[5,4-c]pyridin-2-yl)piperazin-1-yl]methyl]morpholin-4-yl]quinoline-8-carbonitrile;

5-[(2S,6R)-2-[[3-(6,7-dihydro-5H-pyrrolo[3,4-d]pyrimidin-2-ylamino)pyrrolidin-1-yl]methyl]-6-methyl-morpholin-4-yl]quinoline-8-carbonitrile;

5-[(2R,6S)-2-methyl-6-[[4-(4,5,6,7-tetrahydrothiazolo[5,4-c]pyridin-2-yl)-1,4-diazepan-1-yl]methyl]morpholin-4-yl]quinoline-8-carbonitrile;

5-[(2R,6S)-2-methyl-6-[[4-(6-methyl-7,8-dihydro-5H-1,6-naphthyridin-2-yl)piperazin-1-yl]methyl]morpholin-4-yl]quinoline-8-carbonitrile;

5-[(2S,6R)-2-[[(6R)-6-hydroxy-4-(5,6,7,8-tetrahydro-1,6-naphthyridin-2-yl)-1,4-diazepan-1-yl]methyl]-6-methyl-morpholin-4-yl]quinoline-8-carbonitrile;

5-[(2S,6R)-2-[[(6S)-6-hydroxy-4-(5,6,7,8-tetrahydro-1,6-naphthyridin-2-yl)-1,4-diazepan-1-yl]methyl]-6-methyl-morpholin-4-yl]quinoline-8-carbonitrile;

5-[(2R,6S)-2-methyl-6-[[1-(5,6,7,8-tetrahydro-1,6-naphthyridin-2-yl)-1,6-diazaspiro[3.3] heptan-6-yl]methyl]morpholin-4-yl]quinoline-8-carbonitrile;

5-[(2S,6R)-2-[[9-(6,7-dihydro-5H-pyrrolo[3,4-b]pyridin-3-yl)-3-oxa-7,9-diazabicyclo[3.3.1]nonan-7-yl]methyl]-6-methyl-morpholin-4-yl]quinoline-8-carbonitrile;

5-[(2S,6R)-2-[[3-(isoindolin-5-ylamino)pyrrolidin-1-yl]methyl]-6-methyl-morpholin-4-yl]quinoline-8-carbonitrile;

5-[(2R,6S)-2-methyl-6-[[4-(5,6,7,8-tetrahydropyrido[4,3-d]pyrimidin-2-yl)-1,4-diazepan-1-yl]methyl]morpholin-4-yl]quinoline-8-carbonitrile;

5-[(2R,6S)-2-methyl-6-[[4-(5,6,7,8-tetrahydropyrido[3,4-b]pyrazin-3-yl)piperazin-1-yl]methyl]morpholin-4-yl]quinoline-8-carbonitrile;

5-[(2R,6S)-2-methyl-6-[[4-(5-methyl-6,7-dihydro-5H-pyrrolo[3,4-b]pyridin-3-yl)piperazin-1-yl]methyl]morpholin-4-yl]quinoline-8-carbonitrile;

5-[(2S,6R)-2-[[[1-(6,7-dihydro-5H-pyrrolo[3,4-d]pyrimidin-2-yl)azetidin-3-yl]amino]methyl]-6-methyl-morpholin-4-yl]quinoline-8-carbonitrile;

5-[(2S,6R)-2-[[[1-(6,7-dihydro-5H-pyrrolo[3,4-b]pyridin-3-yl)azetidin-3-yl]amino]methyl]-6-methyl-morpholin-4-yl]quinoline-8-carbonitrile;

5-[(2R,6S)-2-methyl-6-[[8-(1,2,3,4-tetrahydroisoquinolin-6-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,7-naphthyridin-2-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,7-naphthyridin-3-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,6-naphthyridin-3-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-2,6-naphthyridin-3-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydro-1,6-naphthyridin-2-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydropyrido[3,4-b]pyrazin-2-yl)-5-oxa-2,8-diazaspiro[3.5]nonan-2-yl]methyl]morpholin-4-yl]quinoline-8-carbonitrile;

5-[(2R,6S)-2-methyl-6-[[8-(5,6,7,8-tetrahydropyrido[4,3-d]pyrimidin-2-yl)-5-oxa-2,8-diazaspiro[3.5]nonan-2-yl]methyl]morpholin-4-yl]quinoline-8-carbonitrile;

5-[(2S,6R)-2-[[(4aR,7aR)-4-(5,6,7,8-tetrahydro-1,7-naphthyridin-3-yl)-2,3,4a,5,7,7a-hexahydropyrrolo[3,4-b][1,4]oxazin-6-yl]methyl]-6-methylmorpholin-4-yl]quinoline-8-carbonitrile;

cis-5-[(2R,6S)-2-methyl-6-[[4-(5,6,7,8-tetrahydro-1,6-naphthyridin-2-yl)-2,3,4a,5,7,7a-hexahydropyrrolo[3,4-b][1,4]oxazin-6-yl]methyl]morpholin-4-yl]quinoline-8-carbonitrile;

trans-5-[(2R,6S)-2-methyl-6-[[3-(5,6,7,8-tetrahydro-1,6-naphthyridin-2-yl)-3,7-diazabicyclo[4.2.0]octan-7-yl]methyl]morpholin-4-yl]quinoline-8-carbonitrile;

5-[(2S,6R)-2-[[3,3-dimethyl-4-(5,6,7,8-tetrahydro-1,6-naphthyridin-3-yl)piperazin-1-yl]methyl]-6-methyl-morpholin-4-yl]quinoline-8-carbonitrile;

5-[(2R,6S)-2-methyl-6-[[3-(5,6,7,8-tetrahydropyrido[4,3-d]pyrimidin-2-ylamino)pyrrolidin-1-yl]methyl]morpholin-4-yl]quinoline-8-carbonitrile;

5-[(2S,6R)-2-[[4-(4-methoxy-1,2,3,4-tetrahydroisoquinolin-6-yl)piperazin-1-yl]methyl]-6-methyl-morpholin-4-yl]quinoline-8-carbonitrile;

5-[(2S,6R)-2-[[4-(4-hydroxy-2-methyl-3,4-dihydro-1H-isoquinolin-6-yl)piperazin-1-yl]methyl]-6-methyl-morpholin-4-yl]quinoline-8-carbonitrile;

5-[(2R,6S)-2-methyl-6-[[4-(3-methyl-5,6,7,8-tetrahydropyrido[3,4-b]pyrazin-2-yl)piperazin yl]methyl]morpholin-4-yl]quinoline-8-carbonitrile;

5-[(2R,6S)-2-methyl-6-[[4-(5,6,7,8-tetrahydropyrido[4,3-d]pyrimidin-4-yl)piperazin yl]methyl]morpholin-4-yl]quinoline-8-carbonitrile;

5-[(2R,6S)-2-methyl-6-[[4-(5,6,7,8-tetrahydro-2,6-naphthyridin-1-yl)piperazin-1-yl]methyl]morpholin-4-yl]quinoline-8-carbonitrile;

5-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-[(7R)-7-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-[(7S)-7-methyl-6,7-dihydro-5H-pyrrolo[3,4-b]pyridin-2-yl]piperazin-1-yl]methyl]morpholin-4-yl]quinoline-8-carbonitrile;

5-[(2R,6S)-2-methyl-6-[[4-[(7S)-7-methyl-6,7-dihydro-5H-pyrrolo[3,4-b]pyridin-3-yl]piperazin-1-yl]methyl]morpholin-4-yl]quinoline-8-carbonitrile;

5-[(2R,6S)-2-methyl-6-[[4-[(7R)-7-methyl-6,7-dihydro-5H-pyrrolo[3,4-b]pyridin-3-yl]piperazin-1-yl]methyl]morpholin-4-yl]quinoline-8-carbonitrile;

5-[(2R,6S)-2-methyl-6-[[4-(5,6,7,8-tetrahydro-1,7-naphthyridin-2-yl)piperazin-1-yl]methyl]morpholin-4-yl]quinoline-8-carbonitrile;

5-[(2R,6S)-2-methyl-6-[[4-[(6R)-6-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(6S)-6-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoline-8-carbonitrile;

5-[(2R,6S)-2-methyl-6-[[4-[(5R)-5-methyl-5,6,7,8-tetrahydro-2,6-naphthyridin-3-yl]piperazin-1-yl]methyl]morpholin-4-yl]quinoline-8-carbonitrile;

5-[(2R,6S)-2-methyl-6-[[4-[(5S)-5-methyl-5,6,7,8-tetrahydro-2,6-naphthyridin-3-yl]piperazin-1-yl]methyl]morpholin-4-yl]quinoline-8-carbonitrile;

5-[(2R,6S)-2-methyl-6-[[4-[(7S)-7-methyl-5,6,7,8-tetrahydro-2,6-naphthyridin-3-yl]piperazin-1-yl]methyl]morpholin-4-yl]quinoline-8-carbonitrile;

5-[(2R,6S)-2-methyl-6-[[4-[(7R)-7-methyl-5,6,7,8-tetrahydro-2,6-naphthyridin-3-yl]piperazin-1-yl]methyl]morpholin-4-yl]quinoline-8-carbonitrile;

8-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoxaline-5-carbonitrile;

8-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoxaline-5-carbonitrile;

8-[(2R,6S)-2-methyl-6-[[4-(5,6,7,8-tetrahydro-2,6-naphthyridin-3-yl)piperazin-1-yl]methyl]morpholin-4-yl]quinoxaline-5-carbonitrile;

8-[(2R,6S)-2-methyl-6-[[4-[(7S)-7-methyl-5,6,7,8-tetrahydro-2,6-naphthyridin-3-yl]piperazin-1-yl]methyl]morpholin-4-yl]quinoxaline-5-carbonitrile;

8-[(2R,6S)-2-methyl-6-[[4-[(7R)-7-methyl-5,6,7,8-tetrahydro-2,6-naphthyridin-3-yl]piperazin-1-yl]methyl]morpholin-4-yl]quinoxaline-5-carbonitrile;

8-[(2R,6S)-2-methyl-6-[[4-[(6R)-6-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-[(6S)-6-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoxaline-5-carbonitrile;

8-[(2R,6S)-2-methyl-6-[[4-[(5R)-5-methyl-5,6,7,8-tetrahydro-2,6-naphthyridin-3-yl]piperazin-1-yl]methyl]morpholin-4-yl]quinoxaline-5-carbonitrile;

8-[(2R,6S)-2-methyl-6-[[4-[(5S)-5-methyl-5,6,7,8-tetrahydro-2,6-naphthyridin-3-yl]piperazin-1-yl]methyl]morpholin-4-yl]quinoxaline-5-carbonitrile;

(2R,6S)-4-(8-methoxyquinoxalin-5-yl)-2-methyl-6-[[4-(5,6,7,8-tetrahydro-2,6-naphthyridin-3-yl)piperazin-1-yl]methyl]morpholine;

2-methyl-8-[(2R,6S)-2-methyl-6-[[4-(5,6,7,8-tetrahydro-2,6-naphthyridin-3-yl)piperazin yl]methyl]morpholin-4-yl]quinoxaline-5-carbonitrile;

(2R,6S)-2-methyl-6-[[4-(5,6,7,8-tetrahydro-2,6-naphthyridin-3-yl)piperazin-1-yl]methyl]-4-[8-(trifluoromethyl)quinoxalin-5-yl]morpholine;

(2R,6S)-2-methyl-4-(8-methylquinoxalin-5-yl)-6-[[4-[(5R)-5-methyl-5,6,7,8-tetrahydro-2,6-naphthyridin-3-yl]piperazin-1-yl]methyl]morpholine;

(2R,6S)-2-methyl-4-(8-methylquinoxalin-5-yl)-6-[[4-[(5S)-5-methyl-5,6,7,8-tetrahydro-2,6-naphthyridin-3-yl]piperazin-1-yl]methyl]morpholine;

2,3-dideuterio-8-[(2R,6S)-2-methyl-6-[[4-[(8S)-8-methyl-5,6,7,8-tetrahydro-2,7-naphthyridin-3-yl]piperazin-1-yl]methyl]morpholin-4-yl]quinoxaline-5-carbonitrile;

2,3-dideuterio-8-[(2R,6S)-2-methyl-6-[[4-[(8R)-8-methyl-5,6,7,8-tetrahydro-2,7-naphthyridin-3-yl]piperazin-1-yl]methyl]morpholin-4-yl]quinoxaline-5-carbonitrile;

2,3-dideuterio-8-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoxaline-5-carbonitrile;

2,3-dideuterio-8-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoxaline-5-carbonitrile;

2-deuterio-5-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]quinoline-8-carbonitrile;

2-deuterio-5-[(2R,6S)-2-methyl-6-[[4-[(5S)-5-methyl-6,7-dihydro-5H-pyrrolo[3,4-b]pyridin-2-yl]piperazin-1-yl]methyl]morpholin-4-yl]quinoline-8-carbonitrile;

1-methyl-4-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]-1,8-naphthyridin-2-one;

1-isopropyl-4-[(2R,6S)-2-methyl-6-[[4-[(5R)-5-methyl-6,7-dihydro-5H-pyrrolo[3,4-b]pyridin-2-yl]piperazin-1-yl]methyl]morpholin-4-yl]-1,8-naphthyridin-2-one; and 1-methyl-4-[(2R,6S)-2-methyl-6-[[4-(5,6,7,8-tetrahydro-2,6-naphthyridin-3-yl)piperazin-1-yl]methyl]morpholin-4-yl]-1,8-naphthyridin-2-one;

or a pharmaceutically acceptable salt, enantiomer or diastereomer thereof.

14. A pharmaceutical composition comprising a compound of claim 1, or a pharmaceutically acceptable salt thereof, and a therapeutically inert carrier.

15. A method for the treatment of systemic lupus erythematosus or lupus nephritis in a mammal in need thereof, which method comprises administering to the mammal a therapeutically effective amount of a compound as defined in claim 1, or pharmaceutically acceptable salt thereof.

16. A pharmaceutical composition comprising a compound of claim 13, or a pharmaceutically acceptable salt thereof, and a therapeutically inert carrier.

17. A method for the treatment of systemic lupus erythematosus or lupus nephritis in a mammal in need thereof, which method comprises administering to the mammal a therapeutically effective amount of a compound as defined in claim 13, or pharmaceutically acceptable salt thereof.

* * * * *